US011390914B2

(12) United States Patent
Fu et al.

(10) Patent No.: US 11,390,914 B2
(45) Date of Patent: Jul. 19, 2022

(54) METHODS AND COMPOSITIONS FOR WHOLE TRANSCRIPTOME AMPLIFICATION

(71) Applicant: Cellular Research, Inc., Menlo Park, CA (US)

(72) Inventors: Glenn Fu, Menlo Park, CA (US); Craig Betts, Menlo Park, CA (US); Christina Fan, Menlo Park, CA (US); Gretchen Yinbon Lam, Menlo Park, CA (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 15/134,967

(22) Filed: Apr. 21, 2016

(65) Prior Publication Data
US 2016/0312276 A1    Oct. 27, 2016

Related U.S. Application Data

(60) Provisional application No. 62/196,782, filed on Jul. 24, 2015, provisional application No. 62/151,583, filed on Apr. 23, 2015.

(51) Int. Cl.
*C12Q 1/68* (2018.01)
*C12Q 1/6855* (2018.01)
*C12Q 1/6806* (2018.01)
*C12Q 1/6837* (2018.01)

(52) U.S. Cl.
CPC ......... *C12Q 1/6855* (2013.01); *C12Q 1/6806* (2013.01); *C12Q 1/6837* (2013.01)

(58) Field of Classification Search
None
See application file for complete search history.

(56) References Cited

U.S. PATENT DOCUMENTS

| | | | |
|---|---|---|---|
| 4,510,244 A | 4/1985 | Parks et al. | |
| 4,725,536 A | 2/1988 | Fritsch et al. | |
| 5,124,246 A | 6/1992 | Urdea et al. | |
| 5,149,625 A | 9/1992 | Church et al. | |
| 5,200,314 A | 4/1993 | Urdea | |
| 5,308,990 A | 5/1994 | Takahashi et al. | |
| 5,424,186 A | 6/1995 | Fodor et al. | |
| 5,424,413 A | 6/1995 | Hogan et al. | |
| 5,445,934 A | 8/1995 | Fodor et al. | |
| 5,604,097 A | 2/1997 | Brenner | |
| 5,635,352 A | 6/1997 | Urdea et al. | |
| 5,635,400 A | 6/1997 | Brenner | |
| 5,648,245 A | 7/1997 | Fire et al. | |
| 5,654,413 A | 8/1997 | Brenner | |
| 5,656,731 A | 8/1997 | Urdea | |
| 5,658,737 A | 8/1997 | Nelson et al. | |
| 5,714,330 A | 2/1998 | Brenner et al. | |
| 5,744,305 A | 4/1998 | Fodor et al. | |
| 5,759,778 A | 6/1998 | Li et al. | |
| 5,763,175 A | 6/1998 | Brenner | |
| 5,800,992 A | 9/1998 | Fodor et al. | |
| 5,830,712 A | 11/1998 | Rampersad et al. | |
| 5,846,719 A | 12/1998 | Brenner et al. | |
| 5,854,033 A | 12/1998 | Lizardi | |
| 5,871,928 A | 2/1999 | Fodor et al. | |
| 5,925,525 A | 7/1999 | Fodor et al. | |
| 5,935,793 A | 8/1999 | Wong | |
| 5,962,271 A | 10/1999 | Chenchick et al. | |
| 5,962,272 A | 10/1999 | Chenchick et al. | |
| 5,968,740 A | 10/1999 | Fodor et al. | |
| 5,981,176 A | 11/1999 | Wallace | |
| 5,981,179 A | 11/1999 | Lorinez et al. | |
| 6,013,445 A | 1/2000 | Albrecht et al. | |
| 6,040,138 A | 3/2000 | Lockhart et al. | |
| 6,046,005 A | 4/2000 | Ju et al. | |
| 6,060,596 A | 5/2000 | Lerner et al. | |
| 6,064,755 A | 5/2000 | Some | |
| 6,114,149 A | 9/2000 | Fry et al. | |
| 6,117,631 A | 9/2000 | Nilsen | |
| 6,124,092 A | 9/2000 | O'neill et al. | |
| 6,138,077 A | 10/2000 | Brenner | |
| 6,140,489 A | 10/2000 | Brenner | |
| 6,172,214 B1 | 1/2001 | Brenner | |
| 6,197,506 B1 | 3/2001 | Fodor et al. | |
| 6,197,554 B1 | 3/2001 | Lin et al. | |
| 6,214,558 B1 | 4/2001 | Shuber et al. | |
| 6,235,475 B1 | 5/2001 | Brenner et al. | |
| 6,235,483 B1 | 5/2001 | Wolber et al. | |
| 6,265,163 B1 | 7/2001 | Albrecht et al. | |
| 6,268,152 B1 | 7/2001 | Fodor et al. | |
| 6,284,460 B1 | 9/2001 | Fodor et al. | |
| 6,284,485 B1 | 9/2001 | Boyle | |

(Continued)

FOREIGN PATENT DOCUMENTS

| | | |
|---|---|---|
| CA | 2474509 | 2/2003 |
| DE | 102008025656 | 12/2009 |

(Continued)

OTHER PUBLICATIONS

"Viruses" (Wikipedia.com, accessed Nov. 24, 2012). (Year: 2012).*
"How many species of bacteria are there" (wisegeek.com; accessed Jan. 21, 2014). (Year: 2014).*
"Fungi," (Wikipedia.com; accessed Jun. 3, 2013). (Year: 2013).*
"Plant," (Wikipedia.com; accessed Aug. 28, 2015). (Year: 2015).*
"Mammal," (Wikipedia.com; accessed Sep. 22, 2011). (Year: 2011).*
"Murinae," (Wikipedia.com, accessed Mar. 18, 2013). (Year: 2013).*
"Fish," (Wikipedia.com, accessed Nov. 2, 2014). (Year: 2014).*
"Archaea," Wikipedia.com (accessed May 11, 2016). (Year: 2016).*

(Continued)

*Primary Examiner* — Bradley L. Sisson
(74) *Attorney, Agent, or Firm* — Sheppard, Mullin, Richter & Hampton LLP

(57) ABSTRACT

The disclosure provides for methods, compositions, systems, devices, and kits for whole transcriptome amplification using stochastic barcodes.

23 Claims, 60 Drawing Sheets

Specification includes a Sequence Listing.

(56) References Cited

U.S. PATENT DOCUMENTS

| | | |
|---|---|---|
| 6,309,822 B1 | 10/2001 | Fodor et al. |
| 6,309,823 B1 | 10/2001 | Cronin et al. |
| 6,326,148 B1 | 12/2001 | Pauletti et al. |
| 6,355,431 B1 | 3/2002 | Chee et al. |
| 6,355,432 B1 | 3/2002 | Fodor et al. |
| 6,372,813 B1 | 4/2002 | Johnson et al. |
| 6,395,491 B1 | 5/2002 | Fodor et al. |
| 6,406,848 B1 | 6/2002 | Bridgham et al. |
| 6,436,675 B1 | 8/2002 | Welch et al. |
| 6,440,667 B1 | 8/2002 | Fodor et al. |
| 6,440,706 B1 | 8/2002 | Vogelstein et al. |
| 6,451,536 B1 | 9/2002 | Fodor et al. |
| 6,458,530 B1 | 10/2002 | Morris et al. |
| 6,468,744 B1 | 10/2002 | Cronin et al. |
| 6,480,791 B1 | 11/2002 | Strathmann |
| 6,489,114 B2 | 12/2002 | Laayoun et al. |
| 6,489,116 B2 | 12/2002 | Wagner |
| 6,492,121 B2 | 12/2002 | Kurane et al. |
| 6,500,620 B2 | 12/2002 | Yu et al. |
| 6,512,105 B1 | 1/2003 | Hogan et al. |
| 6,514,699 B1 | 2/2003 | O'neill et al. |
| 6,544,739 B1 | 4/2003 | Fodor et al. |
| 6,551,784 B2 | 4/2003 | Fodor et al. |
| 6,576,424 B2 | 6/2003 | Fodor et al. |
| 6,600,996 B2 | 7/2003 | Webster et al. |
| 6,629,040 B1 | 9/2003 | Goodlett et al. |
| 6,653,077 B1 | 11/2003 | Brenner |
| 6,753,147 B2 | 6/2004 | Vogelstein et al. |
| 6,787,308 B2 | 9/2004 | Balasubramanian et al. |
| 6,808,906 B2 | 10/2004 | Shen et al. |
| 6,849,404 B2 | 2/2005 | Park et al. |
| 6,852,488 B2 | 2/2005 | Fodor et al. |
| 6,858,412 B2 | 2/2005 | Willis et al. |
| 6,890,741 B2 | 5/2005 | Fan et al. |
| 6,946,251 B2 | 9/2005 | Kurn |
| 6,974,669 B2 | 12/2005 | Mirkin et al. |
| 7,022,479 B2 | 4/2006 | Wagner |
| 7,034,145 B2 | 4/2006 | Shen et al. |
| 7,155,050 B1 | 12/2006 | Sloge |
| 7,294,466 B2 | 11/2007 | McMillan |
| 7,323,309 B2 | 1/2008 | Mirkin et al. |
| 7,393,665 B2 | 7/2008 | Brenner |
| 7,407,757 B2 | 8/2008 | Brenner |
| 7,424,368 B2 | 9/2008 | Huang et al. |
| 7,432,055 B2 | 10/2008 | Pemov et al. |
| 7,470,515 B2 | 12/2008 | Rashtchian et al. |
| 7,473,767 B2 | 1/2009 | Dimitrov |
| 7,476,786 B2 | 1/2009 | Chan et al. |
| 7,537,897 B2 | 5/2009 | Brenner et al. |
| 7,544,473 B2 | 6/2009 | Brenner |
| 7,635,566 B2 | 12/2009 | Brenner |
| 7,638,612 B2 | 12/2009 | Rashtchian et al. |
| 7,718,403 B2 | 5/2010 | Kamberov et al. |
| 7,771,946 B2 | 8/2010 | Kurn |
| 7,822,555 B2 | 10/2010 | Huang et al. |
| 7,824,856 B2 | 11/2010 | Monforte |
| 7,824,889 B2 | 11/2010 | Vogelstein et al. |
| 7,915,015 B2 | 3/2011 | Vogelstein et al. |
| 7,985,546 B2 | 7/2011 | Church et al. |
| 8,071,311 B2 | 12/2011 | Kurn |
| 8,110,351 B2 | 2/2012 | Bosnes |
| 8,114,681 B2 | 2/2012 | Martin et al. |
| 8,148,068 B2 | 4/2012 | Brenner |
| 8,168,385 B2 | 5/2012 | Brenner |
| 8,206,913 B1 | 6/2012 | Kamberov et al. |
| 8,241,850 B2 | 8/2012 | Brenner |
| 8,298,767 B2 | 10/2012 | Brenner et al. |
| 8,318,433 B2 | 11/2012 | Brenner |
| 8,367,051 B2 | 2/2013 | Matyjaszewski et al. |
| 8,420,324 B2 | 4/2013 | Rashtchian et al. |
| 8,445,205 B2 | 5/2013 | Brenner |
| 8,470,996 B2 | 6/2013 | Brenner |
| 8,476,018 B2 | 7/2013 | Brenner |
| 8,481,292 B2 | 7/2013 | Casbon et al. |
| 8,535,889 B2 | 9/2013 | Larson et al. |
| 8,563,274 B2 | 10/2013 | Brenner et al. |
| 8,603,749 B2 | 12/2013 | Gillevet |
| 8,679,756 B1 | 3/2014 | Brenner et al. |
| 8,685,678 B2 | 4/2014 | Casbon et al. |
| 8,685,753 B2 | 4/2014 | Martin et al. |
| 8,715,967 B2 | 5/2014 | Casbon et al. |
| 8,722,368 B2 | 5/2014 | Casbon et al. |
| 8,728,766 B2 | 5/2014 | Casbon et al. |
| 8,741,606 B2 | 6/2014 | Casbon et al. |
| 8,835,110 B2 | 9/2014 | Wang et al. |
| 8,835,358 B2 | 9/2014 | Fodor et al. |
| 8,841,071 B2 | 9/2014 | Link |
| 8,856,410 B2 | 10/2014 | Park |
| 9,150,852 B2 | 10/2015 | Samuels et al. |
| 9,181,582 B2 | 11/2015 | Kurn |
| 9,228,229 B2 | 1/2016 | Olson et al. |
| 9,290,808 B2 | 3/2016 | Fodor et al. |
| 9,290,809 B2 | 3/2016 | Fodor et al. |
| 9,297,047 B2 * | 3/2016 | Furchak ............... C12Q 1/6886 |
| 9,315,857 B2 | 4/2016 | Fu et al. |
| 9,371,598 B2 | 6/2016 | Chee |
| 9,582,877 B2 | 2/2017 | Fu et al. |
| 9,593,365 B2 | 3/2017 | Frisen et al. |
| 9,644,204 B2 | 5/2017 | Hindson et al. |
| 9,689,024 B2 | 6/2017 | Hindson et al. |
| 9,695,468 B2 | 7/2017 | Hindson et al. |
| 9,787,810 B1 | 10/2017 | Chiang |
| 9,850,515 B2 | 12/2017 | McCoy et al. |
| 9,868,979 B2 | 1/2018 | Chee et al. |
| 9,879,313 B2 | 1/2018 | Chee et al. |
| 9,905,005 B2 | 2/2018 | Fu et al. |
| 9,938,523 B2 | 4/2018 | LaBaer |
| 9,951,386 B2 | 4/2018 | Hindson et al. |
| 9,988,660 B2 | 6/2018 | Rashtchian et al. |
| 10,011,872 B1 | 7/2018 | Belgrader et al. |
| 10,017,761 B2 | 7/2018 | Weissman et al. |
| 10,023,910 B2 | 7/2018 | Drmanac et al. |
| 10,030,267 B2 | 7/2018 | Hindson et al. |
| 10,041,116 B2 | 8/2018 | Hindson et al. |
| 10,131,958 B1 | 11/2018 | Fan et al. |
| 10,138,518 B2 * | 11/2018 | Chun ................... C12Q 1/6853 |
| 10,151,003 B2 | 12/2018 | Fan et al. |
| 10,208,343 B2 | 2/2019 | Hindson et al. |
| 10,227,648 B2 | 3/2019 | Hindson et al. |
| 10,246,703 B2 | 4/2019 | Church et al. |
| 10,253,364 B2 | 4/2019 | Hindson et al. |
| 10,273,541 B2 | 4/2019 | Hindson et al. |
| 10,288,608 B2 | 5/2019 | Kozlov et al. |
| 10,294,511 B2 | 5/2019 | Sanches-Kuiper et al. |
| 10,308,982 B2 | 6/2019 | Chee |
| 10,323,278 B2 | 6/2019 | Belgrader et al. |
| 10,337,061 B2 | 7/2019 | Hindson et al. |
| 10,344,329 B2 | 7/2019 | Hindson et al. |
| 2001/0024784 A1 | 9/2001 | Wagner |
| 2001/0036632 A1 | 11/2001 | Yu et al. |
| 2002/0019005 A1 | 2/2002 | Kamb |
| 2002/0051986 A1 | 5/2002 | Baez et al. |
| 2002/0065609 A1 * | 5/2002 | Ashby ................ C12Q 1/6809 702/20 |
| 2002/0072058 A1 | 6/2002 | Voelker et al. |
| 2002/0094116 A1 | 7/2002 | Forst et al. |
| 2002/0106666 A1 | 8/2002 | Hayashizaki |
| 2002/0132241 A1 | 9/2002 | Fan et al. |
| 2002/0168665 A1 | 11/2002 | Okawa |
| 2002/0172953 A1 | 11/2002 | Mirkin et al. |
| 2002/0187480 A1 | 12/2002 | Brandon |
| 2002/0192687 A1 | 12/2002 | Mirkin et al. |
| 2003/0003490 A1 | 1/2003 | Fan et al. |
| 2003/0013091 A1 | 1/2003 | Dimitrov |
| 2003/0032049 A1 | 2/2003 | Wagner |
| 2003/0049616 A1 | 3/2003 | Brenner et al. |
| 2003/0077611 A1 | 4/2003 | Slepnev |
| 2003/0082818 A1 | 5/2003 | Bahnson et al. |
| 2003/0087242 A1 | 5/2003 | Mirkin et al. |
| 2003/0104436 A1 | 6/2003 | Morris et al. |
| 2003/0165935 A1 | 9/2003 | Vann et al. |
| 2003/0175908 A1 | 9/2003 | Linnarsson et al. |
| 2003/0186251 A1 | 10/2003 | Dunn et al. |
| 2003/0207296 A1 | 11/2003 | Park et al. |

(56) References Cited

U.S. PATENT DOCUMENTS

| | | |
|---|---|---|
| 2003/0207300 A1 | 11/2003 | Matray et al. |
| 2004/0047769 A1 | 3/2004 | Tanaami |
| 2004/0096368 A1 | 5/2004 | Davis |
| 2004/0096892 A1 | 5/2004 | Wang et al. |
| 2004/0121342 A1 | 6/2004 | McKeown |
| 2004/0146901 A1 | 7/2004 | Morris et al. |
| 2004/0157243 A1 | 8/2004 | Huang et al. |
| 2004/0209298 A1* | 10/2004 | Kamberov ............ C12Q 1/686 435/6.14 |
| 2004/0224325 A1 | 11/2004 | Knapp et al. |
| 2004/0259118 A1 | 12/2004 | Macevicz |
| 2005/0019776 A1 | 1/2005 | Callow et al. |
| 2005/0032110 A1 | 2/2005 | Shen et al. |
| 2005/0048500 A1 | 3/2005 | Lawton |
| 2005/0053952 A1 | 3/2005 | Hong et al. |
| 2005/0105077 A1 | 5/2005 | Padmanabhan |
| 2005/0170373 A1 | 8/2005 | Monforte |
| 2005/0175993 A1 | 8/2005 | Wei |
| 2005/0196760 A1 | 9/2005 | Pemov et al. |
| 2005/0214825 A1 | 9/2005 | Stuelpnagel |
| 2005/0250146 A1 | 11/2005 | McMillan |
| 2005/0250147 A1 | 11/2005 | Macevicz |
| 2006/0002824 A1 | 1/2006 | Chang et al. |
| 2006/0035258 A1 | 2/2006 | Tadakamalla et al. |
| 2006/0040297 A1 | 2/2006 | Leamon et al. |
| 2006/0041385 A1 | 2/2006 | Bauer |
| 2006/0073506 A1 | 4/2006 | Christians et al. |
| 2006/0211030 A1 | 9/2006 | Brenner |
| 2006/0263709 A1 | 11/2006 | Matsumura et al. |
| 2006/0263789 A1 | 11/2006 | Kincaid |
| 2006/0280352 A1 | 12/2006 | Muschler |
| 2006/0281092 A1 | 12/2006 | Wille et al. |
| 2006/0286570 A1* | 12/2006 | Rowlen ............... C12Q 1/6816 435/6.12 |
| 2007/0020640 A1 | 1/2007 | Mccloskey et al. |
| 2007/0031829 A1* | 2/2007 | Yasuno ............... C12Q 1/6886 435/6.12 |
| 2007/0042400 A1* | 2/2007 | Choi .................. C12N 15/10 435/6.12 |
| 2007/0042419 A1* | 2/2007 | Barany ............... C12Q 1/6813 435/6.12 |
| 2007/0065823 A1 | 3/2007 | Dressman et al. |
| 2007/0065844 A1 | 3/2007 | Golub et al. |
| 2007/0105090 A1 | 5/2007 | Cassidy et al. |
| 2007/0117121 A1 | 5/2007 | Hutchison |
| 2007/0117134 A1 | 5/2007 | Kou |
| 2007/0117177 A1 | 5/2007 | Luo et al. |
| 2007/0133856 A1 | 6/2007 | Dutta-Choudhury |
| 2007/0172873 A1 | 7/2007 | Brenner et al. |
| 2007/0178478 A1 | 8/2007 | Dhallan et al. |
| 2007/0202523 A1 | 8/2007 | Becker et al. |
| 2008/0038727 A1 | 2/2008 | Spier |
| 2008/0070303 A1 | 3/2008 | West et al. |
| 2008/0119736 A1 | 5/2008 | Dentinger |
| 2008/0194414 A1 | 8/2008 | Albert et al. |
| 2008/0261204 A1 | 10/2008 | Lexow |
| 2008/0268508 A1 | 10/2008 | Sowlay |
| 2008/0269068 A1 | 10/2008 | Church et al. |
| 2008/0274458 A1 | 11/2008 | Latham et al. |
| 2008/0299609 A1 | 12/2008 | Kwon et al. |
| 2008/0318802 A1 | 12/2008 | Brenner |
| 2009/0053669 A1 | 2/2009 | Liu et al. |
| 2009/0061513 A1 | 3/2009 | Andersson et al. |
| 2009/0105959 A1 | 4/2009 | Braverman et al. |
| 2009/0131269 A1 | 5/2009 | Martin et al. |
| 2009/0137407 A1 | 5/2009 | Church et al. |
| 2009/0220385 A1 | 9/2009 | Brown |
| 2009/0226891 A2 | 9/2009 | Nova et al. |
| 2009/0252414 A1 | 10/2009 | Suzuki |
| 2009/0253586 A1 | 10/2009 | Nelson et al. |
| 2009/0283676 A1 | 11/2009 | Skoglund |
| 2009/0290151 A1 | 11/2009 | Agrawal |
| 2009/0298709 A1 | 12/2009 | Ma |
| 2010/0069250 A1 | 3/2010 | White, III |
| 2010/0105049 A1 | 4/2010 | Ehrich et al. |
| 2010/0105112 A1 | 4/2010 | Holtze et al. |
| 2010/0105886 A1 | 4/2010 | Woudenberg et al. |
| 2010/0120098 A1 | 5/2010 | Grunenwald et al. |
| 2010/0120630 A1 | 5/2010 | Huang et al. |
| 2010/0136544 A1 | 6/2010 | Agresti et al. |
| 2010/0159533 A1 | 6/2010 | Lipson et al. |
| 2010/0167354 A1 | 7/2010 | Kurn |
| 2010/0184076 A1 | 7/2010 | Lawton |
| 2010/0255471 A1 | 10/2010 | Clarke |
| 2010/0267028 A1 | 10/2010 | Pasche |
| 2010/0291666 A1 | 11/2010 | Collier et al. |
| 2010/0300895 A1 | 12/2010 | Nobile et al. |
| 2010/0323348 A1 | 12/2010 | Hamady et al. |
| 2010/0330574 A1 | 12/2010 | Whitman |
| 2011/0038507 A1 | 2/2011 | Hager |
| 2011/0059436 A1 | 3/2011 | Hardin et al. |
| 2011/0059556 A1 | 3/2011 | Strey et al. |
| 2011/0070584 A1 | 3/2011 | Wohlgemuth et al. |
| 2011/0072889 A1 | 3/2011 | Albitar et al. |
| 2011/0160078 A1 | 6/2011 | Fodor et al. |
| 2011/0201507 A1 | 8/2011 | Rava et al. |
| 2011/0230358 A1 | 9/2011 | Rava |
| 2011/0244455 A1 | 10/2011 | Larson et al. |
| 2011/0245111 A1 | 10/2011 | Chee |
| 2011/0263457 A1 | 10/2011 | Krutzik et al. |
| 2011/0294689 A1 | 12/2011 | Namsaraev |
| 2011/0312511 A1 | 12/2011 | Winquist et al. |
| 2012/0004132 A1 | 1/2012 | Zhang et al. |
| 2012/0010091 A1 | 1/2012 | Linnarson |
| 2012/0014977 A1* | 1/2012 | Furihata ............. C07K 14/4748 424/185.1 |
| 2012/0034607 A1 | 2/2012 | Rothberg |
| 2012/0040843 A1 | 2/2012 | Ducree et al. |
| 2012/0045844 A1 | 2/2012 | Rothberg et al. |
| 2012/0058520 A1 | 3/2012 | Hayashida |
| 2012/0058902 A1 | 3/2012 | Livingston et al. |
| 2012/0065081 A1 | 3/2012 | Chee |
| 2012/0071331 A1 | 3/2012 | Casbon |
| 2012/0087862 A1 | 4/2012 | Hood et al. |
| 2012/0142018 A1 | 6/2012 | Jiang |
| 2012/0149603 A1 | 6/2012 | Cooney |
| 2012/0156675 A1 | 6/2012 | Lueerssen et al. |
| 2012/0163681 A1 | 6/2012 | Lohse |
| 2012/0165219 A1* | 6/2012 | Van Der Zaag ...... C12Q 1/6834 506/9 |
| 2012/0173159 A1 | 7/2012 | Davey et al. |
| 2012/0190020 A1 | 7/2012 | Oliphant et al. |
| 2012/0202293 A1 | 8/2012 | Martin et al. |
| 2012/0220022 A1 | 8/2012 | Ehrlich et al. |
| 2012/0220494 A1 | 8/2012 | Samuels |
| 2012/0231972 A1* | 9/2012 | Golyshin ................ C12Q 1/00 506/11 |
| 2012/0252012 A1* | 10/2012 | Armougom ............ C12Q 1/689 435/6.11 |
| 2012/0253689 A1* | 10/2012 | Rogan ..................... G06F 19/22 702/20 |
| 2012/0316074 A1 | 12/2012 | Saxonov |
| 2012/0322681 A1 | 12/2012 | Kung et al. |
| 2013/0005585 A1 | 1/2013 | Anderson et al. |
| 2013/0022977 A1 | 1/2013 | Lapidus et al. |
| 2013/0045994 A1 | 2/2013 | Shinozuka et al. |
| 2013/0116130 A1 | 5/2013 | Fu et al. |
| 2013/0190206 A1 | 7/2013 | Leonard |
| 2013/0203047 A1 | 8/2013 | Casbon et al. |
| 2013/0210643 A1 | 8/2013 | Casbon et al. |
| 2013/0210659 A1 | 8/2013 | Watson et al. |
| 2013/0224743 A1 | 8/2013 | Casbon et al. |
| 2013/0225418 A1 | 8/2013 | Watson |
| 2013/0225623 A1* | 8/2013 | Buxbaum ............... A61K 31/44 514/277 |
| 2013/0237458 A1 | 9/2013 | Casbon et al. |
| 2013/0267424 A1 | 10/2013 | Casbon et al. |
| 2013/0274117 A1 | 10/2013 | Church |
| 2013/0323732 A1 | 12/2013 | Anderson et al. |
| 2014/0057799 A1 | 2/2014 | Johnson |
| 2014/0066318 A1 | 3/2014 | Frisen et al. |
| 2014/0147860 A1 | 5/2014 | Kaduchak |
| 2014/0155274 A1 | 6/2014 | Xie et al. |

(56) References Cited

U.S. PATENT DOCUMENTS

| | | |
|---|---|---|
| 2014/0155295 A1 | 6/2014 | Hindson et al. |
| 2014/0178438 A1 | 6/2014 | Sahin et al. |
| 2014/0194324 A1 | 7/2014 | Gormley et al. |
| 2014/0206079 A1 | 7/2014 | Malinoski |
| 2014/0206547 A1 | 7/2014 | Wang |
| 2014/0216128 A1 | 8/2014 | Neat |
| 2014/0227684 A1 | 8/2014 | Hindson et al. |
| 2014/0227705 A1 | 8/2014 | Vogelstein et al. |
| 2014/0228239 A1 | 8/2014 | McCoy et al. |
| 2014/0228255 A1 | 8/2014 | Hindson et al. |
| 2014/0235506 A1 | 8/2014 | Hindson et al. |
| 2014/0243242 A1 | 8/2014 | Nicol et al. |
| 2014/0244742 A1 | 8/2014 | Yu et al. |
| 2014/0272952 A1 | 9/2014 | May et al. |
| 2014/0274811 A1 | 9/2014 | Arnold |
| 2014/0287963 A1 | 9/2014 | Hindson et al. |
| 2014/0303005 A1 | 10/2014 | Samuels et al. |
| 2014/0309945 A1 | 10/2014 | Park et al. |
| 2014/0315211 A1 | 10/2014 | Sugino et al. |
| 2014/0357500 A1 | 12/2014 | Vigneault et al. |
| 2014/0378322 A1 | 12/2014 | Hindson et al. |
| 2014/0378345 A1 | 12/2014 | Hindson et al. |
| 2014/0378349 A1 | 12/2014 | Hindson et al. |
| 2014/0378350 A1 | 12/2014 | Hindson et al. |
| 2015/0005185 A1 | 1/2015 | Fodor et al. |
| 2015/0005199 A1 | 1/2015 | Hindson et al. |
| 2015/0005200 A1* | 1/2015 | Hindson ............ C12N 15/1065 506/31 |
| 2015/0011396 A1* | 1/2015 | Schroeder .......... C12N 15/1093 506/26 |
| 2015/0017654 A1 | 1/2015 | Gorfinkel et al. |
| 2015/0066385 A1 | 3/2015 | Schnall-levin et al. |
| 2015/0072867 A1 | 3/2015 | Soldatov et al. |
| 2015/0099661 A1 | 4/2015 | Fodor et al. |
| 2015/0099673 A1 | 4/2015 | Fodor et al. |
| 2015/0111256 A1 | 4/2015 | Church et al. |
| 2015/0118680 A1 | 4/2015 | Fodor et al. |
| 2015/0119255 A1 | 4/2015 | Fodor et al. |
| 2015/0119256 A1 | 4/2015 | Fodor et al. |
| 2015/0119257 A1 | 4/2015 | Fodor et al. |
| 2015/0119258 A1 | 4/2015 | Fodor et al. |
| 2015/0119290 A1 | 4/2015 | Fodor et al. |
| 2015/0133319 A1 | 5/2015 | Fu et al. |
| 2015/0141292 A1 | 5/2015 | Fodor et al. |
| 2015/0152409 A1 | 6/2015 | Seitz et al. |
| 2015/0203897 A1 | 7/2015 | Robons et al. |
| 2015/0211050 A1 | 7/2015 | Iafrate et al. |
| 2015/0218620 A1 | 8/2015 | Behlke et al. |
| 2015/0225777 A1 | 8/2015 | Hindson et al. |
| 2015/0225778 A1 | 8/2015 | Hindson et al. |
| 2015/0247182 A1 | 9/2015 | Faham et al. |
| 2015/0259734 A1 | 9/2015 | Asbury et al. |
| 2015/0298091 A1 | 10/2015 | Weitz |
| 2015/0299784 A1 | 10/2015 | Fan et al. |
| 2015/0307874 A1 | 10/2015 | Jaitin |
| 2015/0329852 A1 | 11/2015 | Nolan |
| 2015/0360193 A1 | 12/2015 | Fan et al. |
| 2015/0376609 A1 | 12/2015 | Hindson et al. |
| 2016/0010151 A1 | 1/2016 | Fan et al. |
| 2016/0017320 A1 | 1/2016 | Wang et al. |
| 2016/0026758 A1 | 1/2016 | Jabara et al. |
| 2016/0053253 A1 | 2/2016 | Salathia et al. |
| 2016/0055632 A1 | 2/2016 | Fu et al. |
| 2016/0060682 A1 | 3/2016 | Pregibon et al. |
| 2016/0068889 A1 | 3/2016 | Gole et al. |
| 2016/0122751 A1 | 5/2016 | LaBaer |
| 2016/0122753 A1 | 5/2016 | Mikkelsen |
| 2016/0138091 A1 | 5/2016 | Chee et al. |
| 2016/0145677 A1 | 5/2016 | Chee et al. |
| 2016/0145683 A1 | 5/2016 | Fan et al. |
| 2016/0201125 A1 | 7/2016 | Samuels et al. |
| 2016/0208322 A1 | 7/2016 | Anderson et al. |
| 2016/0222378 A1 | 8/2016 | Fodor et al. |
| 2016/0232291 A1 | 8/2016 | Kyriazopoulou-Panagiotopoulou et al. |
| 2016/0244742 A1 | 8/2016 | Linnarsson et al. |
| 2016/0244828 A1 | 8/2016 | Mason |
| 2016/0253584 A1 | 9/2016 | Fodor et al. |
| 2016/0257993 A1 | 9/2016 | Fu et al. |
| 2016/0265027 A1 | 9/2016 | Sanches-Kuiper et al. |
| 2016/0265069 A1 | 9/2016 | Fan et al. |
| 2016/0289669 A1 | 10/2016 | Fan et al. |
| 2016/0289670 A1 | 10/2016 | Samuels et al. |
| 2016/0289740 A1 | 10/2016 | Fu et al. |
| 2016/0298180 A1 | 10/2016 | Chee |
| 2016/0320720 A1 | 11/2016 | Fan et al. |
| 2016/0326584 A1 | 11/2016 | Fodor et al. |
| 2016/0355879 A1 | 12/2016 | Kamberov et al. |
| 2016/0376583 A1 | 12/2016 | Fodor et al. |
| 2016/0376648 A1 | 12/2016 | Fodor et al. |
| 2017/0044525 A1 | 2/2017 | Kaper et al. |
| 2017/0073730 A1 | 3/2017 | Betts et al. |
| 2017/0154421 A1 | 6/2017 | Fu et al. |
| 2017/0192013 A1 | 7/2017 | Agresti et al. |
| 2017/0260584 A1 | 9/2017 | Zheng et al. |
| 2017/0275669 A1 | 9/2017 | Weissleder et al. |
| 2017/0314067 A1 | 11/2017 | Shum et al. |
| 2017/0337459 A1 | 11/2017 | Fodor et al. |
| 2017/0342405 A1 | 11/2017 | Fu et al. |
| 2017/0342465 A1 | 11/2017 | Shum et al. |
| 2017/0342484 A1 | 11/2017 | Shum et al. |
| 2017/0344866 A1 | 11/2017 | Fan et al. |
| 2018/0002764 A1 | 1/2018 | Fan et al. |
| 2018/0016634 A1 | 1/2018 | Hindson et al. |
| 2018/0024139 A1 | 1/2018 | Peikon et al. |
| 2018/0030522 A1 | 2/2018 | Kamberov et al. |
| 2018/0037942 A1 | 2/2018 | Fu et al. |
| 2018/0057873 A1 | 3/2018 | Zhou et al. |
| 2018/0094312 A1 | 4/2018 | Hindson et al. |
| 2018/0094314 A1 | 4/2018 | Hindson et al. |
| 2018/0094315 A1 | 4/2018 | Hindson et al. |
| 2018/0105808 A1 | 4/2018 | Mikkelsen et al. |
| 2018/0112266 A1 | 4/2018 | Hindson et al. |
| 2018/0127743 A1 | 5/2018 | Vigneault et al. |
| 2018/0142292 A1 | 5/2018 | Hindson et al. |
| 2018/0163201 A1 | 6/2018 | Larson |
| 2018/0179590 A1 | 6/2018 | Belgrader et al. |
| 2018/0179591 A1 | 6/2018 | Belgrader et al. |
| 2018/0201923 A1 | 7/2018 | LaBaer |
| 2018/0201980 A1 | 7/2018 | Chee et al. |
| 2018/0208975 A1 | 7/2018 | Peterson et al. |
| 2018/0230527 A1 | 8/2018 | Fang et al. |
| 2018/0251825 A1 | 9/2018 | Stoeckius et al. |
| 2018/0258482 A1 | 9/2018 | Hindson et al. |
| 2018/0258500 A1 | 9/2018 | Fan et al. |
| 2018/0276332 A1 | 9/2018 | Fan et al. |
| 2018/0282803 A1 | 10/2018 | Belgrader et al. |
| 2018/0002738 A1 | 11/2018 | Wang et al. |
| 2018/0320241 A1 | 11/2018 | Nolan et al. |
| 2018/0340170 A1 | 11/2018 | Belhocine et al. |
| 2018/0371536 A1 | 12/2018 | Fu et al. |
| 2019/0025304 A1 | 1/2019 | Vigneault et al. |
| 2019/0032129 A1 | 1/2019 | Hindson et al. |
| 2019/0095578 A1 | 3/2019 | Shum et al. |
| 2019/0119726 A1 | 4/2019 | Shum et al. |
| 2019/0136316 A1 | 5/2019 | Hindson et al. |
| 2019/0136317 A1 | 5/2019 | Hindson et al. |
| 2019/0136319 A1 | 5/2019 | Hindson et al. |
| 2019/0177788 A1 | 6/2019 | Hindson et al. |
| 2019/0177800 A1 | 6/2019 | Boutet et al. |
| 2019/0203270 A1 | 7/2019 | Amit et al. |
| 2019/0203291 A1 | 7/2019 | Hindson et al. |
| 2019/0218276 A1 | 7/2019 | Regev et al. |
| 2019/0218607 A1 | 7/2019 | Love et al. |
| 2019/0221287 A1* | 7/2019 | Tsujimoto ............ C12Q 1/6876 |
| 2019/0221292 A1* | 7/2019 | Tsujimoto ............ C12Q 1/686 |
| 2019/0256888 A1 | 8/2019 | Weissleder et al. |
| 2019/0256907 A1 | 8/2019 | Ryan et al. |

(56) References Cited

U.S. PATENT DOCUMENTS

| | | |
|---|---|---|
| 2019/0292592 A1 | 9/2019 | Shum et al. |
| 2020/0109437 A1 | 4/2020 | Chang et al. |

FOREIGN PATENT DOCUMENTS

| | | |
|---|---|---|
| EP | 0 799 897 | 10/1997 |
| EP | 1 473 080 | 11/2004 |
| EP | 1 647 600 | 4/2006 |
| EP | 1 845 160 | 10/2007 |
| EP | 2036989 | 3/2009 |
| EP | 1379693 | 5/2009 |
| EP | 2204456 | 7/2010 |
| EP | 2431465 | 3/2012 |
| EP | 2203749 | 8/2012 |
| EP | 2511708 | 10/2012 |
| EP | 2538220 | 12/2012 |
| EP | 2 623 613 | 8/2013 |
| EP | 1745155 | 10/2014 |
| EP | 2 805 769 | 11/2014 |
| EP | 2556171 | 9/2015 |
| EP | 2970958 | 12/2017 |
| EP | 3263715 | 1/2018 |
| EP | 3136103 | 8/2018 |
| EP | 2954102 | 12/2018 |
| EP | 3428290 | 1/2019 |
| EP | 2970957 | 4/2019 |
| EP | 3058092 | 5/2019 |
| EP | 3256606 | 5/2019 |
| EP | 3327123 | 8/2019 |
| GB | 2293238 A | 3/1996 |
| JP | H04108385 | 4/1992 |
| JP | 2005-233974 | 9/2005 |
| JP | 2007504831 | 3/2007 |
| JP | 2008-256428 | 10/2008 |
| JP | 2013-039275 | 2/2013 |
| WO | WO 89/01050 | 2/1989 |
| WO | WO1996024061 | 8/1996 |
| WO | WO 97/10365 | 3/1997 |
| WO | WO 99/15702 | 4/1999 |
| WO | WO 99/28505 | 6/1999 |
| WO | WO 00/58516 | 10/2000 |
| WO | WO2001048242 | 7/2001 |
| WO | WO2001053539 | 7/2001 |
| WO | WO2002018643 | 3/2002 |
| WO | WO2002046472 | 6/2002 |
| WO | WO 02/056014 | 7/2002 |
| WO | WO 02/059355 | 8/2002 |
| WO | WO 02/070684 | 9/2002 |
| WO | WO2002072772 | 9/2002 |
| WO | WO2002079490 | 10/2002 |
| WO | WO2002083922 | 10/2002 |
| WO | WO2002101358 | 12/2002 |
| WO | WO2003035829 | 5/2003 |
| WO | WO 04/017374 | 2/2004 |
| WO | WO2004021986 | 3/2004 |
| WO | WO2004033669 | 4/2004 |
| WO | WO2004066185 | 8/2004 |
| WO | WO2004081225 | 9/2004 |
| WO | WO2005017206 | 2/2005 |
| WO | WO2005021731 | 3/2005 |
| WO | WO 05/042759 | 5/2005 |
| WO | WO 05/071110 | 8/2005 |
| WO | WO 05/080604 | 9/2005 |
| WO | WO 05/111242 | 11/2005 |
| WO | WO2005111243 | 11/2005 |
| WO | WO 06/071776 | 7/2006 |
| WO | WO 06/102264 | 9/2006 |
| WO | WO2006137932 | 12/2006 |
| WO | WO 07/087310 | 8/2007 |
| WO | WO 07/087312 | 8/2007 |
| WO | WO 07/147079 | 12/2007 |
| WO | WO2008047428 | 4/2008 |
| WO | WO2008051928 | 5/2008 |
| WO | WO2008057163 | 5/2008 |
| WO | WO 08/096318 | 8/2008 |
| WO | WO2008104380 | 9/2008 |
| WO | WO 08/147428 | 12/2008 |
| WO | WO 08/150432 | 12/2008 |
| WO | WO2009048530 | 4/2009 |
| WO | WO 09/148560 | 12/2009 |
| WO | WO 09/152928 | 12/2009 |
| WO | WO2010059820 | 5/2010 |
| WO | WO 10/117620 | 10/2010 |
| WO | WO2010131645 | 11/2010 |
| WO | WO2011106738 | 9/2011 |
| WO | WO 11/123246 | 10/2011 |
| WO | WO2011127099 | 10/2011 |
| WO | WO 11/143659 | 11/2011 |
| WO | WO 11/155833 | 12/2011 |
| WO | WO 12/038839 | 3/2012 |
| WO | WO 12/042374 | 4/2012 |
| WO | WO 12/047297 | 4/2012 |
| WO | WO 12/048341 | 4/2012 |
| WO | WO2012041802 | 4/2012 |
| WO | WO 12/083225 | 6/2012 |
| WO | WO2012099896 | 7/2012 |
| WO | WO 12/108864 | 8/2012 |
| WO | WO2012103154 | 8/2012 |
| WO | WO2012112804 | 8/2012 |
| WO | WO 12/129363 | 9/2012 |
| WO | WO 12/140224 | 10/2012 |
| WO | WO 12/142213 | 10/2012 |
| WO | WO 12/148477 | 11/2012 |
| WO | WO 12/149042 | 11/2012 |
| WO | WO 12/162267 | 11/2012 |
| WO | WO2012148497 | 11/2012 |
| WO | WO2012156744 | 11/2012 |
| WO | WO 13/019075 | 2/2013 |
| WO | WO2013070990 | 5/2013 |
| WO | WO 13/117595 | 8/2013 |
| WO | WO 13/130674 | 9/2013 |
| WO | WO 13/148525 | 10/2013 |
| WO | WO 13/173394 | 11/2013 |
| WO | WO 13/176767 | 11/2013 |
| WO | WO 13/177206 | 11/2013 |
| WO | WO 13/188831 | 12/2013 |
| WO | WO 13/188872 | 12/2013 |
| WO | WO 13/191775 | 12/2013 |
| WO | WO 14/015084 | 1/2014 |
| WO | WO 14/015098 | 1/2014 |
| WO | WO 14/018460 | 1/2014 |
| WO | WO2014018093 | 1/2014 |
| WO | WO 14/028537 | 2/2014 |
| WO | WO2014065756 | 5/2014 |
| WO | WO 14/093676 | 6/2014 |
| WO | WO 14/108850 | 7/2014 |
| WO | WO 14/124336 | 8/2014 |
| WO | WO 14/124338 | 8/2014 |
| WO | WO 14/126937 | 8/2014 |
| WO | WO2014124046 | 8/2014 |
| WO | WO 14/144495 | 9/2014 |
| WO | WO2014145458 | 9/2014 |
| WO | WO2014176575 | 10/2014 |
| WO | WO 14/201273 | 12/2014 |
| WO | WO 14/210353 | 12/2014 |
| WO | WO2014200767 | 12/2014 |
| WO | WO2014204939 | 12/2014 |
| WO | WO2014210223 | 12/2014 |
| WO | WO2014210225 | 12/2014 |
| WO | WO 15/002908 | 1/2015 |
| WO | WO 15/031691 | 3/2015 |
| WO | WO 15/035087 | 3/2015 |
| WO | WO 15/044428 | 4/2015 |
| WO | WO 15/047186 | 4/2015 |
| WO | WO2015057985 | 4/2015 |
| WO | WO 14/071361 | 5/2015 |
| WO | WO 15/103339 | 7/2015 |
| WO | WO2015117163 | 8/2015 |
| WO | WO 15/134787 | 9/2015 |
| WO | WO2015168161 | 11/2015 |
| WO | WO2015179339 | 11/2015 |
| WO | WO 15/200869 | 12/2015 |
| WO | WO2015200893 | 12/2015 |
| WO | WO2016044227 | 3/2016 |

(56) References Cited

FOREIGN PATENT DOCUMENTS

| | | |
|---|---|---|
| WO | WO2016061517 | 4/2016 |
| WO | WO2016100976 | 6/2016 |
| WO | WO2016118915 | 7/2016 |
| WO | WO2016130578 | 8/2016 |
| WO | WO2016160965 | 8/2016 |
| WO | WO 16/138500 | 9/2016 |
| WO | WO2016138496 | 9/2016 |
| WO | WO2016145409 | 9/2016 |
| WO | WO2016149418 | 9/2016 |
| WO | WO2016160844 | 10/2016 |
| WO | WO2016168825 | 10/2016 |
| WO | WO2016172373 | 10/2016 |
| WO | WO2016190795 | 12/2016 |
| WO | WO2016191272 | 12/2016 |
| WO | WO2017032808 | 3/2017 |
| WO | WO2017040306 | 3/2017 |
| WO | WO2017044574 | 3/2017 |
| WO | WO2017053905 | 3/2017 |
| WO | WO2017079593 | 5/2017 |
| WO | WO2017097939 | 6/2017 |
| WO | WO2017117358 | 7/2017 |
| WO | WO2017139690 | 8/2017 |
| WO | WO2017164936 | 9/2017 |
| WO | WO2017173328 | 10/2017 |
| WO | WO2017205691 | 11/2017 |
| WO | WO2018017949 | 1/2018 |
| WO | WO2018020489 | 2/2018 |
| WO | WO2018031631 | 2/2018 |
| WO | WO2018058073 | 3/2018 |
| WO | WO2018075693 | 4/2018 |
| WO | WO2018111872 | 6/2018 |
| WO | WO2018115852 | 6/2018 |
| WO | WO2018119447 | 6/2018 |
| WO | WO2018140966 | 8/2018 |
| WO | WO2018144240 | 8/2018 |
| WO | WO2018144813 | 8/2018 |
| WO | WO2018174827 | 9/2018 |
| WO | WO2018217862 | 11/2018 |
| WO | WO2018222548 | 12/2018 |
| WO | WO2018226293 | 12/2018 |
| WO | WO2019055852 | 3/2019 |
| WO | WO2019113457 | 6/2019 |
| WO | WO2019113499 | 6/2019 |
| WO | WO2019113506 | 6/2019 |
| WO | WO2019113533 | 6/2019 |
| WO | WO2019118355 | 6/2019 |
| WO | WO2019126789 | 6/2019 |
| WO | WO2019157529 | 8/2019 |
| WO | WO2013137737 | 9/2019 |
| WO | WO2019213237 | 11/2019 |
| WO | WO2019213294 | 11/2019 |
| WO | WO2020028266 | 2/2020 |
| WO | WO2020037065 | 2/2020 |
| WO | WO2020046833 | 3/2020 |
| WO | WO2020097315 | 5/2020 |
| WO | WO2020123384 | 6/2020 |
| WO | WO2020154247 | 7/2020 |
| WO | WO2020167920 | 8/2020 |

OTHER PUBLICATIONS

"Algae," Wikipedia.com (accessed Mar. 4, 2016). (Year: 2016).*
"Protozoa," Wikipedia.com (accessed May 11, 2016). (Year: 2016).*
"List of sequenced bacterial genomes" (Wikipedia.com; accessed Jan. 24, 2014). (Year: 2014).*
"Custom Antibody Services" by Precision Antibody (accessed Apr. 16, 2014). (Year: 2014).*
Sommer and Tautz,"Minimal homology requirements for PCR primers," Nucleic Acids Research, vol. 17, No. 16, 1989, p. 6749. (Year: 1989).*
Forster et al., "A human gut bacterial genome and culture collection for improved metagenomic analyses", Nature Biotechnology, vol. 37, Feb. 2019, 186-192. (Year: 2019).*
Sah et al., "Complete Genome Sequence of a 2019 Novel Coronavirus (SARS-CoV-2) Strain Isolated in Nepal", Microbiology Resource Announcements, vol. 9, Issue 11, pp. 1-3, Mar. 2020. (Year: 2020).*
Centers for Disease Control and Prevention, "New COVID-19 Variants", Jan. 15, 20221, pp. 1-3. (Year: 2021).*
Zeberg et al., "The major genetic risk factor for severe COVID-19 in inherited ffrom Neanderthals", Nature, Sep. 30, 2020, pp. 1-13. (Year: 2020).*
Achim et al., May 2015, High-throughput spatial mapping of single-cell RNA-seq data to tissue of origin. Nature Biotechnology, 33(5):503-511.
Alkan et al., Oct. 2009, Personalized copy number and segmental duplication maps using next-generation sequencing. Nat Genet., 41(10):1061-1067.
Ansorge, 2009, Next-generation DNA sequencing techniques. New Biotechnology, 25(4):195-203.
Atanur et al., Jun. 2010, The genome sequence of the spontaneously hypertensive rat: Analysis and functional significance. Genome Res., 20(6):791-803.
Audic et al., 1997, The Significance of Digital Gene Expression Profiles. Genome Research, 7:986-995.
Bendall et al., May 6, 2011, Single-cell mass cytometry of differential immune and drug responses across a human hematopoietic continuum. Science, 332(6030):687-696.
Bionumbers, Aug. 21, 2010, Useful fundamental numbers in molecular biology, http://bionumbers.hms.harvard.edu/KeyNumbers/aspx, 4 pp.
Blainey, May 2013, The future is now: single-cell genomics of bacteria and archaea, FEMS Microbiol Rev., 37(3):407-427.
Bonaldo et al., Sep. 1996, Normalization and subtraction: two approaches to facilitate gene discovery. Genome Res., 6(9):791-806.
Braha et al., 2000, Simultaneous stochastic sensing of divalent metal ions. Nature Biotechnology, 18:1005-1007.
Bratke et al., Sep. 2005, Differential expression of human granzymes A, B, and K in natural killer cells and during CD8+ T cell differentiation in peripheral blood. Eur J Immunol., 35(9):2608-2616.
Brenner et al., 2000, Gene expression analysis by massively parallel signature sequencing (MPSS) on microbead arrays. Nature Biotechnology, 18:630-634.
Brenner et al., Feb. 15, 2000, In vitro cloning of complex mixtures of DNA on microbeads: physical separation of differentially expressed cDNAs. Proc Natl Acad Sci, 97(4):1665-1670.
Brodin et al., 2015, Challenges with using primer IDs to improve accuracy of next generation sequencing, 19(3):1-12.
Cai, Mar. 2013, Turning single cells in microarrays by super-resolution bar-coding, Brief Funct Genomics, 12(2):75-80.
Carr et al., Dec. 15, 2009, Inferring relative proportions of DNA variants from sequencing electropherograms. Bioinformatics, 25(24):3244-3250.
Casbon et al., Jul. 2011, A method for counting PCR template molecules with application to next-generation sequencing. Nucleic Acids Res., 39(12):e81.
Castellarnau et al., Jan. 2015, Stochastic particle barcoding for single-cell tracking and multiparametric analysis, Small, 11(4):489-498.
Castle et al., Apr. 16, 2010, DNA copy number including telomeres and mitochondria, assayed using next-generation sequencing. BMC Genomics, 11:244. doi: 10.1186/1471-2164-11-244.
Chamberlain et al., Dec. 9, 1988, Deletion screening of the Duchenne muscular dystrophy locus via multiplex DNA amplification. Nucleic Acids Res., 16(23):11141-11156.
Chang et al., Aug. 2002, Detection of allelic imbalance in ascitic supernatant by digital single nucleotide polymorphism analysis. Clin Cancer Res., 8(8):2580-2585.
Chee et al., 1996, Accessing genetic information with high-density DNA arrays, Science, 274:610-614.
Chee, 1991, Enzymatic multiplex DNA sequencing. Nucleic Acids Research, 19(12): 3301-3305.
Chen et al., Apr. 9, 2015, Spatially resolved, highly multiplexed RNA profiling in single cells. Science Express, pp. 1-21.

(56) References Cited

OTHER PUBLICATIONS

Church et al., 1988, Multiplex DNA sequencing. Science, 240:185-188.
Costello et al., Apr. 1, 2013, Discovery and characterization of artifactual mutations in deep coverage targeted capture sequencing data due to oxidative DNA damage during sample preparation. Nucleic Acids Res, 41(6):e67.
COX. May 2001, Bar coding objects with DNA. Analyst, 126(5):545-547.
Craig et al., Oct. 2008, Identification of genetic variants using bar-coded multiplexed sequencing. Nat Methods, 5(10):887-893.
Cusanovich et al., May 7, 2014, Multiplex single-cell profiling of chromatin accessibility by combinatorial cellular indexing. Science Express, pp. 1-9.
Daines et al., Aug. 2009, High-throughput multiplex sequencing to discover copy number variants in *Drosophila*. Genetics, 182(4):935-941.
Dalerba et al., Single-cell dissection of transcriptional heterogeneity in human colon tumors, Nat Biotechnol., 29(12):1120-1127 and Supplementary Material.
D'Antoni et al., May 1, 2006, Rapid quantitative analysis using a single molecule counting approach. Anal Biochem. 352(1):97-109.
Daser et al., 2006, Interrogation of genomes by molecular copy-number counting (MCC). Nature Methods, 3(6):447-453.
De Saizieu et al., 1998, Bacterial transcript imaging by hybridization of total RNA to oligonucleotide arrays. Nature Biotechnology, 16:45-48.
Dirks et al., Oct. 26, 2004, Triggered amplification by hybridization chain reaction., Proc Natl Acad Sci U S A, 101(43), 15275-15278.
Fan et al., Feb. 6, 2015, Combinatorial labeling of single cells for gene expression cytometry. Science, 347(6222):1258367-8.
Fan et al., 2000, Parallel Genotyping of Human SNPs Using Generic High-density Oligonucleotide Tag Arrays. Genome Research, 10:853-860.
Fan et al., 2009, Microfluidic digital PCR enables rapid prenatal diagnosis of fetal aneuploidy. Am Obstet Gynecol. 200:543.e1-543.e7.
Fan et al., Jul. 19, 2012, Non-invasive prenatal measurement of the fetal genome. Nature, 487(7407):320-324.
Fan, Nov. 2010, Molecular counting: from noninvasive prenatal diagnostics to whole-genome haplotyping, doctoral dissertation, Stanford University, 185 pp.
Feldhaus et al., Jan. 15, 2000, Oligonucleotide-conjugated beads for transdominant genetic experiments, Nucleic Acids Res., 28(2):534-543.
Fox-Walsh et al., Oct. 2011, A multiplex RNA-seq strategy to profile poly(A+) RNA: application to analysis of transcription response and 3' end formation., Genomics, 98(4),266-721.
Fu et al., Mar. 18, 2014, Digital encoding of cellular mRNAs enabling precise and absolute gene expression measurement by single-molecule counting. Anal Chem., 86(6):2867-2870.
Fu et al., May 31, 2011, Counting individual DNA molecules by the stochastic attachment of diverse labels. Proc Natl Acad Sci, 108(22):9026-9031.
Gerry et al., 1999, Universal DNA microarray method for multiplex detection of low abundance point mutations. Journal of Molecular Biology, 292(2): 251-262.
Gillespie, 1977, Exact stochastic simulation of coupled chemical reactions. The Journal of Physical Chemistry, 81(25):2340-2361.
Grant et al., Nov. 15, 2002, SNP genotyping on a genome-wide amplified DOP-PCR template. Nucleic Acids Res, 30(22):e125.
Gunderson et al., May 2004, Decoding randomly ordered DNA arrays. Genome Res. 14(5):870-877.
Gundry et al., Jan. 3, 2012, Direct mutation analysis by high-throughput sequencing: from germline to low-abundant, somatic variants. Mutat Res. 729(1-2):1-15.
Gundry et al., Mar. 2012, Direct, genome-wide assessment of DNA mutations in single cells. Nucleic Acids Res., 40(5):2032-40.

Hacia et al., 1999, Determination of ancestral alleles for human single-nucleotide polymorphisms using high-density oligonucleotide arrays. Nature Genetics, 22:164-167.
Haff, 1994, Improved quantitative PCR using nested primers, PCR Methods and Applications, 3:332-337.
Hamady et al., Mar. 2008, Error-correcting barcoded primers for pyrosequencing hundreds of samples in multiplex. Nat Methods, 5(3):235-237.
Harrington et al., 2009, Cross-sectional characterization of HIV-1 env compartmentalization in cerebrospinal fluid over the full disease course, AIDS, 23(8) 907-915.
Hashimshony et al., Sep. 27, 2012, CEL-Seq: single-cell RNA-Seq by multiplexed linear amplification Cell Rep. 2(3):666-673.
Hensel et al., Jul. 21, 1995, Simultaneous identification of bacterial virulence genes by negative selection. Science. 269(5222):400-403.
Hiatt et al., Feb. 2010, Parallel, tag-directed assembly of locally derived short sequence reads. Nat Methods, 7(2):119-122.
Hiatt et al., May 2013, Single molecule molecular inversion probes for targeted, high-accuracy detection of low-frequency variation. Genome Res., 23(5):843-854.
Hollas et al., 2003, A stochastic approach to count RNA molecules using DNA sequencing methods. Lecture Notes in Computer Science, 2812:55-62.
Hug et al., 2003, Measure of the number of molecular of a single mRNA species in a complex mRNA preparation, Journal of Theoretical Biology, 221:615-624.
Ingolia et al., Apr. 10, 2009, Genome-wide analysis in vivo of translation with nucleotide resolution using ribosome profiling. Science, 324(5924):218-223.
Islam et al., 2011, Characterization of the single-cell transcriptional landscape by highly multiplex RNA-seq. Genome Research, 21:1160-1167.
Islam et al., 2014, Quantitative single-cell RNA-seq with unique molecular identifiers, Nature Methods, 11(2):163-168.
Jabara et al., Dec. 3, 2011, Accurate sampling and deep sequencing of the HIV-1 protease gene using a Primer ID, PNAS, 108(50):20166-20171.
Jabara, Apr. 23, 2010, Capturing the cloud: High throughput sequencing of multiple individual genomes from a retroviral population. Biology Lunch Bunch Series, Training Initiatives in Biomedical & Biological Sciences of the University of North Carolina at Chapel Hill.
Kanagawa, 2003, Bias and artifacts in multitemplate polymerase chain reactions (PCR), Journal of Bioscience and Bioengineering, 96(4):317-323.
Kebschull et al., Jul. 17, 2015, Sources of PCR-induced distortions in high-throughput sequencing data sets, Nucleic Acids Research, 15 pp.
Keys et al., Jun. 2015, Primer ID informs next-generation sequencing platforms and reveals preexisting drug resistance mutations in the HIV-1 reverse transcriptase coding domain, AIDS Research and Human Retroviruses, 31(6):658-668.
Kim et al., Jun. 8, 2007, Polony multiplex analysis of gene expression (PMAGE) in mouse hypertrophic cardiomyopathy, Science, 316(5830):1481-1484.
Kinde et al., Jun. 7, 2011, Detection and quantification of rare mutations with massively parallel sequencing, Proc. Natl Acad Sci, 108(23):9530-0535.
Kivioja et al., Jan. 2012, Counting absolute numbers of molecules using unique molecular identifiers. Nature Methods, 9(1):72-76.
Koboldt et al., Sep. 1, 2009, VarScan: variant detection in massively parallel sequencing of individual and pooled samples. Bioinformatics. 25(17):2283-2285.
Konig et al., Jul. 2010, iCLIP reveals the function of hnRNAP particles in splicing at individual nucleotide resolution, Nature Structural & Molecular Biology, 17(7):909-916.
Kotake et al., 1996, A simple nested RT-PCR method for quantitation of the relative amounts of multiple cytokine mRNAs in small tissue samples, Journal of Immunological Methods, 199:193-203.
Kurimoto et al., Mar. 17, 2006, An improved single-cell cDNA amplification method for efficient high-density oligonucleotide microarray analysis, Nucleic Acids Res., 34(5):e42.

(56) References Cited

OTHER PUBLICATIONS

Larson et al., Nov. 2009, A single molecule view of gene expression. Trends Cell Biol. 19(11):630-637.
Leamon et al., Nov. 2003, A massively parallel PicoTiterPlate based platform for discrete picoliter-scale polymerase chain reactions, Electrophoresis, 24(21):3769-3777.
Lee et al., Mar. 21, 2014, Highly multiplexed subcellular RNA sequencing in situ. Science. 343(6177):1360-1363.
Lizardi et al., Jul. 1998, Mutation detection and single-molecule counting using isothermal rolling-circle amplification. Nat Genet. 19(3):225-32.
Lockhart et al., 1996, Expression monitoring by hybridization to high-density oligonucleotide arrays. Nature Biotechnology, 14:1675-1680.
Lovatt et al., Feb. 2014, Transcriptome in vivo analysis (TIVA) of spatially defined single cells in live tissue. Nat Methods. 11(2):190-196.
Lucito et al., 1996, Representational Oligonucleotide Microarray Analysis: A High-Resolution Method to Detect Genome Copy Number Variation. Genome Research, 13: 2291-2305.
Maamar et al., 2007, Noise in Gene Expression Determines Cell Fate in Bacillus subtilis. Science, 317:526-529.
Macaulay et al., 2015, G&T-seq: parallel sequencing of single-cell genomes and transcriptomes. Nature Methods, pp. 1-7.
Macosko et al., 2015, Highly parallel genome-wide expression profiling of individual cells using nanoliter droplets, Cell 161:1202-1214 (and supplemental information).
Makrigiorgos et al., Sep. 2002, A PCR-Based amplification method retaining quantities difference between two complex genomes. Nature Biotech, 20(9):936-939.
Margulies et al., Sep. 15, 2005 Genome sequencing in microfabricated high-density picolitre reactors, Nature, 437:376-380.
McCloskey et al., Dec. 2007, Encoding PCR products with batch-stamps and barcodes. Biochem Genet. 45(11-12):761-767.
Medvedev et al., Nov. 2010, Detecting copy number variation with mated short reads. Genome Res. 20(11):1613-1622.
Mei et al., Mar. 22, 2010, Identification of recurrent regions of Copy-Number Variants across multiple individuals. BMC Bioinformatics. 11:147.
Merriam-Webster, definition of associate,: http://www.merriam-webster.com/dictionary/associate, accessed Apr. 5, 2016.
Miller et al., 2006, Directed evolution by in vitro compartmentalization, Nature Methods, 3:561-570.
Miner et al., 2004, Molecular barcodes detect redundancy and contamination in hairpin-bisulfite PCR, Nucleic Acids Research, 32(17):e135.
Mortazavi et al., 2008, Mapping and quantifying mammalian transcriptomes by RNA-Seq. Nat. Methods. 5:621-628.
Newell et al., Jan. 27, 2012, Cytometry by time-of-flight shows combinatorial cytokine expression and virus-specific cell niches within a continuum of CD8+ T cell phenotypes. Immunity. 36(1):142-152.
Novak et al., Jan. 20, 2011, Single-cell multiplex gene detection and sequencing with microfluidically generated agarose emulsions, Angew Chem Int Ed Engl., 50(2):390-395.
Ogino et al., Nov. 2002, Quantification of PCR bias caused by a single nucleotide polymorphism in SMN gene dosage analysis. J Mol Diagn. 4(4):185-190.
Parameswaran et al., 2007, A pyrosequencing-tailored nucleotide barcode design unveils opportunities for large-scale sample multiplexing. Nucleic Acids Res. 35(19):e130.
Park et al., May 2010, Discovery of common Asian copy number variants using integrated high-resolution array CGH and massively parallel DNA sequencing. Nat Genet. 42(5):400-405.
Picelli et al., Jul. 30, 2014, Tn5 transposase and tagmentation procedures for massively scaled sequencing projects, Genome Research 24(12):2033-2040.
Pihlak et al., 2008, Rapid genome sequencing with short universal tiling probes. Nature Biotechnology, 26:676-684.
Pinkel et al., 2005, Comparative Genomic Hybridization. Annual Review of Genomics and Human Genetics, 6:331-354.
Pleasance et al., Jan. 14, 2010, A small-cell lung cancer genome with complex signatures of tobacco exposure. Nature. 463(7278):184-190.
Plessy et al., Feb. 2013, Population transcriptomics with single-cell resolution: a new field made possible by microfluidics: a technology for high throughput transcript counting and data-driven definition of cell types, Bioessays, 35(2):131-140.
Qiu et al., Oct. 2003, DNA sequence-based "bar codes" for tracking the origins of expressed sequence tags from a maize cDNA library constructed using multiple mRNA sources. Plant Physiol. 133(2):475-481.
Roche Diagnostics GmbH, 2006, Genome Sequencer 20 System: First to the Finish (product brochure), 40 pp.
Sasagawa et al., 2013, Quartz-Seq: a highly reproducible and sensitive single-cell RNA sequencing method, reveals non-genetic gene-expression heterogeneity. Genome Biology, 14:R31.
Sasuga et al., Dec. 2008, Single-cell chemical lysis method for analyses of intracellular molecules using an array of picoliter-scale microwells, Anal Chem, 80(23):9141-9149.
Satija et al., May 2015, Spatial reconstruction of single-cell gene expression data. Nature Biotechnology, 33(5):495-508.
Schmitt et al., Sep. 4, 2012, Detection of ultra-rare mutations by next-generation sequencing. Proc Natl Acad Sci U S A. 109(36):14508-14513.
Sebat et al., 2004, Large-Scale Copy Number Polymorphism in the Human Genome. Science, 305:525-528.
Shalek et al., Jun. 13, 2013, Single-cell transcriptomics reveals bimodality in expression and splicing in immune cells. Nature. 498(7453):236-240.
Shiroguchi et al., Jan. 24, 2012, Digital RNA sequencing minimizes sequence-dependent bias and amplification noise with optimized single-molecule barcodes. Proc Natl Acad Sci U S A. 109(4):1347-1352.
Shoemaker et al., 1996, Quantitative phenotypic analysis of yeast deletion mutants using a highly parallel molecular bar-coding strategy. Nature Genetics, 14:450-456.
Simpson et al., Feb. 15, 2010, Copy number variant detection in inbred strains from short read sequence data. Bioinformatics. 26(4):565-567.
Smith et al., 2010, Highly-multiplexed barcode sequencing: an efficient method for parallel analysis of pooled samples. Nucleic Acids Research, 38(13):e142.
Soumillon et al., Mar. 5, 2014, Characterization of directed differentiation by high-throughput single-cell RNA-Seq, bioRxiv preprint, http://biorxiv.org/content/early/2014/03/05/003236.full.pdf, 13 pp.
Speicher et al., Oct. 2005, The new cytogenetics: blurring the boundaries with molecular biology, Nature Reviews Genetics, 6(10):782-792.
Takahashi et al., Mar. 2006, Novel technique of quantitative nested real-time PCR assay for *Mycobacterium tuberculosis* DNA, Journal of Clinical Microbiology, 44(3):1029-1039.
Tan et al., Apr. 2013, Genome-wide comparison of DNA hydroxymethylation in mouse embryonic stem cells and neural progenitor cells by a new comparative hMeDIP-seq method. Nucleic Acids Res. 41(7):e84.
Taudien et al., Apr. 19, 2010, Haplotyping and copy number estimation of the highly polymorphic human beta-defensin locus on 8p23 by 454 amplicon sequencing. BMC Genomics. 11:252.
The Tibbs Times, UNC bioscience newsletter, Apr. 2010, 17 pp.
Tomaz et al., Aug. 2010, Differential methylation as a cause of allele dropout at the imprinted GNAS locus. Genet Test Mol Biomarkers. 14(4):455-460.
Treutlein et al., May 15, 2014, Reconstructing lineage hierarchies of the distal lung epithelium using single-cell RNA-seq. Nature. 509(7500):371-375.
Velculescu et al., 1995, Serial Analysis of Gene Expression. Science, 270:484-487.
Velculescu et al., 1997, Characterization of the Yeast Transcriptome. Cell, 88:243-251.
Vogelstein et al., 1999, Digital PCR. Proc. Natl. Acad. Sci., 96(16):9236-9241.

(56) References Cited

OTHER PUBLICATIONS

Walker et al., Jan. 1, 1992, Isothermal in vitro amplification of DNA by a restriction enzyme/DNA polymerase system. Proc Natl Acad Sci U S A., 89(1):392-396.
Walsh et al., Jul. 13, 2010, Detection of inherited mutations for breast and ovarian cancer using genomic capture and massively parallel sequencing. Proc Natl Acad Sci U S A. 107(28):12629-12633.
Wang et al., 2009, RNA-Seq: a revolutionary tool for transcriptomics. Nature Reviews Genetics, 10:57-63.
Wang et al., May 21, 2015, Advances and applications of single-cell sequencing technologies, Molecular Cell, 58(4):598-609.
Wang et al., Oct. 2010, iCLIP predicts the dual splicing effects of TIA-RNA interactions, PLoS Biol, 8(10):e1000530.
Weber et al., Sep. 15, 2003, A real-time polymerase chain reaction assay for quantification of allele ratios and correction of amplification bias. Anal Biochem. 320(2):252-258.
Wittes et al., 1999, Searching for Evidence of Altered Gene Expression: a Comment on Statistical Analysis of Microarray Data. Journal of the National Cancer Institute, 91(5):400-401.
Wodicka et al., 1997, Genome-wide expression monitoring in *Saccharomyces cerevisiae*. Nature Biotechnology, 15:1359-1367.
Wojdacz et al., May 16, 2009, Primer design versus PCR bias in methylation independent PCR amplifications. Epigenetics. 4(4):231-234.
Wood et al., Aug. 2010, Using next-generation sequencing for high resolution multiplex analysis of copy number variation from nanogram quantities of DNA from formalin-fixed paraffin-embedded specimens. Nucleic Acids Res. 38(14):e151.
Wu et al., Jan. 2014, Quantitative assessment of single-cell RNA-sequencing methods. Nat Methods. 11(1):41-46.
Yandell et al., Sep. 2011, A probabilistic disease-gene finder for personal genomes. Genome Res. 21(9):1529-1542.
Ye et al., 2001, Fluorescent microsphere-based readout technology for multiplexed human single nucleotide polymorphism analysis and bacterial identification. Human Mutation, 17(4):305-316.
Yoon et al., Sep. 2009, Sensitive and accurate detection of copy number variants using read depth of coverage. Genome Res. 19(9):1586-1592.
Zhang et al., Jun. 19, 2012, DNA-based hybridization chain reaction for amplified bioelectronic signal and ultrasensitive detection of proteins. Anal Chem., 84(12),5392-5399.
Zhang et al., Mar. 20, 2011, The impact of next-generation sequencing on genomics. J Genet Genomics. 38(3):95-109.
Zhao et al., 2005, Homozygous Deletions and Chromosome Amplifications in Human Lung Carcinomas Revealed by Single Nucleotide Polymorphism Array Analysis. Cancer Research, 65:5561-5570.
Zheng et al., Feb. 2016, Haplotyping germline and cancer genomes with high-throughput linked-read sequencing, Nature Biotechnology, 34(3):303-311.
Zhou et al., 2001, Counting alleles reveals a connection between chromosome 18q loss and vascular invasion. Nature Biotechnology, 19:78-81.
International Search Report and Written Opinion dated May 3, 2016 in PCT/US16/018354.
Office action dated Oct. 3, 2013 for U.S. Appl. No. 12/969,581.
Response with allowed claims dated Mar. 4, 2014 for U.S. Appl. No. 12/969,581.
Notice of allowance dated Jun. 19, 2014 for U.S. Appl. No. 12/969,581.
Notice of allowance dated Aug. 22, 2014 for U.S. Appl. No. 12/969,581.
Office action dated Dec. 3, 2015 for U.S. Appl. No. 14/281,706.
Office Action dated May 7, 2015 for U.S. Appl. No. 13/327,526.
Notice of allowance dated Jan. 21, 2016 for U.S. Appl. No. 13/327,526.
Office action dated Feb. 18, 2015 for U.S. Appl. No. 14/540,007.
Office action dated Sep. 24, 2015 for U.S. Appl. No. 14/540,007.
Notice of allowance dated Dec. 15, 2015 for U.S. Appl. No. 14/540,007.
Office action dated Mar. 19, 2015 for U.S. Appl. No. 14/540,018.
Office action dated Oct. 6, 2015 for U.S. Appl. No. 14/540,018.
Notice of allowance dated Dec. 21, 2015 for U.S. Appl. No. 14/540,018.
Office Action dated Feb. 26, 2015 for U.S. Appl. No. 14/540,029.
Office action dated Sep. 1, 2015 for U.S. Appl. No. 14/540,029.
International Search Report and Written Opinion dated Jun. 6, 2012 in PCT/US11/065291.
Restriction Requirement dated Mar. 15, 2016 in U.S. Appl. No. 14/381,488.
Office Action dated May 10, 2016 in U.S. Appl. No. 14/381,488.
International Search Report and Written Opinion dated Sep. 6, 2013 in PCT/US13/028103.
Second Office Action dated Jun. 6, 2016 in Chinese patent application No. 201380022187.9.
European search report and search opinion dated Jul. 17, 2015 for EP Application No. 13755319.4.
Search and Examination Report dated Aug. 6, 2014 for GB patent application No. 1408829.8.
Search and Examination Report dated Jan. 27, 2016 in GB patent application No. 1408829.8.
Examination Report dated Jun. 8, 2016 in GB patent application No. 1408829.8.
Search Report and Written Opinion dated Mar. 1, 2016 in Singapore patent application No. 1120140527W.
International search report and written opinion dated Aug. 16, 2013 for PCT/US2013/027891.
Extended European Search Report dated Dec. 15, 2015 in European patent application No. 13754428.4.
Restriction Requirement dated Mar. 17, 2016 in U.S. Appl. No. 14/472,363.
Office Action dated Apr. 11, 2016 in U.S. Appl. No. 14/472,363.
Office action dated Dec. 31, 2015 for U.S. Appl. No. 14/800,526.
Office action dated Apr. 11, 2016 for U.S. Appl. No. 14/800,526.
International Search Report and Written Opinion dated Feb. 3, 2015 in PCT/US/14/053301.
Search and Examination Report dated Aug. 26, 2015 in GB patent application No. 1511591.8.
Examination Report dated Feb. 19, 2016 in Great Britain patent application No. GB1511591.8.
Office Action dated May 13, 2016 in U.S. Appl. No. 14/508,911.
International search report and written opinion dated Dec. 19, 2014 for PCT Application No. US2014/059542.
International Search Report and Written Opinion dated Jun. 20, 2016 in PCT/US16/14612.
International Search Report and Written Opinion dated Jun. 17, 2016 in PCT/US16/019962.
Invitation to Pay Additional Search Fees dated Jun. 2, 2016 in PCT/US16/019971.
International Search Report and Written Opinion dated Jun. 9, 2016 in PCT/US16/022712.
International search report and written opinion dated May 7, 2012 for PCT/IB2011/003160.
Notice of opposition dated Jul. 22, 2015 for EP Application No. 11810645.9.
Notice of opposition dated Jul. 9, 2015 for EP Application No. 11810645.9.
Anderson, Feb. 11, 2014, Study describes RNA sequencing applications for molecular indexing methods, genomeweb.com, 5 pp.
Bioscribe, Feb. 5, 2015, Massively parallel sequencing technology for single-cell gene expression published (press release), 3 pp.
Brisco et al., Jun. 25, 2012, Quantification of RNA integrity and its use for measurement of transcript number, Nucleic Acids Research, 40(18):e144.
Butkus, Feb. 6, 2014, Cellular research set to launch first gene expression platform using 'molecular indexing' technology, genomeweb.com, 5 pp.
Gong et al., 2010, Massively parallel detection of gene expression in single cells using subnanolitre wells, Lab Chip, 10:2334-2337.
Junker et al., May 21, 2015, Single-cell transcriptomics enters the age of mass production, Molecular Cell, 58:563-564.

(56) References Cited

OTHER PUBLICATIONS

Klein et al., May 21, 2015, Droplet barcoding for single-cell transcriptomics applied to embryonic stem cells, Cell, 161:1187-1201.
Kolodziejczyk et al., May 21, 2015, The technology and biology of single-cell RNA sequencing, Molecular Cell, 58:610-620.
Lamble et al., Nov. 20, 2013, Improved workflows for high throughput library preparation using the transposome-based nextera system, BMC Biotechnology, 13(1):104.
Lee et al., 2010, Large-scale arrays of picolitre chambers for single-cell analysis of large cell populations, Lab Chip, 10:2952-2958.
Liu et al., Single-cell transcriptome sequencing: recent advances and remaining challenges, F1000Research 2016, 5(F1000 Faculty Rev):182, 9 pp.
Marcus et a., 2006, Microfluidic single-cell mRNA isolation and analysis, Ana. Chem. 78:3084-3089.
Martinez et al., Jul. 2012, A microfluidic approach to encapsulate living cells in uniform alginate hydrogel microparticles, Macromol. Biosci, 12(7):946-951.
Nadai et al., 2008, Protocol for nearly full-length sequencing of HIV-1 RNA from plasma, PLoS ONE, 3(1):e1420.
Nagai et al., 2001, Development of a microchamber array for picoleter PCR, Anal. Chem., 73:1043-1047.
Navin et al., 2015, The first five years of single-cell cancer genomics and beyond, Genome Research, 25(10):1499-1507.
Pfaffl et al., Mar. 2004, Determination of stable housekeeping genes, differentially regulated target genes and sample integrity: BestKeeper—Excel-based tool using pair-wise correlations, Biotechnology Letters, 26(6):505-515.
Rajeevan et al., Oct. 2003, Global amplification of sense RNA: a novel method to replicate and archive mRNA for gene expression analysis, Genomics, 82(4):491-497.
Stratagene 1998 Catalog, Gene Characterization Kits, p. 39.
Vandesompele et al., Jun. 18, 2002, Accurate normalization of real-time quantitative RT-PCR data by geometric averaging of multiple internal control genes, Genome Biology, 3(7).
Warren et al., Nov. 21, 2006, Transcription factor profiling in individual hematopoietic progenitors by digital RT-PCR, PNAS, 103(47):17807-17812.
Weiner et al., Apr. 2008, Kits and their unique role in molecular biology: a brief retrospective, BioTechniques, 44:701-704.
White et al., Aug. 23, 2011, High-throughput microfluidic single-cell RT-qPCR, PNAS, 108(34):13999-14004.
Office action dated Jul. 20, 2016 for U.S. Appl. No. 14/281,706.
Office Action dated Oct. 11, 2016 in U.S. Appl. No. 15/224,460.
Office Action dated Aug. 12, 2016 in U.S. Appl. No. 14/381,488.
Examination report dated Jul. 12, 2016 in European patent application No. 13755319.4.
Office action dated Aug. 17, 2016 for U.S. Appl. No. 14/800,526.
Office Action dated Oct. 25, 2015 in U.S. Appl. No. 14/872,337.
Office action dated Sep. 26, 2016 in U.S. Appl. No. 15/167,807.
Examination Report dated Jun. 15, 2016 in Great Britain patent application No. GB1511591.8.
Written Opinion dated Jul. 5, 2016 in PCT/US16/019962.
Written Opinion dated Sep. 27, 2016 in PCT/US16/019962.
International Search Report and Written Opinion dated Aug. 9, 2016 in PCT/US16/019971.
International Search Report and Written Opinion dated Sep. 28, 2016 in PCT/US16/028694.
International Search Report and Written Opinion dated Sep. 27, 2016 in PCT/US16/034473.
Bogdanova et al., Jan. 2008, Normalization of full-length enriched cDNA, Molecular Biosystems, 4(3):205.
Patanjali et al., Mar. 1991, Construction of a uniform-abundance (normalized) CNDA library, Proceedings of the National Academy of Sciences, 88(5):1943-1947.
Office Action dated Feb. 13, 2017 in U.S. Appl. No. 14/381,488.
Office Action dated Dec. 27, 2016 in Chinese patent application No. 201380022187.9.

Official Action dated Dec. 28, 2016 in Japanese patent application No. 2014-558975.
Combined Search and Examination Report dated Feb. 21, 2017 in GB patent application No. 1609740.4.
Office Action dated Jan. 19, 2017 in U.S. Appl. No. 15/055,445.
International Search Report and Written Opinion dated Dec. 5, 2016 in PCT/US16/024783.
International Search Report and Written Opinion dated Jan. 31, 2017 in PCT/US16/050694.
Peng et al., Mar. 11, 2016, Reducing amplification artifacts in high multiplex amplicon sequencing by using molecular barcodes, BMC Genomics, retrieved from the internet: url:http://bmcgenomics.biomedcentral.com/articles/0.1186/s12864-015-1806-8, 14 pp.
Office Action dated May 8, 2017 in U.S. Appl. No. 15/224,460.
Office Action dated Jul. 28, 2017 in U.S. Appl. No. 14/975,441.
Office Action dated Jun. 7, 2017 in U.S. Appl. No. 14/381,488.
Office Action dated Feb. 17, 2017 in Canadian patent application No. 2,865,575.
Fourth Office Action dated Jul. 14, 2017 in Chinese patent application No. 201380022187.9.
Written Opinion dated May 26, 2017 in Singapore patent application No. 11201405274W.
Examination Report dated Apr. 10, 2017 in European patent application No. 14761937.3.
Office Action dated Mar. 24, 2017 in U.S. Appl. No. 15/409,355.
International Search Report and Written Opinion dated Aug. 7, 2017 in PCT/US2017/034576.
Buschmann et al., Aug. 7, 2014, Enhancing the detection of barcoded reads in high throughput DNA sequencing DNA by controlling the false discovery rate, BMC Bioinformatics, 15(1):264.
Jabara et al., Dec. 3, 2011, Accurate sampling and deep sequencing of the HIV-1 protease gene using a Primer ID, Supporting Information, 10.1073/pnas.111004108.
Office Action dated Sep. 8, 2017 in U.S. Appl. No. 15/046,225.
Office Action dated Nov. 16, 2017 in U.S. Appl. No. 14/381,488.
Examination Report No. 1 for standard patent application, dated Oct. 24, 2017, Australian patent application No. 2013226081.
Final Decision dated Aug. 30, 2017 in Japanese patent application No. 2014-558975.
Examination Report dated Oct. 10, 2017 in European patent application No. 14761937.3.
Office Action dated Oct. 16, 2017 in U.S. Appl. No. 15/409,355.
Office Action dated Nov. 9, 2017 in U.S. Appl. No. 15/004,618.
Office Action dated Nov. 1, 2017 in U.S. Appl. No. 15/667,125.
International Search Report and Written Opinion dated Sep. 8, 2017 in PCT/US2017/030097.
Applied Biosystems, Apr. 2008, SOLiD™ System Barcoding, Application Note, 4 pp.
Bontoux et al, "Integrating whole transcriptome assays on a lab-on-a-chip for single cell gene profiling", Lab on a Chip, (2008) vol. 8, No. 3, pp. 443-450.
Brady et al., "Construction of cDNA libraries form single cells", Methods in Enzymology, Academic Press, US, (1993) vol. 225, doi:10.1016/0076-6879(93)25039-5, ISSN 0076-6879, pp. 611-623.
Clontech Laboratories, Inc., May 15, 2007, Super SMART™ PGR cDNA Synthesis Kit User Manual, 39 pp.
Cloonan et al., "Stem cell transcriptome profiling via massive-scale mRNA sequencing", Nature Methods, (Jul. 2008) vol. 5, No. 7, pp. 613-619.
Costa et al., Aug. 22, 2012, Single-tube nested real-time PCR as a new highly sensitive approach to trace hazelnut, J. Agric Food Chem, 60(33):8103-8110.
Di Carlo et al., Dec. 1, 2008, Dynamic single-cell analysis for quantitative biology, Analytical Chemistry, 78(23):7918-7925.
Eberwine et al., "Analysis of gene expression in single live neurons", Proc. Natl. Acad. Sci. USA, (Apr. 1992) vol. 89, No. 7, pp. 3010-3014.
Harbers, "The current status of cDNA cloning", Genomics, (2008) vol. 91, No. 3, pp. 232-242.
Hartmann, "Gene expression profiling of single cells on large-scale oligonucleotide arrays", Nucleic Acids Research, (Oct. 2006) vol. 34, No. 21, p. e143.

(56) References Cited

OTHER PUBLICATIONS

Islam et al, "Highly multiplexed and strand specific single-cell RNA 5' end sequencing", Nature Protocols, (2012) vol. 7, No. 5, pp. 813-828.
Karrer et al., "In situ isolation of mRNA from individual plant cells: creation of cell-specific cDNA libraries.", Proc. Natl. Acad. Sci. USA, (1995) vol. 92, No. 9, pp. 3814-3818.
Ko et al., "RNA-conjugated template-switching RT-PCR method for generating an *Escherichia coli* cDNA library for small RNAs", Journal of Microbiological Methods, (2006) vol. 64, No. 3, pp. 297-304.
Kurimoto et al, "Global single-cell cDNA amplification to provide a template for representative high-density oligonucleotide microarray analysis", Nature Protocols, (2007) vol. 2, No. 3, pp. 739-752.
Maeda et al., "Development of a DNA barcode tagging method for monitoring dynamic changes in gene expression by using an ultra high-throughput sequencer", BioTechniques, (Jul. 2008), vol. 45, No. 1, pp. 95-97.
Mardis, "Next-generation DNA sequencing methods", Annu. Rev. Genomics Hum. Genet., (2008) vol. 9, pp. 387-402.
Marguerat et al, "Next-generation sequencing: applications beyond genomes", Biochemical Society Transactions, (2008) vol. 36, No. 5, pp. 1091-1096.
Meyer et al., "Parallel tagged sequencing on the 454 platform", Nature Protocols, (2008) vol. 3, No. 2, pp. 267-278.
Ozkumur et al., Apr. 3, 2013, Inertial focusing for tumor antigen-dependent and -independent sorting of rare circulating tumor cells, Sci Transl Med, 5(179):1-20.
Shendure et al., "Next-generation DNA sequencing", Nature Biotechnology, (2008) vol. 26, No. 10, pp. 1135-1145.
Song et al., 2013, Design rules for size-based cell sorting and sheathless cell focusing by hydrophoresis, Journal of Chromatography A, 1302:191-196.
Subkhankulova et al., "Comparative evaluation of linear and exponential amplification techniques for expression profiling at the single cell level", Genome Biology, (2006) vol. 7, No. R18, pp. 1-16.
Tang et al, "RNA-Seq analysis to capture the transcriptome landscape of a single cell", Nature Protocols, (2010) vol. 5, No. 3, pp. 516-535.
Zhu et al., "Reverse transcriptase template switching: a SMART approach for full-length cDNA library construction.", BioTechniques, (Apr. 2001) vol. 30, No. 4, pp. 892-897.
Office Action dated May 3, 2018 in U.S. Appl. No. 15/046,225.
Office action dated Jan. 9, 2018 in U.S. Appl. No. 15/217,896.
Office action dated Jan. 12, 2018 in U.S. Appl. No. 15/217,886.
Office action dated Jul. 20, 2018 in U.S. Appl. No. 15/217,886.
Office Action dated May 10, 2018 in U.S. Appl. No. 14/381,488.
Office Action dated Feb. 15, 2018 in Canadian patent application No. 2,865,575.
Extended European Search Report dated Feb. 8, 2018 in patent application No. 17202409.3.
Notice of Reasons for Rejection dated Apr. 2, 2018 in Japanese patent application No. 2014-558975.
Examination Report dated Mar. 16, 2018 in European patent application No. 13754428.4.
Examination Report No. 1 for standard patent application, dated Jul. 20, 2018 Australian patent application No. 2014312208.
Examination Report dated Jan. 3, 2018 in GB patent application No. 1609740.4.
Third Party Observation dated Jun. 14, 2018 in Japanese patent application No. 2016-537867.
Official Action dated Jul. 30, 2018 in Japanese patent application No. 2016-537867.
Office Action dated Dec. 19, 2017 in Chinese patent application No. 201480061859.1.
Notice of Reasons for Rejection dated Aug. 31, 2018 in Japanese patent application No. 2016-520632.
Office Action dated Jul. 25, 2018 in U.S. Appl. No. 15/108,268.
Office Action dated Jul. 5, 2018 in U.S. Appl. No. 15/004,618.
Extended European Search Report dated Jun. 11, 2018 in Euronean patent application No. 16740872.3.
Office Action dated Mar. 8, 2018 in U.S. Appl. No. 15/608,780.
Statement of Opposition of Strawman Limited filed against European Patent No. EP2414548B1 on Jul. 19, 2016.
Statement of Opposition filed against European Patent No. EP2414548B1 on Jul. 26, 2016.
Statement of Opposition filed against European Patent No. EP2414548B1 on Jul. 21, 2016.
Submission dated Jan. 15, 2018 by Strawman Limited in preparation for upcoming oral proceedings in opposition against European Patent No. EP2414548B1.
Submission dated Jan. 15, 2018 by Vossius & Partner in preparation for upcoming oral proceedings in opposition against European Patent No. EP2414548B1.
Third-Party Pre-Issuance Submission filed on Jun. 16, 2018 for U.S. Appl. No. 15/847,752.
Third-Party Pre-Issuance Submission filed on Jun. 6, 2018 for U.S. Appl. No. 15/847,752.
Third-Party Pre-Issuance Submission filed on May 21, 2018 for U.S. Appl. No. 15/847,752.
10X Genomics, Inc., 2019, User Guide: Visium Spatial Gene Expression Reagent Kits, www.10xGenomics.com, 76 pp.
2018 Top 10 Innovations, The Scientist Magazine® (2018). Available at: https://www.thescientist.com/features/2018-top-10-innovations-65140, 16 pp.
Advisory Action dated Nov. 29, 2019 in U.S. Appl. No. 15/084,307.
Advisory Action dated Dec. 2, 2019 in U.S. Appl. No. 15/055,407.
Advisory Action dated Aug. 25, 2020 in U.S. Appl. No. 15/084,307.
Agasti et al., "Photocleavable DNA barcode-antibody conjugates allow sensitive and multiplexed protein analysis in single cell," J Am Chem Soc. 2012, 134(45), 18499-18502.
Alexandra M. Ewing of Richards, Layton and Finger, P.A., Entry of Appearance dated Jan. 18, 2019 in the USDC District of Delaware, C.A. No. 18-1800-RGA, 1 pp.
Anderson, "Study Describes RNA Sequencing Applications for Molecular Indexing Methods," GenomeWeb 2014, 5 pp.
Argrawal et al., "Counting Single Native Biomolecules and Intact Viruses with Color-Coded Nanoparticles," Analytical Chemistry 2006, 78, 1061-1070.
Arslan et al., "An efficient algorithm for the stochastic simulation of the hybridization of DNA to microarrays," BMC Bioinformatics 2009, 10(411), 1-17.
Baek et al., "Development of Hydrogel TentaGel Shell-Core Beads for Ultra-high Throughput Solution Phase Screening of Encoded OBOC Combinatorial Small Molecule Libraries," J. Comb Chem. 2009, 11(1), 91-102.
BD Life Sciences, 2018, BD AbSeq antibody-oligo conjugates, www.bd.com/genomics, 2 pp.
BD Life Sciences, 2018, BD AbSeq on the BD Rhapsody system: Exploration of single-cell gene regulation by simultaneous digital mRNA and protein quantification, www.bd.com/genomics, 7 pp.
Biosciences Product Catalogue, Dynal® Catalog 1999, Oslo, Norway, 49-51.
Bose et al., "Scalable microfluidics for single-cell RNA printing and sequencing," Genome Biology 2015, 16(120), 1-16.
Brinza et al., "Detection of somatic mutations at 0.1% frequency from cfDNA in peripheral blood with a multiplex next-generation sequencing assay," Conference Poster, AACR 107th Annual Meeting, Apr. 16-20, 2016, 1 p.
Buggenum et al., "A covalent and cleavable antibody DNA conjugation strategy for sensitive protein detection via immunoPCR," Scientific Reports 2016, 6(22675), 1-12.
Bustin, "Absolute quantification of mRNA using real-time reverse transcription polymerase chain reaction assays," Journal of Molecular Endocrinology 2000, 25, 169-193.
Cao et al., "Comprehensive single-cell transcriptional profiling of a multicellular organism," Science 2017, 357, 661-667.
Caruccio et al., "Nextera (TM) Technology for NGS DNA Library Preparation: Simultaneous Fragmentation and Tagging by in Vitro Transposition," EpiBio 2009, 16(3), 4-6.

(56) References Cited

OTHER PUBLICATIONS

Chapin et al., "Rapid microRNA Profiling on Encoded Gel Microparticles," Angew Chem Int Ed Engl. 2011, 50(10), 2289-2293.
Civil Cover Sheet filed Nov. 15, 2018 in the USDC for the District of Delaware, C.A. 18-1800-RGA, 1 pp.
Communication of a Notice of Opposition dated Jul. 21, 2016 in European Patent Application No. EP 10762102.1.
Complaint filed in *Becton, Dickinson and Company and Cellular Research Inc. v. 10X Genomics, Inc.* dated Nov. 15, 2018 in the USDC for the District of Delaware, C.A. 18-1800-RGA, 141 pp.
Cotten et al., "Selection of proteins with desired properties from natural proteome libraries using mRNA display," Nature Protocols 2011, 6, 1163-1182.
Custom Antibody Services, Precision Antibody, accessed Apr. 16, 2014, 2 pp.
Day et al., "Immobilization of polynucleotides on magnetic particles," Biochem. J. 1991, 278, 735-740.
Defendant 10X Genomics, Inc.'s Letter to Judge Andrews in Response to Plaintiff's Letter of Supplemental Authority, dated Jul. 11, 2019 in the USDC for the District of Delaware, C.A. 18-1800-RGA, 2 pp.
Defendant 10X Genomics Motion for Admission Pro Hac Vice of Paul Ehrlich, Azra Hadzimehmedovic and Aaron Nathan, Pursuant to Local Rule 83.5, dated May 1, 2019 in the USDC for the District of Delaware, C.A. 18-1800-RGA, 5 pp.
Defendant 10X Genomics, Inc.'s Motion for Admission Pro Hac Vice Pursuant to Local Rule 83.5, dated Jan. 18, 2019 in the USDC District of Delaware, C.A. No. 18-1800-RGA, 5 pp.
Defendant 10X Genomics, Inc.'s Motion to Dismiss Pursuant to Federal Rule of Civil Procedure 12(b)(6), dated Jan. 18, 2019 in the USDC for the District of Delaware, C.A. 18-1800-RGA, 1 pp.
Defendant 10X Genomics, Inc.'s Motion to Dismiss the First Amended Complaint Pursuant to Federal Rule of Civil Procedure 12(b)(6), dated Mar. 1, 2019 in the USDC for the District of Delaware, C.A. 18-1800-RGA, 1 pp.
Defendant 10X Genomics Notice of Service for Initial Disclosures served to Opposing Counsel, dated Jun. 7, 2019 in the USDC for the District of Delaware, C.A. 18-1800-RGA, 2 pp.
Defendant 10X Genomic Inc.'s Notice of Service for Initial Requests for Production and Interrogatories Served to Becton, Dickinson, and Company and Cellular Research, Inc., dated May 31, 2019 in the USDC for the District of Delaware, C.A. 18-1800-RGA, 2 pp.
Defendant 10X Genomics Inc's, Notice of Service of Technical Documents, dated Jul. 8, 2019 in the USDC for the District of Delaware, C.A. 18-1800-RGA, 2 pp.
Defendant 10X Genomics, Inc.'s Opening Brief in Support of Its Motion to Dismiss Pursuant to Federal Rule of Civil Procedure 12(b)(6), dated Jan. 18, 2019 in the USDC District of Delaware, C.A. No. 1:18-cv-01800-RGA, 25 pp.
Defendant 10X Genomics, Inc.'s Opening Brief in Support of Its Motion to Dismiss Pursuant to Federal Rule of Civil Procedure 12(b)(6), dated Mar. 1, 2019 in the USDC District of Delaware, C.A. No. 18-1800 RGA, 26 pp.
Defendant 10X Genomics, Inc.'s [Proposed] Order for Partial Dismissal Pursuant to Federal Rules of Civil Procedure 12(b)(6), dated Jan. 18, 2019 in the USDC District of Delaware, C.A. No. 18-1800-RGA, 1 pp.
Defendant 10X Genomics, Inc's Proposed Order for Dismissal pursuant to Federal Rules of Civil Procedure 12(b)(6), filed Mar. 1, 2019 in the USDC for the District of Delaware, C.A. 18-1800-RGA, 1 pp.
Defendant 10X Genomics Reply Brief in Support of its Motion to Dismiss Pursuant to Federal Rule of Civil Procedure 12(b)(6), dated Apr. 12, 2019 in the USDC for the District of Delaware, C.A. No. 18-1800-RGA, 15 pp.
Defendant 10X Genomics Request for Oral Argument Under D. Del. LR 7.1.4, dated Apr. 18, 2019 in the USDC for the District of Delaware, C.A. 18-1800-RGA 2 pp.
Defendant 10X Genomics Response Letter to Judge Richard G. Andrews re Request for a Rule 16, dated Apr. 16, 2019 in the USDC for the District of Delaware, C.A. 18-1800-RGA, 2 pp.
Defendant 10X Genomics, Inc.'s Rule 7.1 Disclosure Statement, dated Jan. 18, 2019 in the USDC District of Delaware, C.A. No. 18-1800-RGA, 1 pp. 1.
Delley et al., "Combined aptamer and transcriptome sequencing of single cells," bioRxiv 2017, 1-10.
Dube et al., "Mathematical Analysis of Copy Number Variation in a DNA Sample Using Digital PCR on a Nanofluidic Device," PLoS One 2008, 3(8) e2876.
Evanko et al., "Hybridization chain reaction," Nature Methods 2004, 1(3), 186-187.
Ex Parte David H Gelfand, Ivo Glynne Gut, Keith A. Bauer, and Florence Mauger, Appeal No. 2017-001917 (PTAB Aug. 6, 2018).
Ex Parte Olga Ornatsky, Appeal No. 2018-001623 (PTAB Jul. 29, 2019).
Ex Parte Brian Jon Peter, Appeal No. 2017-008386 (PTAB May 29, 2018).
Examination Report dated May 12, 2020 in Australian Patent Application No. 2018220004.
Examination Report dated Sep. 5, 2018 in European Patent Application No. 16710357.1.
Examination Report dated Sep. 26, 2018 in European Patent Application No. 16714081.3.
Examination Report dated Dec. 12, 2018 in European Patent Application No. 16719706.0.
Examination Report dated Jan. 2, 2019 in European Patent Application No. 16757986.1.
Examination Report dated Feb. 6, 2019 in European Patent Application No. 13754428.4.
Examination Report dated Apr. 26, 2019 in European Patent Application No. 16710357.1.
Examination Report dated Jun. 18, 2019 in European Patent Application No. 16710551.9.
Examination Report dated Jul. 24, 2019 in European Patent Application No. 16714081.3.
Examination Report dated Aug. 2, 2019 in European Patent Application No. 17202409.3.
Examination Report dated Oct. 11, 2019 in European Patent Application No. 16757986.1.
Examination Report dated Dec. 4, 2019 in European Patent Application No. 16719706.0.
Examination Report dated Feb. 19, 2020 in European Patent Application No. 16710551.9.
Examination Report dated Mar. 18, 2020 in European Patent Application No. 17202409.3.
Examination Report dated Jul. 6, 2020 in European Patent Application No. 17781265.8.
Examination Report dated Sep. 21, 2020 in European Patent Application No. 18703156.2.
Examination Report dated Mar. 18, 2019 in Singapore Patent Application No. 11201405274W.
Exhibit A filed Jul. 10, 2019 in the USDC for the District of Delaware, C.A. 18-1800-RGA, 25 pp.
Exhibits 12-32 filed Feb. 8, 2019 in the USDC for the District of Delaware, C.A. 18-1800-RGA, 795 pp.
Exhibits A-D filed Jan. 18, 2019 in the USDC District of Delaware, C.A. No. 1:18-cv-01800-RGA, 47 pp.
Exhibits A-E filed Mar. 1, 2019 in the USDC District of Delaware, C.A. No. 18-1800 RGA, 75 pp.
Extended European Search Report dated Mar. 22, 2019 in European Patent Application No. 18195513.9.
Final Office Action dated Jan. 25, 2018 in U.S. Appl. No. 14/381,526.
Final Office Action dated Feb. 19, 2019 in U.S. Appl. No. 14/381,526.
Final Office Action dated Mar. 1, 2019 in U.S. Appl. No. 16/012,584.
Final Office Action dated Apr. 22, 2019 in U.S. Appl. No. 15/987,851.
Final Office Action dated May 2, 2019 in U.S. Appl. No. 16/012,635.
Final Office Action dated May 3, 2019 in U.S. Appl. No. 15/937,713.
Final Office Action dated Sep. 18, 2019 in U.S. Appl. No. 15/055,407.
Final Office Action dated Oct. 2, 2019 in U.S. Appl. No. 15/084,307.
Final Office Action dated Dec. 4, 2019 in U.S. Appl. No. 15/596,364.
Final Office Action dated Jan. 8, 2020 in U.S. Appl. No. 15/459,977.

(56) References Cited

OTHER PUBLICATIONS

Final Office Action dated Jan. 16, 2020 in U.S. Appl. No. 16/012,584.
Final Office Action dated Jan. 29, 2020 in U.S. Appl. No. 14/381,488.
Final Office Action dated Feb. 4, 2020 in U.S. Appl. No. 15/715,028.
Final Office Action dated Mar. 9, 2020 in U.S. Appl. No. 15/987,851.
Final Office Action dated Jun. 5, 2020 in U.S. Appl. No. 15/084,307.
Final Office Action dated Aug. 19, 2020 in U.S. Appl. No. 15/875,816.
Final Office Action dated Sep. 14, 2020 in U.S. Appl. No. 16/789,358.
Final Office Action dated Sep. 22, 2020 in U.S. Appl. No. 16/789,311.
Final Office Action dated Sep. 25, 2020 in U.S. Appl. No. 15/055,407.
First Action Interview Pilot Program Pre-Interview Communication dated Oct. 15, 2018 in U.S. Appl. No. 15/987,851.
First Action Interview Office Action Summary dated Jan. 25, 2019 in U.S. Appl. No. 15/987,851.
Flanigon et al., "Multiplex protein detection with DNA readout via mass spectrometry," N Biotechnol. 2013, 30(2), 153-158.
Forster et al., "A human gut bacterial genome and culture collection for improved metagenomic analyses," Nature Biotechnology 2019, 37, 186-192.
Fu et al., "Molecular indexing enables quantitative targeted RNA sequencing and reveals poor efficiencies in standard library preparation," PNAS 2014, 111(5), 1891-1896.
Gong et al., "Simple Method Prepare Oligonucleotide-Conjugated Antibodies and Its Application in Multiplex Protein Detection in Single Cells," Bioconjugate Chem. 2016, 27, 217-225.
Gu et al., "Complete workflow for detection of low frequency somatic mutations from cell-free DNA using Ion Torrent™ platforms," Conference Poster, AACR 107th Annual Meeting, Apr. 16-20, 2016, 1 p.
Gu et al., "Depletion of abundant sequences by hybridization (DSH): using Cas9 to remove unwanted high-abundance species in sequencing libraries and molecular counting applications," Genome Biology 2016, 17(41) 1-13.
Han et al., "An approach to multiplexing an immunosorbent assay with antibody-oligonucleotide conjugates," Bioconjug Chem. 2010, 21(12), 2190-2196.
Holcomb et al., "Abstract 1853: Single-cell multiplexed profiling of protein-level changes induced by EGFR inhibitor gefitinib," Cancer Res 2016, 76(14 Suppl), Abstract 1853.
How many species of bacteria are there? Wisegeek.org, accessed Jan. 21, 2014, 2 pp.
Hu et al., "Dissecting Cell-Type Composition and Activity-Dependent Transcriptional State in Mammalian Brains by Massively Parallel Single-Nucleus RNA-Seq," Molecular Cell 2017, 68, 1006-1015.
Hu et al., "Single Cell Multi-Omics Technology: Methodology and Application," Frontiers in Cell and Developmental Biology 2018, 6(28), 1-13.
International Preliminary Report on Patentability dated Mar. 26, 2019 in PCT Application No. PCT/US2017/053331.
International Preliminary Report on Patentability dated Aug. 6, 2019 in PCT Application No. PCT/US2018/014385.
International Search Report and Written Opinion dated Mar. 20, 2018 in PCT Application No. PCT/US2017/053331.
International Search Report and Written Opinion dated Mar. 28, 2018 in PCT Application No. PCT/US2018/014385.
International Search Report and Written Opinion dated Jul. 16, 2018 in PCT Application No. PCT/US2018/024602.
International Search Report and Written Opinion dated Jun. 24, 2019 in PCT Application No. PCT/US2019/030175.
International Search Report and Written Opinion dated Oct. 8, 2019 in PCT Application No. PCT/US2019/043949.
International Search Report and Written Opinion dated Oct. 16, 2019 in PCT Application No. PCT/US2019/030245.
International Search Report and Written Opinion dated Nov. 27, 2019 in PCT Application No. PCT/US2019/046549.
International Search Report and Written Opinion dated Dec. 4, 2019 in PCT Application No. PCT/US2019/053868.
International Search Report and Written Opinion dated Jan. 27, 2020 in PCT Application No. PCT/US2019/048179.
International Search Report and Written Opinion dated Mar. 30, 2020 in PCT Application No. PCT/US2019/060243.
International Search Report and Written Opinion dated Mar. 30, 2020 in PCT Application No. PCT/US2019/065237.
International Search Report and Written Opinion dated May 18, 2020 in PCT Application No. PCT/US2020/014339.
International Search Report and Written Opinion dated Jun. 30, 2020 in PCT Application No. PCT/US2020/017890.
Invitation to Pay Fees dated May 16, 2018 in PCT Application No. PCT/US2018/024602.
Invitation to Pay Fees dated Nov. 26, 2019 in PCT Application No. PCT/US2019/048179.
Invitation to Pay Additional Search Fees dated May 7, 2020 in PCT Application No. PCT/US2020/017890.
Jason J. Rawnsley of Richards, Layton and Finger, P.A., Entry of Appearance dated Jan. 18, 2019 in the USDC District of Delaware, C.A. No. 18-1800-RGA, 1 pp.
Jiang et al., "Synthetic spike-in standards for RNA-seq experiments," Genome Res. 2011, 21, 1543-1551.
Joint Stipulation and Order to Extend Time to Respond to Plaintiff's First Amended Complaint, dated Feb. 21, 2019 in the USDC for the District of Delaware, C.A. 18-1800-RGA, 2 pp.
Joint Stipulation and Order to Request Extended Time to File Opposition to Defendant's Motion to Dismiss dated, Mar. 8, 2019 in the USDC District of Delaware, C.A. No. 18-1800 RGA, 2 pp.
Joint Stipulation and Order to Request Extended Time to Submit a proposed Protective Order, dated Jun. 7, 2019 in the USDC for the District of Delaware, C.A. 18-1800-RGA, 1 pp.
Joint Stipulation and Order to Extended Time to Submit Agreed Document Production Protocol, filed Jun. 28, 2019 in the USDC for the District of Delaware, C.A. 18-1800 (RGA), 1 pp.
Joint Stipulation and Order to Request Extended Time to Submit Agreed Document Production Protocol, dated Jul. 11, 2019 in the USDC for the District of Delaware, C.A. 18-1800 (RGA), 1 pp.
Kang et al., "Targeted sequencing with enrichment PCR: a novel diagnostic method for the detection of EGFR mutations," Oncotarget 2015, 6(15), 13742-13749.
Kang et al., "Application of multi-omics in single cells," Ann Biotechnol. 2018, 2(1007), 1-8.
Kausch et al., "Organelle Isolation by Magnetic Immunoabsorption," BioTechniques 1999, 26(2), 336-343.
Kirsebom et al., "Stimuli-Responsive Polymers in the 21st Century: Elaborated Architecture to Achieve High Sensitivity, Fast Response, and Robust Behavior," Journal of Polymer Science: Part B: Polymer Physics 2011, 49, 173-178.
Kooiker & Xue, "cDNA Library Preparation," Cereal Genomics 2013, 1099, 29-40.
Kozarewa & Turner, "96-Plex Molecular Barcoding for the Illumina Genome Analyzer," High-Throughput Next Generation Sequencing. Methods in Molecular Biology (Methods and Applications) 2011, 733, 24 pp. DOI: 10.1007/978-1-61779-089-8_20.
Kozlov et al., "A high-complexity, multiplexed solution-phase assay for profiling protease activity on microarrays," Comb Chem High Throughput Screen 2008, 11(1), 24-35.
Lass-Napiorkowska et al., "Detection methodology based on target molecule-induced sequence-specific binding to a single-stranded oligonucleotide," Anal Chem. 2012, 84(7), 3382-3389.
Lee et al., "Universal process-inert encoding architecture for polymer microparticles," Nature Materials 2014, 13(5), 524-529.
Letter to Judge Richard G. Andrews Requesting a Rule 16 Conference, dated Apr. 15, 2019 in the USDC for the District of Delaware, C.A. 18-1800 (RGA), 1 pp.
Letter to Judge Andrews regarding Agreement on Proposed Scheduling Order, dated May 7, 2019 in the USDC for the District of Delaware, C.A. 18-1800-RGA, 1 pp.
Letter to Judge Andrews regarding Notice of Supplemental Authority, dated Jul. 10, 2019 in the USDC for the District of Delaware, C.A. 18-1800(RGA), 2pp.
Lin et al., "Self-Assembled Combinatorial Encoding Nanoarrays for Multiplexed Biosensin," Nano Lett. 2007, 7(2), 507-512.
Loy et al., "A rapid library preparation method with custom assay designs for detection of variants at 0.1% allelic frequency in liquid biopsy samples," Oct. 2, 2018, 1 p.

(56) References Cited

OTHER PUBLICATIONS

Lundberg et al., "Practical innovations for high-throughput amplicon sequencing," Nature Methods 2013, 10(10), 999-1007.
Lundberg et al., "Supplementary Information for: Practical innovations for high-throughput amplicon sequencing," Nature Methods 2013, 1-24.
Macaulay et al., "G&T-seq: parallel sequencing of single-cell genomes and transcriptomes," Nature Methods 2015, 1-7.
Massachusetts General Hospital, Overview of Illumina Chemistry, http://nextgen.mgh.harvard.edu/IlluminaChemistry.html, downloaded Jan. 28, 2020, 2 pp.
Motion and Order for Admission Pro Hac Vice Pursuant to Local Rule 83.5, dated Jan. 24, 2019 in the USDC District of Delaware, C.A. No. 18-1800-RGA, 7 pp.
Non-Final Office Action dated Jun. 2, 2017 in U.S. Appl. No. 14/381,526.
Non-Final Office Action dated Apr. 6, 2018 in U.S. Appl. No. 15/603,239.
Non-Final Office Action dated Oct. 4, 2018 in U.S. Appl. No. 15/260,106.
Non-Final Office Action dated Oct. 25, 2018 in U.S. Appl. No. 16/012,584.
Non-Final Office Action dated Nov. 5, 2018 in U.S. Appl. No. 16/038,790.
Non-Final Office Action dated Nov. 26, 2018 in U.S. Appl. No. 15/937,713.
Non-Final Office Action dated Jan. 7, 2019 in U.S. Appl. No. 15/055,407.
Non-Final Office Action dated Jan. 14, 2019 in U.S. Appl. No. 16/219,553.
Non-Final Office Action dated Mar. 19, 2019 in U.S. Appl. No. 15/046,225.
Non-Final Office Action dated May 15, 2019 in U.S. Appl. No. 15/084,307.
Non-Final Office Action dated May 23, 2019 in U.S. Appl. No. 15/459,977.
Non-Final Office Action dated Jun. 17, 2019 in U.S. Appl. No. 14/381,488.
Non-Final Office Action dated Jul. 9, 2019 in U.S. Appl. No. 15/596,364.
Non-Final Office Action dated Aug. 20, 2019 for U.S. Appl. No. 15/715,028.
Non-Final Office Action dated Sep. 18, 2019 in U.S. Appl. No. 16/194,819.
Non-Final Office Action dated Nov. 29, 2019 in U.S. Appl. No. 15/937,713.
Non-Final Office Action dated Jan. 17, 2020 in U.S. Appl. No. 15/084,307.
Non-Final Office Action dated Feb. 5, 2020 in U.S. Appl. No. 15/875,816.
Non-Final Office Action dated Mar. 12, 2020 in U.S. Appl. No. 16/789,358.
Non-Final Office Action dated Mar. 17, 2020 in U.S. Appl. No. 15/055,407.
Non-Final Office Action dated Mar. 26, 2020 in U.S. Appl. No. 16/012,635.
Non-Final Office Action dated Mar. 26, 2020 in U.S. Appl. No. 16/789,311.
Non-Final Office Action dated Jun. 8, 2020 in U.S. Appl. No. 15/715,028.
Non-Final Office Action dated Aug. 4, 2020 in U.S. Appl. No. 15/459,977.
Non-Final Office Action dated Aug. 19, 2020 in U.S. Appl. No. 16/374,626.
Non-Final Office Action dated Aug. 25, 2020 in U.S. Appl. No. 14/381,488.
Notice of Allowance dated Mar. 21, 2014 for U.S. Appl. No. 12/969,581.
Notice of Allowance dated Jan. 9, 2019 in U.S. Appl. No. 15/603,239.
Notice of Allowance dated Mar. 20, 2019 in U.S. Appl. No. 16/219,553.
Notice of Allowance dated Mar. 21, 2019 in U.S. Appl. No. 15/993,468.
Notice of Allowance dated May 28, 2019 in U.S. Appl. No. 16/219,553.
Notice of Allowance dated Sep. 24, 2019 in U.S. Appl. No. 15/217,886.
Notice of Allowance dated Nov. 11, 2019 in Japanese Patent Application No. 2017-245295.
Notice of Allowance dated Nov. 29, 2019 in U.S. Appl. No. 16/012,635.
Notice of Allowance dated Dec. 27, 2019 in U.S. Appl. No. 15/260,106.
Notice of Allowance dated Mar. 5, 2020 in U.S. Appl. No. 15/217,886.
Notice of Allowance dated Mar. 27, 2020 in U.S. Appl. No. 15/596,364.
Notice of Allowance dated Mar. 30, 2020 in U.S. Appl. No. 15/937,713.
Notice of Allowance dated Apr. 15, 2020 in U.S. Appl. No. 16/012,635.
Notice, Consent, and Reference of a Civil Action to a Magistrate Judge (Rule 73.1), filed Nov. 15, 2018 in the USDC for the District of Delaware, C.A. 18-1800-RGA, 3 pp.
Notice of Opposition dated Jul. 27, 2016 for European Patent Application No. 10762102.1.
Notice of Reasons for Rejection dated Dec. 5, 2018 in Japanese Patent Application No. 2017-245295.
Notice of Reason for Rejection dated Nov. 21, 2019 in Korean Patent Application No. 10-2016-7008144.
Notice of Reasons for Rejection dated Feb. 25, 2020 in Japanese Patent Application No. 2019-014564.
Notice of Reasons for Rejection dated May 11, 2020 in Japanese Patent Application No. 2017-549390.
Notice of Service of Disclosures to Opposing Counsel, dated Jun. 10, 2019 in the USDC for the District of Delaware, C.A. 18-1800 (RGA), 3 pp.
Notice of Service of Interrogatories and First Request of Documents and Things to Defendant 10X Genomics, Inc., dated Jul. 5, 2019 in the USDC for the District of Delaware, C.A. 18-1800 (RGA), 3 pp.
Notification Prior to Examination dated Nov. 27, 2019 in Israeli Patent Application No. 265478.
Office Action dated Sep. 7, 2018 in Chinese Patent Application No. 201480061859.1.
Office Action dated Dec. 13, 2018 in Canadian Patent Application No. 2,865,575.
Office Action dated Jan. 2, 2019 in Chinese Patent Application No. 201480059505.3.
Office Action dated Mar. 4, 2020 in Canadian Patent Application No. 2,865,575.
Office Action dated Jun. 22, 2020 in Chinese Patent Application No. 201680007351.2.
Office Action dated Jun. 22, 2020 in Chinese Patent Application No. 201680007652.5.
Office Action dated Jun. 23, 2020 in Chinese Patent Application No. 2016800157452.
Office Action dated Jul. 20, 2020 in Japanese Patent Application No. 2018-512152.
Opposition to Defendant's Motion to Dismiss Pursuant to Federal Rule of Civil Procedure 12(b)(6) dated Feb. 15, 2019, in the USDC for the District of Delaware, C.A. 18-800-RGA, 3 pp.
Oral Order by Judge Andrews Canceling Scheduling Conference set for May 8, 2019.
Order Setting Rule 16(b) Conference as Ordered by Judge Andrews Pursuant to Fed. R. Civ. P. 16(b), ruling dated Apr. 17, 2019 in the USDC District of Delaware, C.A. 18-1800-RGA, 1 pp.
Order Scheduling ADR Mediation Teleconference, filed May 13, 2019 in the USDC for the District of Delaware, C.A. 18-1800-RGA, 4pp.
Pérez-Rentero et al., "Synthesis of Oligonucleotides Carrying Thiol Groups Using a Simple Reagent Derived from Threoninol," Molecules 2012, 17, 10026-10045.

(56) References Cited

OTHER PUBLICATIONS

Peterson et al., "Multiplexed quantification of proteins and transcripts in single cells," Nature Biotechnology 2017, 35, 936-939.
Picelli et al., "Single-cell RNA-sequencing: The future of genome biology is now," RNA Biology 2017, 14(5), 637-650.
Plaintiff's Brief in Opposition to Defendant's Motion to Dismiss Pursuant to Fed. R. Civ. P. 12(b)(6), filed Mar. 29, 2019 in the USDC District of Delaware, C.A. No. 18-1800 (RGA), 27 pp.
Plaintiff's First Amended Complaint filed on Feb. 8, 2019, in the USDC for the District of Delaware, C.A. 18-1800-RGA, 178 pp.
Pre-interview communication dated Nov. 27, 2018 in U.S. Appl. No. 16/012,635.
Preissl et al., "Single-nucleus analysis of accessible chromatin in developing mouse forebrain reveals cell-type-specific transcriptional regulation," Nature Neuroscience 2018, 21(3), 432-439.
Proposed Stipulated Protective Order Pursuant to Rule 26(c) of the Federal Rules of Civil Procedure, filed Jun. 20, 2019 In the USDC for the District of Delaware, C.A. 18-1800 (RGA), 26 pp.
Raj et al., "Stochastic mRNA synthesis in mammalian cells," PLoS Biol. 2006, 4(10) 1707-1719.
Raj et al., "Imaging individual mRNA molecules using multiple singly labeled probes," Nature Methods 2008, 5(10), 877-879.
Raj et al., "Single-Molecule Approaches to Stochastic Gene Expression," Annu Rev Biophys 2009, 38, 255-270.
Report on the Filing or Determination of an Action Regarding a Patent or Trademark filed Nov. 15, 2018 in the USDC for the District of Delaware, C.A. 18-1800-RGA, 2 pp.
Restriction Requirement dated Mar. 29, 2019 in U.S. Appl. No. 15/715,028.
Restriction Requirement dated Jun. 19, 2019 in U.S. Appl. No. 15/596,364.
Restriction Requirement dated Sep. 20, 2019 in U.S. Appl. No. 15/875,816.
Rhee et al., "Simultaneous detection of mRNA and protein stem cell markers in live cells," BMC Biotechnology 2009, 9(30), 1-10.
Rule 7.1 Disclosure Statement dated Nov. 15, 2018 in the USDC for the District of Delaware, C.A. 18-1800-RGA, 1 pp.
Sah et al., "Complete Genome Sequence of a 2019 Novel Coronavirus (SARS-CoV-2) Strain Isolated in Nepal," Microbiol Resour Announc. 2020, 9(11), e00169-20, 3 pp.
Sano et al., "Immuno-PCR: Very Sensitive Antigen Detection by Means of Specific Antibody-DNA Conjugates," Science 1992, 258, 120-122.
Scheduling Order pursuant to Local Rule 16.1(b), filed May 7, 2019 in the USDC for the District of Delaware, C.A. 18-1800-RGA, 10 pp.
Scheduling Order Signed by Judge Andrews, dated May 8, 2019 in the USDC for the District of Delaware, C.A. 18-1800-RGA, 10 pp.
Search Report and Written Opinion dated Jan. 26, 2016 in Singapore Patent Application No. 1120140527W.
Search Report and Written Opinion dated Aug. 26, 2020 in Singapore Patent Application No. 10201806890V.
Shahi et al., "Abseq: ultrahigh-throughput single cell protein profiling with droplet microfluidic barcoding," Scientific Reports 2017, 7(44447), 1-10.
S.H.KO, "An 'equalized cDNA library' by the reassociation of short double-stranded cDNAs," Nucleic Acids Res. 1990, 18(19), 5705-5711.
Shortreed et al., "A thermodynamic approach to designing structure-free combinatorial DNA word sets," Nucleic Acids Res. 2005, 33(15), 4965-4977.
Shum et al., "Quantitation of mRNA Transcripts and Proteins Using the BD Rhapsody™ Single-Cell Analysis System," Adv Exp Med Biol. 2019,1129, 63-79.
Soares et al., "Construction and characterization of a normalized cDNA library," Proc. Natl., Acad. Sci. 1994, 91, 9228-9232.
Sogin et al., "Microbial diversity in the deep sea and the underexplored 'rare biosphere'," PNAS 2008, 103(32), 12115-12120.
Sommer et al., "Minimal homology requirements for PCR primers," Nucleic Acids Research 1989, 17(16), 6749.
Stipulated Protective Order Pursuant to Rule 26(c) of the Federal Rules of Civil Procedure, dated Jun. 21, 2019 in the USDC for the District of Delaware, C.A. 18-1800 (RGA), 26 pp.
Stipulation and Order to Extend Time to File Opposition to Motion to Dismiss, and Reply in Support of the Motion, dated Jan. 28, 2019 in the USDC for the District of Delaware, C.A. 18-1800-RGA, 2 pp.
Stoeckius et al., "Large-scale simultaneous measurement of epitopes and transcriptomes in single cells," Nature Methods 2017, 14(9), 865-868.
Summons in a Civil Action to Defendant 10X Genomics, Inc. filed Nov. 16, 2018 in the USDC for the District of Delaware, Civil Action No. 18-1800, 2 pp.
Sun et al., "Ultra-deep profiling of alternatively spliced *Drosophila* Dscam isoforms by circularization-assisted multi-segment sequencing," EMBO J. 2013, 32(14), 2029-2038.
Ullal et al., "Cancer cell profiling by barcoding allows multiplexed protein analysis in fine needle aspirates," Sci Transl Med. 2014, 6(219), 22 pp.
Unopposed Motion to Extend Time for Defendant's Response, dated Dec. 4, 2018 in the USDC for the District of Delaware, C.A. 18-1800-(RGA), 2 pp.
Vollbrecht et al., "Validation and comparison of two NGS assays for the detection of EGFR T790M resistance mutation in liquid biopsies of NSCLC patients," Oncotarget 2018, 9(26), 18529-18539.
Wang et al., "Combining Gold Nanoparticles with Real-Time Immuno-PCR for Analysis of HIV p24 Antigens," Proceedings of ICBBE 2007, 1198-1201.
Weibrecht et al., "Proximity ligation assays: a recent addition to the proteomics toolbox," Expert Rev. Proteomics 2010, 7(3), 401-409.
Zagordi et al., "Error correction of next-generation sequencing data and reliable estimation of HIV quasispecies," Nucleic Acids Research 2010, 38(21), 7400-7409.
Zhou et al., "Photocleavable Peptide-Oligonucleotide Conjugates for Protein Kinase Assays by MALDI-TOF MS," Mol. BioSyst. 2012, 8, 2395-2404.

* cited by examiner

| SAMPLE | YIELD WTA |
|---|---|
| 100NG | 2.34µG |
| 10NG | 750NG |
| 1NG | 198NG |

FIG. 6C

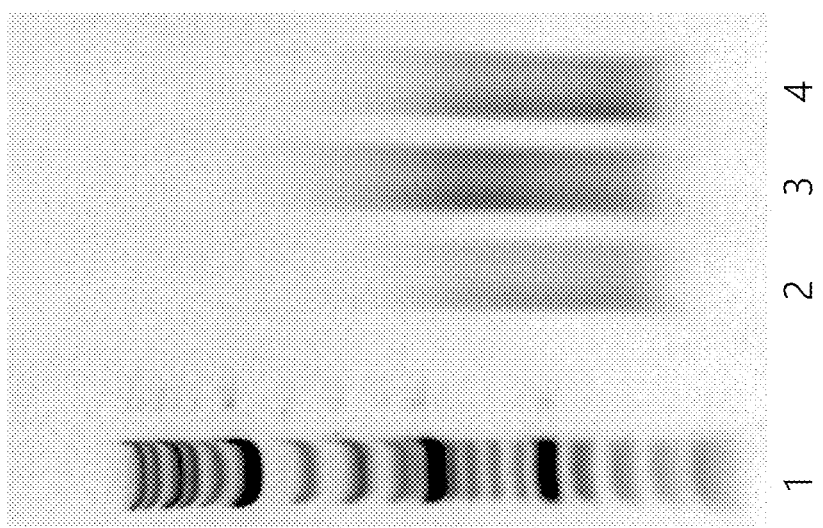

FIG. 17

ILLUMINA READ 1
SEQ ID NO:16

5' CCCTACACGACGCTCTTCCGATCTIIIIIIIINNNNNNNT$_{18}$V

1705

1715

*
         CTTCCGATCGCGCGATCGC               3' SEQ ID NO:17
3' GATGTGCTGCGAGAAGGCTAGCG-PO$_4$          5' SEQ ID NO:18
                1710

****
5' GCTCTTCCGGATCGC                         3' SEQ ID NO:19
3' GATGTGCTGCGAGAAGGCTAGCG-PO$_4$          5' SEQ ID NO:20

RT PRIMER SEQUENCE

CBO122/103
HIGH SUPPRESSION

CBO123/106
LOW SUPPRESSION

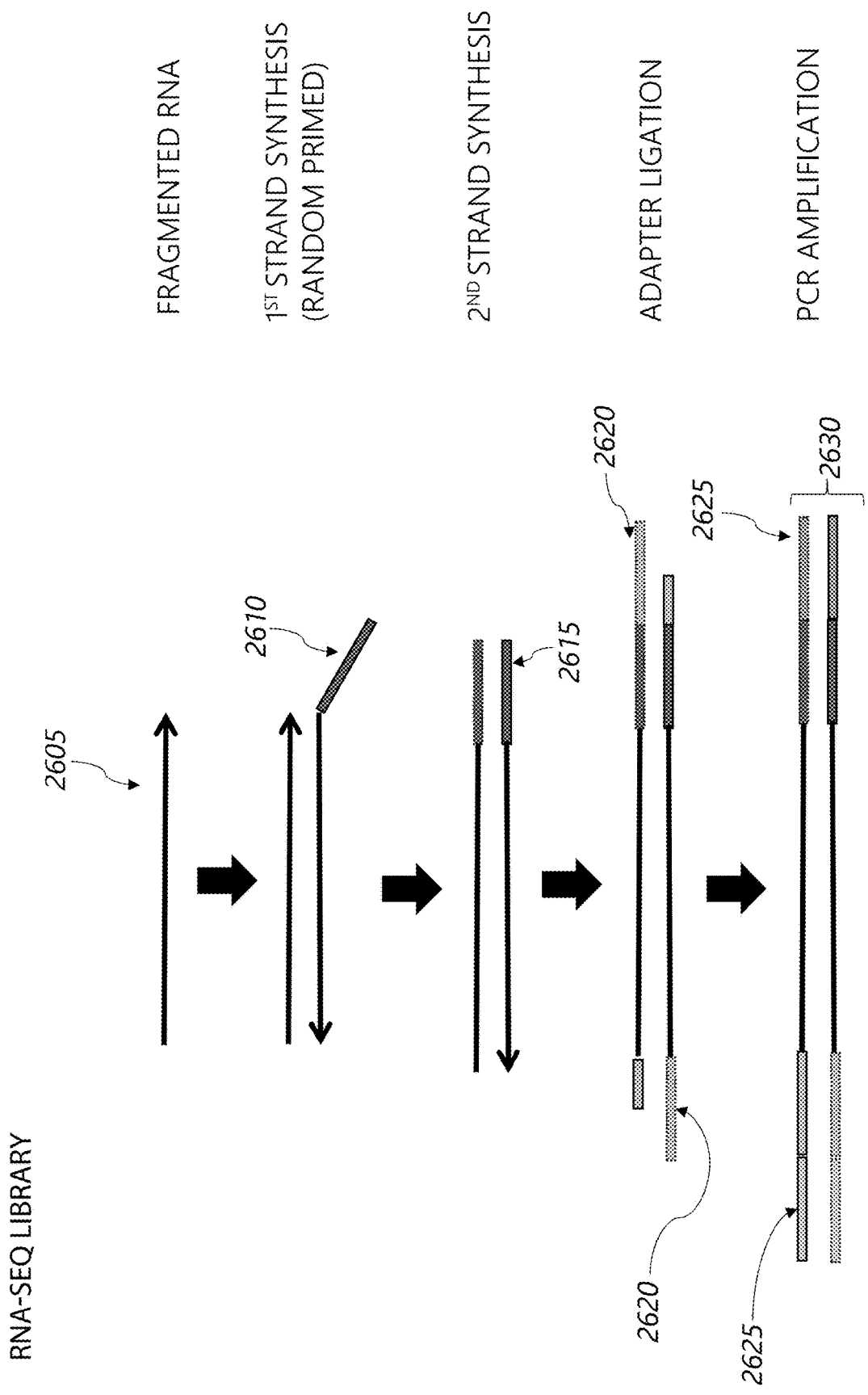
FIG. 26 RNA-SEQ LIBRARY

WTAX03_ORIGINAL 2ND STRAND WTA PROTOCOL ON FLIPPED
PLATES_JPW_SAT
6/6/2015
DILUTED RNA TO 370PG/ML SO THAT EACH WELL WILL GET 1NG RNA
IN 2.7ML RUNNING UHRR (A-D) AND HBRR (E-H) IN HALVES OF THE PLATE

| | RNA DILUTION | |
|---|---|---|
| 1 | 80 X | REAGENT |
| 0.1 | 8 µL | 10NG/µL HBRR OR UHRR |
| 2.6 | 208 µL | WATER |
| 2.7 | 216 µL | TOTAL |

ALIQUOT 50µL TO EIGHT TUBES
ADD 2.7µL DILUTED RNA TO EACH WELL OF THE PLATE
HEAT TO 65°C FOR 3MIN, THEN ICE FOR 5 MIN

ADDED 2.3µL PROTOSCRIPTII/BUFFER MASTERMIX TO EACH TUBE

| | PROTOSCRIPTII MASTERMIX | |
|---|---|---|
| 1 | 129.6 X | REAGENT |
| 2 | 259.2 µL | 5X PROTOSCIPT BUFFER |
| 0.1 | 12.96 µL | MURINE RNASE INHIBITOR |
| 0.2 | 25.92 µL | PROTOSCRIPTII |
| 2.3 | 298.08 µL | TOTAL |

ALIQUOT 35µL TO EIGHT TUBES
ADD 2.3µL PROTOSCRIPTII MIX TO EACH WELL OF AN ENTIRE PLATE BY
MULTICHANNEL PIPETTOR
INCUBATE 42°C FOR 30MIN
INCUBATE 80°C FOR 5MIN
HOLD AT 4°C

COMBINE ALL WELLS TOGETHER (CAME OUT TO ~900µL)
CLEAN UP WITH AN EQUAL VOLUME OF AMPUREXP BEADS
ELUTE IN 68µL WATER (SHOULD TEST TRIS-TWEEN IN THE FUTURE SINCE
IT'S EASIER TO ELUTE WITH

FIG. 29A

2ND STRAND SYNTHESIS
ADDED (EACH REAGENT INDIVIDUALLY FOLLOWED BY GENTLE MIXING)
ASSEMBLY ON ICE AND MAKE SURE
NOT TO GET ABOVE 16°C

| 2ND STRAND SYNTHESIS MIX | | |
|---|---|---|
| 1 | 1 X | REAGENT |
| 68 | 68 μL | ELUTED CDNA |
| 8 | 8 μL | 10X 2ND STRAND SYNTHESIS BUFFER |
| 4 | 4 μL | 2ND STRAND ENZYME MIX |
| 80 | 80 μL | TOTAL |

INCUBATE 2.5HRS AT 16°C
ADDED 1ML 3U/μL T4 DNA POLYMERASE AND INCUBATED 5MIN AT 16°C
BLUNT THE CDNA)

TRANSFER TO ICE
ADDED 5μL 0.5M EDTA AND MIXED TO STOP ALL ENZYMATIC ACTIVITY
CLEANED UP WITH 100μL AMPUREXP
ELUTED IN 37μL WATER

ADAPTER LIGATION
ADDED (EACH INDIVIDUALLY FOLLOWED BY GENTLE MIXING)

| LIGATION MIX | | |
|---|---|---|
| 1 | 1 X | REAGENT |
| 37 | 37 μL | BLUNTED CDNA |
| 10 | 10 μL | 5X QUICK LIGATION REACTION BUFFER |
| 1 | 1 μL | QUICK T4 DNA LIGASE |
| 2 | 2 μL | 5μM ANEALED CBO123/106 |
| 50 | 50 μL | TOTAL |

INCUBATE 30MIN @ 23°C IN A THERMOCYCLE

CLEANED UP WITH 50μL AMPUREXP
ELUTED IN 50μL WATER

WTA AMPLIFICATION
ADDED 150μL WTA MASTERMIX TO THE TUBES, SPLIT INTO CYCLING
CONDITIONS

| WTA MASTERMIX | | | | | |
|---|---|---|---|---|---|
| | | | 98°C | 30S | |
| 1 | 4X | REAGENT | 98°C | 10S | |
| 11.5 | 46 μL | WATER | 58°C | 15S | 15X |
| 1 | 4 μL | 30μM CBO40 | 72°C | 3MIN | |
| 25 | 100 μL | 2X Q5 HOTSTART MASTER | 72°C | 5MIN | |
| 37.5 | 150 μL | TOTAL | 4°C | HOLD | |

COMBINE ALL FOUR PCR REACTIONS IN A 1.5ML TUBE
CLEAN UP WITH 200μL AMPUREXP
ELUTE IN 30μL 10MM TRIS 0.05% TWEEN-20

NANODROP: 44.8NG/UL
30UL=1344NG TOTAL

FIG. 29B

WTAX04_REPEATING 10PG/WELL PROTOCOL
6/6/2015
DILUTED RNA TO 3.70FG/µL SO THAT EACH WELL WILL GET 10PG RNA IN 2.7µL
RUNNING UHRR (A-D) AND HBRR (E-H) IN HALVES OF THE PLATE

| RNA DILUTION | | |
|---|---|---|
| 1 | 200 X | REAGENT |
| 0.01 | 2 µL | 1NG/µL HBRR OR UHRR |
| 2.69 | 538 µL | WATER |
| 2.7 | 540 µL | TOTAL |

ALIQUOT 50µL TO EIGHT TUBES
ADD 2.7µL DILUTED RNA TO EACH WELL OF THE PLATE
HEAT TO 65°C FOR 3MIN, THEN ICE FOR 5 MIN

ADDED 2.3µL PROTOSCRIPTII/BUFFER MASTERMIX TO EACH TUBE

| PROTOSCRIPTII MASTERMIX | | |
|---|---|---|
| 1 | 129.6 X | REAGENT |
| 2 | 259.2 µL | 5X PROTOSCIPT BUFFER |
| 0.1 | 12.96 µL | MURINE RNASE INHIBITOR |
| 0.2 | 25.92 µL | PROTOSCRIPTII |
| 2.3 | 298.08 µL | TOTAL |

ALIQUOT 35µL TO EIGHT TUBES
ADD 2.3µL PROTOSCRIPTII MIX TO EACH WELL OF AN ENTIRE PLATE BY MULTICHANNEL PIPETTOR
INCUBATE 42°C FOR 30MIN
INCUBATE 80°C FOR 5MIN
HOLD AT 4°C

COMBINE ALL WELLS TOGETHER (CAME OUT TO ~900ML)
CLEAN UP WITH AN EQUAL VOLUME OF AMPUREXP BEADS
ELUTE IN 68µL WATER

FIG. 30A

2ND STRAND SYNTHESIS
ADDED (EACH REAGENT INDIVIDUALLY FOLLOWED BY GENTLE MIXING)

| | | 2ND STRAND SYNTHESIS MIX |
|---|---|---|
| 1 | 1 X | REAGENT |
| 68 | 68 µL | ELUTED CDNA |
| 8 | 8 µL | 10X 2ND STRAND SYNTHESIS BUFFER |
| 4 | 4 µL | 2ND STRAND ENZYME MIX |
| 80 | 80 µL | TOTAL |

INCUBATE 2.5HRS AT 16°C
AT 2 HRS AND 25 MINUTES, ADD 1UL 3U/UL T4 DNA POLYMERASE, -
MIX, SPIN, RETURN TO THERMALCYCLER
ADDED 5µL 0.5M EDTA AND MIXED TO STOP ALL ENZYMATIC ACTIVITY
CLEANED UP WITH 100µL AMPUREXP
ELUTED IN 37µL WATER

ADAPTER LIGATION
ADDED (EACH INDIVIDUALLY FOLLOWED BY GENTLE MIXING)

| | | LIGATION MIX |
|---|---|---|
| 1 | 1 X | REAGENT |
| 37 | 37 µL | BLUNTED CDNA |
| 10 | 10 µL | 5X QUICK LIGATION REACTION BUFFER |
| 1 | 1 µL | QUICK T4 DNA LIGASE |
| 2 | 2 µL | 5µM ANEALED CBO123/106 |
| 50 | 50 µL | TOTAL |

INCUBATE 30MIN @ ROOM TEMP

CLEANED UP WITH 50µL AMPUREXP
ELUTED IN 45µL WATER

WTA AMPLIFICATION
ADDED 150µL WTA MASTERMIX TO THE TUBES, CYCLING CONDITIONS

| | | WTA MASTERMIX | | | |
|---|---|---|---|---|---|
| | | | 98°C | 30S | |
| 1 | 4X | REAGENT | 98°C | 10S | |
| 11.5 | 46 µL | WATER | 58°C | 15S | 20X |
| 1 | 4 µL | 30µM CBO40 | 72°C | 3MIN | |
| 25 | 100 µL | 2X Q5 HOTSTART MASTERM | 72°C | 5MIN | |
| 37.5 | 150 µL | TOTAL | 4°C | HOLD | |

COMBINE ALL FOUR PCR REACTIONS IN A 1.5ML TUBE
CLEAN UP WITH 200µL AMPUREXP
ELUTE IN 30µL 10MM TRIS 0.05% TWEEN-20

NANODROP: 24NG/UL
30UL=720NG TOTAL

METHODS AND COMPOSITIONS FOR WHOLE TRANSCRIPTOME AMPLIFICATION

RELATED APPLICATIONS

This application claims the benefit under 35 U.S.C. § 119(e) of U.S. Provisional Patent Application Ser. No. 62/196,782, filed Jul. 24, 2015, and U.S. Provisional Patent Application Ser. No. 62/151,583, filed Apr. 23, 2015, the contents of these related applications are incorporated herein by reference in their entireties for all purposes.

REFERENCE TO SEQUENCE LISTING

The present application is being filed along with a Sequence Listing in electronic format. The Sequence Listing is provided as a file entitled BDCRI-014A_Sequence_Listing.TXT, created Apr. 21, 2016, which is 6.96 Kb in size. The information in the electronic format of the Sequence Listing is incorporated herein by reference in its entirety.

BACKGROUND

Methods and compositions for labeling nucleic acid molecules for amplification or sequencing have been developed. Sometimes a sample provides too little starting materials for performing counting of nucleic acid molecules in the sample. Amplification can increase the amount of materials for downstream analysis methods, such as stochastic counting. Herein described are methods, compositions, kits, and systems for whole transcriptome amplification (WTA), including counting of nucleic acid molecules in samples using stochastic barcodes.

SUMMARY

Some embodiments disclosed herein provide methods for labeling a plurality of targets from a sample, comprising: hybridizing the plurality of targets from the sample with a plurality of nucleic acids each comprising a first universal label; extending the plurality of nucleic acids to generate a plurality of first strand polynucleotides; synthesizing a plurality of second strand polynucleotides using the plurality of first strand polynucleotides as templates to generate a plurality of double-stranded polynucleotides; ligating an adaptor to the plurality of double-stranded polynucleotides, wherein said adaptor comprises a second universal label; and amplifying the plurality of double-stranded polynucleotides using the first universal label and the second universal label, thereby generating a plurality of amplicons comprising the plurality of targets. In some embodiments, each of the plurality of nucleic acids comprises a stochastic barcode. In some embodiments, said stochastic barcode comprises a molecular label, a cellular label, a target-specific region, or any combination thereof. In some embodiments, said target-specific region comprises an oligo dT sequence, a random sequence, a target-specific sequence, or any combination thereof. In some embodiments, the plurality of targets are DNAs. In some embodiments, the plurality of targets are mRNAs. In some embodiments, synthesizing the plurality of second strand polynucleotides comprises nicking the plurality of mRNAs with an RNase, thereby generating one or more mRNA primers. In some embodiments, said RNase is RNaseH. In some embodiments, at least one of said one or more mRNA primers is at least 15 nucleotides in length. In some embodiments, the methods further comprise extending said one or more mRNA primers with a polymerase, thereby generating extended segments. In some embodiments, said polymerase has 5'-3' exonuclease activity. In some embodiments, said polymerase comprises DNA Pol I. In some embodiments, the methods further comprise ligating said extended segments with a ligase, thereby generating a second strand polynucleotide. In some embodiments, the methods further comprise extending said one or more mRNA primers with a strand displacing polymerase, thereby generating an extended second strand. In some embodiments, the methods further comprise removing said one or more mRNA primers from the extended second strand. In some embodiments, the plurality of targets are nucleic acids from a single cell. In some embodiments, the plurality of amplicons comprises a whole transcriptome amplification (WTA) product. In some embodiments, said adaptor is a double stranded polynucleotide. In some embodiments, said adaptor comprises an AsiSI site. In some embodiments, said adaptor is a partially double stranded polynucleotide. In some embodiments, the methods further comprise blunt ending at least one of said plurality of double-stranded polynucleotides. In some embodiments, the methods further comprise adding an A overhang to said plurality of double-stranded polynucleotides. In some embodiments, the methods further comprise synthesizing a plurality of third strand polynucleotides from the plurality of second strand polynucleotides. In some embodiments, each of the plurality of nucleic acids is immobilized on a solid support. In some embodiments, said solid support is a bead. In some embodiments, at least two of said plurality of nucleic acids immobilized on a single solid support comprises different molecular labels. In some embodiments, said plurality of nucleic acids attached to a solid support comprises the same cellular label. In some embodiments, the sample comprises a single cell. In some embodiments, the sample comprises a plurality of cells. In some embodiments, the first universal label and the second universal label are the same. In some embodiments, the first universal label and the second universal label are different. In some embodiments, each one of the plurality of amplicons comprises at least part of the first universal label, the second universal label, or both.

Some embodiments disclosed herein provide methods for labeling a plurality of targets from a sample comprising: hybridizing the plurality of targets from the sample with a plurality of nucleic acids each comprising a first universal label; extending the plurality of nucleic acids to generate a plurality of first strand polynucleotides, wherein the plurality of first stand polynucleotides and the plurality of targets form a plurality of double-stranded polynucleotides; fragmenting the plurality of double-stranded polynucleotides using a first transposome to generate a plurality of double stranded polynucleotides that are ligated with a first adaptor, wherein said first adaptor comprises a second universal label, and wherein the first transposome comprises a first transposase and the first adaptor; and amplifying the plurality of double-stranded polynucleotides that are ligated with the first adaptor using the first universal label and the second universal label, thereby generating a plurality of amplicons comprising the plurality of targets. In some embodiments, the methods further comprise fragmenting the plurality of double-stranded polynucleotides using a second transposome to generate a plurality of double stranded polynucleotides that are ligated with the first adaptor and a second adaptor, wherein said second adaptor comprises a third universal label, and wherein the second transposome comprises a second transposase and the second adaptor. In some embodiments, the first transposase and the second transposase are the same. In some embodiments, the first transposase and the second transposase are different. In some embodiments, the first adaptor and the second adaptor are the same. In some embodiments, the first adaptor and the second adaptor are different. In some embodiments, the methods further comprise synthesizing a plurality of second strand polynucleotides using the plurality of first strand polynucleotides as templates. In some embodiments, said first adaptor comprises a stochastic barcode. In some embodiments, said second universal label is a transposome sequence. In some embodiments, said first adaptor comprises a sequencing primer binding site. In some embodiments, said sequencing primer is P7 or P5. In some embodiments, said second adaptor comprises a stochastic barcode. In some embodiments, said third universal label is a transposome sequence. In some embodiments, said second adaptor comprises a sequencing primer binding site. In some embodiments, said sequencing primer is P7 or P5. In some embodiments, each of the plurality of nucleic acids is immobilized on a solid support. In some embodiments, said solid support is a bead. In some embodiments, the methods comprise purifying double-stranded polynucleotides that are immobilized on beads, wherein the double-stranded polynucleotides are double-stranded polynucleotides that are ligated with the first adaptor, the second adaptor, or both.

Some embodiments disclosed herein provide kits comprising: a plurality of solid supports, wherein each of the sloid support comprises a plurality of nucleic acids each comprising a first universal label sequence; an nucleic acid adaptor comprising a second universal label sequence; and an enzyme, wherein the enzyme is a ligase or a transposase. In some embodiments, said enzyme is a ligase. In some embodiments, said enzyme is a transposase. In some embodiments, said plurality of nucleic acids comprises different molecular labels. In some embodiments, said plurality of nucleic acids comprises the same cellular label. In some embodiments, said plurality of solid supports is a plurality of beads. In some embodiments, the kits comprise one or more additional enzymes selected from the group consisting of a reverse transcriptase, a DNA polymerase, an RNase, an exonuclease, or any combination thereof. In some embodiments, the kits further comprise a substrate. In some embodiments, said substrate comprises microwells.

Some embodiments disclosed herein provide methods for labeling a plurality of target sequences from a single cell, comprising: providing the single cell to a partition comprising a solid support immobilized with a plurality of nucleic acids each comprising a first universal label; lysing the single cell to release the plurality of target sequences; hybridizing the plurality of target sequences from the single cell with the plurality of nucleic acids; extending the plurality of nucleic acids to generate a plurality of first strand polynucleotides; adding an adaptor sequence to the plurality of first strand polynucleotides, wherein said adaptor sequence comprises a second universal label; and amplifying the plurality of first strand polynucleotides using the first universal label and the second universal label, thereby generating a plurality of amplicons comprising the plurality of target sequences. In some embodiments, said adaptor sequence is added by a transposome. In some embodiments, said transposome comprises a transposase and the adaptor sequence. In some embodiments, said adaptor is added by a ligation step. In some embodiments, the plurality of target sequences are mRNAs. In some embodiments, the methods further comprise synthesizing a plurality of second strand polynucleotides using the plurality of first strand polynucleotides as templates. In some embodiments, synthesizing the plurality of second strand polynucleotides comprises nicking the plurality of mRNAs with an RNase, thereby generating one or more mRNA primers. In some embodiments, said RNase is RNaseH. In some embodiments, at least one of said one or more mRNA primers is at least 15 nucleotides in length. In some embodiments, the methods further comprise extending said one or more mRNA primers with a polymerase, thereby generating extended segments. In some embodiments, said polymerase has 5'-3' exonuclease activity. In some embodiments, said polymerase comprises DNA Pol I. In some embodiments, the methods further comprise ligating said extended segments with a ligase, thereby generating a second strand polynucleotide. In some embodiments, the methods further comprise extending said one or more mRNA primers with a strand displacing polymerase, thereby generating an extended second strand. In some embodiments, the methods further comprise removing said one or more mRNA primers from the extended second strand. In some embodiments, the plurality of amplicons comprises a whole transcriptome amplification (WTA) product. In some embodiments, the WTA product comprises at least 10% of the mRNAs in the single cell. In some embodiments, the WTA product comprises at least 50% of the mRNAs in the single cell. In some embodiments, the WTA product comprises at least 90% of the mRNAs in the single cell. In some embodiments, each of the plurality of amplicons comprises a stochastic barcode. In some embodiments, said stochastic barcode comprises a molecular label, a cellular label, a target-specific region, or any combination thereof. In some embodiments, the methods further comprise sequencing the plurality of amplicons to generate a plurality of sequencing reads comprising a molecular label, a cellular label, a target-specific region, or any combination thereof. In some embodiments, the methods further comprise analyzing the plurality of sequencing reads using the cellular label. In some embodiments, the methods further comprise analyzing the plurality of sequencing reads using the molecular label. In some embodiments, said partition is a microwell.

Some embodiments disclosed herein provide systems for generating a whole transcriptome amplification (WTA) product from a plurality of single cells comprising: a substrate comprising a plurality of partitions each comprising a single cell and a solid support immobilized with a plurality of nucleic acids, wherein each of the plurality of nucleic acids comprises: a first universal label; a cellular label; and a molecular label; an nucleic acid adaptor comprising a second universal label sequence; and an enzyme, wherein the enzyme is a ligase or a transposase. In some embodiments, the substrate is a microwell array. In some embodiments, said plurality of cells comprises a one or more different cell types. In some embodiments, said one or more cell types are selected from the group consisting of: brain cells, heart cells, cancer cells, circulating tumor cells, organ cells, epithelial cells, metastatic cells, benign cells, primary cells, and circulatory cells, or any combination thereof.

In one aspect, the disclosure provides for a composition comprising: a quasi-symmetric stochastically barcoded nucleic acid comprising: a stochastic barcode sequence comprising a first universal label; a second strand synthesis primer sequence comprising a second universal label, wherein the second universal label is at most 99% identical to the first universal label. In some embodiments, the quasi-symmetric stochastically barcoded nucleic acid is capable of undergoing suppression PCR. In some embodiments, the strand synthesis primer sequence further comprises a restriction site. In some embodiments, the second universal label is a subset of the first universal label. In some embodiments, the second universal label is shorter than the first universal label. In some embodiments, the second universal label is shorter than the first universal label by at least 1 nucleotide. In some embodiments, the second universal label is shorter than the first universal label by at least 2 nucleotides. In some embodiments, the at least 2 nucleotides are located at the 5' end of the second universal label. In some embodiments, the at least 2 nucleotides are located at the 3' end of the second universal label. In some embodiments, the at least 2 nucleotides are located in between the 3' and 5' end the second universal label. In some embodiments, the second universal label comprises a mismatch compared to the first universal label. In some embodiments, the second universal label hybridizes to at least 80% of the first universal label. In some embodiments, the second universal label is at most 99% identical to the first universal label over at least 90% of the length of the first universal label. In some embodiments, the second universal label is not identical to the first universal label. In some embodiments, the stochastic barcode comprises a target binding region, a molecular label, a cellular label, and a universal label, or any combination thereof. In some embodiments, the target-binding region comprises a sequence selected from the group consisting of: oligo dT, a random multimer, and a gene-specific sequence. In some embodiments, the first universal label is a first sequencing read primer sequence. In some embodiments, the whole transcriptome amplification tag further comprises a sequence complementary to a homopolymer tail, a gene-specific sequence, or a random multimer. In some embodiments, the stochastically barcoded nucleic acid comprises a homopolymer tail. In some embodiments, the second strand synthesis primer sequence further comprises a restriction endonuclease cleavage site. In some embodiments, the first universal label is at one end of the quasi-symmetric stochastically barcoded nucleic acid and wherein the second universal label is at another end of the quasi-symmetric stochastically barcoded nucleic acid. In some embodiments, the first universal label is at the 3' end of the quasi-symmetric stochastically barcoded nucleic acid and the second universal label is at the 5' end of the quasi-symmetric stochastically barcoded nucleic acid. In some embodiments, the quasi-symmetric stochastically barcoded nucleic acid is single stranded. In some embodiments, the quasi-symmetric stochastically barcoded nucleic acid is double-stranded.

In one aspect, the disclosure provides for a method for breaking symmetry in a barcoded nucleic acid comprising: generating a quasi-symmetric stochastically barcoded nucleic acid, comprising a stochastic barcode sequence, a first universal label and a second universal label, wherein the second universal label is at most 99% identical to the first universal label; and identifying 3' and 5' sequencing reads from the quasi-symmetric stochastically barcoded nucleic acid, thereby breaking the symmetry of the quasi-symmetric stochastically barcoded nucleic acid. In some embodiments, the generating comprises contacting a target RNA with a stochastic barcode. In some embodiments, the stochastic barcode comprises a cellular label, a molecular label, the first universal label, and a target-binding region, or any combination thereof. In some embodiments, the method further comprises reverse transcribing the stochastic barcode, thereby generating a stochastically labelled cDNA comprising a complementary sequence of the target RNA. In some embodiments, the method further comprises appending a 3' homopolymer tail to the stochastically labelled cDNA. In some embodiments, the 3' homopolymer tail is from 2-10 nucleotides in length. In some embodiments, the 3' homopolymer tail is a poly A tail. In some embodiments, the method further comprises performing second strand synthesis with a second strand synthesis primer comprising a sequence complementary to the homopolymer tail and the second universal label, thereby generating the quasi-symmetric stochastically barcoded nucleic acid. In some embodiments, the sequence complementary to the homopolymer tail comprises a poly T sequence. In some embodiments, the sequence complementary to the homopolymer tail comprises a poly U sequence. In some embodiments, the primer further comprises a restriction endonuclease cleavage site. In some embodiments, the method further comprises amplifying the quasi-symmetric stochastically barcoded nucleic acid with a whole transcriptome amplification primer. In some embodiments, the whole transcriptome amplification primer hybridizes to a portion of the second universal label. In some embodiments, the whole transcriptome amplification primer hybridizes to at least 18 nucleotides of the second universal label. In some embodiments, the whole transcriptome amplification primer hybridizes to at most 18 nucleotides of the second universal label. In some embodiments, the whole transcriptome amplification primer hybridizes to about 18 nucleotides from the 5' end of the second universal label. In some embodiments, further comprising cleaving the restriction endonuclease cleavage site with a restriction endonuclease, thereby generating an asymmetric stochastically barcoded nucleic acid. In some embodiments, the asymmetric stochastically barcoded nucleic acid does not comprise the second universal label. In some embodiments, the generating the 3' and 5' sequencing reads comprises contacting the asymmetric stochastically barcoded nucleic acid with a degenerate primer, thereby generating an asymmetric read product. In some embodiments, the degenerate primer comprises a gene-specific sequence, a random-multimer sequence, and a third universal label, or any combination thereof. In some embodiments, the third universal label is a sequencing primer binding site. In some embodiments, the third universal label is different than the first universal label. In some embodiments, the method further comprises amplifying the asymmetric read product with library amplification primers. In some embodiments, a primer of the library amplification primer does not bind to the second universal label. In some embodiments, the library amplification primers bind to the first universal label and the third universal label. In some embodiments, the method further comprises performing second strand synthesis with a degenerate primer comprising the second universal label and a random multimer sequence, thereby generating the quasi-symmetric stochastically barcoded nucleic acid. In some embodiments, the quasi-symmetric stochastically barcoded nucleic acid is single-stranded. In some embodiments, the method further comprises amplifying the quasi-symmetric stochastically barcoded nucleic acid with a whole transcriptome amplification primer. In some embodiments, the whole transcriptome amplification primer hybridizes to a portion of the second universal label. In some embodiments, the whole transcriptome amplification primer hybridizes to at least 18 nucleotides of the second universal label. In some embodiments, the whole transcriptome amplification primer hybridizes to at most 18 nucleotides of the second universal label. In some embodiments, the whole transcriptome amplification primer hybridizes to about 18 nucleotides from the 5' end of the second universal label. In some embodiments, the identifying comprises sequencing the 3' and 5' sequencing reads. In some embodiments, the 3' sequencing reads comprise a stochastic barcode sequence. In some embodiments, the 3' sequencing reads further comprise the first universal label, a cellular label, and a portion of the sequence of the nucleic acid, or any combination thereof. In some embodiments, the 5' sequencing reads comprise a restriction endonuclease cleavage site, and the second universal label, or any combination thereof. In some embodiments, the number of 3' sequencing reads is at least 2-fold the number of 5' sequence reads. In some embodiments, the number of 5' sequencing reads is less than 1,000. In some embodiments, the generating comprises adding a cleavage site and the second universal label through template switching. In some embodiments, the generating comprises adding a cleavage site and the second universal label through in vitro transcription. In some embodiments, the identifying sequencing reads comprises determining the sequence of a portion of the sequence of the stochastic barcode and the nucleic acid. In some embodiments, the sequencing reads are at least 25 nucleotides in length. In some embodiments, the sequencing reads are at least 75 nucleotides in length. In some embodiments, the barcoded nucleic acid is from a sample. In some embodiments, the sample comprises a single cell. In some embodiments, the sample comprises a plurality of cells. In some embodiments, the plurality of cells comprises a one or more different cell types. In some embodiments, the one or more cell types are selected from the group consisting of: brain cells, heart cells, cancer cells, circulating tumor cells, organ cells, epithelial cells, metastatic cells, benign cells, primary cells, and circulatory cells, or any combination thereof. In some embodiments, the sample comprises a solid tissue. In some embodiments, the sample is obtained from a subject. In some embodiments, the subject is a subject selected from the group consisting of: a human, a mammal, a dog, a rat, a mouse, a fish, a fly, a worm, a plant, a fungi, a bacterium, a virus, a vertebrate, and an invertebrate. In some embodiments, the targets are deoxyribonucleic acid molecules. In some embodiments, the method further comprises isolating a single cell and a single bead into a plurality of wells on a substrate, wherein a single well of the plurality of wells has the single cell and the single bead. In some embodiments, the substrate comprises at least 1,000 wells. In some embodiments, the single bead comprises a plurality of stochastic barcodes. In some embodiments, the method further comprises hybridizing targets from the single cell to the stochastic barcodes. In some embodiments, individual stochastic barcodes of the plurality of stochastic barcodes have different molecular labels. In some embodiments, individual stochastic barcodes of the plurality of stochastic barcodes have the same cellular label. In some embodiments, individual stochastic barcodes of the plurality of stochastic barcodes comprise a molecular label, a cellular label, the first universal label, and a target-binding region, or any combination thereof. In some embodiments, stochastic barcodes in different wells of the plurality of wells have different cellular labels. In some embodiments, the method further comprises removing the bead. In some embodiments, the removing is performed with a magnet.

In one aspect, the disclosure provides for a kit comprising: a set of stochastic barcodes, wherein each stochastic barcode of the set of stochastic barcodes comprise a target-specific region; a molecular label; a cellular label; and a first universal label; a second strand synthesis primer comprising a second universal label, wherein the second universal label is at most 99% identical to the first universal label; and an enzyme. In some embodiments, individual stochastic barcodes of the set of stochastic barcodes comprise different molecular labels. In some embodiments, individual stochastic barcodes of the set of stochastic barcodes comprise the same cellular labels. In some embodiments, the target-specific region comprises a sequence selected from the group consisting of: an oligo dT, a random multimer, and a gene-specific sequence. In some embodiments, the enzyme is selected from the group consisting of: a reverse transcriptase, a terminal transferase, an RNase inhibitor, a DNA polymerase, a restriction endonuclease, and an exonuclease, or any combination thereof. In some embodiments, the kit further comprises a whole transcriptome amplification primer. In some embodiments, the whole transcriptome amplification primer hybridizes to a portion of the second universal label. In some embodiments, the whole transcriptome amplification primer hybridizes to at least 18 nucleotides of the second universal label. In some embodiments, the whole transcriptome amplification primer hybridizes to at most 18 nucleotides of the second universal label. In some embodiments, the whole transcriptome amplification primer hybridizes to about 18 nucleotides from the 5' end of the second universal label. In some embodiments, the second universal label differs by at least one nucleotide from the first universal label. In some embodiments, the second universal label is shorter than the first universal label by at least one nucleotide. In some embodiments, the second universal label is shorter than the first universal label by at least two nucleotides. In some embodiments, the second universal label is shorter than the first universal label by two nucleotides. In some embodiments, the second universal label comprises a sequence that is a subset of the sequence of the first universal label. In some embodiments, the second strand synthesis primer comprises a cleavage site. In some embodiments, the cleavage site comprises a restriction endonuclease cleavage site. In some embodiments, the kit further comprises instructions for use. In some embodiments, the kit further comprises one or more universal primers. In some embodiments, the one or more universal primers are adapted to hybridize to the first and second universal label, the first universal label, or the second universal label. In some embodiments, the kit further comprises a set of gene-specific primers. In some embodiments, the kit further comprises reagents for a reverse transcription reaction. In some embodiments, the kit further comprises reagents for a polymerase chain reaction. In some embodiments, the kit further comprises reagents for a restriction endonuclease cleavage reaction. In some embodiments, the set of stochastic barcodes are attached to a solid support. In some embodiments, the solid support comprises a bead. In some embodiments, the kit further comprises a substrate. In some embodiments, the substrate comprises microwells.

In one aspect, the disclosure provides for a method for whole transcriptome amplification using adaptor ligation comprising: contacting one or more mRNA targets a sample with a nucleic acid comprising a first universal label; performing reverse transcription and second strand synthesis, thereby generating a labeled cDNA; ligating an adaptor to labeled cDNA, thereby generating a quasi-symmetric cDNA, wherein the adaptor comprises a second universal label; and amplifying the adaptor ligated cDNA with a whole transcriptome amplification primer, thereby generating a whole-transcriptome amplified product. In some embodiments, the nucleic acid comprises a stochastic barcode. In some embodiments, the stochastic barcode comprises a molecular label, a cellular label, a target-specific region, or any combination thereof. In some embodiments, the target-specific region comprises an oligo dT sequence. In some embodiments, the second strand synthesis comprises nicking the mRNA with an RNAse, thereby generating mRNA primers. In some embodiments, the RNase is RNaseH. In some embodiments, the mRNA primers are at least 15 nucleotides in length. In some embodiments, the method further comprises extending the mRNA primers with a polymerase, thereby generating extended segments. In some embodiments, the polymerase comprises 5'-3' exonuclease activity. In some embodiments, the polymerase comprises DNA Pol I. In some embodiments, the method further comprises ligating the extended segments with a ligase, thereby generating a second strand. In some embodiments, the adaptor is double stranded. In some embodiments, the adaptor comprises a restriction endonuclease cleavage site. In some embodiments, the second universal label is a subset of the first universal label. In some embodiments, the second universal label is shorter than the first universal label. In some embodiments, the second universal label is shorter than the first universal label by at least 1 nucleotide. In some embodiments, the second universal label is shorter than the first universal label by at least 2 nucleotides. In some embodiments, the at least 2 nucleotides are located at the 5' end of the second universal label. In some embodiments, the at least 2 nucleotides are located at the 3' end of the second universal label. In some embodiments, the at least 2 nucleotides are located in between the 3' and 5' end the second universal label. In some embodiments, the second universal label comprises a mismatch compared to the first universal label. In some embodiments, the second universal label hybridizes to at least 80% of the first universal label. In some embodiments, the second universal label is at most 99% identical to the first universal label over at least 90% of the length of the first universal label. In some embodiments, the second universal label is not identical to the first universal label. In some embodiments, the ligating comprises ligating the adaptor to both strands of the labeled cDNA. In some embodiments, the adaptor comprises a single 5' phosphorylation site. In some embodiments, after the ligating, the quasi-symmetric cDNA comprises the same sequence at the 3' end of each strand. In some embodiments, the same sequence comprises a second universal primer sequence. In some embodiments, the whole transcriptome amplification primer comprises a sequence complementary to the second universal primer sequence on the adaptor. In some embodiments, the whole transcriptome amplification primer comprises a sequence complementary to the first universal primer sequence on the adaptor. In some embodiments, the amplifying comprises suppressive PCR. In some embodiments, the amplifying comprises semi-suppressive PCR. In some embodiments, the amplifying comprises linear amplification of one strand and exponential amplification of the other strand of the quasi-symmetric cDNA. In some embodiments, the method is not gene-specific. In some embodiments, the amplifying is not gene-specific. In some embodiments, at least 5% of the mRNA targets are amplified. In some embodiments, at least 10% of the mRNA targets are amplified. In some embodiments, at least 15% of the mRNA targets are amplified. In some embodiments, the method further comprises sequencing the whole transcriptome amplified product. In some embodiments, the method further comprises counting the number of molecules of the mRNA targets. In some embodiments, the counting comprises counting the number of unique molecular labels for each whole transcriptome amplified product with the sequence of the mRNA target.

In one aspect, the disclosure provides for a method for second strand synthesis comprising: contacting an mRNA target in a sample with a nucleic acid comprising a first universal label; reverse transcribing the mRNA target into a labeled single stranded cDNA; synthesizing a second strand with a strand displacing polymerase off the labeled single-stranded cDNA; and generating a third strand from the second strand with a sequence comprising the first universal label, thereby generating a double-stranded labeled cDNA. In some embodiments, the nucleic acid comprises a stochastic barcode. In some embodiments, the stochastic barcode comprises a molecular label, a cellular label, a target-specific region, and a universal label, or any combination thereof. In some embodiments, the contacting comprises hybridizing a target-specific region of the nucleic acid to the mRNA. In some embodiments, the target-specific region comprises an oligo dT sequence. In some embodiments, after the reverse transcribing the labeled single stranded cDNA is hybridized to the mRNA target. In some embodiments, the synthesizing comprises nicking the mRNA with an RNAse, thereby generating mRNA primers. In some embodiments, the RNase is RNaseH. In some embodiments, the mRNA primers are at least 15 nucleotides in length. In some embodiments, the method further comprises extending the mRNA primers with the strand displacing polymerase, thereby generating extended segments. In some embodiments, the extended segments comprise the mRNA primer. In some embodiments, the method further comprises removing the mRNA primer. In some embodiments, the removing comprises removing with an exonuclease. In some embodiments, the generating comprises extending the first universal label to incorporate the sequence of the second strand. In some embodiments, the method further comprises blunting the end of the double-stranded cDNA. In some embodiments, the method further comprises adding an A overhang to the double-stranded cDNA. In some embodiments, the method further comprises ligating an adaptor to the double-stranded cDNA, thereby generating a quasi-symmetric cDNA. In some embodiments, the adaptor is double stranded. In some embodiments, the adaptor comprises a restriction endonuclease cleavage site. In some embodiments, the adaptor comprises a second universal label. In some embodiments, the second universal label is a subset of the first universal label. In some embodiments, the second universal label is shorter than the first universal label. In some embodiments, the second universal label is shorter than the first universal label by at least 1 nucleotide. In some embodiments, the second universal label is shorter than the first universal label by at least 2 nucleotides. In some embodiments, the at least 2 nucleotides are located at the 5' end of the second universal label. In some embodiments, the at least 2 nucleotides are located at the 3' end of the second universal label. In some embodiments, the at least 2 nucleotides are located in between the 3' and 5' end the second universal label. In some embodiments, the second universal label comprises a mismatch compared to the first universal label. In some embodiments, the second universal label hybridizes to at least 80% of the first universal label. In some embodiments, the second universal label is at most 99% identical to the first universal label over at least 90% of the length of the first universal label. In some embodiments, the second universal label is not identical to the first universal label. In some embodiments, the ligating comprises ligating the adaptor to both strands of the labeled cDNA. In some embodiments, after the ligating, the adaptor ligated cDNA comprises the same sequence at the 3' end of each strand. In some embodiments, the same sequence comprises a second universal primer sequence. In some embodiments, the method further comprises amplifying the quasi-symmetric cDNA with a whole transcriptome amplification primer. In some embodiments, the whole transcriptome amplification primer comprises a sequence complementary to a second universal primer sequence on the adaptor. In some embodiments, the amplifying comprises suppressive PCR. In some embodiments, the amplifying comprises semi-suppressive PCR. In some embodiments, the amplifying comprises linear amplification of one strand and exponential amplification of the other strand of the adaptor ligated cDNA. In some embodiments, the method is not gene-specific. In some embodiments, the amplifying is not gene-specific.

In one aspect the disclosure provides for a kit comprising: a set of stochastic barcodes, wherein each stochastic barcode of the set of stochastic barcodes comprise a target-specific region; a molecular label; a cellular label; and a first universal label; an adaptor comprising a second universal label, wherein the second universal label is at most 99% identical to the first universal label; and an enzyme. In some embodiments, individual stochastic barcodes of the set of stochastic barcodes comprise different molecular labels. In some embodiments, individual stochastic barcodes of the set of stochastic barcodes comprise the same cellular labels. In some embodiments, the target-specific region comprises a sequence selected from the group consisting of: an oligo dT, a random multimer, and a gene-specific sequence. In some embodiments, the enzyme is selected from the group consisting of: a reverse transcriptase, a terminal transferase, an RNase inhibitor, a DNA polymerase, an RNase, a restriction endonuclease, and an exonuclease, or any combination thereof. In some embodiments, the kit further comprises a whole transcriptome amplification primer. In some embodiments, the whole transcriptome amplification primer hybridizes to a portion of the second universal label. In some embodiments, the whole transcriptome amplification primer hybridizes to at least 10 nucleotides of the first universal label. In some embodiments, the whole transcriptome amplification primer hybridizes to at most 10 nucleotides of the first universal label. In some embodiments, the whole transcriptome amplification primer hybridizes to about 10 nucleotides from the 5' end of the first universal label. In some embodiments, the second universal label differs by at least one nucleotide from the first universal label. In some embodiments, the second universal label is shorter than the first universal label by at least one nucleotide. In some embodiments, the second universal label is shorter than the first universal label by at least two nucleotides. In some embodiments, the second universal label is shorter than the first universal label by two nucleotides. In some embodiments, the second universal label comprises a sequence that is a subset of the sequence of the first universal label. In some embodiments, the adaptor comprises a cleavage site. In some embodiments, the cleavage site comprises a restriction endonuclease cleavage site. In some embodiments, the kit further comprises instructions for use. In some embodiments, the kit further comprises one or more universal primers. In some embodiments, the one or more universal primers are adapted to hybridize to the first and second universal label, the first universal label, or the second universal label. In some embodiments, the kit further comprises reagents for a reverse transcription reaction. In some embodiments, the kit further comprises reagents for a polymerase chain reaction. In some embodiments, the kit further comprises reagents for a restriction endonuclease cleavage reaction. In some embodiments, the set of stochastic barcodes are attached to a solid support. In some embodiments, the solid support comprises a bead. In some embodiments, the kit further comprises a substrate. In some embodiments, the substrate comprises microwells.

In one aspect, the disclosure provides for a method for generating a strand specific sequencing library comprising: contacting an RNA fragment with a primer comprising a first sequence; generating a double-stranded cDNA that incorporates the first sequence; ligating an adaptor to the double-stranded cDNA, thereby generating an asymmetric adaptor ligated cDNA, wherein the sequencing reads of the asymmetric adaptor ligated cDNA indicate strand specificity. In some embodiments, the first sequence comprises a portion of a first sequencing primer sequence. In some embodiments, the first sequence comprises a sample barcode. In some embodiments, the first sequence comprises a molecular barcode. In some embodiments, the generating comprises reverse transcription, second strand synthesis. In some embodiments, the adaptor is double-stranded. In some embodiments, the adaptor ligates to the 3' end, the 5' end, or both the 3' and 5' end of the double-stranded cDNA. In some embodiments, the adaptor comprises a second sequence. In some embodiments, the second sequence comprises a portion of a second sequencing primer sequence. In some embodiments, the second sequence comprises a sample barcode. In some embodiments, the method further comprises amplifying the asymmetric adaptor ligated cDNA, thereby generating asymmetric amplicons. In some embodiments, the amplifying comprises PCR amplification with a first primer and a second primer. In some embodiments, the first primer hybridizes to at least a portion of the first sequence. In some embodiments, the second primer hybridizes to at least a portion of a second sequence. In some embodiments, the first and second primers comprise additional sequences to be added to the adaptor ligated cDNA. In some embodiments, the additional sequences comprise additional flow cell sequences. In some embodiments, the additional sequences comprise additional sequencing primer sequences. In some embodiments, the additional sequences comprise sample barcodes. In some embodiments, the method further comprises incorporating a universal sequence into the RNA. In some embodiments, the incorporating comprises using a PolyA polymerase. In some embodiments, the some of the reads incorporate the sequence of the adaptor. In some embodiments, the reads correspond to a first strand of the double-stranded cDNA. In some embodiments, the some of the reads incorporate the sequence of the first sequence. In some embodiments, the reads correspond to a second strand of the double-stranded cDNA. In some embodiments, the strand specificity is determined by whether a read of the sequencing reads comprises the sequence of the adaptor or the first sequence. In some embodiments, the RNA is selected from the group consisting of: an mRNA, a non-coding RNA, a lncRNA, a miRNA, a double-stranded RNA, and a single-stranded RNA. In some embodiments, the method does not comprise degrading one strand of the double-stranded cDNA. In some embodiments, the method further comprises sequencing the amplicon.

In one aspect the disclosure provides for a method for generating a strand-specific sequencing library comprising: contacting a DNA fragment with a primer comprising a first sequence; extending the primer, thereby generating a copy of the DNA sequence; and ligating an adaptor to one end of the copy of the DNA sequence, wherein the adaptor comprises a second sequence, thereby generating an asymmetric adaptor ligated cDNA, wherein the sequencing reads of the asymmetric adaptor ligated cDNA indicate strand specificity. In some embodiments, the first sequence comprises a portion of a first sequencing primer sequence. In some embodiments, the first sequence comprises a sample barcode. In some embodiments, the first sequence comprises a molecular barcode. In some embodiments, the generating comprises reverse transcription, second strand synthesis. In some embodiments, the adaptor is double-stranded. In some embodiments, the adaptor ligates to the 3' end, the 5' end, or both the 3' and 5' end of the double-stranded cDNA. In some embodiments, the second sequence comprises a portion of a second sequencing primer sequence. In some embodiments, the second sequence comprises a sample barcode. In some embodiments, the method further comprises amplifying the asymmetric adaptor ligated cDNA, thereby generating asymmetric amplicons. In some embodiments, the amplifying comprises PCR amplification with a first primer and a second primer. In some embodiments, the first primer hybridizes to at least a portion of the first sequence. In some embodiments, the second primer hybridizes to at least a portion of a second sequence. In some embodiments, the first and second primers comprise additional sequences to be added to the adaptor ligated cDNA. In some embodiments, the additional sequences comprise additional flow cell sequences. In some embodiments, the additional sequences comprise additional sequencing primer sequences. In some embodiments, the additional sequences comprise sample barcodes. In some embodiments, the method further comprises incorporating a universal sequence into the RNA. In some embodiments, the incorporating comprises using a terminal transferase. In some embodiments, the some of the reads incorporate the sequence of the adaptor. In some embodiments, the reads correspond to a first strand of the double-stranded cDNA. In some embodiments, the some of the reads incorporate the sequence of the first sequence. In some embodiments, the reads correspond to a second strand of the double-stranded cDNA. In some embodiments, the strand specificity is determined by whether a read of the sequencing reads comprises the sequence of the adaptor or the first sequence. In some embodiments, the method does not comprise degrading one strand of the double-stranded cDNA.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIGS. 6A, 6B and 6C depict the efficiency and mass yield of an exemplary adaptor ligation method used in Example 1.

FIG. 8A shows efficiency using the second strand synthesis method as described in FIGS. 15A and 15B. FIG. 8B shows efficiency using the nicking and extension method as described in FIGS. 16A and 16B.

FIGS. 9A and 9B depict (A) an agarose gel and (B) mass yield of the product in FIG. 8B.

FIG. 17 depicts exemplary adaptors used in the methods of the disclosure.

FIG. 20A is a PCA plot that clearly separates the UHRR (Universal Human Reference RNA) wells from the Human Brain Reference RNA (HBRR) wells;

FIG. 20B is a heatmap of the genes used for PCA along with hierarchical clustering that shows all of the like RNA types clustering together.

FIG. 26 illustrates an exemplary embodiment of RNA-seq library preparation using the adaptor ligation method of the disclosure.

FIGS. 29A and 29B show an exemplary experimental protocol for analyzing 1 ng of RNA with the whole transcriptome methods of the disclosure.

FIGS. 30A and 30B show an exemplary experimental protocol for analyzing 10 pg of RNA with the whole transcriptome methods of the disclosure.

DETAILED DESCRIPTION

Definitions

Figure 1A:
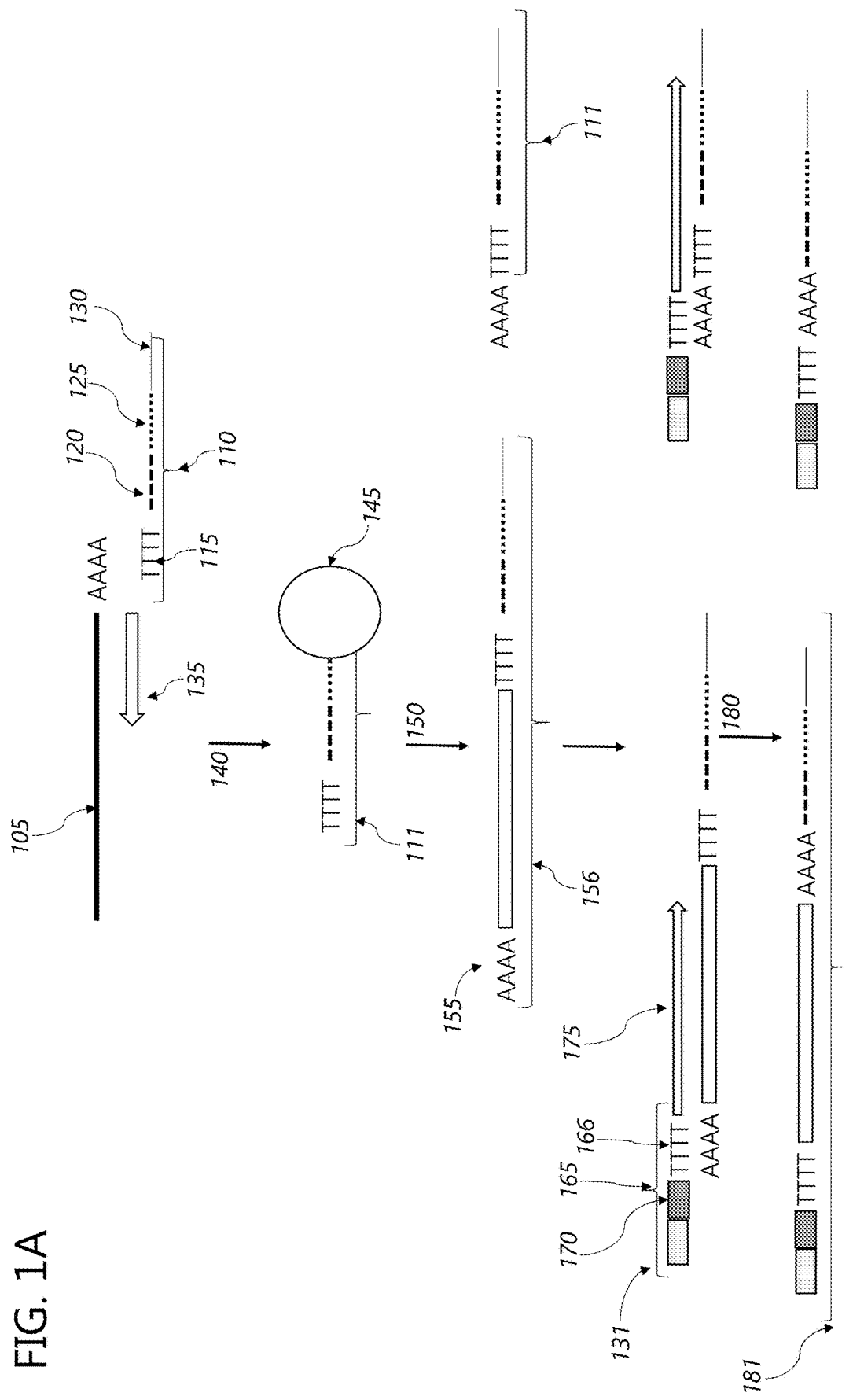
FIGS. 1A and 1B illustrate an exemplary embodiment of the homopolymer tailing method of the disclosure.

Unless otherwise defined, all technical terms used herein have the same meaning as commonly understood by one of ordinary skill in the art in the field to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

As used herein the term "transcriptome" refers to the set of all transcripts, such as messenger RNA (mRNA) molecules, small interfering RNA (siRNA) molecules, transfer RNA (tRNA) molecules, ribosomal RNA (rRNA) molecules, in a sample, for example, a single cell or a population of cells. In some embodiments, transcriptome not only refers to the species of transcripts, such as mRNA species, but also the amount of each species in the sample. In some embodiments, a transcriptome includes each mRNA molecule in the sample, such as all the mRNA molecules in a single cell.

As used herein the term "associated" or "associated with" can mean that two or more species are identifiable as being co-located at a point in time. An association can mean that two or more species are or were within a similar container. An association can be an informatics association, where for example digital information regarding two or more species is stored and can be used to determine that one or more of the species were co-located at a point in time. An association can also be a physical association. In some instances two or more associated species are "tethered", "attached", or "immobilized" to one another or to a common solid or semisolid surface. An association may refer to covalent or non-covalent means for attaching labels to solid or semisolid supports such as beads. An association may comprise hybridization between a target and a label.

As used herein, the term "complementary" can refer to the capacity for precise pairing between two nucleotides. For example, if a nucleotide at a given position of a nucleic acid is capable of hydrogen bonding with a nucleotide of another nucleic acid, then the two nucleic acids are considered to be complementary to one another at that position. Complementarity between two single-stranded nucleic acid molecules may be "partial," in which only some of the nucleotides bind, or it may be complete when total complementarity exists between the single-stranded molecules. A first nucleotide sequence can be said to be the "complement" of a second sequence if the first nucleotide sequence is complementary to the second nucleotide sequence. A first nucleotide sequence can be said to be the "reverse complement" of a second sequence, if the first nucleotide sequence is complementary to a sequence that is the reverse (i.e., the order of the nucleotides is reversed) of the second sequence. As used herein, the terms "complement", "complementary", and "reverse complement" can be used interchangeably. It is understood from the disclosure that if a molecule can hybridize to another molecule it may be the complement of the molecule that is hybridizing.

As used herein, the term "digital counting" can refer to a method for estimating a number of target molecules in a sample. Digital counting can include the step of determining a number of unique labels that have been associated with targets in a sample. This stochastic methodology transforms the problem of counting molecules from one of locating and identifying identical molecules to a series of yes/no digital questions regarding detection of a set of predefined labels.

As used herein, the term "first universal label" can refer to a label that is universal for barcodes of the disclosure. A first universal label can be a sequencing primer binding site (e.g., a read primer binding site, i.e., for an Illumina sequencer).

As used herein, the term "label" or "labels" can refer to nucleic acid codes associated with a target within a sample. A label can be, for example, a nucleic acid label. A label can be an entirely or partially amplifiable label. A label can be entirely or partially sequencable label. A label can be a portion of a native nucleic acid that is identifiable as distinct. A label can be a known sequence. A label can comprise a junction of nucleic acid sequences, for example a junction of a native and non-native sequence. As used herein, the term "label" can be used interchangeably with the terms, "index", "tag," or "label-tag." Labels can convey information. For example, in various embodiments, labels can be used to determine an identity of a sample, a source of a sample, an identity of a cell, and/or a target.

As used herein, the term "non-depleting reservoirs" can refer to a pool of stochastic barcodes made up of many different labels. A non-depleting reservoir can comprise large numbers of different stochastic barcodes such that when the non-depleting reservoir is associated with a pool of targets each target is likely to be associated with a unique stochastic barcode. The uniqueness of each labeled target molecule can be determined by the statistics of random choice, and depends on the number of copies of identical target molecules in the collection compared to the diversity of labels. The size of the resulting set of labeled target molecules can be determined by the stochastic nature of the barcoding process, and analysis of the number of stochastic barcodes detected then allows calculation of the number of target molecules present in the original collection or sample. When the ratio of the number of copies of a target molecule present to the number of unique stochastic barcodes is low, the labeled target molecules are highly unique (i.e. there is a very low probability that more than one target molecule will have been labeled with a given label).

As used herein, a "nucleic acid" can generally refer to a polynucleotide sequence, or fragment thereof. A nucleic acid can comprise nucleotides. A nucleic acid can be exogenous or endogenous to a cell. A nucleic acid can exist in a cell-free environment. A nucleic acid can be a gene or fragment thereof. A nucleic acid can be DNA. A nucleic acid can be RNA. A nucleic acid can comprise one or more analogs (e.g. altered backgone, sugar, or nucleobase). Some non-limiting examples of analogs include: 5-bromouracil, peptide nucleic acid, xeno nucleic acid, morpholinos, locked nucleic acids, glycol nucleic acids, threose nucleic acids, dideoxynucleotides, cordycepin, 7-deaza-GTP, florophores (e.g. rhodamine or flurescein linked to the sugar), thiol containing nucleotides, biotin linked nucleotides, fluorescent base analogs, CpG islands, methyl-7-guanosine, methylated nucleotides, inosine, thiouridine, pseudourdine, dihydrouridine, queuosine, and wyosine. "Nucleic acid", "polynucleotide, "target polynucleotide", and "target nucleic acid" can be used interchangeably.

A nucleic acid can comprise one or more modifications (e.g., a base modification, a backbone modification), to provide the nucleic acid with a new or enhanced feature (e.g., improved stability). A nucleic acid can comprise a nucleic acid affinity tag. A nucleoside can be a base-sugar combination. The base portion of the nucleoside can be a heterocyclic base. The two most common classes of such heterocyclic bases are the purines and the pyrimidines. Nucleotides can be nucleosides that further include a phosphate group covalently linked to the sugar portion of the nucleoside. For those nucleosides that include a pentofuranosyl sugar, the phosphate group can be linked to the 2', the 3', or the 5' hydroxyl moiety of the sugar. In forming nucleic acids, the phosphate groups can covalently link adjacent nucleosides to one another to form a linear polymeric compound. In turn, the respective ends of this linear polymeric compound can be further joined to form a circular compound; however, linear compounds are generally suitable. In addition, linear compounds can have internal nucleotide base complementarity and can therefore fold in a manner as to produce a fully or partially double-stranded compound. Within nucleic acids, the phosphate groups can commonly be referred to as forming the internucleoside backbone of the nucleic acid. The linkage or backbone of the nucleic acid can be a 3' to 5' phosphodiester linkage.

A nucleic acid can comprise a modified backbone and/or modified internucleoside linkages. Modified backbones can include those that retain a phosphorus atom in the backbone and those that do not have a phosphorus atom in the backbone. Suitable modified nucleic acid backbones containing a phosphorus atom therein can include, for example, phosphorothioates, chiral phosphorothioates, phosphorodithioates, phosphotriesters, aminoalkylphosphotriesters, methyl and other alkyl phosphonates such as 3'-alkylene phosphonates, 5'-alkylene phosphonates, chiral phosphonates, phosphinates, phosphoramidates including 3'-amino phosphoramidate and aminoalkylphosphoramidates, phosphorodiamidates, thionophosphoramidates, thionoalkylphosphonates, thionoalkylphosphotriesters, selenophosphates, and boranophosphates having normal 3'-5' linkages, 2'-5' linked analogs, and those having inverted polarity wherein one or more internucleotide linkages is a 3' to 3', a 5' to 5' or a 2' to 2' linkage.

A nucleic acid can comprise polynucleotide backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These can include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and CH2 component parts.

A nucleic acid can comprise a nucleic acid mimetic. The term "mimetic" can be intended to include polynucleotides wherein only the furanose ring or both the furanose ring and the internucleotide linkage are replaced with non-furanose groups, replacement of only the furanose ring can also be referred as being a sugar surrogate. The heterocyclic base moiety or a modified heterocyclic base moiety can be maintained for hybridization with an appropriate target nucleic acid. One such nucleic acid can be a peptide nucleic acid (PNA). In a PNA, the sugar-backbone of a polynucleotide can be replaced with an amide containing backbone, in particular an aminoethylglycine backbone. The nucleotides can be retained and are bound directly or indirectly to aza nitrogen atoms of the amide portion of the backbone. The backbone in PNA compounds can comprise two or more linked aminoethylglycine units which gives PNA an amide containing backbone. The heterocyclic base moieties can be bound directly or indirectly to aza nitrogen atoms of the amide portion of the backbone.

A nucleic acid can comprise a morpholino backbone structure. For example, a nucleic acid can comprise a 6-membered morpholino ring in place of a ribose ring. In some of these embodiments, a phosphorodiamidate or other non-phosphodiester internucleoside linkage can replace a phosphodiester linkage.

A nucleic acid can comprise linked morpholino units (i.e. morpholino nucleic acid) having heterocyclic bases attached to the morpholino ring. Linking groups can link the morpholino monomeric units in a morpholino nucleic acid. Non-ionic morpholino-based oligomeric compounds can have less undesired interactions with cellular proteins. Morpholino-based polynucleotides can be nonionic mimics of nucleic acids. A variety of compounds within the morpholino class can be joined using different linking groups. A further class of polynucleotide mimetic can be referred to as cyclohexenyl nucleic acids (CeNA). The furanose ring normally present in a nucleic acid molecule can be replaced with a cyclohexenyl ring. CeNA DMT protected phosphoramidite monomers can be prepared and used for oligomeric compound synthesis using phosphoramidite chemistry. The incorporation of CeNA monomers into a nucleic acid chain can increase the stability of a DNA/RNA hybrid. CeNA oligoadenylates can form complexes with nucleic acid complements with similar stability to the native complexes. A further modification can include Locked Nucleic Acids (LNAs) in which the 2'-hydroxyl group is linked to the 4' carbon atom of the sugar ring thereby forming a 2'-C,4'-C-oxymethylene linkage thereby forming a bicyclic sugar moiety. The linkage can be a methylene (—CH2-), group bridging the 2' oxygen atom and the 4' carbon atom wherein n is 1 or 2. LNA and LNA analogs can display very high duplex thermal stabilities with complementary nucleic acid (Tm=+3 to +10° C.), stability towards 3'-exonucleolytic degradation and good solubility properties.

A nucleic acid can also include nucleobase (often referred to simply as "base") modifications or substitutions. As used herein, "unmodified" or "natural" nucleobases can include the purine bases, (e.g. adenine (A) and guanine (G)), and the pyrimidine bases, (e.g. thymine (T), cytosine (C) and uracil (U)). Modified nucleobases can include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH3) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-aminoadenine, 8-azaguanine and 8-azaadenine, 7-deazaguanine and 7-deazaadenine and 3-deazaguanine and 3-deazaadenine. Modified nucleobases can include tricyclic pyrimidines such as phenoxazine cytidine(1H-pyrimido(5,4-b)(1,4)benzoxazin-2 (3H)-one), phenothiazine cytidine (1H-pyrimido(5,4-b)(1,4) benzothiazin-2(3H)-one), G-clamps such as a substituted phenoxazine cytidine (e.g. 9-(2-aminoethoxy)-H-pyrimido (5,4-(b) (1,4)benzoxazin-2(3H)-one), carbazole cytidine (2H-pyrimido(4,5-b)indol-2-one), pyridoindole cytidine (Hpyrido(3',':4,5)pyrrolo[2,3-d]pyrimidin-2-one).

As used herein, the term "quasi-symmetric stochastically barcoded nucleic acid" can refer to a molecule comprising a stochastic barcode of the disclosure and ends that are symmetric enough to hybridize together to form a panhandle structure (e.g., for suppression PCR), but may not be identical. A quasi-symmetric stochastically barcoded nucleic acid can behave like a symmetric nucleic acid, but have an asymmetric sequence.

As used herein, the term "sample" can refer to a composition comprising targets. Suitable samples for analysis by the disclosed methods, devices, and systems include cells, single cells, tissues, organs, or organisms.

As used herein, the term "sampling device" or "device" can refer to a device which may take a section of a sample and/or place the section on a substrate. A sample device can refer to, for example, a fluorescence activated cell sorting (FACS) machine, a cell sorter machine, a biopsy needle, a biopsy device, a tissue sectioning device, a microfluidic device, a blade grid, and/or a microtome.

As used herein, the term "second universal label" can refer to a label that is universal for barcodes of the disclosure. A second universal label can be a modified version of a sequencing primer binding site (e.g., a read primer binding site, i.e., for an Illumina sequencer). A second universal label can be a modified version of a label of the disclosure (e.g., first universal label).

As used herein, the term "solid support" can refer to discrete solid or semi-solid surfaces to which a plurality of stochastic barcodes may be attached. A solid support can encompass any type of solid, porous, or hollow sphere, ball, bearing, cylinder, or other similar configuration composed of plastic, ceramic, metal, or polymeric material (e.g., hydrogel) onto which a nucleic acid can be immobilized (e.g., covalently or non-covalently). A solid support can comprise a discrete particle that may be spherical (e.g., microspheres) or have a non-spherical or irregular shape, such as cubic, cuboid, pyramidal, cylindrical, conical, oblong, or disc-shaped, and the like. A plurality of solid supports spaced in an array may not comprise a substrate. A solid support can be used interchangeably with the term "bead."

A solid support can refer to a "substrate." A substrate can be a type of solid support. A substrate can refer to a continuous solid or semi-solid surface on which the methods of the disclosure may be performed. A substrate can refer to an array, a cartridge, a chip, a device, and a slide, for example. As used herein, "solid support" and "substrate" can be used interchangeably.

As used herein, the term "stochastic barcode" can refer to a polynucleotide sequence comprising labels of the disclosure. A stochastic barcode can be a polynucleotide sequence that can be used for stochastic barcoding. Stochastic barcodes can be used to quantify targets within a sample. Stochastic barcodes can be used to control for errors which may occur after a label is associated with a target. For example, a stochastic barcode can be used to assess amplification or sequencing errors. A stochastic barcode associated with a target can be called a stochastic barcode-target or stochastic barcode-tag-target.

As used herein, the term "stochastic barcoding" can refer to the random labeling (e.g., barcoding) of nucleic acids. Stochastic barcoding can utilize a recursive Poisson strategy to associate and quantify labels associated with targets. As used herein, the term "stochastic barcoding" can be used interchangeably with "stochastic labeling."

As used here, the term "target" can refer to a composition which can be associated with a stochastic barcode. Exemplary suitable targets for analysis by the disclosed methods, devices, and systems include oligonucleotides, DNA, RNA, mRNA, microRNA, tRNA, and the like. Targets can be single or double stranded. In some embodiments targets can be proteins. In some embodiments targets are lipids.

The term "reverse transcriptase" can refer to a group of enzymes having reverse transcriptase activity (i.e., that catalyze synthesis of DNA from an RNA template). In general, such enzymes include, but are not limited to, retroviral reverse transcriptase, retrotransposon reverse transcriptase, retroplasmid reverse transcriptase, retron reverse transcriptase, bacterial reverse transcriptase, group II intron-derived reverse transcriptase, and mutants, variants or derivatives thereof. Non-retroviral reverse transcriptase include non-LTR retrotransposon reverse transcriptase, retroplasmid reverse transcriptase, retron reverse transcriptase, and group II intron reverse transcriptase. Examples of group II intron reverse transcriptase include the *Lactococcus lactis* Ll.LtrB intron reverse transcriptase, the *Thermosynechococcus elongatus* TeI4c intron reverse transcriptase, or the *Geobacillus stearothermophilus* GsI-IIC intron reverse transcriptase. Other classes of reverse transcriptase can include many classes of non-retroviral reverse transcriptase (i.e., retrons, group II introns, and diversity-generating retroelements among others).

The term "template switching" can refer to the ability of a reverse transcriptase to switch from an initial nucleic acid sequence template to the 3' end of a new nucleic acid sequence template having little or no complementarity to the 3' end of the nucleic acid synthesized from the initial template. Nucleic acid copies of a target polynucleotide can be made using template switching. Template switching allows, e.g., a DNA copy to be prepared using a reverse transcriptase that switches from an initial nucleic acid sequence template to the 3' end of a new nucleic acid sequence template having little or no complementarity to the 3' end of the DNA synthesized from the initial template, thereby allowing the synthesis of a continuous product DNA that directly links an adaptor sequence to a target oligonucleotide sequence without ligation. Template switching can comprise ligation of adaptor, homopolymer tailing (e.g., polyadenylation), random primer, or an oligonucleotide that the polymerase can associate with.

Stochastic Barcodes

Figure 4:
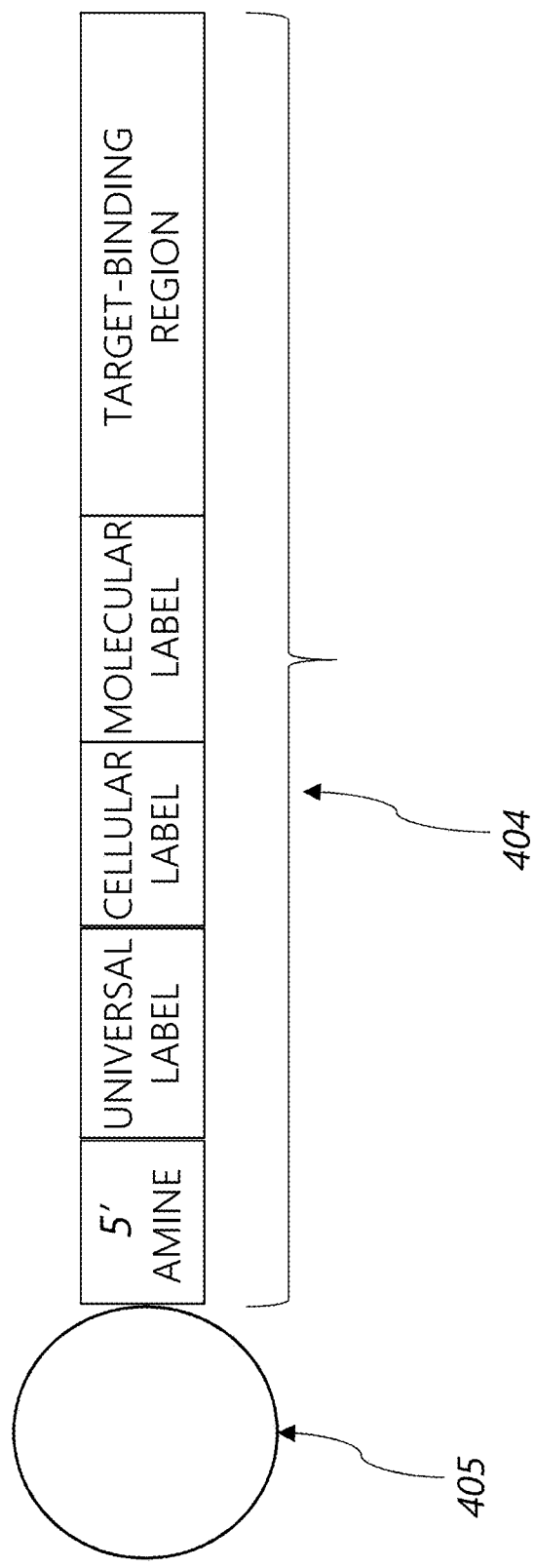
FIG. 4 depicts an exemplary stochastic barcode of the disclosure.

As used herein, the term "stochastic barcode" refers to a polynucleotide sequence that can be used to stochastically label (e.g., barcode, tag) a target. A stochastic barcode can comprise one or more labels. Exemplary labels can include a universal label, a cellular label, a molecular label, a sample label, a plate label, a spatial label, and/or a pre-spatial label. FIG. 4 illustrates an exemplary stochastic barcode of the disclosure. A stochastic barcode 404 can comprise a 5'amine that may link the stochastic barcode to a solid support 405. In some embodiments, the stochastic barcode can comprise a universal label, a dimension label, a spatial label, a cellular label, and/or a molecular label. In some embodiments, the universal label can be 5'-most label. In some embodiments, the molecular label can be the 3'-most label. In some embodiments, the spatial label, dimension label, and the cellular label can be in any order. In some embodiments, the universal label, the spatial label, the dimension label, the cellular label, and the molecular label are in any order. In some embodiments, the stochastic barcode can comprise a target-binding region. In some embodiments, the target-binding region can interact with a target (e.g., target nucleic acid, RNA, mRNA, DNA) in a sample. For example, a target-binding region can comprise an oligo dT sequence which can interact with poly-A tails of mRNAs. In some embodiments, the labels of the stochastic barcode (e.g., universal label, dimension label, spatial label, cellular label, and molecular label) can be separated by, or by about, 1, 2, 3, 4, 5, 6, 7, 8, 9, 10, 11, 12, 13, 14, 15, 16, 17, 18, 19, or 20 or more nucleotides.

A stochastic barcode can, for example, comprise one or more universal labels. The one or more universal labels can be the same for all stochastic barcodes in the set of stochastic barcodes (e.g., attached to a given solid support). In some embodiments, the one or more universal labels can be the same for all stochastic barcodes attached to a plurality of beads. In some embodiments, a universal label can comprise a nucleic acid sequence that is capable of hybridizing to a sequencing primer. In some embodiments, sequencing primers can be used for sequencing stochastic barcodes comprising a universal label. In some embodiments, sequencing primers (e.g., universal sequencing primers) can comprise sequencing primers associated with high-throughput sequencing platforms. In some embodiments, the universal label can comprise a nucleic acid sequence that is capable of hybridizing to a PCR primer. In some embodiments, the universal label can comprise a nucleic acid sequence that is capable of hybridizing to a sequencing primer and a PCR primer. In some embodiments, the nucleic acid sequence of the universal label that is capable of hybridizing to a sequencing or PCR primer can be referred to as a primer binding site. In some embodiments, the universal label can comprise a sequence that can be used to initiate transcription of the stochastic barcode. In some embodiments, the universal label can comprise a sequence that may be used for extension of the stochastic barcode or a region within the stochastic barcode. In some embodiments, the universal label can be, or can be at least about, 1, 2, 3, 4, 5, 10, 15, 20, 25, 30, 35, 40, 45, 50 or more nucleotides in length. In some embodiments, the universal label can comprise at least about 10 nucleotides. In some embodiments, the universal label can be, or can be at most about, 1, 2, 3, 4, 5, 10, 15, 20, 25, 30, 35, 40, 45, 50 or more nucleotides in length. In some embodiments, a cleavable linker or modified nucleotide can be part of the universal label sequence to enable the stochastic barcode to be cleaved off from the support. As used herein, a universal label can be used interchangeably with "universal PCR primer."

In some embodiments, the stochastic barcode can comprise one or more dimension labels. A dimension label can comprise a nucleic acid sequence that provides information about a dimension in which the stochastic labeling occurred. For example, the dimension label can provide information about the time at which a target was stochastically barcoded. In some embodiments, the dimension label can be associated with a time of stochastic barcoding in a sample. In some embodiments, the dimension label can activated at the time of stochastic labeling. In some embodiments, different dimension labels can be activated at different times. In some embodiments, the dimension label provides information about the order in which targets, groups of targets, and/or samples were stochastically barcoded. For example, a population of cells can be stochastically barcoded at the G0 phase of the cell cycle. In some embodiments, the cells can be pulsed again with stochastic barcodes at the G1 phase of the cell cycle. The cells can be pulsed again with stochastic barcodes at the S phase of the cell cycle, and so on. Stochastic barcodes at each pulse (e.g., each phase of the cell cycle), can comprise different dimension labels. In this way, the dimension label provides information about which targets were labelled at which phase of the cell cycle. In some embodiments, dimension labels can interrogate many different biological times. Exemplary biological times can include, but are not limited to, the cell cycle, transcription (e.g., transcription initiation), and transcript degradation. In another example, a sample (e.g., a cell, a population of cells) can be stochastically labeled before and/or after treatment with a drug and/or therapy. The changes in the number of copies of distinct targets can be indicative of the sample's response to the drug and/or therapy.

The dimension label can be activatable. For example, an activatable dimension label can be activated at a specific timepoint. The activatable dimension label can be constitutively activated (e.g., not turned off). The activatable dimension label can be reversibly activated (e.g., the activatable dimension label can be turned on and turned off). The dimension label can be reversibly activatable at least 1, 2, 3, 4, 5, 6, 7, 8, 9, or 10 or more times. The dimension label can be reversibly activatable at least 1, 2, 3, 4, 5, 6, 7, 8, 9, or 10 or more times. The dimension label can be activated with fluorescence, light, a chemical event (e.g., cleavage, ligation of another molecule, addition of modifications (e.g., pegylated, sumoylated, acetylated, methylated, deacetylated, demethylated), a photochemical event (e.g., photocaging), and introduction of a non-natural nucleotide.

The dimension label can be identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support can comprise the same dimension label. In some embodiments, at least 60% of stochastic barcodes on the same solid support can comprise the same dimension label. In some embodiments, at least 95% of stochastic barcodes on the same solid support can comprise the same dimension label.

There can be $10^4$, $10^5$, $10^6$, $10^7$, $10^8$, $10^9$, $10^{10}$, or more unique dimension label sequences represented in a plurality of solid supports (e.g., beads). A dimension label can be at least, or at least about, 1, 2, 3, 4, 5, 10, 15, 20, 25, 30, 35, 40, 45, 50 or more nucleotides in length. In some embodiments, the dimension label can be, or be at most about, 300, 200, 100, 90, 80, 70, 60, 50, 40, 30, 20, 15, 12, 10, 9, 8, 7, 6, 5, 4 or fewer or more nucleotides in length. In some embodiments, the dimension label comprises from about 5 to about 200 nucleotides. In some embodiments, the dimension label comprises from about 10 to about 150 nucleotides. In some embodiments, the dimension label comprises from about 20 to about 125 nucleotides in length.

A stochastic barcode can comprise one or more spatial labels. A spatial label can comprise a nucleic acid sequence that provides information about the spatial orientation of a target molecule which is associated with the stochastic barcode. In some embodiments, the spatial label can be associated with a coordinate in a sample. In some embodiments, the coordinate can be a fixed coordinate. For example a coordinate can be fixed in reference to a substrate. In some embodiments, the spatial label can be in reference to a two or three-dimensional grid. In some embodiments, the coordinate can be fixed in reference to a landmark. In some embodiments, the landmark can be identifiable in space. In some embodiments, the landmark can be a structure which can be imaged. In some embodiments, the landmark can be a biological structure, for example an anatomical landmark. In some embodiments, the landmark can be a cellular landmark, for instance an organelle. In some embodiments, the landmark can be a non-natural landmark such as a structure with an identifiable identifier such as a color code, bar code, magnetic property, fluorescents, radioactivity, or a unique size or shape. In some embodiments, the spatial label can be associated with a physical partition (e.g. a well, a container, or a droplet). In some instances, multiple spatial labels are used together to encode one or more positions in space.

The spatial label can be identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support can comprise the same spatial label. In some embodiments, at least 60% of stochastic barcodes on the same solid support can comprise the same spatial label. In some embodiments, at least 95% of stochastic barcodes on the same solid support can comprise the same spatial label.

There can be $10^4$, $10^6$, $10^6$, $10^7$, $10^8$, $10^9$, $10^{10}$, or more unique spatial label sequences represented in a plurality of solid supports (e.g., beads). A spatial label can be, or be at least about, 1, 2, 3, 4, 5, 10, 15, 20, 25, 30, 35, 40, 45, 50 or more nucleotides in length. The spatial label can be, or be at most about, 300, 200, 100, 90, 80, 70, 60, 50, 40, 30, 20, 15, 12, 10, 9, 8, 7, 6, 5, 4 or fewer or more nucleotides in length. In some embodiments, the spatial label comprises from about 5 to about 200 nucleotides. In some embodiments, the spatial label comprises from about 10 to about 150 nucleotides. In some embodiments, the spatial label comprises from about 20 to about 125 nucleotides in length.

Stochastic barcodes can comprise one or more cellular label (i.e., sample label). As used herein, the terms "sample label" and "cellular label" are used interchangeably. A cellular label can comprise a nucleic acid sequence that provides information for determining which target nucleic acid originated from which cell. In some embodiments, the cellular label is identical for all stochastic barcodes attached to a given solid support (e.g., bead), but different for different solid supports (e.g., beads). In some embodiments, at least 60%, 70%, 80%, 85%, 90%, 95%, 97%, 99% or 100% of stochastic barcodes on the same solid support can comprise the same cellular label. In some embodiments, at least 60% of stochastic barcodes on the same solid support can comprise the same cellular label. In some embodiment, at least 95% of stochastic barcodes on the same solid support can comprise the same cellular label.

There can be $10^4$, $10^6$, $10^6$, $10^7$, $10^8$, $10^9$, $10^{10}$, or more unique cellular label sequences represented in a plurality of solid supports (e.g., beads). The cellular label can be, or be at least about, 1, 2, 3, 4, 5, 10, 15, 20, 25, 30, 35, 40, 45, 50 or more nucleotides in length. The cellular label can be, or be at most about, 300, 200, 100, 90, 80, 70, 60, 50, 40, 30, 20, 15, 12, 10, 9, 8, 7, 6, 5, 4 or fewer or more nucleotides in length. In some embodiments, the cellular label comprises from about 5 to about 200 nucleotides. In some embodiments, the cellular label comprises from about 10 to about 150 nucleotides. In some embodiments, the cellular label comprises from about 20 to about 125 nucleotides in length.

Stochastic barcodes can comprise one or more molecular labels. A molecular label can comprise a nucleic acid sequence that provides identifying information for the specific type of target nucleic acid species hybridized to the stochastic barcode. The molecular label can comprise a nucleic acid sequence that provides a counter for the specific occurrence of the target nucleic acid species hybridized to the stochastic barcode (e.g., target-binding region). In some embodiments, a diverse set of molecular labels are attached to a given solid support (e.g., bead). In some embodiments, there can be $10^4$, $10^6$, $10^6$, $10^7$, $10^8$, $10^9$, $10^{10}$, or more unique molecular label sequences attached to a given solid support (e.g., bead). In some embodiments, there can be as many as $10^5$ or more unique molecular label sequences attached to a given solid support (e.g., bead). In some embodiments, there can be $10^4$, $10^6$, $10^6$, $10^7$, $10^8$, $10^9$, $10^{10}$, or more unique molecular label sequences attached to a given solid support (e.g., bead). In some embodiments, there can be as many as $10^2$, $10^3$, $10^4$, $10^6$, $10^6$, $10^7$, $10^8$, $10^9$, $10^{10}$, or more unique molecular label sequences attached to a given solid support (e.g., bead). In some embodiments, there can be as many as 10, $10^2$, $10^3$, $10^4$, $10^6$ or more unique molecular label sequences attached to a given solid support (e.g., bead). The molecular label can be, or be at least about, 1, 2, 3, 4, 5, 10, 15, 20, 25, 30, 35, 40, 45, 50 or more nucleotides in length. The molecular label can be, or be at most about, 300, 200, 100, 90, 80, 70, 60, 50, 40, 30, 20, 15, 12, 10, 9, 8, 7, 6, 5, 4 or fewer nucleotides in length.

A stochastic barcode can comprise one or more target binding regions. In some embodiments, a target binding region can comprise a nucleic acid sequence that hybridizes specifically to a target (e.g., target nucleic acid, target molecule, e.g., a cellular nucleic acid to be analyzed), for example to a specific gene sequence. In some embodiments, the target binding region can comprise a nucleic acid sequence that can attach (e.g., hybridize) to a specific location of a specific target nucleic acid. In some embodiments, the target binding region can comprise a nucleic acid sequence that is capable of specific hybridization to a restriction site overhang (e.g. an EcoRI sticky-end overhang). The stochastic barcode can then ligate to any nucleic acid molecule comprising a sequence complementary to the restriction site overhang.

A target-binding region can, for example, hybridize with a target of interest. For example, the target-binding region can comprise an oligo dT which can hybridize with mRNAs comprising poly-adenylated ends. A target-binding region can be gene-specific. For example, the target-binding region can be configured to hybridize to a specific region of a target. The target-binding region can be, or be at least, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 or more nucleotides in length. The target-binding region can be, or be at most, 1, 2, 3, 4, 5, 6, 7, 8, 9, 10, 11, 12, 13, 14, 15, 16, 17, 18, 19, 20, 21, 22, 23, 24, 25, 26 27, 28, 29, or 30 or more nucleotides in length. A target-binding region can be from 5-30 nucleotides in length. When a stochastic barcode comprises a gene-specific target-binding region, the stochastic barcode can be referred to as a gene-specific stochastic barcode.

A target binding region can comprise one or more non-specific target nucleic acid sequences. A non-specific target nucleic acid sequence can refer to a sequence that may bind to multiple target nucleic acids, independent of the specific sequence of the target nucleic acid. For example, the target binding region can comprise a random multimer sequence, or an oligo-dT sequence that hybridizes to the poly-A tail on mRNA molecules. A random multimer sequence can be, for example, a random dimer, trimer, quatramer, pentamer, hexamer, septamer, octamer, nonamer, decamer, or higher multimer sequence of any length. In some embodiments, the target binding region is the same for all stochastic barcodes attached to a given bead. In some embodiments, the target binding regions for the plurality of stochastic barcodes attached to a given bead can comprise two or more different target binding sequences. The target binding region can be, or be at least about, 5, 10, 15, 20, 25, 30, 35, 40, 45, 50 or more nucleotides in length. The target binding region can be, or be at most about, 5, 10, 15, 20, 25, 30, 35, 40, 45, 50 or more nucleotides in length.

A stochastic barcode can comprise one or more orientation properties which can be used to orient (e.g., align) the stochastic barcodes. The stochastic barcode can comprise one or more moieties for isoelectric focusing. In some embodiments, different stochastic barcodes can comprise different isoelectric focusing points. For example, in some embodiments, when these stochastic barcodes are introduced to a sample, the sample can undergo isoelectric focusing in order to orient the stochastic barcodes into a known way. In this way, the orientation property can be used to develop a known map of stochastic barcodes in a sample. Exemplary orientation properties can include, electrophoretic mobility (e.g., based on size of the stochastic barcode), isoelectric point, spin, conductivity, and/or self-assembly. For example, stochastic barcodes can comprise an orientation property of self-assembly, which can self-assemble into a specific orientation (e.g., nucleic acid nanostructure) upon activation.

A stochastic barcode can comprise one or more affinity properties. For example, a spatial label can comprise an affinity property. The affinity property can include, in some embodiments, a chemical and/or biological moiety that can facilitate binding of the stochastic barcode to another entity (e.g., cell receptor). For example, an affinity property can comprise an antibody. In some embodiments, the antibody can be specific for a specific moiety (e.g., receptor) on a sample. In some embodiments, the antibody can guide the stochastic barcode to a specific cell type or molecule. Targets at and/or near the specific cell type or molecule can be stochastically labeled. An affinity property can also provide spatial information in addition to the nucleotide sequence of the spatial label because the antibody can guide the stochastic barcode to a specific location. The antibody can be a therapeutic antibody, a monoclonal antibody, or a polyclonal antibody. The antibody can be humanized, or chimeric. The antibody can be a naked antibody or a fusion antibody.

The antibody can refer to a full-length (i.e., naturally occurring or formed by normal immunoglobulin gene fragment recombinatorial processes) immunoglobulin molecule (e.g., an IgG antibody) or an immunologically active (i.e., specifically binding) portion of an immunoglobulin molecule, like an antibody fragment.

The antibody can, in some embodiments, be an antibody fragment. An antibody fragment can be, for example, a portion of an antibody such as F(ab')2, Fab', Fab, Fv, sFv and the like. The antibody fragment can, in some embodiments, bind with the same antigen that is recognized by the full-length antibody. The antibody fragment, in some embodiments, can include isolated fragments consisting of the variable regions of antibodies, such as the "Fv" fragments consisting of the variable regions of the heavy and light chains and recombinant single chain polypeptide molecules in which light and heavy variable regions are connected by a peptide linker ("scFv proteins"). Exemplary antibodies can include, but are not limited to, antibodies for antibodies for cancer cells, antibodies for viruses, antibodies that bind to cell surface receptors (CD8, CD34, CD45), and therapeutic antibodies.

The cellular label and/or any label of the disclosure can further comprise a unique set of nucleic acid sub-sequences of defined length, e.g. 7 nucleotides each (equivalent to the number of bits used in some Hamming error correction codes), which are designed to provide error correction capability. The set of error correction sub-sequences comprise 7 nucleotide sequences can be designed such that any pairwise combination of sequences in the set exhibits a defined "genetic distance" (or number of mismatched bases), for example, a set of error correction sub-sequences may be designed to exhibit a genetic distance of 3 nucleotides. In some embodiments, the length of the nucleic acid sub-sequences used for creating error correction codes can vary, for example, they can be at least 3 nucleotides, at least 7 nucleotides, at least 15 nucleotides, or at least 31 nucleotides in length. In some embodiments, nucleic acid sub-sequences of other lengths may be used for creating error correction codes.

Stochastic barcodes can, in some embodiments, comprise error-correcting sequences (e.g., Hamming codes) in them for error-correction. A Hamming code can refer an arithmetic process that identifies unique binary codes based upon inherent redundancy that are capable of correcting single bit errors. For example, a Hamming code can be matched with a nucleic acid barcode in order to screen for single nucleotide errors occurring during nucleic acid amplification. The identification of a single nucleotide error by using a Hamming code, thereby can allow for the correction of the nucleic acid barcode.

When a stochastic barcode comprises more than one of a type of label (e.g., more than one cellular label or more than one molecular label), the labels can be interspersed with a linker label sequence. For example, the linker label sequence can be, or be at least about, 5, 10, 15, 20, 25, 30, 35, 40, 45, 50 or more nucleotides in length. In some embodiments, the linker label sequence can be, or be at most about, 5, 10, 15, 20, 25, 30, 35, 40, 45, 50 or more nucleotides in length. In some embodiments, the linker label sequence is 12 nucleotides in length. The linker label sequence can be used, in some embodiments, to facilitate the synthesis of the stochastic barcode. In some embodiments, the linker label can comprise an error-correcting (e.g., Hamming) code.

Quasi-Symmetric Stochastically Barcoded Nucleic Acids

The disclosure provides for compositions comprising quasi-symmetric stochastically barcoded nucleic acids. A quasi-symmetric stochastically barcoded nucleic acid can comprise a stochastic barcode of the disclosure. A quasi-symmetric stochastically barcoded nucleic acid can comprise two ends that are quasi-symmetric. A quasi-symmetric stochastically barcoded nucleic acid can comprise a nucleic acid of any target sequence and/or of any length. For example, a quasi-symmetric stochastically barcoded nucleic acid can be RNA (e.g., mRNA, miRNA, tRNA, lncRNA, non-coding RNA, coding RNA, and the like), DNA (e.g., genomic DNA, intron, exon, coding region, non-coding region, and the like), or a combination thereof. The quasi-symmetric stochastically barcoded nucleic acid can be, or be at least, 10, 50, 100, 150, 200, 250, 300, 350, 400, 450, 500, 550, 600, 650, 700, 750, 800, 850, 900, 950, or 1000 or more nucleotides in length. The quasi-symmetric stochastically barcoded nucleic acid can be, or be at most, 10, 50, 100, 150, 200, 250, 300, 350, 400, 450, 500, 550, 600, 650, 700, 750, 800, 850, 900, 950, or 1000 or more nucleotides in length.

The quasi-symmetric stochastically barcoded nucleic acid can comprise two ends that are quasi-symmetric. The two ends can comprise universal labels (e.g., a universal label on the stochastic barcode (herein, a first universal label), and a universal label from the adaptor (herein a second universal label)). The universal label of the adaptor (e.g., second universal label) can be the same as the universal label on the stochastic barcode (e.g. on the 5' end of the single-stranded cDNA molecule, e.g., first universal label). The second universal label can comprise a sequence that is a subset of the first universal label. For example, the second universal label can comprise at least 10, 20, 30, 40, 50, 60, 70, 80, 90, 95, or 100% of the sequence of the first universal label. The second universal label can comprise at most 10, 20, 30, 40, 50, 60, 70, 80, 90, 95, or 100% of the sequence of the first universal label. The second universal label can be, or be at least, 1, 2, 3, 4, 5, 6, 7, 8, 9, or 10 or more nucleotides shorter or longer than the first universal label. The second universal label can be, or be at most, 1, 2, 3, 4, 5, 6, 7, 8, 9, or 10 or more nucleotides shorter or longer than the first universal label. In some embodiments, the second universal label is shorter than the first universal label by 2 nucleotides. The universal label can differ from the first universal label by at least 1, 2, 3, 4, 5, 6, 7, 8, 9, or 10 or more nucleotides. The universal label can differ from the first universal label by at most 1, 2, 3, 4, 5, 6, 7, 8, 9, or 10 or more nucleotides. The second universal label can be at most 99, 98, 7, 96, 95, 94, 93, 92, 91 or 90% or less identical to the first universal label. The second universal label may not be identical to said first universal label. The second universal label can hybridize to the first universal label over at least 50, 60, 70, 80, 90, 91, 92, 93, 94, 95, 96, 97, 98, 99, or 100% of said first universal label. The second universal label can be, or be at most, 99% identical to the first universal label over 50, 60, 70, 80, 90, 91, 92, 93, 94, 95, 96, 97, 98, 99, or 100% of the first universal label. The sequence of the first universal label can be a sequencing primer binding site (e.g., Illumina read 2 sequence). The sequence of the second universal label can be a modified sequencing primer binding site (e.g., Illumina modified read 2 sequence).

In some embodiments, the first universal label and the second universal label are able to hybridize to each other (e.g., for use in suppression PCR). In some embodiments, the first and second universal labels can hybridize with at least 1, 2, 3, 4, 5, 6, 7, 8, 9, or 10 or more mismatches. In some embodiments, the first and second universal labels can hybridize with at most 1, 2, 3, 4, 5, 6, 7, 8, 9, or 10 or more mismatches. The extent of hybridization can relate to the amount of suppression occurring during suppression PCR. For example, sequences that can hybridize strongly can be suppressed more than sequences that hybridize weakly.

Solid Supports

The stochastic barcodes disclosed herein can be attached to a solid support (e.g., bead, substrate). As used herein, the terms "tethered", "attached", and "immobilized" are used interchangeably, and can refer to covalent or non-covalent means for attaching stochastic barcodes to a solid support. Any of a variety of different solid supports can be used as solid supports for attaching pre-synthesized stochastic barcodes or for in situ solid-phase synthesis of stochastic barcode.

In some embodiments, a solid support is a bead (e.g., a magnetic or polymer bead). The bead can encompass any type of solid, porous, or hollow sphere, ball, bearing, cylinder, or other similar configuration composed of plastic, ceramic, metal, or polymeric material onto which a nucleic acid may be immobilized (e.g., covalently or non-covalently). The bead can comprise a discrete particle that may be spherical (e.g., microspheres) or have a non-spherical or irregular shape, such as cubic, cuboid, pyramidal, cylindrical, conical, oblong, or disc-shaped, and the like. The bead can be non-spherical in shape.

Beads disclosed herein can comprise one or more of a variety of materials including, but not limited to, paramagnetic materials (e.g. magnesium, molybdenum, lithium, and tantalum), superparamagnetic materials (e.g. ferrite ($Fe_3O_4$; magnetite) nanoparticles), ferromagnetic materials (e.g. iron, nickel, cobalt, some alloys thereof, and some rare earth metal compounds), ceramic, plastic, glass, polystyrene, silica, methylstyrene, acrylic polymers, titanium, latex, sepharose, agarose, hydrogel, polymer, cellulose, nylon, and any combination thereof.

The diameter of the beads can vary, for example be, or be at least about, 5 µm, 10 µm, 20 µm, 25 µm, 30 µm, 35 µm, 40 µm, 45 µm or 50 µm. The diameter of the beads can be at most about 5 µm, 10 µm, 20 µm, 25 µm, 30 µm, 35 µm, 40 µm, 45 µm or 50 µm. In some embodiments, the diameter of the bead can be related to the diameter of the wells of the substrate. For example, the diameter of the bead can be at least 10, 20, 30, 40, 50, 60, 70, 80, 90 or 100% longer or shorter than the diameter of the well. The diameter of the bead can be at most 10, 20, 30, 40, 50, 60, 70, 80, 90 or 100% longer or shorter than the diameter of the well. The diameter of the bead can be related to the diameter of a cell (e.g., a single cell entrapped by the a well of the substrate). The diameter of the bead can be at least 10, 20, 30, 40, 50, 60, 70, 80, 90, 100, 150, 200, 250, or 300% or more longer or shorter than the diameter of the cell. The diameter of the bead can be at most 10, 20, 30, 40, 50, 60, 70, 80, 90, 100, 150, 200, 250, or 300% or more longer or shorter than the diameter of the cell.

The bead can be attached to and/or embedded in a substrate. For example, the bead can be attached to and/or embedded in a gel, hydrogel, polymer and/or matrix. The spatial position of the bead within a substrate (e.g., gel, matrix, scaffold, or polymer) can be identified using the spatial label present on the stochastic barcode on the bead which can serve as a location address.

Examples of beads can include, but are not limited to, streptavidin beads, agarose beads, magnetic beads, Dynabeads®, MACS® microbeads, antibody conjugated beads (e.g., anti-immunoglobulin microbead), protein A conjugated beads, protein G conjugated beads, protein A/G conjugated beads, protein L conjugated beads, oligodT conjugated beads, silica beads, silica-like beads, anti-biotin microbead, anti-fluorochrome microbead, and BcMag™ Carboxy-Terminated Magnetic Beads.

In some embodiments, the bead can be associated with (e.g. impregnated with) quantum dots or fluorescent dyes to make it fluorescent in one fluorescence optical channel or multiple optical channels. In some embodiments, the bead can be associated with iron oxide or chromium oxide to make it paramagnetic or ferromagnetic. In some embodiments, the bead can be identifiable. In some embodiments, the bead can be imaged using a camera. In some embodiments, the bead can have a detectable code associated with the bead. For example, the bead can comprise an RFID tag. In some embodiments, the bead comprises a detectable tag (e.g., UPC code, electronic barcode, etched identifier). In some embodiments, the bead can change size, for example due to swelling in an organic or inorganic solution. The bead can be hydrophobic or hydrophilic. In some embodiments, the bead is biocompatible.

A solid support (e.g., bead) can be visualized. The solid support can comprise a visualizing tag (e.g., fluorescent dye). The solid support (e.g., bead) can be, for example, etched with an identifier (e.g., a number). In some embodiments, the identifier can be visualized through imaging the solid supports (e.g., beads).

A solid support can be made of, or comprise, one or more insoluble, semi-soluble, and insoluble materials. The solid support may be referred to as "functionalized" when it includes a linker, a scaffold, a building block, or other reactive moiety attached thereto, whereas a solid support may be "nonfunctionalized" when it lack such a reactive moiety attached thereto. The solid support can be employed free in solution, such as in a microtiter well format; in a flow-through format, such as in a column; or in a dipstick.

The solid support can comprise a membrane, paper, plastic, coated surface, flat surface, glass, slide, chip, or any combination thereof. The solid support can, for example, take the form of resins, gels, microspheres, or other geometric configurations. The solid support can, for example, comprise silica chips, microparticles, nanoparticles, plates, arrays, capillaries, flat supports such as glass fiber filters, glass surfaces, metal surfaces (steel, gold silver, aluminum, silicon and copper), glass supports, plastic supports, silicon supports, chips, filters, membranes, microwell plates, slides, plastic materials including multiwell plates or membranes (e.g., formed of polyethylene, polypropylene, polyamide, polyvinylidenedifluoride), and/or wafers, combs, pins or needles (e.g., arrays of pins suitable for combinatorial synthesis or analysis) or beads in an array of pits or nanoliter wells of flat surfaces such as wafers (e.g., silicon wafers), wafers with pits with or without filter bottoms.

The solid support can, for example, comprise a polymer matrix (e.g., gel, hydrogel). In some embodiments, the polymer matrix is able to permeate intracellular space (e.g., around organelles). In some embodiments, the polymer matrix is able to be pumped throughout the circulatory system.

The solid support can be a biological molecule. For example, the solid support can be a nucleic acid, a protein, an antibody, a histone, a cellular compartment, a lipid, a carbohydrate, and the like. In some embodiments, solid supports that are biological molecules can be amplified, translated, transcribed, degraded, and/or modified (e.g., pegylated, sumoylated, acetylated, methylated). A solid support that is a biological molecule can, for example, provide spatial and time information in addition to the spatial label that is attached to the biological molecule. For example, a biological molecule can comprise a first confirmation when unmodified, but can change to a second confirmation when modified. The different conformations can expose stochastic barcodes of the disclosure to targets. For example, a biological molecule can comprise stochastic barcodes that are unaccessible due to folding of the biological molecule. Upon modification of the biological molecule (e.g., acetylation), the biological molecule can change conformation to expose the stochastic labels. The timing of the modification can provide another time dimension to the method of stochastic barcoding of the disclosure.

In some embodiments, the biological molecule comprising stochastic barcodes of the disclosure can be located in the cytoplasm of a cell. Upon activation, the biological molecule can move to the nucleus, whereupon stochastic barcoding can take place. In this way, modification of the biological molecule can encode additional space-time information for the targets identified by the stochastic barcodes.

The dimension label can provide information about space-time of a biological event (e.g., cell division). For example, a dimension label can be added to a first cell, the first cell can divide generating a second daughter cell, the second daughter cell can comprise all, some or none of the dimension labels. The dimension labels can be activated in the original cell and the daughter cell. In this way, the dimension label can provide information about time of stochastic barcoded in distinct spaces.

Substrates

A substrate can refer to a type of solid support. A substrate can refer to a solid support that can comprise stochastic barcodes of the disclosure. A substrate can comprise a plurality of microwells. A microwell can comprise a small reaction chamber of defined volume. A microwell can entrap one or more cells. In some embodiments, a microwell can entrap only one cell. In some embodiments, a microwell can entrap one or more solid supports. In some embodiments, a microwell can entrap only one solid support. In some embodiments, a microwell entraps a single cell and a single solid support (e.g., bead). In some embodiments, a microwell is sized that it can only entrap a single cell. In some embodiments, a microwell is sized that it can only entrap a single solid support (e.g., a bead). In some embodiments, a microwell is sized that it can only entrap a single cell and a single solid support (e.g. a bead).

The microwells of a microwell array can be fabricated in a variety of shapes and sizes. Well geometries can include, but are not limited to, cylindrical, conical, hemispherical, rectangular, or polyhedral (e.g., three dimensional geometries comprised of several planar faces, for example, hexagonal columns, octagonal columns, inverted triangular pyramids, inverted square pyramids, inverted pentagonal pyramids, inverted hexagonal pyramids, or inverted truncated pyramids). The microwells can comprise a shape that combines two or more of these geometries. For example, a microwell may be partly cylindrical, with the remainder having the shape of an inverted cone. A microwell can include two side-by-side cylinders, one of larger diameter (e.g. that corresponds roughly to the diameter of the beads) than the other (e.g. that corresponds roughly to the diameter of the cells), that are connected by a vertical channel (that is, parallel to the cylinder axes) that extends the full length (depth) of the cylinders. The opening of the microwell can be at the upper surface of the substrate. The opening of the microwell can be at the lower surface of the substrate. The closed end (or bottom) of the microwell can be flat. The closed end (or bottom) of the microwell can have a curved surface (e.g., convex or concave). The shape and/or size of the microwell can be determined based on the types of cells or solid supports to be trapped within the microwells.

The portion of the substrate between the wells can have a topology. For example, the portion of the substrate between the wells can be rounded. The portion of the substrate between the wells can be pointed. The spacing portion of the substrate between the wells can be flat. The portion of the substrate between the wells may not be flat. In some instances, the portion of the substrate between wells is rounded. In other words, the portion of the substrate that does not comprise a well can have a curved surface. The curved surface can be fabricated such that the highest point (e.g., apex) of the curved surface can be at the furthest point between the edges of two or more wells (e.g., equidistant from the wells). The curved surface can be fabricated such that the start of the curved surface is at the edge of a first microwell and creates a parabola that ends at the end of a second microwell. This parabola can be extended in 2 dimensions to capture microwells nearby on the hexagonal grid of wells. The curved surface can be fabricated such that the surface between the wells is higher and/or curved than the plane of the opening of the well. The height of the curved surface can be, or be at least, 0.1, 0.5, 1, 1.5, 2, 2.5, 3, 3.5, 4, 4.5, 5, 5.5, 6, 6.5, or 7 or more micrometers. The height of the curved surface can be, or be at most, 0.1, 0.5, 1, 1.5, 2, 2.5, 3, 3.5, 4, 4.5, 5, 5.5, 6, 6.5, or 7 or more micrometers.

Microwell dimensions can be, for example, characterized in terms of the diameter and depth of the well. As used herein, the diameter of the microwell refers to the largest circle that can be inscribed within the planar cross-section of the microwell geometry. The diameter of the microwells can range from about 1-fold to about 10-fold the diameter of the cells or solid supports to be trapped within the microwells. The microwell diameter can be at least 1-fold, at least 1.5-fold, at least 2-fold, at least 3-fold, at least 4-fold, at least 5-fold, or at least 10-fold the diameter of the cells or solid supports to be trapped within the microwells. The microwell diameter can be at most 10-fold, at most 5-fold, at most 4-fold, at most 3-fold, at most 2-fold, at most 1.5-fold, or at most 1-fold the diameter of the cells or solid supports to be trapped within the microwells. The microwell diameter can be about 2.5-fold the diameter of the cells or solid supports to be trapped within the microwells.

The diameter of the microwells can be, for example, specified in terms of absolute dimensions. For example, the diameter of the microwells can range from about 5 to about 60 micrometers. The microwell diameter can be at least 5 micrometers, at least 10 micrometers, at least 15 micrometers, at least 20 micrometers, at least 25 micrometers, at least 30 micrometers, at least 35 micrometers, at least 40 micrometers, at least 45 micrometers, at least 50 micrometers, or at least 60 micrometers. The microwell diameter can be at most 60 micrometers, at most 50 micrometers, at most 45 micrometers, at most 40 micrometers, at most 35 micrometers, at most 30 micrometers, at most 25 micrometers, at most 20 micrometers, at most 15 micrometers, at most 10 micrometers, or at most 5 micrometers. The microwell diameter can be about 30 micrometers.

The microwell depth can be chosen to provide efficient trapping of cells and solid supports. The microwell depth can be chosen to provide efficient exchange of assay buffers and other reagents contained within the wells. The ratio of diameter to height (i.e., aspect ratio) can be chosen such that once a cell and solid support settle inside a microwell, they will not be displaced by fluid motion above the microwell. The dimensions of the microwell can be chosen such that the microwell has sufficient space to accommodate a solid support and a cell of various sizes without being dislodged by fluid motion above the microwell. The depth of the microwells can range from about 1-fold to about 10-fold the diameter of the cells or solid supports to be trapped within the microwells. The microwell depth can be at least 1-fold, at least 1.5-fold, at least 2-fold, at least 3-fold, at least 4-fold, at least 5-fold, or at least 10-fold the diameter of the cells or solid supports to be trapped within the microwells. The microwell depth can be at most 10-fold, at most 5-fold, at most 4-fold, at most 3-fold, at most 2-fold, at most 1.5-fold, or at most 1-fold the diameter of the cells or solid supports to be trapped within the microwells. The microwell depth can be about 2.5-fold the diameter of the cells or solid supports to be trapped within the microwells.

The depth of the microwells can be, for example, specified in terms of absolute dimensions. For example, the depth of the microwells can range from about 10 to about 60 micrometers. The microwell depth can be at least 10 micrometers, at least 20 micrometers, at least 25 micrometers, at least 30 micrometers, at least 35 micrometers, at least 40 micrometers, at least 50 micrometers, or at least 60 micrometers. The microwell depth can be at most 60 micrometers, at most 50 micrometers, at most 40 micrometers, at most 35 micrometers, at most 30 micrometers, at most 25 micrometers, at most 20 micrometers, or at most 10 micrometers. The microwell depth can be about 30 micrometers.

The volume of the microwells can vary, for example ranging from about 200 picometers$^3$ to about 120,000 picometers$^3$. The microwell volume can be at least 200 picometers$^3$, at least 500 picometers$^3$, at least 1,000 picometers$^3$, at least 10,000 picometers$^3$, at least 25,000 picometers$^3$, at least 50,000 picometers$^3$, at least 100,000 picometers$^3$, or at least 120,000 picometers$^3$. The microwell volume can be at most 120,000 picometers$^3$, at most 100,000 picometers$^3$, at most 50,000 picometers$^3$, at most 25,000 picometers$^3$, at most 10,000 picometers$^3$, at most 1,000 picometers$^3$, at most 500 picometers$^3$, or at most 200 picometers$^3$. The microwell volume can be about 25,000 picometers$^3$. The microwell volume can fall within any range bounded by any of these values (e.g. from about 18,000 picometers$^3$ to about 30,000 picometers$^3$).

The volume of the microwell can also vary, for example, be at least 5, 10, 15, 20, 25, 30, 35 40, 45 or 50 or more nanoliters$^3$. The volume of the microwell can be at most 5, 10, 15, 20, 25, 30, 35 40, 45 or 50 or more nanoliters$^3$. The volume of liquid that can fit in the microwell can be at least 5, 10, 15, 20, 25, 30, 35 40, 45 or 50 or more nanoliters$^3$. The volume of liquid that can fit in the microwell can be at most 5, 10, 15, 20, 25, 30, 35 40, 45 or 50 or more nanoliters$^3$. The volume of the microwell can be at least 5, 10, 15, 20, 25, 30, 35 40, 45 or 50 or more picoliters$^3$. The volume of the microwell can be at most 5, 10, 15, 20, 25, 30, 35 40, 45 or 50 or more picoliters$^3$. The volume of liquid that can fit in the microwell can be at least 5, 10, 15, 20, 25, 30, 35 40, 45 or 50 or more picoliters$^3$. The volume of liquid that can fit in the microwell can be at most 5, 10, 15, 20, 25, 30, 35 40, 45 or 50 or more picoliters$^3$.

The volumes of the microwells can be further characterized in terms of the variation in volume from one microwell to another. The coefficient of variation (expressed as a percentage) for microwell volume can range from about 1% to about 10%. The coefficient of variation for microwell volume can be at least 1%, at least 2%, at least 3%, at least 4%, at least 5%, at least 6%, at least 7%, at least 8%, at least 9%, or at least 10%. The coefficient of variation for microwell volume can be at most 10%, at most 9%, at most 8%, at most 7%, at most 6%, at most 5%, at most 4%, at most 3%, at most 2%, or at most 1%. The coefficient of variation for microwell volume can have any value within a range encompassed by these values, for example between about 1.5% and about 6.5%. In some embodiments, the coefficient of variation of microwell volume can be about 2.5%.

The ratio of the volume of the microwells to the surface area of the beads (or to the surface area of a solid support to which stochastic barcode oligonucleotides may be attached) used in the methods, devices, and systems of the present disclosure can range, for example, from about 2.5 to about 1,520 micrometers. The ratio can be at least 2.5, at least 5, at least 10, at least 100, at least 500, at least 750, at least 1,000, or at least 1,520. The ratio can be at most 1,520, at most 1,000, at most 750, at most 500, at most 100, at most 10, at most 5, or at most 2.5. The ratio can be about 67.5. The ratio of microwell volume to the surface area of the bead (or solid support used for immobilization) can fall within any range bounded by any of these values (e.g. from about 30 to about 120).

The wells of the microwell array can be arranged in a one dimensional, two dimensional, or three-dimensional array. A three dimensional array can be achieved, for example, by stacking a series of two or more two dimensional arrays (that is, by stacking two or more substrates comprising microwell arrays).

The pattern and spacing between microwells can be chosen to optimize the efficiency of trapping a single cell and single solid support (e.g., bead) in each well, as well as to maximize the number of wells per unit area of the array. The microwells can be distributed according to a variety of random or non-random patterns. For example, they can be distributed entirely randomly across the surface of the array substrate, or they can be arranged in a square grid, rectangular grid, hexagonal grid, or the like. In some instances, the microwells are arranged hexagonally. The center-to-center distance (or spacing) between wells can vary from about 5 micrometers to about 75 micrometers. In some instances, the spacing between microwells is about 10 micrometers. In other embodiments, the spacing between wells is at least 5 micrometers, at least 10 micrometers, at least 15 micrometers, at least 20 micrometers, at least 25 micrometers, at least 30 micrometers, at least 35 micrometers, at least 40 micrometers, at least 45 micrometers, at least 50 micrometers, at least 55 micrometers, at least 60 micrometers, at least 65 micrometers, at least 70 micrometers, or at least 75 micrometers. The microwell spacing can be at most 75 micrometers, at most 70 micrometers, at most 65 micrometers, at most 60 micrometers, at most 55 micrometers, at most 50 micrometers, at most 45 micrometers, at most 40 micrometers, at most 35 micrometers, at most 30 micrometers, at most 25 micrometers, at most 20 micrometers, at most 15 micrometers, at most 10 micrometers, at most 5 micrometers. The microwell spacing can be about 55 micrometers. The microwell spacing can fall within any range bounded by any of these values (e.g. from about 18 micrometers to about 72 micrometers).

The microwell array can comprise surface features between the microwells that are designed to help guide cells and solid supports into the wells and/or prevent them from settling on the surfaces between wells. Examples of suitable surface features can include, but are not limited to, domed, ridged, or peaked surface features that encircle the wells or straddle the surface between wells.

The total number of wells in the microwell array can be determined by the pattern and spacing of the wells and the overall dimensions of the array. The number of microwells in the array can range from about 96 to about 5,000,000 or more. The number of microwells in the array can be at least 96, at least 384, at least 1,536, at least 5,000, at least 10,000, at least 25,000, at least 50,000, at least 75,000, at least 100,000, at least 500,000, at least 1,000,000, or at least 5,000,000. The number of microwells in the array can be at most 5,000,000, at most 1,000,000, at most 75,000, at most 50,000, at most 25,000, at most 10,000, at most 5,000, at most 1,536, at most 384, or at most 96 wells. The number of microwells in the array can be about 96. The number of microwells can be about 150,000. The number of microwells in the array can fall within any range bounded by any of these values (e.g. from about 100 to about 325,000).

Microwell arrays can be fabricated using any of a number of fabrication techniques. Examples of fabrication methods that may be used include, but are not limited to, bulk micromachining techniques such as photolithography and wet chemical etching, plasma etching, or deep reactive ion etching; micro-molding and micro-embossing; laser micromachining; 3D printing or other direct write fabrication processes using curable materials; and similar techniques.

Microwell arrays can be fabricated from any of a number of substrate materials. The choice of material can depend on the choice of fabrication technique, and vice versa. Examples of suitable materials can include, but are not limited to, silicon, fused-silica, glass, polymers (e.g. agarose, gelatin, hydrogels, polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, thiol-ene based resins, metals or metal films (e.g. aluminum, stainless steel, copper, nickel, chromium, and titanium), and the like. In some instances, the microwell comprises optical adhesive. In some instances, the microwell is made out of optical adhesive. In some instances, the microwell array comprises and/or is made out of PDMS. In some instances, the microwell is made of plastic. A hydrophilic material can be desirable for fabrication of the microwell arrays (e.g. to enhance wettability and minimize non-specific binding of cells and other biological material). Hydrophobic materials that can be treated or coated (e.g. by oxygen plasma treatment, or grafting of a polyethylene oxide surface layer) can also be used. The use of porous, hydrophilic materials for the fabrication of the microwell array may be desirable in order to facilitate capillary wicking/venting of entrapped air bubbles in the device. The microwell array can be fabricated from a single material. The microwell array can comprise two or more different materials that have been bonded together or mechanically joined.

Microwell arrays can be fabricated using substrates of any of a variety of sizes and shapes. For example, the shape (or footprint) of the substrate within which microwells are fabricated may be square, rectangular, circular, or irregular in shape. The footprint of the microwell array substrate can be similar to that of a microtiter plate. The footprint of the microwell array substrate can be similar to that of standard microscope slides, e.g. about 75 mm long×25 mm wide (about 3" long×1" wide), or about 75 mm long×50 mm wide (about 3" long×2" wide). The thickness of the substrate within which the microwells are fabricated can range from about 0.1 mm thick to about 10 mm thick, or more. The thickness of the microwell array substrate can be at least 0.1 mm thick, at least 0.5 mm thick, at least 1 mm thick, at least 2 mm thick, at least 3 mm thick, at least 4 mm thick, at least 5 mm thick, at least 6 mm thick, at least 7 mm thick, at least 8 mm thick, at least 9 mm thick, or at least 10 mm thick. The thickness of the microwell array substrate can be at most 10 mm thick, at most 9 mm thick, at most 8 mm thick, at most 7 mm thick, at most 6 mm thick, at most 5 mm thick, at most 4 mm thick, at most 3 mm thick, at most 2 mm thick, at most 1 mm thick, at most 0.5 mm thick, or at most 0.1 mm thick. The thickness of the microwell array substrate can be about 1 mm thick. The thickness of the microwell array substrate can be any value within these ranges, for example, the thickness of the microwell array substrate can be between about 0.2 mm and about 9.5 mm. The thickness of the microwell array substrate can be uniform.

A variety of surface treatments and surface modification techniques may be used to alter the properties of microwell array surfaces. Examples can include, but are not limited to, oxygen plasma treatments to render hydrophobic material surfaces more hydrophilic, the use of wet or dry etching techniques to smooth (or roughen) glass and silicon surfaces, adsorption or grafting of polyethylene oxide or other polymer layers (such as pluronic), or bovine serum albumin to substrate surfaces to render them more hydrophilic and less prone to non-specific adsorption of biomolecules and cells, the use of silane reactions to graft chemically-reactive functional groups to otherwise inert silicon and glass surfaces, etc. Photodeprotection techniques can be used to selectively activate chemically-reactive functional groups at specific locations in the array structure, for example, the selective addition or activation of chemically-reactive functional groups such as primary amines or carboxyl groups on the inner walls of the microwells may be used to covalently couple oligonucleotide probes, peptides, proteins, or other biomolecules to the walls of the microwells. The choice of surface treatment or surface modification utilized can depend both or either on the type of surface property that is desired and on the type of material from which the microwell array is made.

The openings of microwells can be sealed, for example, during cell lysis steps to prevent cross hybridization of target nucleic acid between adjacent microwells. A microwell (or array of microwells) can be sealed or capped using, for example, a flexible membrane or sheet of solid material (i.e. a plate or platten) that clamps against the surface of the microwell array substrate, or a suitable bead, where the diameter of the bead is larger than the diameter of the microwell.

A seal formed using a flexible membrane or sheet of solid material can comprise, for example, inorganic nanopore membranes (e.g., aluminum oxides), dialysis membranes, glass slides, coverslips, elastomeric films (e.g. PDMS), or hydrophilic polymer films (e.g., a polymer film coated with a thin film of agarose that has been hydrated with lysis buffer).

Solid supports (e.g., beads) used for capping the microwells can comprise any of the solid supports (e.g., beads) of the disclosure. In some instances, the solid supports are cross-linked dextran beads (e.g., Sephadex). Cross-linked dextran can range from about 10 micrometers to about 80 micrometers. The cross-linked dextran beads used for capping can be from 20 micrometers to about 50 micrometers. In some embodiments, the beads can be at least about 10, 20, 30, 40, 50, 60, 70, 80 or 90% larger than the diameter of the microwells. The beads used for capping can be at most about 10, 20, 30, 40, 50, 60, 70, 80 or 90% larger than the diameter of the microwells.

The seal or cap may allow buffer to pass into and out of the microwell, while preventing macromolecules (e.g., nucleic acids) from migrating out of the well. A macromolecule of at least about 1, 2, 3, 4, 5, 6, 7, 8, 9, 10, 12, 13, 14, 15, 16, 17, 18, 19, or 20 or more nucleotides may be blocked from migrating into or out of the microwell by the seal or cap. A macromolecule of at most about 1, 2, 3, 4, 5, 6, 7, 8, 9, 10, 12, 13, 14, 15, 16, 17, 18, 19, or 20 or more nucleotides may be blocked from migrating into or out of the microwell by the seal or cap.

Solid supports (e.g., beads) can be distributed among a substrate. Solid supports (e.g., beads) can be distributed among wells of the substrate, removed from the wells of the substrate, or otherwise transported through a device comprising one or more microwell arrays by means of centrifugation or other non-magnetic means. A microwell of a substrate can be pre-loaded with a solid support. A microwell of a substrate can hold at least 1, 2, 3, 4, or 5 or more solid supports. A microwell of a substrate can hold at most 1, 2, 3, 4, or 5 or more solid supports. In some instances, a microwell of a substrate can hold one solid support.

Individual cells and beads can be compartmentalized using alternatives to microwells, for example, a single solid support and single cell could be confined within a single droplet in an emulsion (e.g. in a droplet digital microfluidic system).

Cells could potentially be confined within porous beads that themselves comprise the plurality of tethered stochastic barcodes. Individual cells and solid supports can be compartmentalized in any type of container, microcontainer, reaction chamber, reaction vessel, or the like.

Single cell stochastic barcoding can be performed without the use of microwells. Single cell, stochastic barcoding assays can be performed without the use of any physical container. For example, stochastic barcoding without a physical container can be performed by embedding cells and beads in close proximity to each other within a polymer layer or gel layer to create a diffusional barrier between different cell/bead pairs. In another example, stochastic barcoding without a physical container can be performed in situ, in vivo, on an intact solid tissue, on an intact cell, and/or subcellularly.

Microwell arrays can be a consumable component of the assay system. Microwell arrays may be reusable. Microwell arrays can be configured for use as a stand-alone device for performing assays manually, or they may be configured to comprise a fixed or removable component of an instrument system that provides for full or partial automation of the assay procedure. In some embodiments of the disclosed methods, the bead-based libraries of stochastic barcodes can be deposited in the wells of the microwell array as part of the assay procedure. In some embodiments, the beads can be pre-loaded into the wells of the microwell array and provided to the user as part of, for example, a kit for performing stochastic barcoding and digital counting of nucleic acid targets.

In some embodiments, two mated microwell arrays can be provided, one pre-loaded with beads which are held in place by a first magnet, and the other for use by the user in loading individual cells. Following distribution of cells into the second microwell array, the two arrays can be placed face-to-face and the first magnet removed while a second magnet is used to draw the beads from the first array down into the corresponding microwells of the second array, thereby ensuring that the beads rest above the cells in the second microwell array and thus minimizing diffusional loss of target molecules following cell lysis, while maximizing efficient attachment of target molecules to the stochastic barcodes on the bead.

Microwell arrays of the disclosure can be pre-loaded with solid supports (e.g., beads). Each well of a microwell array can comprise a single solid support. At least 10, 20, 30, 40, 50, 60, 70, 80, 90, or 100% of the wells in a microwell array can be pre-loaded with a single solid support. At most 10, 20, 30, 40, 50, 60, 70, 80, 90, or 100% of the wells in a microwell array can be pre-loaded with a single solid support. The solid support can comprise stochastic barcodes of the disclosure. Cellular labels of stochastic barcodes on different solid supports can be different. Cellular labels of stochastic barcodes on the same solid support can be the same.

Three-Dimensional Substrates

A three-dimensional array can be any shape. A three-dimensional substrate can be made of any material used in a substrate of the disclosure. In some instances, a three-dimensional substrate comprises a DNA origami. DNA origami structures incorporate DNA as a building material to make nanoscale shapes. The DNA origami process can involve the folding of one or more long, "scaffold" DNA strands into a particular shape using a plurality of rationally designed "staple DNA strands. The sequences of the staple strands can be designed such that they hybridize to particular portions of the scaffold strands and, in doing so, force the scaffold strands into a particular shape. The DNA origami can include a scaffold strand and a plurality of rationally designed staple strands. The scaffold strand can have any sufficiently non-repetitive sequence.

The sequences of the staple strands can be selected such that the DNA origami has at least one shape to which stochastic labels can be attached. In some embodiments, the DNA origami can be of any shape that has at least one inner surface and at least one outer surface. An inner surface can be any surface area of the DNA origami that is sterically precluded from interacting with the surface of a sample, while an outer surface is any surface area of the DNA origami that is not sterically precluded from interacting with the surface of a sample. In some embodiments, the DNA origami has one or more openings (e.g., two openings), such that an inner surface of the DNA origami can be accessed by particles (e.g., solid supports). For example, in certain embodiments the DNA origami has one or more openings that allow particles smaller than 10 micrometers, 5 micrometers, 1 micrometer, 500 nm, 400 nm, 300 urn, 250 nm, 200 nm, 150 nm, 100 nm, 75 nm, 50 nm, 45 nm or 40 nm to contact an inner surface of the DNA origami.

The DNA origami can change shape (conformation) in response to one or more certain environmental stimuli. Thus an area of the DNA origami can be an inner surface when the DNA origami takes on some conformations, but can be an outer surface when the device takes on other conformations. In some embodiments, the DNA origami can respond to certain environmental stimuli by taking on a new conformation.

In some embodiments, the staple strands of the DNA origami can be selected such that the DNA origami is substantially barrel- or tube-shaped. The staples of the DNA origami can be selected such that the barrel shape is closed at both ends or is open at one or both ends, thereby permitting particles to enter the interior of the barrel and access its inner surface. In certain embodiments, the barrel shape of the DNA origami can be a hexagonal tube.

In some embodiments, the staple strands of the DNA origami can be selected such that the DNA origami has a first domain and a second domain, wherein the first end of the first domain is attached to the first end of the second domain by one or more single-stranded DNA hinges, and the second end of the first domain is attached to the second domain of the second domain by the one or more molecular latches. The plurality of staples can be selected such that the second end of the first domain becomes unattached to the second end of the second domain if all of the molecular latches are contacted by their respective external stimuli. Latches can be formed from two or more staple stands, including at least one staple strand having at least one stimulus-binding domain that is able to bind to an external stimulus, such as a nucleic acid, a lipid or a protein, and at least one other staple strand having at least one latch domain that binds to the stimulus binding domain. The binding of the stimulus-binding domain to the latch domain supports the stability of a first conformation of the DNA origami.

Synthesis of Stochastic Barcodes on Solid Supports and Substrates

A stochastic barcode can be synthesized on a solid support (e.g., bead). Pre-synthesized stochastic barcodes (e.g., comprising the 5'amine that can link to the solid support) can be attached to solid supports (e.g., beads) through any of a variety of immobilization techniques involving functional group pairs on the solid support and the stochastic barcode. The stochastic barcode can comprise a functional group. The solid support (e.g., bead) can comprise a functional group. The stochastic barcode functional group and the solid support functional group can comprise, for example, biotin, streptavidin, primary amine(s), carboxyl(s), hydroxyl(s), aldehyde(s), ketone(s), and any combination thereof. A stochastic barcode can be tethered to a solid support, for example, by coupling (e.g. using 1-Ethyl-3-(3-dimethylaminopropyl) carbodiimide) a 5' amino group on the stochastic barcode to the carboxyl group of the functionalized solid support. Residual non-coupled stochastic barcodes can be removed from the reaction mixture by performing multiple rinse steps. In some embodiments, the stochastic barcode and solid support are attached indirectly via linker molecules (e.g. short, functionalized hydrocarbon molecules or polyethylene oxide molecules) using similar attachment chemistries. The linkers can be cleavable linkers, e.g. acid-labile linkers or photo-cleavable linkers.

The stochastic barcodes can be synthesized on solid supports (e.g., beads) using any of a number of solid-phase oligonucleotide synthesis techniques, such as phosphodiester synthesis, phosphotriester synthesis, phosphite triester synthesis, and phosphoramidite synthesis. Single nucleotides can be coupled in step-wise fashion to the growing, tethered stochastic barcode. A short, pre-synthesized sequence (or block) of several oligonucleotides can be coupled to the growing, tethered stochastic barcode.

Stochastic barcodes can be synthesized by interspersing step-wise or block coupling reactions with one or more rounds of split-pool synthesis, in which the total pool of synthesis beads is divided into a number of individual smaller pools which are then each subjected to a different coupling reaction, followed by recombination and mixing of the individual pools to randomize the growing stochastic barcode sequence across the total pool of beads. Split-pool synthesis is an example of a combinatorial synthesis process in which a maximum number of chemical compounds are synthesized using a minimum number of chemical coupling steps. The potential diversity of the compound library thus created is determined by the number of unique building blocks (e.g. nucleotides) available for each coupling step, and the number of coupling steps used to create the library. For example, a split-pool synthesis comprising 10 rounds of coupling using 4 different nucleotides at each step will yield $4^{10}=1,048,576$ unique nucleotide sequences. In some embodiments, split-pool synthesis can be performed using enzymatic methods such as polymerase extension or ligation reactions rather than chemical coupling. For example, in each round of a split-pool polymerase extension reaction, the 3' ends of the stochastic barcodes tethered to beads in a given pool can be hybridized with the 5'ends of a set of semi-random primers, e.g. primers having a structure of 5'-$(M)_k$-$(X)_i$-$(N)_j$-3', where $(X)_i$ is a random sequence of nucleotides that is i nucleotides long (the set of primers comprising all possible combinations of $(X)_i$), $(N)_j$ is a specific nucleotide (or series of j nucleotides), and $(M)_k$ is a specific nucleotide (or series of k nucleotides), wherein a different deoxyribonucleotide triphosphate (dNTP) is added to each pool and incorporated into the tethered oligonucleotides by the polymerase.

The number of stochastic barcodes conjugated to or synthesized on a solid support can comprise at least 100, 1000, 10000, or 1000000 or more stochastic barcodes. The number of stochastic barcodes conjugated to or synthesized on a solid support can comprise at most 100, 1000, 10000, or 1000000 or more stochastic barcodes. The number of oligonucleotides conjugated to or synthesized on a solid support such as a bead can be at least 1, 2, 3, 4, 5, 6, 7, 8, 9, or 10-fold more than the number of target nucleic acids in a cell. The number of oligonucleotides conjugated to or synthesized on a solid support such as a bead can be at most 1, 2, 3, 4, 5, 6, 7, 8, 9, or 10-fold more than the number of target nucleic acids in a cell. At least 10, 20, 30, 40, 50, 60, 70, 80, 90 or 100% of the stochastic barcode can be bound by a target nucleic acid. At most 10, 20, 30, 40, 50, 60, 70, 80, 90 or 100% of the stochastic barcode can be bound by a target nucleic acid. At least 1, 2, 3, 4, 5, 6, 7, 8, 9, 10, 20, 30, 40, 50, 60, 70, 80, 90 or 100 or more different target nucleic acids can be captured by the stochastic barcode on the solid support. At most 1, 2, 3, 4, 5, 6, 7, 8, 9, 10, 20, 30, 40, 50, 60, 70, 80, 90 or 100 or more different target nucleic acids can be captured by the stochastic barcode on the solid support.

Samples

Cells

A sample for use in the method, compositions, systems, and kits of the disclosure can comprise one or more cells. In some embodiments, the cells are cancer cells excised from a cancerous tissue, for example, breast cancer, lung cancer, colon cancer, prostate cancer, ovarian cancer, pancreatic cancer, brain cancer, melanoma and non-melanoma skin cancers, and the like. In some instances, the cells are derived from a cancer but collected from a bodily fluid (e.g. circulating tumor cells). Non-limiting examples of cancers can include, adenoma, adenocarcinoma, squamous cell carcinoma, basal cell carcinoma, small cell carcinoma, large cell undifferentiated carcinoma, chondrosarcoma, and fibrosarcoma.

In some embodiments, the cells are cells that have been infected with virus and contain viral oligonucleotides. In some embodiments, the viral infection can be caused by a virus selected from the group consisting of double-stranded DNA viruses (e.g. adenoviruses, herpes viruses, pox viruses), single-stranded (+ strand or "sense") DNA viruses (e.g. parvoviruses), double-stranded RNA viruses (e.g. reoviruses), single-stranded (+ strand or sense) RNA viruses (e.g. picornaviruses, togaviruses), single-stranded (− strand or antisense) RNA viruses (e.g. orthomyxoviruses, rhabdoviruses), single-stranded ((+ strand or sense) RNA viruses with a DNA intermediate in their life-cycle) RNA-RT viruses (e.g. retroviruses), and double-stranded DNA-RT viruses (e.g. hepadnaviruses). Exemplary viruses can include, but are not limited to, SARS, HIV, coronaviruses, Ebola, Malaria, Dengue, Hepatitis C, Hepatitis B, and Influenza.

In some embodiments, the cells are bacterial cells. These can include cells from gram-positive bacterial and/or gram-negative bacteria. Examples of bacteria that may be analyzed using the disclosed methods, devices, and systems include, but are not limited to, Actinomedurae, *Actinomyces israelii, Bacillus anthracis, Bacillus cereus, Clostridium botulinum, Clostridium difficile, Clostridium perfringens, Clostridium tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like. Gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Heliobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like. Other bacteria may include *Myobacterium avium, Myobacterium leprae, Myobacterium tuberculosis, Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium,* Meningococci and the like.

In some embodiments, the cells are cells from fungi. Non-limiting examples of fungi that may be analyzed using the disclosed methods, devices, and systems include, but are not limited to, Aspergilli, Candidae, *Candida albicans, Coccidioides immitis,* Cryptococci, and combinations thereof.

In some embodiments, the cells are cells from protozoans or other parasites. Examples of parasites to be analyzed using the methods, devices, and systems of the present disclosure include, but are not limited to, *Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii,* Trypanosomae, trapezoidal amoeba, worms (e.g., helminthes), particularly parasitic worms including, but not limited to, Nematoda (roundworms, e.g., whipworms, hookworms, pinworms, ascarids, filarids and the like), Cestoda (e.g., tapeworms).

As used herein, the term "cell" can refer to one or more cells. In some embodiments, the cells are normal cells, for example, human cells in different stages of development, or human cells from different organs or tissue types (e.g. white blood cells, red blood cells, platelets, epithelial cells, endothelial cells, neurons, glial cells, fibroblasts, skeletal muscle cells, smooth muscle cells, gametes, or cells from the heart, lungs, brain, liver, kidney, spleen, pancreas, thymus, bladder, stomach, colon, small intestine). In some embodiments, the cells can be undifferentiated human stem cells, or human stem cells that have been induced to differentiate. In some embodiments, the cells can be fetal human cells. The fetal human cells can be obtained from a mother pregnant with the fetus. In some embodiments, the cells are rare cells. A rare cell can be, for example, a circulating tumor cell (CTC), circulating epithelial cell, circulating endothelial cell, circulating endometrial cell, circulating stem cell, stem cell, undifferentiated stem cell, cancer stem cell, bone marrow cell, progenitor cell, foam cell, mesenchymal cell, trophoblast, immune system cell (host or graft), cellular fragment, cellular organelle (e.g. mitochondria or nuclei), pathogen infected cell, and the like.

In some embodiments, the cells are non-human cells, for example, other types of mammalian cells (e.g. mouse, rat, pig, dog, cow, or horse). In some embodiments, the cells are other types of animal or plant cells. In some embodiments, the cells can be any prokaryotic or eukaryotic cells.

In some embodiments, a first cell sample is obtained from a person not having a disease or condition, and a second cell sample is obtained from a person having the disease or condition. In some embodiments, the persons are different. In some embodiments, the persons are the same but cell samples are taken at different time points. In some embodiments, the persons are patients, and the cell samples are patient samples. The disease or condition can be a cancer, a bacterial infection, a viral infection, an inflammatory disease, a neurodegenerative disease, a fungal disease, a parasitic disease, a genetic disorder, or any combination thereof.

In some embodiments, cells suitable for use in the presently disclosed methods can range in size, for example ranging from about 2 micrometers to about 100 micrometers in diameter. In some embodiments, the cells can have diameters of at least 2 micrometers, at least 5 micrometers, at least 10 micrometers, at least 15 micrometers, at least 20 micrometers, at least 30 micrometers, at least 40 micrometers, at least 50 micrometers, at least 60 micrometers, at least 70 micrometers, at least 80 micrometers, at least 90 micrometers, or at least 100 micrometers. In some embodiments, the cells can have diameters of at most 100 micrometers, at most 90 micrometers, at most 80 micrometers, at most 70 micrometers, at most 60 micrometers, at most 50 micrometers, at most 40 micrometers, at most 30 micrometers, at most 20 micrometers, at most 15 micrometers, at most 10 micrometers, at most 5 micrometers, or at most 2 micrometers. The cells can have a diameter of any value within a range, for example from about 5 micrometers to about 85 micrometers. In some embodiments, the cells have diameters of about 10 micrometers.

In some embodiments, the cells are sorted prior to associating one or more of the cells with a bead and/or in a microwell. For example the cells can be sorted by fluorescence-activated cell sorting or magnetic-activated cell sorting, or e.g., by flow cytometry. The cells can be filtered by size. In some instances a retentate contains the cells to be associated with the bead. In some instances the flow through contains the cells to be associated with the bead.

Methods of Whole Transcriptome Amplification

The disclosure provides methods for whole transcriptome amplification of a sample. "Whole transcriptome amplification" as used herein can refer to the amplification of all or a fraction of the transcriptome of a sample, such as a single cell. Amplification can be accomplished using various PCR or non-PCR based methods as disclosed herein.

The methods for whole transcriptome amplification disclosed herein can amplify a plurality of targets (including but not limited to mRNA, micro RNA, siRNA, tRNA, rRNA, and any combination thereof) in a sample, such as a single cell. In some embodiments, the methods disclosed herein for whole transcriptome amplification can amplify all or a fraction of the transcripts, or the species of transcripts, in a sample, such as a single cell. "A species of transcripts" as used herein refers to all the transcripts from a single gene, or genetic locus. In some embodiments, a transcriptome can comprise at least 100, 1,000, 10,000, 100,000, 1,000,000 or more species of transcripts in a sample, such as a single cell. In some embodiments, a transcriptome can comprise at least 100, 1,000, 10,000, 100,000, 1,000,000, 10,000,000, 100,000,000 or more transcripts in a sample, such as a single cell. In some embodiments, the methods disclosed herein for whole transcriptome amplification can produce a WTA product comprising at least 1%, 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, 80%, 90%, 95%, or 100% of transcripts in a sample, such as a single cell. In some embodiments, the methods disclosed herein for whole transcriptome amplification can produce a WTA product comprising at least 1%, 2%, 3%, 4%, 5%, 6%, 7%, 8%, 9%, 10%, 11%, 12%, 13%, 14%, 15%, 16%, 17%, 18%, 19%, 20%, 30%, 40%, 50%, 60%, 70%, 80%, 90%, 95%, or 100% of the species of transcripts in a sample, such as a single cell.

In some embodiments, for whole transcriptome amplification, one or more universal primer binding sites can be added to the targets, such as mRNA molecules, in a sample. In various embodiments, the methods disclosed herein comprise labeling a plurality of targets, such as mRNA molecules, in a sample. In some embodiments, labeling the plurality of targets comprises adding a stochastic barcode to one or more of the plurality of targets. The stochastic barcode can comprise one or more universal labels that comprise binding sites for amplification primers, such as PCR primers. In some embodiments, the stochastic barcodes can comprise a universal label, a molecular label, a cellular label, a spatial label, a target-specific region, or any combination thereof. The stochastic barcodes can be added to the targets in a sequence dependent or preferably, sequence independent manner.

Quasi-Symmetric Stochastic Barcodes

Figure 1B:
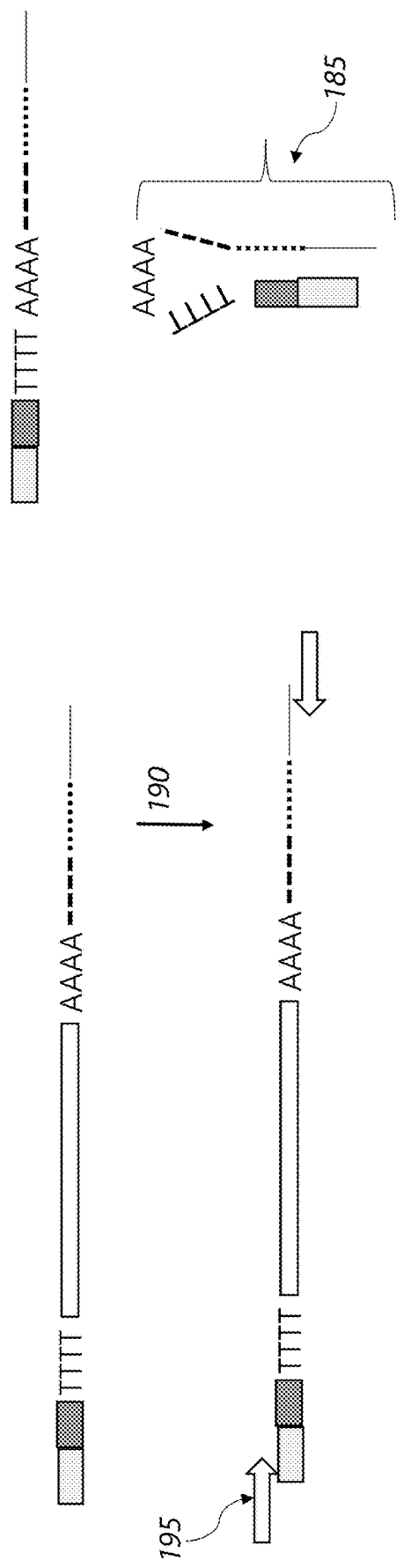

Methods for whole transcriptome amplification using quasi-symmetric stochastic barcodes are provided. A non-limiting embodiment of the method is shown in FIGS. 1A and 1B. In FIGS. 1A and 1B, a target 105 can comprise a poly-A tail. A target 105 can be an mRNA. The target 105 can be hybridized to a stochastic barcode 110. The stochastic barcode 110 can comprise a number of labels. For example, the stochastic barcode 110 can comprise a target-specific region (e.g., oligo dT for binding to poly-A tails of mRNAs) 115, a molecular label 120, a cellular label 125, and a first universal label 130. The stochastic barcode 110 can be reverse transcribed 135 using a reverse transcriptase, thereby generating a labelled-cDNA molecule. Excess stochastic barcodes 111 can be treated at step 140 with a degradation enzyme 145. The degradation enzyme 145 can be, for example, an exonuclease. The labelled-cDNA molecule can be tailed in step 150. Tailing can comprise, for example, homopolymer tailing. For example, a homopolymer tail 155 can be appended to the 3' end of the labelled-cDNA molecule, thereby generating a tailed molecule 156. In some instances, excess stochastic barcodes 111 that were resistant to exonuclease can be tailed as well.

The tailed molecule 156 can be contacted with a second strand synthesis primer 165. The second strand synthesis primer 165 can comprise a region 166 that is complementary to the homopolymer tail 155. The second strand synthesis primer 165 can comprise a restriction site 170. The second strand synthesis primer 165 can comprise a second universal label 131. The second universal label 131 can be shorter than the first universal label 130. The second universal label 131 can be different than the first universal label 130. The second strand synthesis primer can be extended 175, thereby generating at step 180 a quasi-symmetric stochastically barcoded nucleic acid 181. In some instances, the excess stochastic barcode 111 can be tailed and extended as well.

The excess stochastic barcode 111 that is tailed and extended can, in some embodiments, form a panhandle structure 185. The panhandle structure can be formed by hybridization of the first and second universal labels 130 and 131 on each end of the tailed and extended excess stochastic barcode 111. The panhandle structure 185 can prevent amplification of the tailed and extended excess stochastic barcode.

The quasi-symmetric stochastically barcoded nucleic acid 181 can be amplified 190. Amplification can be performed, for example, with a WTA (whole transcriptome amplification) primer 195. The WTA primer 195 can hybridize with the first and second universal labels 130 and 131. The quasi-symmetric stochastically barcoded nucleic acid 181 can be amplified, for example, with a whole transcriptome amplification primer, thereby producing a quasi-symmetric stochastically barcoded amplicon.

Figure 2A:
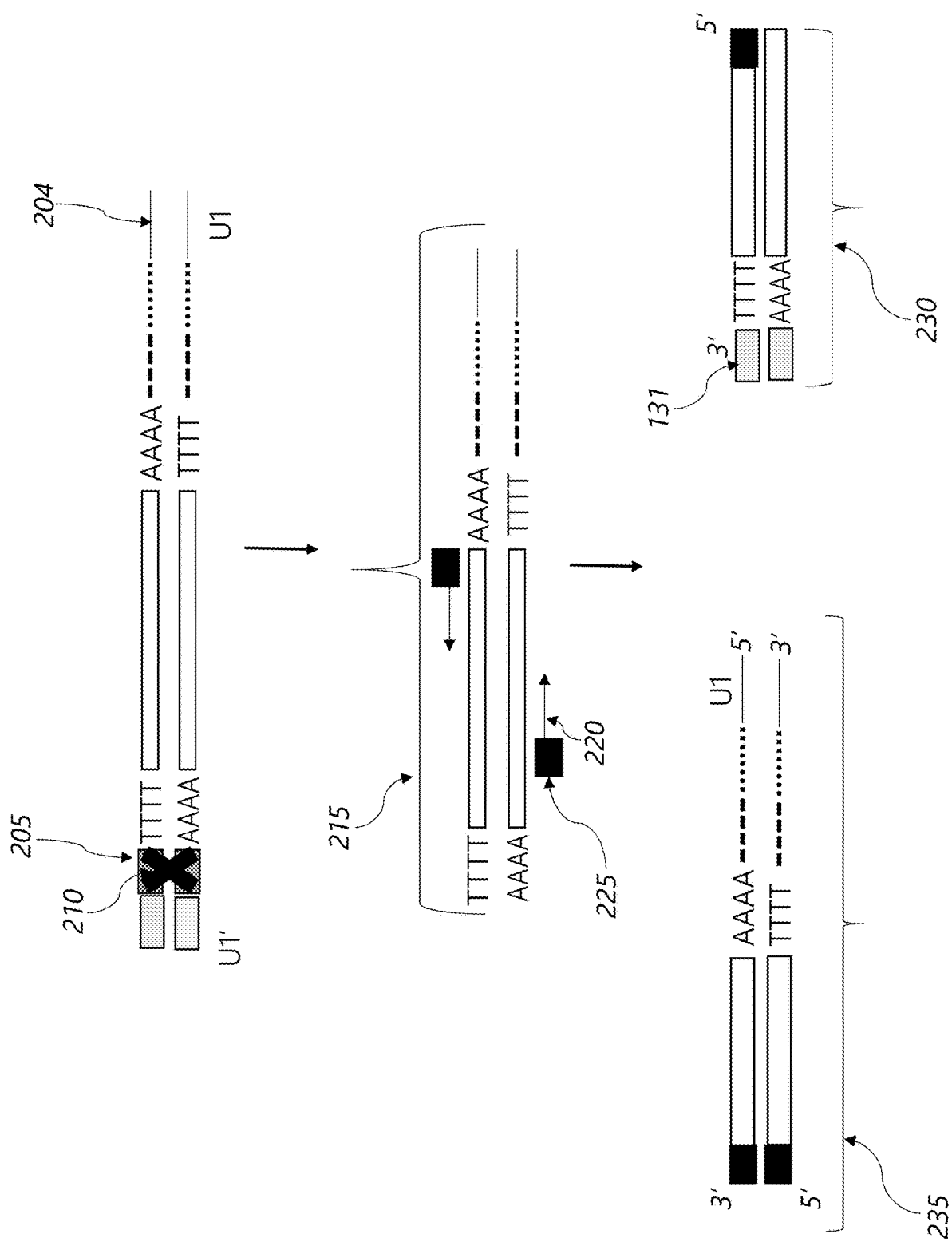
FIGS. 2A and 2B illustrate an exemplary embodiment for breaking symmetry of a quasi-symmetric stochastically barcode nucleic acid.
Figure 2B:
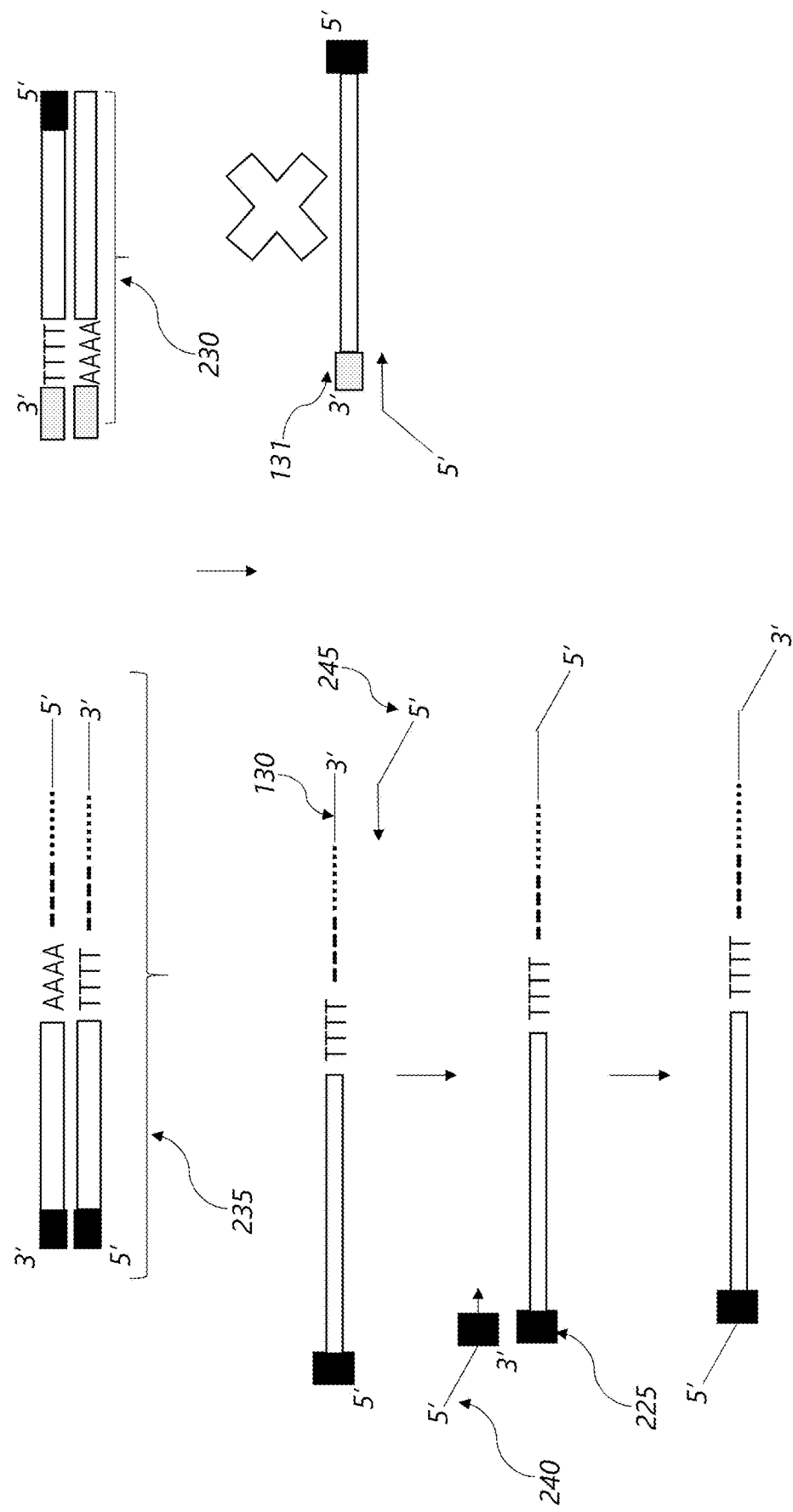

The WTA amplified quasi-symmetric stochastically barcoded nucleic acid can be prepared for a sequencing library (e.g., for generating sequencing reads). For example, as shown in FIGS. 2A and 2B, the restriction site 205 can be cleaved at step 210, thereby generating an asymmetric stochastically barcoded nucleic acid 215. The asymmetric stochastically barcoded nucleic acid 215 can be amplified with a degenerate primer 220. The degenerate primer 220 can comprise a polynucleotide sequence can comprise a third universal label 225. The third universal label 225 can be different from the first and second universal labels 130 and 131. The degenerate primer 220 can comprise a random multimer sequence. The random multimer sequence can hybridize randomly to the sense and/or anti-sense strand of the asymmetric stochastically barcoded nucleic acid. For example, two products can be made. When the degenerate primer amplifies off the sense strand it can generate a 5' product 230. The 5' product 230 can, for example, comprise the second universal sequence 131 if the restriction digest 210 is not performed to completion. In this way, the second universal label 131 can be a second mechanism for breaking the symmetry of the quasi-symmetric stochastically barcoded nucleic acid 181. When the degenerate primer amplifies off the anti-sense strand it can generate a 3' product 235. The 3' product 235 can comprise the sequence of the stochastic barcode.

The 3' and 5' products 230 and 235 can be used for downstream sequencing library preparation. For example, the 3' and 5' products 230 and 235 can be amplified with sequencing library amplification primers 240/245. One of the sequencing library amplification primers 240 can hybridize to the third universal label 225. One of the sequencing library amplification primers 245 can hybridize to the first universal label 130. The sequencing library amplification primers 245 may not be able to hybridize to the second universal label 131. The sequencing library amplification primers 245 may hybridize less efficiently to the second universal label 131. Amplification of the 5' product 230 may not occur. Amplification of the 5' product 230 may occur less efficiently. In this way, the second universal label 131 can be a mechanism for breaking the symmetry of the quasi-symmetric stochastically barcoded nucleic acid 181. The 3' product can be the majority product subjected to a sequencing reaction. The results of the sequencing reaction can be more useful and efficient because only the 3' product is sequenced, thereby generating the data comprising the stochastic barcode. The sequencing data can be used in downstream methods of the disclosure such as binning, counting, and estimating the number of original target mRNAs in a single cell.

Cell Lysis

Following the distribution of cells and stochastic barcodes, the cells can be lysed to liberate the target molecules. Cell lysis can be accomplished by any of a variety of means, for example, by chemical or biochemical means, by osmotic shock, or by means of thermal lysis, mechanical lysis, or optical lysis. Cells can be lysed by addition of a cell lysis buffer comprising a detergent (e.g. SDS, Li dodecyl sulfate, Triton X-100, Tween-20, or NP-40), an organic solvent (e.g. methanol or acetone), or digestive enzymes (e.g. proteinase K, pepsin, or trypsin), or any combination thereof. To increase the association of a target and a stochastic barcode, the rate of the diffusion of the target molecules can be altered by for example, reducing the temperature and/or increasing the viscosity of the lysate.

Association of Stochastic Barcodes to Targets

Following lysis of the cells and release of nucleic acid molecules therefrom, the nucleic acid molecules can randomly associate with the stochastic barcodes of the co-localized solid support. Association can comprise hybridization of a stochastic barcode's target recognition region to a complementary portion of the target nucleic acid molecule (e.g., oligo dT of the stochastic barcode can interact with a poly-A tail of a target). The assay conditions used for hybridization (e.g. buffer pH, ionic strength, temperature, etc.) can be chosen to promote formation of specific, stable hybrids.

In some embodiments, the methods disclosed herein can comprise placing the stochastic barcodes in close proximity with the sample, lysing the sample, associating distinct targets with the stochastic barcodes, amplifying the targets and/or digitally counting the targets. The method can, in some embodiments, further comprise analyzing and/or visualizing the information obtained from the spatial labels on the stochastic barcodes. The stochastic barcodes can be associated with the targets using a variety of methods, such as primer-based extension or transcription, ligation, transposome-based ligation, or any combination thereof. In some embodiments, a sample can comprise a total amount of targets that is, is about, is less than, 1 pg, 2 pg, 3 pg, 4 pg, 5 pg, 6 pg, 7 pg, 8 pg, 9 pg, 10 pg, 20 pg, 30 pg, 40 pg, 50 pg, 60 pg, 70 pg, 80 pg, 90 pg, 100 pg, 200 pg, 300 pg, 400 pg, 500 pg, 600 pg, 700 pg, 800 pg, 900 pg, 1 ng, or a range between any two of the above values.

Attachment can further comprise ligation of a stochastic barcode's target recognition region and a portion of the target nucleic acid molecule. For example, the target binding region can comprise a nucleic acid sequence that can be capable of specific hybridization to a restriction site overhang (e.g. an EcoRI sticky-end overhang). The assay procedure can further comprise treating the target nucleic acids with a restriction enzyme (e.g. EcoRI) to create a restriction site overhang. The stochastic barcode can then be ligated to any nucleic acid molecule comprising a sequence complementary to the restriction site overhang. A ligase (e.g., T4 DNA ligase) may be used to join the two fragments.

The labeled targets from a plurality of cells (or a plurality of samples) (e.g., target-barcode molecules) can be subsequently pooled, for example by retrieving the stochastic barcodes and/or the beads to which the target-barcode molecules are attached. The retrieval of solid support-based collections of attached target-barcode molecules can be implemented by use of magnetic beads and an externally-applied magnetic field. Once the target-barcode molecules have been pooled, all further processing may proceed in a single reaction vessel. Further processing can include, for example, reverse transcription reactions, amplification reactions, cleavage reactions, dissociation reactions, and/or nucleic acid extension reactions. Further processing reactions may be performed within a single microwell containing a reaction mixture and/or a sample such as a single cell, that is, without first pooling the labeled target nucleic acid molecules from a plurality of cells.

Excess stochastic barcodes can be degraded with an enzyme. The enzyme can be a nuclease such as, for example, an exonuclease or an endonuclease. Exemplary nucleases can include DNase I, Cas9 nuclease, Endonuclease III, endonuclease IV, endonuclease III, endonuclease IV, endonuclease V, endonuclease VIII, exonuclease I, exonuclease III, exonuclease I, exonuclease V, micrococcal nuclease, T7 endonuclease, T7 exonuclease, uracil glycosylase inhibitor, and uracil DNA glycosylase. In some embodiments, at least 10, 20, 30, 40, 50, 60, 70, 80, 90 or 100% of the excess barcodes can be degraded with an enzyme (e.g., exonuclease). In some embodiments, at most 10, 20, 30, 40, 50, 60, 70, 80, 90 or 100% of the excess barcodes can be degraded with an enzyme (e.g., exonuclease). In some embodiments, at least 10, 20, 30, 40, 50, 60, 70, 80, 90 or 100% of the excess barcodes may escape degradation with an enzyme (e.g., exonuclease). In some embodiments, at most 10, 20, 30, 40, 50, 60, 70, 80, 90 or 100% of the excess barcodes may escape degradation with an enzyme (e.g., exonuclease).

A sample comprising, for example, a cell, organ, or tissue thin section, can be contacted with stochastic barcodes. In some embodiments, the stochastic barcodes can be immobilized on a solid support. The solid supports can be free floating. The solid supports can be embedded in a semi-solid or solid array. The stochastic barcodes may not be associated with solid supports. The stochastic barcodes can be individual nucleotides. The stochastic barcodes can be associated with a substrate. When stochastic barcodes are in close proximity to targets, the targets can hybridize to the stochastic barcode. The stochastic barcodes can be contacted at a non-depletable ratio such that each distinct target can associate with a distinct stochastic barcode of the disclosure. To ensure efficient association between the target and the stochastic barcode, the targets can be crosslinked to the stochastic barcode.

The probability that two distinct targets of a sample can contact the same unique stochastic barcode can be at least $10^{-6}$, $10^{-5}$, $10^{-4}$, $10^{-1}$, $10^{-2}$, or $10^{-1}$ or more. The probability that two distinct targets of a sample can contact the same unique stochastic barcode can be at most $10^{-6}$, $10^{-5}$, $10^{-4}$, $10^{-1}$, $10^{-2}$, or $10^{-1}$ or more. The probability that two targets of the same gene from the same cell can contact the same stochastic barcode can be at least $10^{-6}$, $10^{-5}$, $10^{-4}$, $10^{-1}$, $10^{-2}$, or $10^{-1}$ or more. The probability that two targets of the same gene from the same cell can contact the same stochastic barcode can be at most $10^{-6}$, $10^{-5}$, 10-4, $10^{-1}$, $10^{-2}$, or $10^{-1}$ or more.

In some embodiments, cells from a population of cells can be separated (e.g., isolated) into wells of a substrate of the disclosure. The population of cells can be diluted prior to separating. For example, the population of cells can be diluted such that at least 1, 5, 10, 15, 20, 25, 30, 35, 40, 45, 50, 55, 60, 65, 70, 75, 80, 85, 90, 95 or 100% of wells of the substrate receive a single cell. In some embodiments, the population of cells can be diluted such that at most 1, 5, 10, 15, 20, 25, 30, 35, 40, 45, 50, 55, 60, 65, 70, 75, 80, 85, 90, 95 or 100% of wells of the substrate receive a single cell. In some embodiments, the population of cells can be diluted such that the number of cells in the diluted population is at least 1, 5, 10, 15, 20, 25, 30, 35, 40, 45, 50, 55, 60, 65, 70, 75, 80, 85, 90, 95 or 100% of the number of wells on the substrate. In some embodiments, the population of cells can be diluted such that the number of cells in the diluted population is at least 1, 5, 10, 15, 20, 25, 30, 35, 40, 45, 50, 55, 60, 65, 70, 75, 80, 85, 90, 95 or 100% of the number of wells on the substrate. In some embodiments, the population of cells is diluted such that the number of cell is about 10% of the number of wells in the substrate.

Distribution of single cells into wells of the substrate can follow a Poisson distribution. For example, there can be, or can be at least, a 0.1, 0.5, 1, 2, 3, 4, 5, 6, 7, 8, 9 or 10% or more probability that a well of the substrate has more than one cell. In some embodiments, there can be at least a 0.1, 0.5, 1, 2, 3, 4, 5, 6, 7, 8, 9 or 10% or more probability that a well of the substrate has more than one cell. Distribution of single cells into wells of the substrate can be random. Distribution of single cells into wells of the substrate can be non-random. The cells can be separated such that a well of the substrate receives only one cell.

Stochastic Barcodes on Solid Supports

The methods of whole transcriptome amplification disclosed herein can, in some embodiments, comprise steps of removing non-stochastically labeled targets or non-targets, etc. In some embodiments, the stochastic barcoding (e.g., labeling, indexing) step of the methods of the disclosure can be performed on a solid support. In some embodiments, the methods disclosed herein can comprise a step of removing non-stochastically labeled targets, non-targets such as DNA, or other cellular components or reagents. In some embodiments, the removing can comprise washing the solid support after contacting the solid support, such as beads, with the targets from a sample. In some embodiments, the removing can comprise washing the solid support after extension of the stochastic barcodes on the solid support. In some embodiments, the washing can comprising collected the solid supports, such as beads, from the reaction mixture.

Figure 3A:
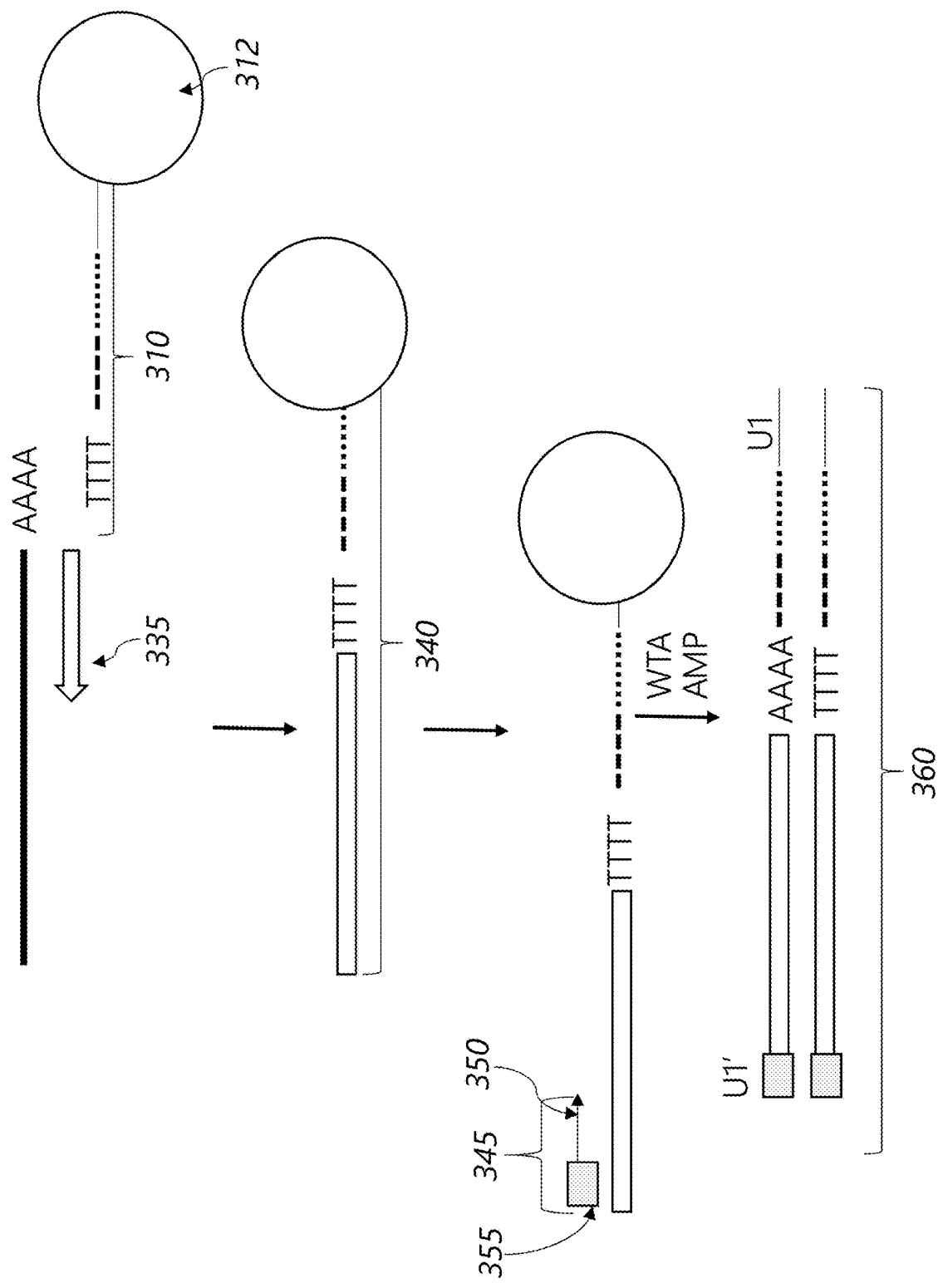
FIGS. 3A, 3B, and 3C illustrate an exemplary embodiment for the random priming method of the disclosure.
Figure 3B:
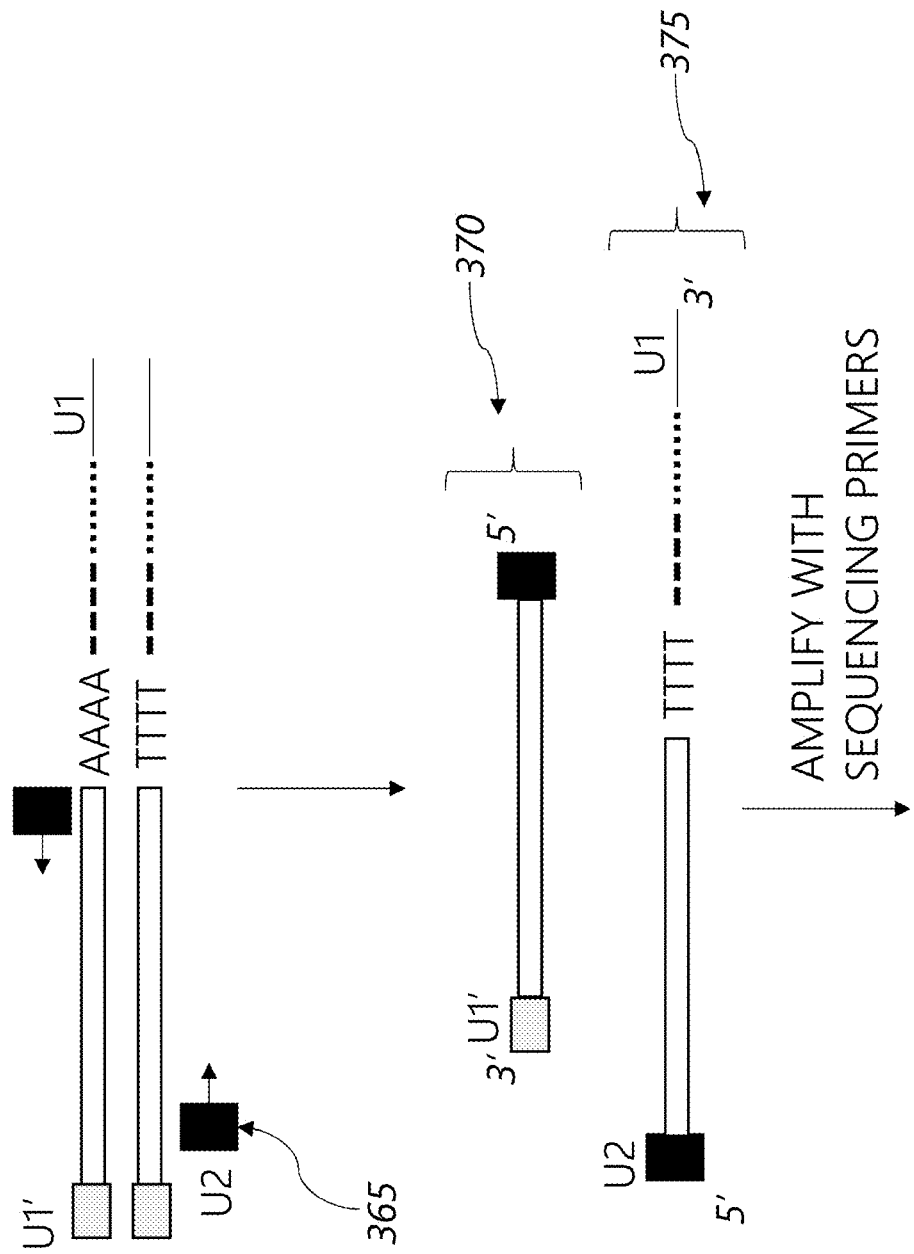
Figure 3C:
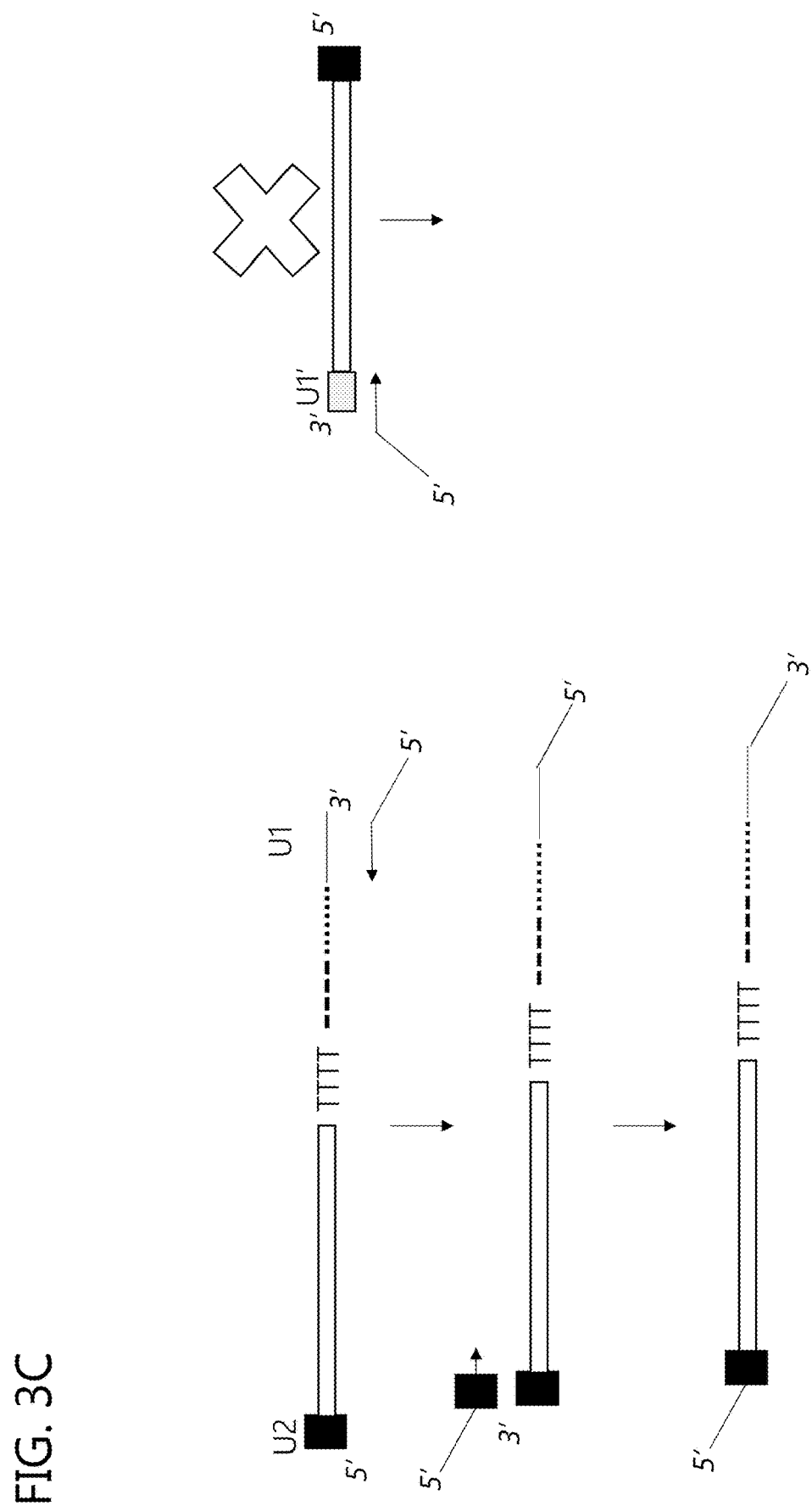

As shown in FIGS. 3A, 3B, and 3C, the stochastic barcode 310 can be attached (e.g., conjugated, covalently attached, non-covalently attached) to a solid support 312. A reverse transcription reaction 335 can be performed on the solid support 312. Excess stochastic barcodes 310 attached to the solid support 312 can be removed (e.g., by washing, by magnets). The reverse transcription reaction 335 can produce a first strand labelled cDNA 340. The first strand labelled cDNA 340 can be contacted with a second strand synthesis primer 345. The second strand synthesis primer 345 can comprise a random multimer sequence 350. The second strand synthesis primer 345 can comprise a second universal label 355. The second strand synthesis primer 345 can be extended (e.g., by primer extension), thereby generating a quasi-symmetric double-stranded labelled cDNA 360. The quasi-symmetric double-stranded labelled cDNA 360 can be amplified, for example, with a whole transcriptome amplification primer, thereby producing a quasi-symmetric stochastically barcoded amplicon. The method can be continued as described in FIGS. 2A and 2B, wherein the quasi-symmetric stochastically barcoded amplicon can be contacted with a degenerate primer 365 and undergo random priming. The degenerate primer can comprise a third universal label (U2). The 3' (375) and 5' (370) products resulting from the random priming with the degenerate primer can be amplified with sequencing library amplification primers. The 3' product 375 can be favored. The reaction can be sequenced and subjected to downstream methods of the disclosure such as sequencing, counting, and estimating the number of target mRNAs in a single cell.

Reverse Transcription

In some embodiments, cDNA synthesis, such as by reverse-transcription, can be used to associate stochastic barcodes to targets, e.g., mRNAs. For example, the stochastic target-barcode conjugate can comprise the stochastic barcode and a complementary sequence of all or a portion of the target nucleic acid (i.e. a stochastically barcoded cDNA molecule). Reverse transcription of the associated RNA molecule can occur by the addition of a reverse transcription primer along with the reverse transcriptase. The reverse transcription primer can be an oligo-dT primer, a random hexanucleotide primer, or a target-specific oligonucleotide primer. Oligo-dT primers can be 12-18 nucleotides in length and bind to the endogenous poly-A tail at the 3' end of mammalian mRNA. Random hexanucleotide primers can bind to mRNA at a variety of complementary sites. Target-specific oligonucleotide primers typically selectively prime the mRNA of interest.

Figure 5:
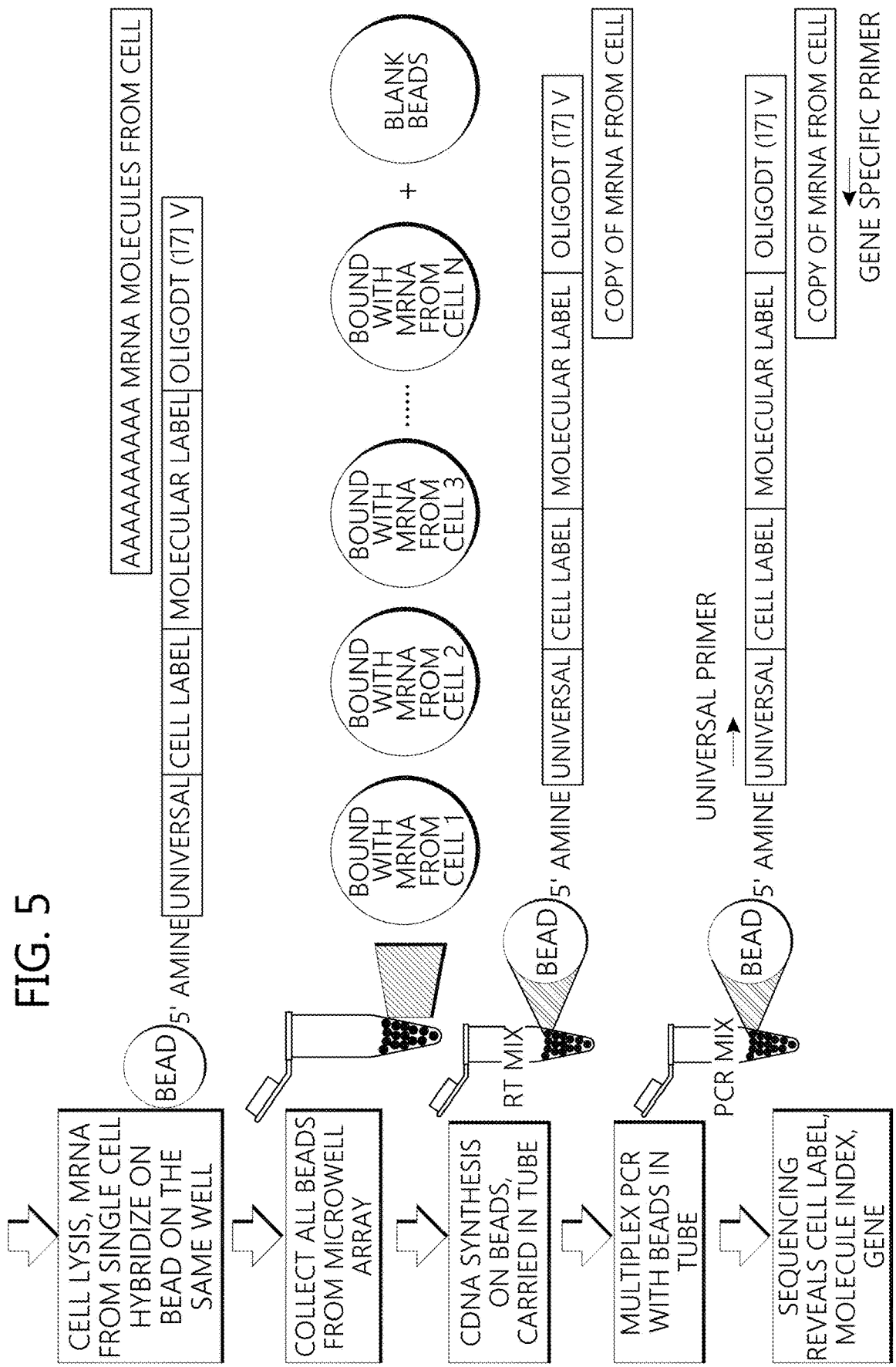
FIG. 5 depicts a schematic of an exemplary embodiment of the stochastic barcoding method of the disclosure.

FIG. 5 illustrates an exemplary embodiment of the stochastic barcoding method of the disclosure. A sample (e.g., section of a sample, thin slice, or one or more cells) can be contacted with a solid support comprising a stochastic barcode. Targets in the sample can be associated with the stochastic barcodes. The solid supports can be collected. cDNA synthesis can be performed on the solid support. cDNA synthesis can be performed off the solid support. cDNA synthesis can incorporate the label information from the labels in the stochastic barcode into the new cDNA target molecule being synthesized, thereby generating a target-barcode molecule. The target-barcode molecules can be amplified using PCR. The sequence of the targets and the labels of the stochastic barcode on the target-barcode molecule can be determined by sequencing methods.

After the synthesis of a first cDNA strand, various methods can be used to synthesize a second strand to produce a double-stranded cDNA. Preferably, the second strand synthesis may not be conducted in a target-specific manner. For example, a random primer can be used that binds to the first cDNA strand, and can be extended using a DNA polymerase. In some embodiments, homopolyer tailing can be used for second strand synthesis. In some embodiments, second strand synthesis can be conducted in a primer-independent manner.

Second Strand Synthesis Using Homopolymer Tailing

In some embodiments, the methods disclosed herein provide for homopolymer tailing of the single-stranded cDNA molecules obtained after reverse transcription. Homopolymer tailing can comprise reaction with a terminal deoxynucleotide transferase (TdT) in the presence of a selected dNTP, to form a homopolymer region at the 3' cDNA ends. The homopolymer tailing reaction can be performed on the RNA/cDNA duplex or single-stranded cDNA. If the RNA strand is present, the efficiency of the reaction can, in some embodiments, be enhanced by initial digestion with a 5' exonuclease, to expose the 3' fragment ends, or by carrying out the reaction in the presence of cobalt ions. The homopolymer tail can comprise a polyA tail, a polyT tail, a polyU tail, a polyC tail, and/or a polyG tail.

The homopolymer tailing reaction can introduce at least 1, 2, 3, 4, 5, 6, 7, 8, 9, 10, 11, 12, 13, 14, 15, 16, 17, 18, 19, or 20 or more nucleotides to the cDNA. The homopolymer tailing reaction can introduce at most 1, 2, 3, 4, 5, 6, 7, 8, 9, 10, 11, 12, 13, 14, 15, 16, 17, 18, 19, or 20 or more nucleotides to the cDNA. The enzymes, (e.g., RNase and/or TdT) and selected dNTP are removed, for example, by cDNA fragment precipitation. In some instances, excess stochastic barcodes that escaped degradation by the exonuclease enzyme can be homopolymer tailed. These can be considered reaction side products.

The single-stranded cDNA can be contacted with a second strand synthesis primer to initiate second strand synthesis, thereby generating a double-stranded labelled cDNA. The second strand synthesis primer can comprise a region complementary to the homopolymer tail (e.g., it can bind to the homopolymer tail sequence). For example, if the homopolymer tail is comprised of adenines, then the region complementary to the homopolymer tail can comprise thymidines. The length of the region complementary to the homopolymer tail can be the same as the homopolymer tail. The length of the region complementary to the homopolymer tail can be, or be at least, 10, 20, 30, 40, 50, 60, or 70% or more shorter than the homopolymer tail. The length of the region complementary to the homopolymer tail can be, or be at most, 10, 20, 30, 40, 50, 60, or 70% or more shorter than the homopolymer tail. The length of the region complementary to the homopolymer tail can be, or be at least, 10, 20, 30, 40, 50, 60, or 70% or more longer than the homopolymer tail. The length of the region complementary to the homopolymer tail can be, or be at most, 10, 20, 30, 40, 50, 60, or 70% or more longer than the homopolymer tail.

The second strand synthesis primer can comprise a cleavage site. The cleavage site can be a restriction endonuclease cleavage site. Exemplary restriction endonuclease can comprise BamH1, EcoR1, AleI, ApaI, BglII, BsaI, KpnI, or any endonuclease cleaving enzyme.

The second strand synthesis primer can comprise a second universal label. The universal label of the second strand synthesis primer (e.g., second universal label) can be the same as the universal label on the stochastic barcode (e.g. on the 5' end of the single-stranded cDNA molecule, i.g., first universal label). The second universal label can comprise a sequence that is a subset of the first universal label. For example, the second universal label can comprise at least 10, 20, 30, 40, 50, 60, 70, 80, 90, 95, or 100% of the sequence of the first universal label. The second universal label can comprise at most 10, 20, 30, 40, 50, 60, 70, 80, 90, 95, or 100% of the sequence of the first universal label. The second universal label can be, or be at least, 1, 2, 3, 4, 5, 6, 7, 8, 9, or 10 or more nucleotides shorter or longer than the first universal label. The second universal label can be at most 1, 2, 3, 4, 5, 6, 7, 8, 9, or 10 or more nucleotides shorter or longer than the first universal label. In some instances, the second universal label is shorter than the first universal label by 2 nucleotides. The universal label can differ from the first universal label by at least 1, 2, 3, 4, 5, 6, 7, 8, 9, or 10 or more nucleotides. The universal label can differ from the first universal label by at most 1, 2, 3, 4, 5, 6, 7, 8, 9, or 10 or more nucleotides. The second universal label can be, or be at most, 99, 98, 7, 96, 95, 94, 93, 92, 91 or 90% or less identical to said first universal label. The second universal label may not be identical to said first universal label. The second universal label can hybridize to said first universal label over at least 50, 60, 70, 80, 90, 91, 92, 93, 94, 95, 96, 97, 98, 99, or 100% of said first universal label. The second universal label can be at most 99% identical to said first universal label over 50, 60, 70, 80, 90, 91, 92, 93, 94, 95, 96, 97, 98, 99, or 100% of said first universal label. The sequence of the first universal label can be a sequencing primer binding site (e.g., Illumina read 2 sequence). The sequence of the second universal label can be a modified sequencing primer binding site (e.g., Illumina modified read 2 sequence).

In some instances, the first universal label and the second universal label are able to hybridize to each other (e.g., for use in suppression PCR). The first and second universal labels can hybridize with at least 1, 2, 3, 4, 5, 6, 7, 8, 9, or 10 or more mismatches. The first and second universal labels can hybridize with at most 1, 2, 3, 4, 5, 6, 7, 8, 9, or 10 or more mismatches. The extent of hybridization can relate to the amount of suppression occurring during suppression PCR. For example, sequences that can hybridize strongly can be suppressed more than sequences that hybridize weakly.

The second strand synthesis primer can be extended (e.g., using primer extension) over the length of the first cDNA strand, thereby generating a quasi-symmetric stochastically barcoded nucleic acid. The quasi-symmetric stochastically barcoded nucleic acid can comprise the sequence of the second strand synthesis primer, the second universal label, and the labelled cDNA molecule (e.g., first cDNA strand, i.e., including the sequence of the target-binding region and the stochastic barcode). In this way the quasi-symmetric stochastically barcoded nucleic acid can comprise a universal label at each end of the molecule.

In some instances, the second strand synthesis primer can anneal to the homopolymer tail on the tailed excess stochastic barcode. The second strand synthesis primer can be extended to generate a synthesized second strand cDNA molecule that incorporates the sequence of the excess stochastic barcode. In some instances, the synthesized second strand cDNA molecule may not comprise a target (e.g., target polynucleotide).

Second Strand Synthesis with Random Priming

In some embodiments, as exemplified in FIGS. 3A, 3B, and 3C, the methods of the disclosure may not comprise homopolymer tailing. The methods of the disclosure can provide for random priming. The method can comprise contacting a target nucleic acid (e.g., target RNA, target polyadenylated transcript, target mRNA) with a stochastic barcode of the disclosure. For example, the stochastic barcode can comprise an oligo dT region which can hybridize with the poly-A tail of the target nucleic acid. The stochastic barcode can be attached to a solid support. The stochastic barcode may not be attached to a solid support. The target RNA can be reverse transcribed using the stochastic barcode as a primer, thereby resulting in a single-stranded labelled cDNA molecule.

Excess stochastic barcodes can be degraded with an enzyme. The enzyme can be a nuclease such as, for example, an exonuclease or an endonuclease. Exemplary nucleases can include DNase I, Cas9 nuclease, Endonuclease III, endonuclease IV, endonuclease III, endonuclease IV, endonuclease V, endonuclease VIII, exonuclease I, exonuclease III, exonuclease I, exonuclease V, micrococcal nuclease, T7 endonuclease, T7 exonuclease, uracil glycosylase inhibitor, and uracil DNA glycosylase. At least 10, 20, 30, 40, 50, 60, 70, 80, 90 or 100% of the excess barcodes can be degraded with an enzyme (e.g., exonuclease). At most 10, 20, 30, 40, 50, 60, 70, 80, 90 or 100% of the excess barcodes can be degraded with an enzyme (e.g., exonuclease). At least 10, 20, 30, 40, 50, 60, 70, 80, 90 or 100% of the excess barcodes may escape degradation with an enzyme (e.g., exonuclease). At most 10, 20, 30, 40, 50, 60, 70, 80, 90 or 100% of the excess barcodes may escape degradation with an enzyme (e.g., exonuclease). In some embodiments, when excess barcodes are attached to a solid support (e.g., bead), the beads can be removed. Removal can occur by, for example, washing, or the use of magnets. At least 10, 20, 30, 40, 50, 60, 70, 80, 90 or 100% of the excess beads/stochastic barcodes can be removed. At most 10, 20, 30, 40, 50, 60, 70, 80, 90 or 100% of the excess beads/stochastic barcodes can be removed.

In some embodiments, the single-stranded labelled cDNA molecule (i.e., resulting from the reverse transcription reaction) can be attached to the solid support. In some embodiments, the single-stranded labelled cDNA molecule (i.e., resulting from the reverse transcription reaction) may not be attached to the solid support.

In some embodiments, the single-stranded labelled cDNA molecule can be contacted with a second strand synthesis primer of the disclosure. In some embodiments, the second strand synthesis primer can comprise a second universal label (e.g., as described above).

In some embodiments, the second strand synthesis primer can comprise a random multimer sequence. The random multimer sequence can, for example, be at least 1, 2, 3, 4, 5, 6, 7, 8, 9, 10, 11, 12, 13, 14, 15, 16, 17, 18, 19 or 20 or more nucleotides in length. In some embodiments, the random multimer sequence can be at most 1, 2, 3, 4, 5, 6, 7, 8, 9, 10, 11, 12, 13, 14, 15, 16, 17, 18, 19 or 20 or more nucleotides in length. In some embodiments, the random multimer sequence can hybridize to a random location on the single-stranded labelled cDNA.

In some embodiments, the second strand synthesis primer can be extended (e.g., using primer extension) over the length of the first cDNA strand, thereby generating a quasi-symmetric stochastically barcoded nucleic acid. The quasi-symmetric stochastically barcoded nucleic acid can, for example, comprise the sequence of the second strand synthesis primer and the labelled cDNA molecule (e.g., first cDNA strand, i.e., including the sequence of the target-binding region and the stochastic barcode). In this way the quasi-symmetric stochastically barcoded nucleic acid can comprise a universal label at each end of the molecule. In some embodiments, the quasi-symmetric stochastically barcoded nucleic acid can be amplified, for example using polymerase chain reaction and a whole transcriptome amplification primer that bind to the first and second universal labels.

Second Strand Synthesis with No Priming

In some embodiments, the methods of the disclosure generate a second strand off a first strand (e.g., reverse transcription reaction) without the use of an added primer. For example, as described in the methods shown in FIG. 15 second strand synthesis can occur with the use of an RNase, DNA Pol I polymerase, and a ligase. The RNase can nick the mRNA strand hybridized to the first strand generated from the reverse transcription reaction, thereby generating nicked mRNA primers. In some embodiments, the RNase can nick the mRNA strand at one or more specific locations. In some embodiments, the RNase can nick the mRNA strand at non-specific locations. The nicked mRNA primers can, for example, be, or be at least, 5, 10, 15, 20, 25, 30, 35, 40, 45, or 50 or more nucleotides in length. In some embodiments, the nicked mRNA primers can be, or be at most, 5, 10, 15, 20, 25, 30, 35, 40, 45, or 50 or more nucleotides in length.

The nicked mRNA primers can, for example, serve as a starting point for extension of the first strand. Extension can occur with a polymerase (e.g., DNA Pol I). The polymerase can degrade downstream mRNA primers (e.g., according to the Gubler Hoffman method of second strand synthesis). In some embodiments, this method of second strand synthesis can be gene-independent. For example, this method of second strand synthesis may not use a gene-specific primer.

Second Strand Synthesis with a Strand Displacement Polymerase

In some instances, the methods of the disclosure generate a second strand off a first strand (e.g., reverse transcription reaction) without the use of an added primer. For example, as described in the methods shown in FIGS. 16A and 16B, second strand synthesis can occur with the use of an RNase and a strand displacing polymerase. The RNase can nick the mRNA strand hybridized to the first strand generated from the reverse transcription reaction, thereby generating nicked mRNA primers. The RNase can, for example, nick the mRNA strand at one or more specific locations. In some embodiments, the RNase can nick the mRNA strand at non-specific locations. The nicked mRNA primers can be, or be at least, 5, 10, 15, 20, 25, 30, 35, 40, 45, or 50 or more nucleotides in length. The nicked mRNA primers can be, or be at most, 5, 10, 15, 20, 25, 30, 35, 40, 45, or 50 or more nucleotides in length.

The nicked mRNA primers can, for example, serve as a starting point for extension of the first strand. Extension can occur with a strand displacing polymerase (e.g., phi29, Bst DNA Polymerase, Large Fragment, Klenow (Exo-)). The polymerase can extend through a downstream mRNA primer, thereby releasing single-stranded cDNAs, some of which comprise 5' mRNA primer sequences, of varying lengths. The lengths of the second strand can be proportional to the distance from the 3' end where the mRNA was nicked. In some embodiments, this method of second strand synthesis can be gene-independent. For example, this method of second strand synthesis may not use a gene-specific primer.

Third Strand Synthesis

Figure 16A:
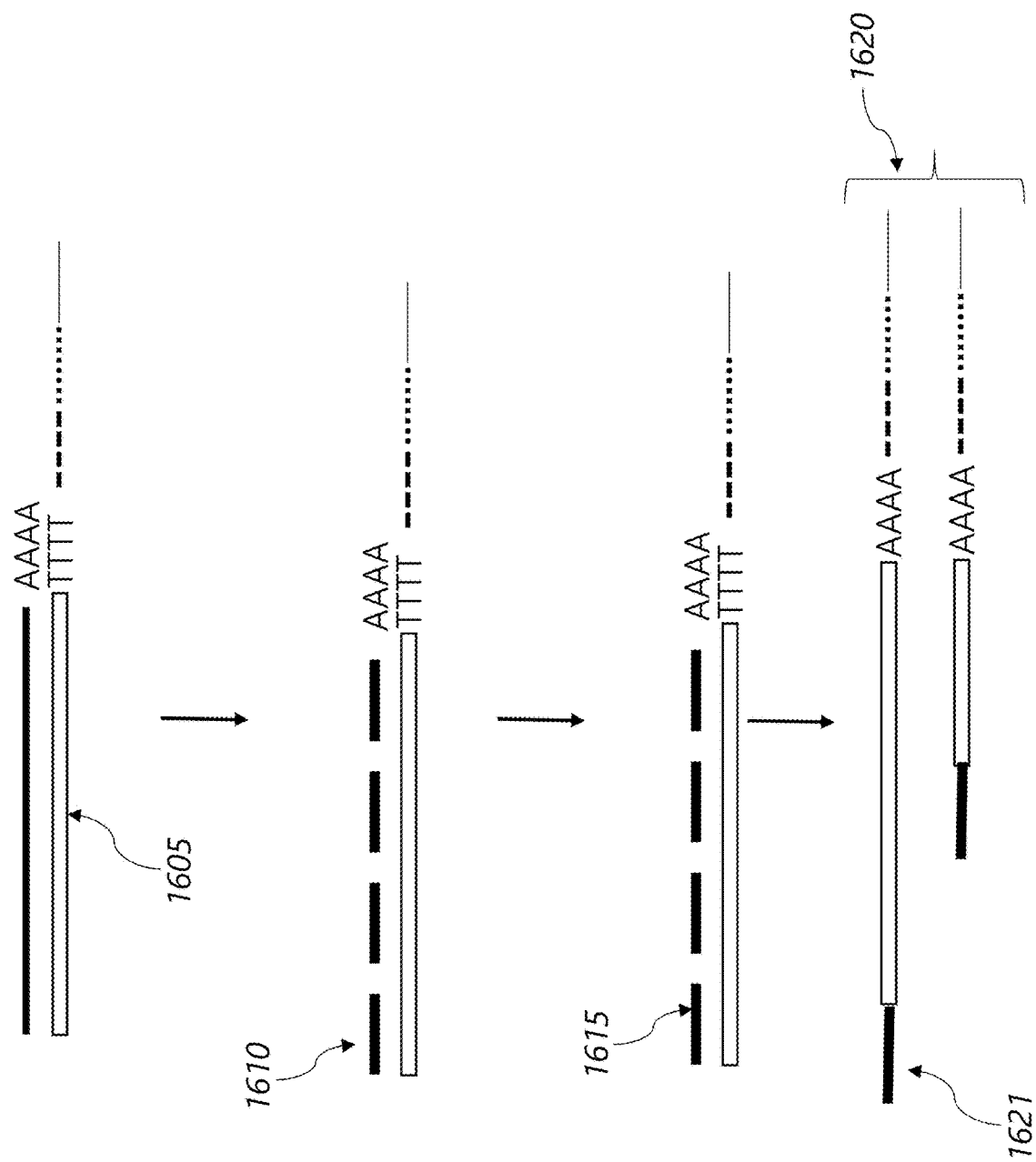
FIGS. 16A and 16B depict an exemplary embodiment of the RNase priming method of the disclosure.
Figure 16B:
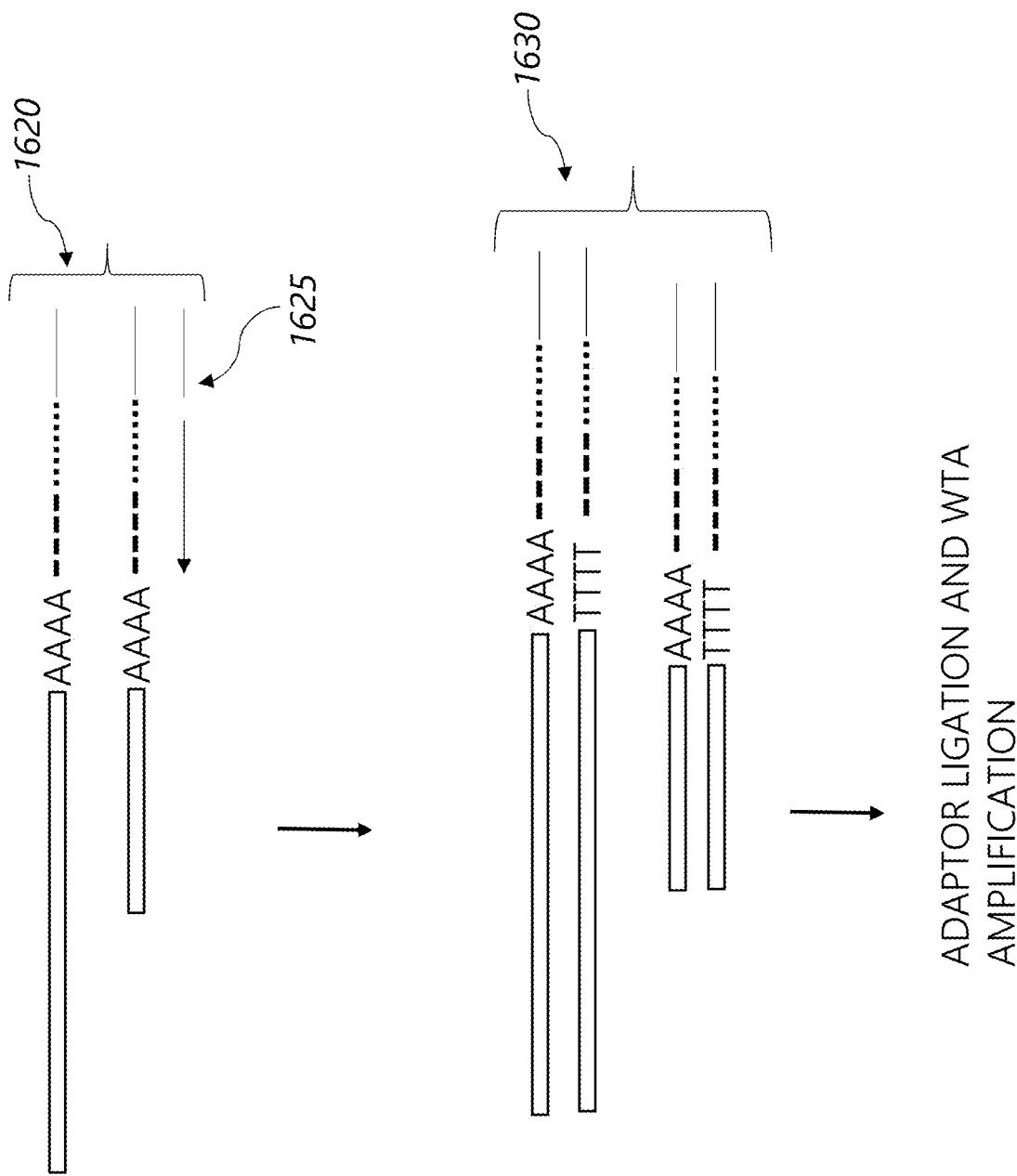

In some embodiments, as disclosed in FIGS. 16A and 16B, a third strand can be generated from the single-stranded second strands generated from the strand displacing polymerase as described above. The third strand can be generated by using a primer. The primer can comprise a universal sequence (e.g., a first universal sequence, i.e., the universal sequence of the stochastic barcode used for labeling the mRNA). The primer can be extended, thereby generating a double-stranded cDNA (e.g., comprising a second and third strand).

Adaptor Ligation

In some embodiments, adaptor ligation can be used to associate stochastic barcodes, e.g., universal label, molecular label, cellular label, spatial label, or any combination thereof, to targets. In some embodiments, adaptors can be ligated to the targets, with or without a stochastic barcode. For example, adaptors can be ligated to a double-stranded cDNA, a mRNA/cDNA hybrid, etc. Adaptors can comprise a first universal primer sequence of the disclosure, a second universal primer sequence of the disclosure, a stochastic barcode of the disclosure, a restriction endonuclease cleavage site, or any combination thereof. In some embodiments, the adaptor comprises a second universal primer sequence of the disclosure and a restriction endonuclease binding site. In some embodiments, an adaptor can be ligated to one end of a nucleic acid molecule, e.g., a double stranded cDNA molecule or an mRNA/cDNA hybrid molecule. In some embodiments, an adaptor can be ligated to the end of a nucleic acid molecule that is not immobilized on a solid support, such as a bead. In some embodiments, both ends of a nucleic acid molecule can be ligated with adaptors that are the same or different. In some embodiments, the nucleic acid molecule can be blunt-ended before the adaptors are legated.

The term "adaptor" can refer to a single stranded, partially double-stranded, or double-stranded oligonucleotide of at least 10, 15, 20 or 25 bases that can be attached to the end of a nucleic acid. Adaptor sequences can be synthesized using for example, priming sites, the complement of a priming site, and recognition sites for endonucleases, common sequences and promoters. The adaptor can be entirely or substantially double stranded. A double stranded adaptor can comprise two oligonucleotides that are at least partially complementary. The adaptor can be phosphorylated or unphosphorylated on one or both strands. The adaptor can have a double stranded section and a single stranded overhang section that is completely or partially complementary to an overhang (e.g., generated by a restriction enzyme, or a polymerase enzyme). The overhang in the adaptor can be, for example, 4 to 8 bases. For example, when DNA is digested with the restriction enzyme EcoRI, the resulting double stranded fragments are flanked at either end by the single stranded overhang 5'-AATT-3', an adaptor that carries a single stranded overhang 5'-AATT-3' can hybridize to the fragment through complementarity between the overhanging regions. This "sticky end" hybridization of the adaptor to the fragment facilitates ligation of the adaptor to the fragment; however, blunt ended ligation is also possible. Blunt ends can be converted to sticky ends using, for example, the exonuclease activity of the Klenow fragment. For example when DNA is digested with PvuII the blunt ends can be converted to a two base pair overhang by incubating the fragments with Klenow in the presence of dTTP and dCTP. Overhangs can also be converted to blunt ends by filling in an overhang or removing an overhang.

Adaptors of the disclosure can be designed such that once attached (e.g., ligated) to the stochastically barcoded nucleic acid, they can be involved in suppression and/or semi-suppression PCR amplification (e.g., the resulting quasi-symmetric stochastically barcoded nucleic acid with the adaptor can undergo suppression and/or semi-suppression PCR). In some embodiments, adaptors of the disclosure can be designed to comprise a stochastic barcode such that the adaptors can be used to stochastically barcode a nucleic acid.

In some embodiments, the adaptor can have a structure that can enhance suppression (suppressive structure of adaptor) or inhibit suppression (permissive structure of adaptor). For example, the adaptor can be tuned, e.g., by changes in its sequence, to affect the level of suppression. The level of suppression can be related to the amount of amplification of artifacts in the sample.

In some embodiments, the equilibrium constant associated with the formation of the suppressive and the permissive structures, and, therefore, the efficiency of suppression of particular DNA fragments during PCR, can be related to, for example, differences in melting temperature of the suppressive and permissive structures, length of the suppression adaptor, and primary structure of the adaptor. If the suppressor sequence portion of the adapter is roughly equal to or longer than the primer binding portion, then the suppressive structure can be preferentially formed due to the higher melting temperatures of the suppressive structure versus the permissive structure. If the suppressor portion is about one half, or less, the length of the primer binding portion, or is absent altogether, then the amplification permissive structure can be formed. The suppressive structure can have a melting temperature at least 0.1%, 0.5%, 1%, 2%, 3%, 4%, 5%, 6%, 7%, 8%, 9%, or 10% or more than the permissive structure. The suppressive structure can have a melting temperature at most 0.1%, 0.5%, 1%, 2%, 3%, 4%, 5%, 6%, 7%, 8%, 9%, or 10% or more than the permissive structure. The suppressive structure can have a melting temperature at least 0.01-fold, 0.05-fold, 0.1-fold, 0.5-fold, or 1-fold or more than the permissive structure. The suppressive structure can have a melting temperature at most 0.01-fold, 0.05-fold, 0.1-fold, 0.5-fold, or 1-fold or more than the permissive structure.

In addition to sequence length, the differences in melting temperatures of the suppressive and permissive structures can be determined by the relative ratio of guanosine and cytidine residues to adenosine and thymidine residues (hereinafter this ratio is referred to as the GC content of the sequence) in the primer binding and suppressor sequence portion of the adapter. For an adapter having a primer binding portion and a suppressor portion of fixed length, the higher the GC content of the suppressor portion, the greater the efficiency of suppression that can be achieved (using the same primer binding portion of the adapter).

In some embodiments, the longer the suppressor portion of the adaptor, the more efficient the suppression when used in conjunction with the same primer binding portion of the adapter. The suppressor portion of the adaptor can be, or be at least, 1, 2, 4, 6, 8, 10, 12, 14, 16, 18, 20, 22, 24, 26, 28, 30, 32, 34, 36, 38, or 40 or more nucleotides in length. The suppressor portion of the adaptor can be, or be at most, 1, 2, 4, 6, 8, 10, 12, 14, 16, 18, 20, 22, 24, 26, 28, 30, 32, 34, 36, 38, or 40 or more nucleotides in length.

In some embodiments, the adaptor does not comprise any sequences that can result in the formation of "hairpins" or other secondary structures which can, for example, prevent adapter ligation and/or primer extension.

In some instances, adaptors of the disclosure can be the adaptors described in FIG. 17. The adaptor can comprise a sequencing primer sequence (e.g., Illumina Read 1 (IR1)) sequence. The WTA primer of the disclosure can hybridize to a subsequence of the sequencing primer sequence 1705.

An adaptor of the disclosure can comprise a suppression sequence 1710 and a restriction enzyme binding site 1715. In some embodiments, the adaptor can be designed such that there is a mismatch between the RT primer sequence and the adaptor, see "*". For example, the number of mismatches can be, or be at least, 1, 2, 3, 4, 5, 6, 7, 8, 9, or 10 or more. In some embodiments, the number of mismatches can be at most 1, 2, 3, 4, 5, 6, 7, 8, 9, or 10 or more. In some embodiments, the number of mismatches is 1. In some embodiments, the number of mismatches is 4. In some embodiments, the suppression sequence can comprise at least 1, 2, 3, 4, 5, 6, 7, 8, 9, or 10 or more nucleotides. In some embodiments, the suppression sequence can comprise at most 1, 2, 3, 4, 5, 6, 7, 8, 9, or 10 or more nucleotides. In some embodiments, a low suppression adaptor can comprise more mismatches with the RT primer sequence, thereby reducing the ability of the pan-handle structure to form, thereby limiting suppression. In some embodiments, a high suppression adaptor can comprise fewer mismatches with the RT primer sequence, thereby increasing the ability of the pan-handle structure to form, thereby increasing suppression.

Adaptors can be ligated to double-stranded cDNAs of the disclosure. Ligation methods can include using T4 DNA Ligase which catalyzes the formation of a phosphodiester bond between juxtaposed 5' phosphate and 3' hydroxyl termini in duplex DNA or RNA with blunt and sticky ends; Taq DNA Ligase which catalyzes the formation of a phosphodiester bond between juxtaposed 5' phosphate and 3' hydroxyl termini of two adjacent oligonucleotides which are hybridized to a complementary target DNA; E. coli DNA ligase which catalyzes the formation of a phosphodiester bond between juxtaposed 5'-phosphate and 3'-hydroxyl termini in duplex DNA containing cohesive ends; and T4 RNA ligase which catalyzes ligation of a 5' phosphoryl-terminated nucleic acid donor to a 3' hydroxyl-terminated nucleic acid acceptor through the formation of a 3' to 5' phosphodiester bond, substrates include single-stranded RNA and DNA as well as dinucleoside pyrophosphates; or any other methods known in the art. Different enzymes generate different overhangs and the overhang of the adaptor can be targeted to ligate to fragments generated by selected restriction enzymes.

In some embodiments, a double stranded adaptor is used and only one strand of the adaptor is ligated to the double-stranded cDNA. Ligation of one strand of an adaptor can be selectively blocked. To block ligation, for example, one strand of the adaptor can be designed to introduce a gap of one or more nucleotides between the 5' end of that strand of the adaptor and the 3' end of the target nucleic acid. Absence of a phosphate from the 5' end of an adaptor can block ligation of that 5' end to an available 3'OH. Ligation of an adaptor to a double-stranded labeled cDNA of the disclosure can result in a quasi-symmetric nucleic acid (e.g., one or more strands of the nucleic acid comprises a first and second universal label, as shown in FIGS. 15A and 15B, 1575).

Figure 15A:
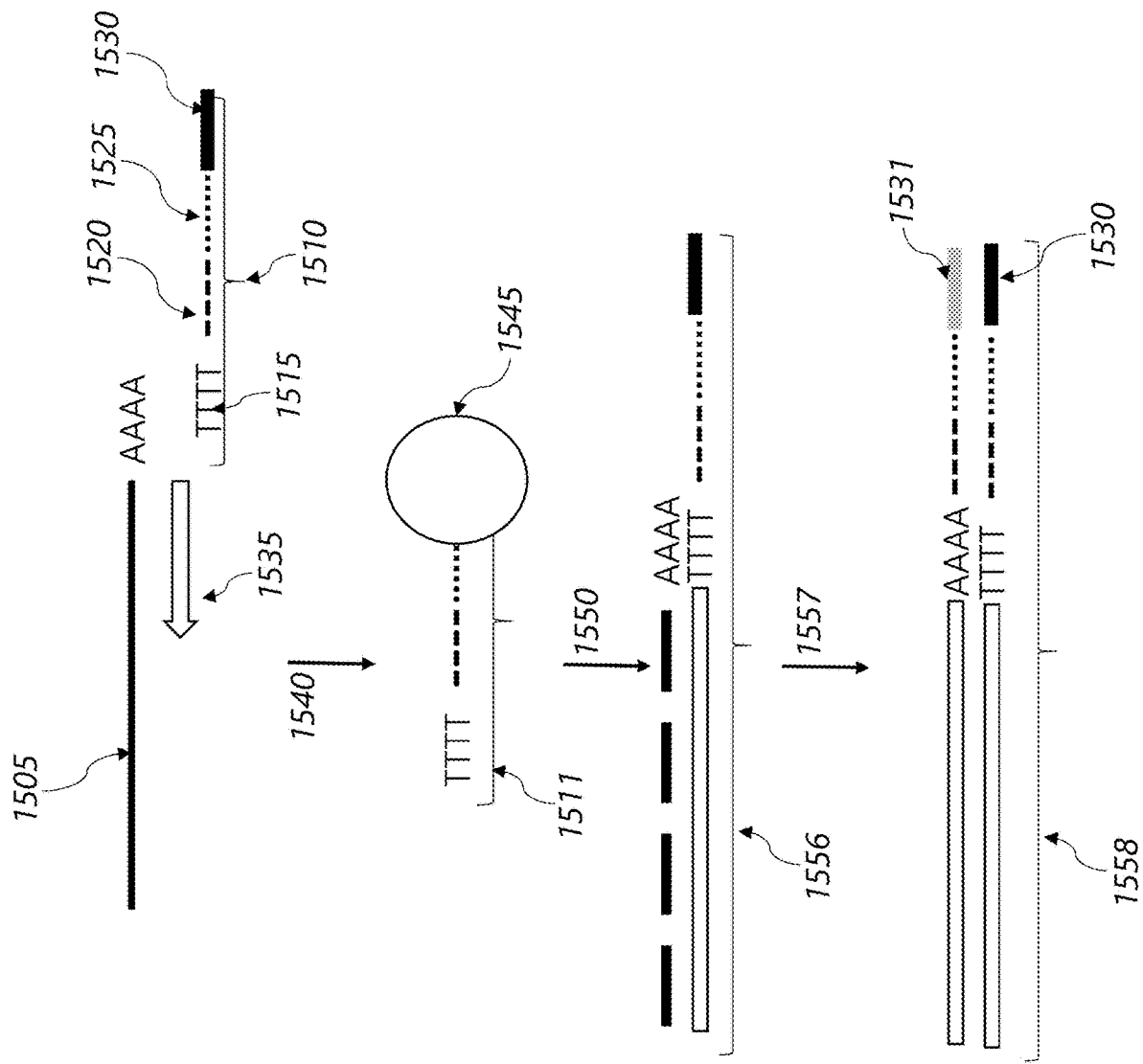
FIGS. 15A and 15B depict an exemplary embodiment of the adaptor ligation method of the disclosure.
Figure 15B:
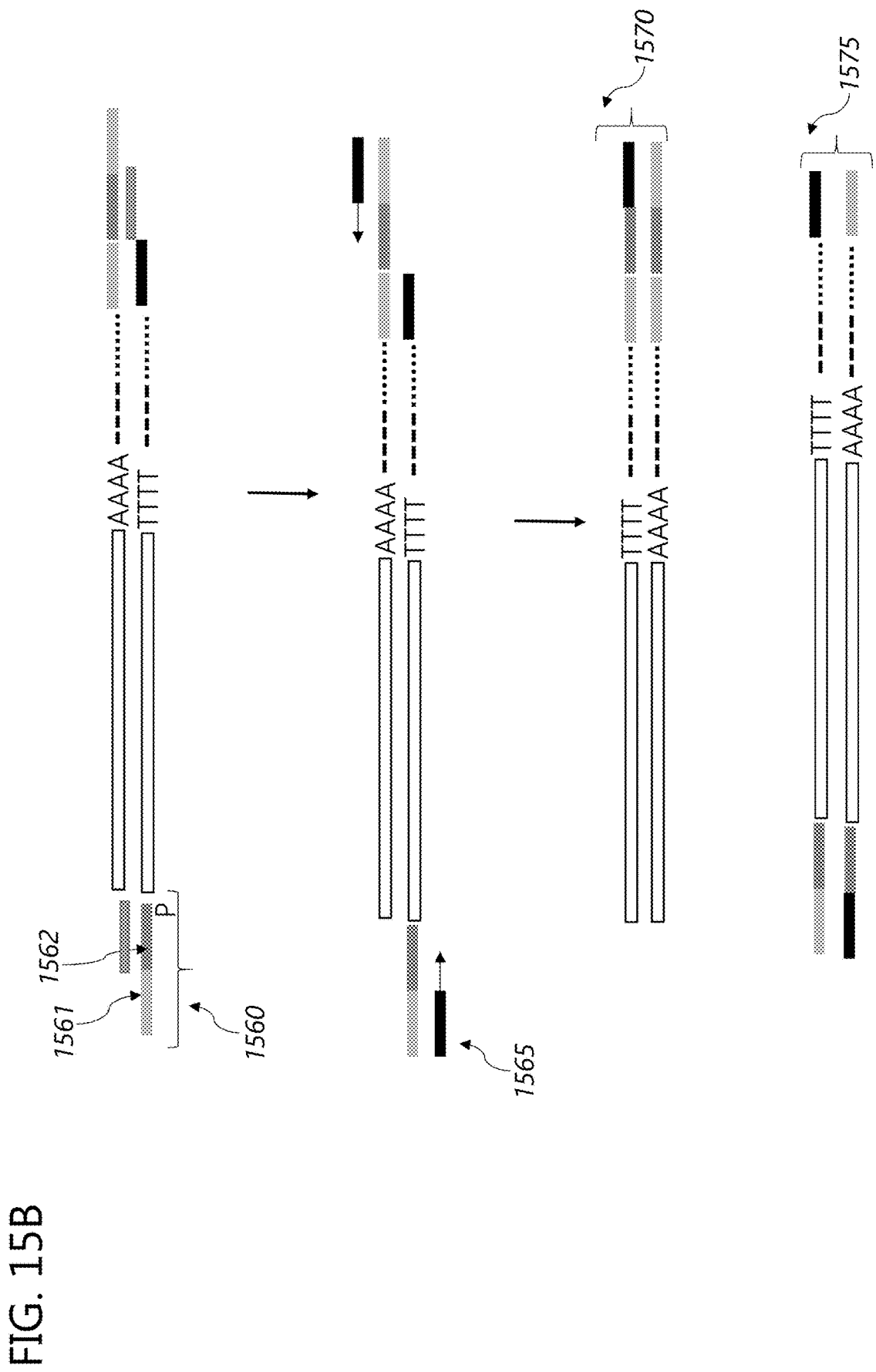

In some embodiments, whole transcriptome amplification can be performed using an adaptor ligation method as described in FIGS. 15A and 15B. A target 1505 can comprise a poly-A tail. A target 1505 can be an mRNA. The target 1505 can be hybridized to a stochastic barcode 1510. The stochastic barcode 1510 can comprise a number of labels. For example, a stochastic barcode 1510 can comprise a target-specific region (e.g., oligo dT for binding to poly-A tails of mRNAs) 1515, a molecular label 1520, a cellular label 1525, and a first universal label 1530. The stochastic barcode can be reverse transcribed 1535 using a reverse transcriptase, thereby generating a labelled-cDNA molecule 1556. Excess stochastic barcodes 1511 can be treated 1540 with a degradation enzyme 1545. The degradation enzyme 1545 can be an exonuclease.

The labelled-cDNA molecule 1556 can undergo second strand synthesis 1557 thereby generating a double-stranded labeled cDNA molecule 1558. Second strand synthesis can be performed by contacting the labelled cDNA molecule-mRNA hybrid with a nicking enzyme (e.g., RNaseH) that can nick the mRNA hybridized to the labelled cDNA molecule 1556, thereby generating nicked mRNA. The nicked mRNA can be used as a primer and extended using a polymerase (e.g., DNA Pol I), thereby incorporating the sequence of the first strand. The polymerase can comprise 5'-3' exonuclease activity. The polymerase can degrade the downstream mRNA nicks that serve as the primers for the second strand synthesis. A ligase can be used to ligate the extended sequences together, thereby generating a second strand (e.g., double-stranded labeled cDNA molecule 1558).

The double-stranded labeled cDNA molecule 1558 can comprise a sequence 1531 that is complementary to the first universal label 1530. The double-stranded labeled cDNA molecule 1558 can be contacted with an adaptor 1560. The adaptor 1560 can be double-stranded. The adaptor 1560 can comprise a restriction endonuclease cleavage site 1562. The adaptor 1560 can comprise a second universal primer sequence 1561 (that is the same as 1531). The adaptor 1560 can comprise a 3' overhang. The adaptor 1560 can comprise a free 5' phosphate (P) which can ligate to the 3' hydroxyl of the double-stranded labelled-cDNA molecule 1558. The adaptor 1560 can ligate to both strands of the double-stranded labelled cDNA molecule 1558.

The product can be amplified using one or more WTA amplification primers 1565. The product can be amplified such that one strand is linearly amplified 1570 and one strand is exponentially amplified 1575. The linearly amplified strand 1570 can comprise the amplifiable universal sequence at one end. The exponentially amplifiable strand 1575 can comprise universal sequences at both ends. The exponentially amplifiable strand 1575 can comprise different universal sequences at both ends, thereby generating a quasi-symmetric stochastically barcoded nucleic acid. The WTA amplified product (e.g., quasi-symmetric stochastically barcoded nucleic acid) 1575 can be subjected to downstream methods of the disclosure such as random priming and/or sequencing.

In some embodiments, the second strand can be synthesized using a strand displacement step. As shown in FIG. 16, an mRNA can be reverse transcribed into a cDNA using a stochastic barcode primer (as shown in FIGS. 15A and 15B), thereby generating a labeled cDNA 1605. The labeled cDNA 1605 can be treated with a nicking enzyme such as RNaseH that can nick the RNA 1610. The nicked RNAs 1610 can serve as primers for extension, thereby copying the sequencing of the labeled cDNA 1605. The nicked RNAs 1610 can be extended with a strand displacing polymerase. The resulting strand displacement fragments 1620 can comprise an RNA end 1621 that was the primer for the extension reaction. The method can include an RNA removal step to remove the RNA from the primer/strand displacement fragments 1620. The stochastic barcode of the strand displacement fragments 1620 can be the complement of the original barcode. The strand displacement fragments 1620 can comprise a blunt end. The strand displacement fragments 1620 can be extended with a nucleic acid 1625 comprising a sequence or a complementary sequence to the original universal sequence of the stochastic barcode, (See FIGS. 15A and 15B) thereby generating a double-stranded whole transcriptome amplification product 1630. The double-stranded whole transcriptome amplification product 1630 can comprise a blunt end or an A-overhang. The double-stranded whole transcriptome amplification product 1630 can be subject to downstream methods of the disclosure such as adaptor ligation (See FIGS. 15A and 15B) and whole transcriptome amplification, which can generate a quasi-symmetric stochastically barcoded nucleic acid of the disclosure.

Adaptor Ligation with Solid Support

In some embodiments, whole transcriptome amplification can be performed using adaptor ligation methods with a solid support, such as beads. As disclosed herein, stochastic barcodes immobilized on a solid support, such as beads, can be used to label a plurality of targets from a sample, such as a single cell. In some embodiments, all the stochastic barcodes on a bead comprise the same cellular label. In some embodiments, the stochastic barcodes on a bead comprise different molecular labels.

An exemplary embodiment of adaptor ligation with solid support is shown in FIGS. 31A-31D. In FIGS. 31A-31D, a target mRNA comprises a poly-A tail. The target can be hybridized to a stochastic barcode immobilized on a bead 3125. The stochastic barcode can comprise a number of labels. For example, a stochastic barcode can comprise a target-specific region (e.g., oligo dT for binding to poly-A tails of mRNAs) 3120, a molecular label 3115, a cellular label 3110, and a first universal label 3105. The stochastic barcode can be reverse transcribed 3130 using a reverse transcriptase, thereby generating a labelled-cDNA molecule 3135 that is immobilized on the bead. Excess stochastic barcodes can be removed 3140 with a degradation enzyme. The degradation enzyme can be an exonuclease.

The labelled-cDNA molecule 3135 can undergo second strand synthesis 3150 thereby generating a double-stranded labeled cDNA molecule 3155. Second strand synthesis can be performed by contacting the labelled cDNA molecule-mRNA hybrid with a nicking enzyme (e.g., RNaseH) that can nick the mRNA hybridized to the labelled cDNA molecule 3135, thereby generating nicked mRNA. The nicked mRNA can be used as a primer and extended using a polymerase (e.g., DNA Pol I), thereby incorporating the sequence of the first strand. The polymerase can comprise 5'-3' exonuclease activity. The polymerase can degrade the downstream mRNA nicks that serve as the primers for the second strand synthesis. A ligase can be used to ligate the extended sequences together, thereby generating a second strand (e.g., double-stranded labeled cDNA molecule 3155).

The double-stranded labeled cDNA molecule 3155 can be end-polished at step 3160 and A-tailed 3165 at the free end to prepare for adaptor ligation. The double-stranded labeled cDNA molecule 3155 can be contacted with an adaptor 3170. The adaptor can be single stranded, partially double-stranded, or fully double-stranded. The adaptor can comprise a restriction site 3185, for example, an AsiSI site. The adaptor can comprise a 5' overhang which can comprise a second universal primer sequence 3175. The adaptor can comprise a free 5' phosphate (P) which can ligate to the 3' hydroxyl of the double-stranded labelled-cDNA molecule 3155. The adaptor can ligate to both strands of the double-stranded labelled cDNA molecule 3155.

Optionally, the ligation product can be used as a template for third strand synthesis 3190. A CBO40 primer 3195 can be used to hybridize to the second universal primer sequence 3175 to synthesize the third strand. The third strand synthesis product can be WTA amplified using one or more WTA amplification primers, for example, a CBO40 primer, and a DNA polymerase, for example, KAPA Fast2G. The WTA amplified product can be subjected to downstream methods of the disclosure such as random priming and/or sequencing.

Adaptor Ligation Using a Transposome

In some embodiments, the adaptor ligation step can be accomplished using a transposome-based approach. Transposome-based adaptor ligation can be used to label targets in a sample in a variety of ways. For example, transposome-based adaptor ligation can be used to label targets that comprise stochastic barcodes, which can be immobilized on a solid support, on one end. In some embodiments, transposome-based adaptor ligation can be used to label targets that comprise no stochastic barcodes on either end. Therefore, transposome-based adaptor ligation can be used to stochastically label targets on one or both ends. In some embodiments, transposome-based adaptor ligation can be used to label the targets with a universal label, a molecular label, a cellular label, a spatial label, or any combination thereof. In some embodiments, two adaptors can be ligated to a target on both ends, which can be the same or different.

In some embodiments, the targets can be double-stranded cDNA molecules produced by reverse transcription and second strand synthesis methods as disclosed herein. In some embodiments, no second strand synthesis is needed before adding the adaptor loaded transposase to the targets, which can be mRNA/cDNA hybrids. In some embodiments, the transposome can randomly fragment the targets. For example, the transposome can fragment the targets into fragments having a size that is, is about, is less than, is more than, 20 nt, 30 nt, 40 nt, 50 nt, 60 nt, 70 nt, 80 nt, 90 nt, 100 nt, 200 nt, 300 nt, 400 nt, 500 nt, or a range between any two of the above values.

In some embodiments, targets that are immobilized on a solid support can be ligated using a transposome, so that the solid support can be used to remove fragments that are not immobilized on the solid support. In some embodiments, targets that are immobilized on a solid support can be ligated using a transposome, so that the solid support can be used to remove fragments that are immobilized on the solid support.

The adaptors disclosed herein can be loaded into a transposase, which is added to the targets, such as stochastically barcoded molecules. In some embodiments, the transposase can be the Tn5 transposase, or a hyperactive derivative thereof, as disclosed in Adey et al., Genome Biology (2010) 11.R119, the content of which is hereby incorporated by reference in its entirety. In some embodiments, the adaptor can comprise a wild-type transposon DNA sequence, or derivative thereof.

As shown in FIGS. 32A-32E, a target mRNA can comprise a poly-A tail. The target can be hybridized to a stochastic barcode immobilized on a bead 3225. The stochastic barcode can comprise a number of labels. For example, a stochastic barcode can comprise a target-specific region (e.g., oligo dT for binding to poly-A tails of mRNAs) 3220, a molecular label 3215, a cellular label 3210, and a first universal label 3205. The stochastic barcode can be reverse transcribed 3230 using a reverse transcriptase, thereby generating a labelled-cDNA molecule 3235 that is immobilized on the bead. Excess stochastic barcodes can be removed 3240 with a degradation enzyme. The degradation enzyme can be an exonuclease.

The labelled-cDNA molecule 3235 can undergo second strand synthesis 3250 thereby generating a double-stranded labeled cDNA molecule 3255. Second strand synthesis can be performed by contacting the labelled cDNA molecule-mRNA hybrid with a nicking enzyme (e.g., RNaseH) that can nick the mRNA hybridized to the labelled cDNA molecule 3135, thereby generating nicked mRNA. The nicked mRNA can be used as a primer and extended using a polymerase (e.g., DNA Pol I), thereby incorporating the sequence of the first strand. The polymerase can comprise 5'-3' exonuclease activity. The polymerase can degrade the downstream mRNA nicks that serve as the primers for the second strand synthesis. A ligase can be used to ligate the extended sequences together, thereby generating a second strand (e.g., double-stranded labeled cDNA molecule 3255).

The double-stranded labeled cDNA molecule 3255 can be treated with a transposome 3260 (e.g., Nextera or Nextera XT from Illumina) for adaptor ligation. The double-stranded labeled cDNA molecule 3155 can be contacted with a transposome 3265 that is loaded with an adaptor 3270. The double-stranded labeled cDNA molecule 3155 can be contacted with a second transposome 3275 that is loaded with a second adaptor 3280. The transposome can fragment 3290 the double-stranded labeled cDNA molecule 3255 and ligate the double stranded adaptor. The double stranded adaptor can comprise a universal primer binding sequence, for example, a transposase primer. In some embodiments, the transposome-based adaptor ligation can be conducted on an mRNA-cDNA hybrid. Therefore, no second strand synthesis is needed.

The adaptor ligated product can be amplified 3295 using one or more library amplification primers, for example, an ILR2 primer and a transposase primer to generate an indexed library. A second amplification step can be used to finish creating a sequencing library using full-length P5 and P7 primers. P5 and P7 primers are used in generating sequencing libraries for the HiSeq and MiSeq platforms by Illumina.

Adaptor Ligation by Template Switching

Figure 21:
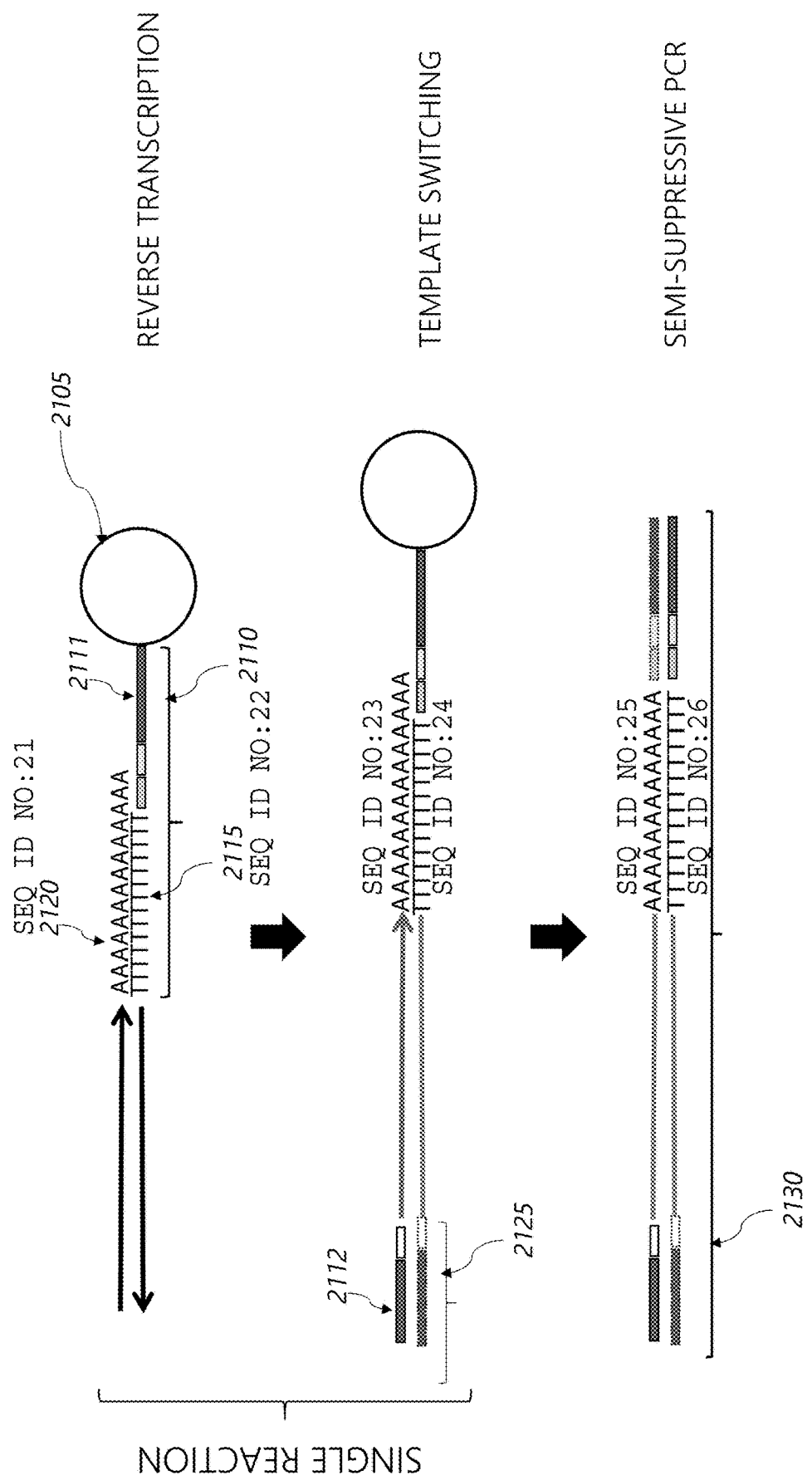
FIG. 21 shows a schematic illustrating an exemplary embodiment of the whole transcriptome amplification method of the disclosure using template switching.

In some embodiments, the disclosure provides for methods of adaptor addition to a stochastically barcoded molecule using template switching. As shown in FIG. 21, an mRNA 2120 can be contact to a stochastic barcode 2110 that can be conjugated to a solid support (e.g., bead) 2105. The stochastic barcode 2110 can comprise any label of the disclosure (e.g., a molecular label, a cellular label, and a universal label 2111) and a target-specific region 2115. The mRNA 2120 can be reverse transcribed into a cDNA. An adaptor 2125 (e.g., adaptor of the disclosure) can be added to the cDNA using template switching. Second strand synthesis can occur on the adaptor-added cDNA, thereby resulting in a double-stranded cDNA 2130 that can undergo semi-suppressive PCR. The double-stranded cDNA 2130 can undergo semi-suppressive PCR because the adaptor can comprise a sequence 2112 that is at least partially complementary to the universal label 2111. The double-stranded cDNA 2130 can be referred to as a quasi-symmetric stochastically barcoded nucleic acid.

Amplification with Whole Transcriptome Amplification Primer

The stochastically barcoded nucleic acid (e.g., comprising a homopolymer tail or an adaptor, generated from random priming, or generated from the non-priming second strand and third strand synthesis or adaptor ligation methods of the disclosure) can be amplified using a whole transcriptome amplification primer. In some embodiments, the whole transcriptome amplification primer can be, or be at least, 1, 2, 3, 4, 5, 6, 7, 8, 9, 10, 11, 12, 13, 14, 15, 16 17, 18, 19, 20, 21, 22, 23, 24, 25, 26, 27, 28, 29, or 30 or more nucleotides in length. In some embodiments, the whole transcriptome amplification primer can be at most 1, 2, 3, 4, 5, 6, 7, 8, 9, 10, 11, 12, 13, 14, 15, 16 17, 18, 19, 20, 21, 22, 23, 24, 25, 26, 27, 28, 29, or 30 or more nucleotides in length. In some embodiments, the whole transcriptome amplification primer can bind to at least 1, 2, 3, 4, 5, 6, 7, 8, 9, 10, 11, 12, 13, 14, 15, 16 17, 18, 19, 20, 21, 22, 23, 24, 25, 26, 27, 28, 29, or 30 or more nucleotides of the first and second universal labels. In some embodiments, the whole transcriptome amplification primer can bind to at most 1, 2, 3, 4, 5, 6, 7, 8, 9, 10, 11, 12, 13, 14, 15, 16 17, 18, 19, 20, 21, 22, 23, 24, 25, 26, 27, 28, 29, or 30 or more nucleotides of the first and second universal labels. The whole transcriptome amplification primer may not bind to the entirety of the first and/or second universal labels. In some instances, the whole transcriptome amplification primer binds to 18 nucleotides of the first and/or second universal labels.

Amplification with a whole transcriptome amplification primer can generate a whole transcriptome amplicon. The whole transcriptome amplicon can be quasi-symmetric. The whole transcriptome amplicon can be stored (e.g., at −20° C., −80° C.). The whole transcriptome amplicons can represent an immortalized library of transcripts from a sample (e.g. single cell).

Amplification

One or more nucleic acid amplification reactions can be performed to create multiple copies of the stochastically barcoded nucleic acid (e.g., comprising a homopolymer tail or an adaptor, generated from random priming, or generated from the non-priming second strand and third strand synthesis or adaptor ligation methods of the disclosure). Amplification can be performed in a multiplexed manner, wherein multiple target nucleic acid sequences are amplified simultaneously. The amplification reaction can be used to add sequencing adaptors to the nucleic acid molecules. The amplification reactions can comprise amplifying at least a portion of a sample label, if present. The amplification reactions can comprise amplifying at least a portion of the cellular and/or molecular label. The amplification reactions can comprise amplifying at least a portion of a sample tag, a cellular label, a spatial label, a molecular label, a target nucleic acid, or a combination thereof. The amplification reactions can comprise amplifying at least 1%, 2%, 3%, 4%, 5%, 6%, 7%, 8%, 9%, 10%, 15%, 20%, 25%, 30%, 35%, 40%, 45%, 50%, 55%, 60%, 65%, 70%, 75%, 80%, 85%, 90%, 95%, 97%, or 100% of the plurality of nucleic acids in a sample, such as a single cell. The method can further comprise conducting one or more cDNA synthesis reactions to produce one or more cDNA copies of target-barcode molecules comprising a sample label, a cellular label, a spatial label, and/or a molecular label.

In some embodiments, amplification can be performed using a polymerase chain reaction (PCR). As used herein, PCR can refer to a reaction for the in vitro amplification of specific DNA sequences by the simultaneous primer extension of complementary strands of DNA. As used herein, PCR can encompass derivative forms of the reaction, including but not limited to, RT-PCR, real-time PCR, nested PCR, quantitative PCR, multiplexed PCR, digital PCR, and assembly PCR.

Amplification of the labeled nucleic acids can comprise non-PCR based methods. Examples of non-PCR based methods include, but are not limited to, multiple displacement amplification (MDA), transcription-mediated amplification (TMA), whole transcriptome amplification (WTA), whole genome amplification (WGA), nucleic acid sequence-based amplification (NASBA), strand displacement amplification (SDA), real-time SDA, rolling circle amplification, or circle-to-circle amplification. Other non-PCR-based amplification methods include multiple cycles of DNA-dependent RNA polymerase-driven RNA transcription amplification or RNA-directed DNA synthesis and transcription to amplify DNA or RNA targets, a ligase chain reaction (LCR), and a QP replicase (QP) method, use of palindromic probes, strand displacement amplification, oligonucleotide-driven amplification using a restriction endonuclease, an amplification method in which a primer is hybridized to a nucleic acid sequence and the resulting duplex is cleaved prior to the extension reaction and amplification, strand displacement amplification using a nucleic acid polymerase lacking 5' exonuclease activity, rolling circle amplification, and ramification extension amplification (RAM). In some embodiments, the amplification may not produce circularized transcripts.

Suppression PCR can be used for amplification methods of the disclosure. Suppression PCR can refer to the selective exclusion of molecules less than a certain size flanked by terminal inverted repeats, due to their inefficient amplification when the primer(s) used for amplification correspond(s) to the entire repeat or a fraction of the repeat. The reason for this can lie in the equilibrium between productive PCR primer annealing and nonproductive self-annealing of the fragment's complementary ends. At a fixed size of a flanking terminal inverted repeat, the shorter the insert, the stronger the suppression effect and vice versa. Likewise, at a fixed insert size, the longer the terminal inverted repeat, the stronger the suppression effect.

Suppression PCR can use adapters that are ligated to the end of a DNA fragment prior to PCR amplification. Upon melting and annealing, single-stranded DNA fragments having self-complementary adapters at the 5'- and 3'-ends of the strand can form suppressive "tennis racquet" shaped structures that suppress amplification of the fragments during PCR.

In some embodiments, the methods disclosed herein further comprise conducting a polymerase chain reaction on the labeled nucleic acid (e.g., labeled-RNA, labeled-DNA, labeled-cDNA) to produce a stochastically labeled-amplicon. The labeled-amplicon can be double-stranded molecule. The double-stranded molecule can comprise a double-stranded RNA molecule, a double-stranded DNA molecule, or a RNA molecule hybridized to a DNA molecule. One or both of the strands of the double-stranded molecule can comprise a sample label, a spatial label, a cellular label, and/or a molecular label. The stochastically labeled-amplicon can be a single-stranded molecule. The single-stranded molecule can comprise DNA, RNA, or a combination thereof. The nucleic acids of the disclosure can comprise synthetic or altered nucleic acids.

Amplification can comprise use of one or more non-natural nucleotides. Non-natural nucleotides can comprise photolabile or triggerable nucleotides. Examples of non-natural nucleotides can include, but are not limited to, peptide nucleic acid (PNA), morpholino and locked nucleic acid (LNA), as well as glycol nucleic acid (GNA) and threose nucleic acid (TNA). Non-natural nucleotides can be added to one or more cycles of an amplification reaction. The addition of the non-natural nucleotides can be used to identify products as specific cycles or time points in the amplification reaction.

Conducting the one or more amplification reactions can comprise the use of one or more primers. The one or more primers can comprise at least 1, 2, 3, 4, 5, 6, 7, 8, 9, 10, 11, 12, 13, 14, or 15 or more nucleotides. The one or more primers can comprise at least 1, 2, 3, 4, 5, 6, 7, 8, 9, 10, 11, 12, 13, 14, or 15 or more nucleotides. The one or more primers can comprise less than 12-15 nucleotides. The one or more primers can anneal to at least a portion of the plurality of stochastically labeled targets. The one or more primers can anneal to the 3' end or 5' end of the plurality of stochastically labeled targets. The one or more primers can anneal to an internal region of the plurality of stochastically labeled targets. The internal region can be, or be at least about, 50, 100, 150, 200, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 650, 700, 750, 800, 850, 900 or 1000 nucleotides from the 3' ends the plurality of stochastically labeled targets. The one or more primers can comprise a fixed panel of primers. The one or more primers can comprise at least one or more custom primers. The one or more primers can comprise at least one or more control primers. The one or more primers can comprise at least one or more gene-specific primers.

The one or more primers can comprise any universal primer of the disclosure. The universal primer can anneal to a universal primer binding site. The one or more custom primers can anneal to a first sample label, a second sample label, a spatial label, a cellular label, a molecular label, a target, or any combination thereof. The one or more primers can comprise a universal primer and a custom primer. The custom primer can be designed to amplify one or more targets. The targets can comprise a subset of the total nucleic acids in one or more samples. The targets can comprise a subset of the total stochastically labeled targets in one or more samples. The one or more primers can comprise at least 96 or more custom primers. The one or more primers can comprise at least 960 or more custom primers. The one or more primers can comprise at least 9600 or more custom primers. The one or more custom primers can anneal to two or more different labeled nucleic acids. The two or more different labeled nucleic acids can correspond to one or more genes.

Any amplification scheme can be used in the methods of the present disclosure. For example, in one scheme, the first round PCR can amplify molecules (e.g., attached to the bead) using a gene specific primer and a primer against the universal Illumina sequencing primer 1 sequence. The second round of PCR can amplify the first PCR products using a nested gene specific primer flanked by Illumina sequencing primer 2 sequence, and a primer against the universal Illumina sequencing primer 1 sequence. The third round of PCR adds P5 and P7 and sample index to turn PCR products into an Illumina sequencing library. Sequencing using 150 bp×2 sequencing can reveal the cell label and molecular index on read 1, the gene on read 2, and the sample index on index 1 read.

Amplification can be performed in one or more rounds. In some instances there are multiple rounds of amplification. Amplification can comprise two or more rounds of amplification. The first amplification can be an extension off X' to generate the gene specific region. The second amplification can occur when a sample nucleic hybridizes to the newly generated strand.

In some embodiments hybridization does not need to occur at the end of a nucleic acid molecule. In some embodiments a target nucleic acid within an intact strand of a longer nucleic acid is hybridized and amplified. For example a target within a longer section of genomic DNA or mRNA. A target can be more than 50 nt, more than 100 nt, or more that 1000 nt from an end of a polynucleotide.

Library Preparation

The disclosure provides for methods for library preparation. In some embodiments, the stochastically barcoded nucleic acid (e.g., comprising a homopolymer tail or an adaptor, generated from random priming, or generated from the non-priming second strand and third strand synthesis or adaptor ligation methods of the disclosure) and/or the whole transcriptome amplicons therefrom, or the quasi-symmetric stochastically barcoded nucleic acid and/or the whole transcriptome amplicons therefrom, can be used for library preparation. In some instances, the stochastically barcoded nucleic acid (e.g., comprising a homopolymer tail or an adaptor, generated from random priming, or generated from the non-priming second strand and third strand synthesis or adaptor ligation methods of the disclosure) and/or the whole transcriptome amplicons therefrom, or the quasi-symmetric stochastically barcoded nucleic acid and/or the whole transcriptome amplicons (e.g., resulting from whole transcriptome amplification of the quasi-symmetric stochastically barcoded nucleic acid) can comprise a restriction endonuclease cleavage site. Cleavage of the restriction endonuclease cleavage site can occur with a restriction endonuclease as disclosed herein. Treatment with a restriction endonuclease can result in at least 10, 20, 30, 40, 50, 60, 70, 80, 90 or 100% cleavage of the restriction site. Treatment with a restriction endonuclease can result in at most 10, 20, 30, 40, 50, 60, 70, 80, 90 or 100% cleavage of the restriction site. Cleavage of the quasi-symmetric stochastically barcoded nucleic acid and/or the whole transcriptome amplicons can represent a first mechanism for breaking the symmetry of the quasi-symmetric stochastically barcoded nucleic acid. Cleavage can result in an asymmetric stochastically barcoded nucleic acid and/or an asymmetric whole transcriptome amplicon (these terms, as used herein, can be used interchangeably). The quasi-symmetric stochastically barcoded nucleic acid and/or amplicon of the quasi-symmetric stochastically barcoded nucleic acid may not be cleaved.

The stochastically barcoded nucleic acid (e.g., comprising a homopolymer tail or an adaptor, generated from random priming, or generated from the non-priming second strand and third strand synthesis or adaptor ligation methods of the disclosure) and/or the whole transcriptome amplicons therefrom, or the asymmetric stochastically barcoded nucleic acid, quasi-symmetric stochastically barcoded nucleic acid and/or amplicon (e.g., uncleaved amplicon, i.e., amplicon of the quasi-symmetric stochastically barcoded nucleic acid) can be subjected to random priming. In some embodiments, a degenerate primer comprising a random multimer sequence and a third universal label can be contacted to the stochastically barcoded nucleic acid and/or amplicon. For example, the random multimer sequence can be, or be at least, 1, 2, 3, 4, 5, 6, 7, 8, 9, 10, 11, 12, 13, 14, 15, 16, 17, 18, 19 or 20 or more nucleotides in length. In some embodiments, the random multimer sequence can be at most 1, 2, 3, 4, 5, 6, 7, 8, 9, 10, 11, 12, 13, 14, 15, 16, 17, 18, 19 or 20 or more nucleotides in length. The random multimer sequence can hybridize to a random location on the stochastically barcoded nucleic acid and/or amplicon.

The third universal label of the primer oligonucleotide can be identical to the first and/or second universal labels of the disclosure. The third universal label of the primer oligonucleotide can be different from the first and/or second universal labels of the disclosure. The third universal label of the primer oligonucleotide can differ from the first and/or second universal labels by at least 1, 2, 3, 4, 5, 6, 7, 8, 9, or 10 or more nucleotides. The third universal label of the primer oligonucleotide can differ from the first and/or second universal labels by at most 1, 2, 3, 4, 5, 6, 7, 8, 9, or 10 or more nucleotides. The third universal label can comprise a sequencing primer binding site. For example, the first and/or second universal labels can comprise a first sequencing primer binding site (e.g., Illumina read 2 primer). The third universal label can comprise a second sequencing primer binding site (e.g., Illumina read 1 primer).

The random multimer can hybridize to either the sense and/or antisense strand of the stochastically barcoded nucleic acid and/or amplicon. The degenerate primer can be extended (e.g., with primer extension), thereby generating 3' and 5' read products (e.g., products that can generate 3' and 5' reads on a sequencer). 3' and 5' read products can be referred to as asymmetric read products. Some of the read products can comprise the sequence of the target nucleic acid, the stochastic barcode, and the first universal label (e.g., the 3' read products). Some of the polynucleotide products can comprise the sequence of the target nucleic acid and the second universal label (and the restriction cleavage site, if cleavage was not efficient), (e.g., 5' read products).

The read products can be amplified with sequencing library amplification primers. Sequencing library amplification primers can refer to primers used for addition of sequences that can be used in sequencing reactions (e.g., sequencing flow cell primers). A first primer of the sequencing library amplification primers can hybridize to the third universal label (e.g., on the degenerate primer used in random priming). A second primer of the sequencing library amplification primers can hybridize to the first universal label. The second primer may not be able to hybridize to the second universal label (e.g., because of the difference in sequence between the first universal label and the second universal label). In some embodiments, the 5' read product may not be amplified by the first sequencing library amplification primer. In some embodiments, the 5' read product can be amplified by the first sequencing library amplification primer less efficiently. In some embodiments, the 5' read product can be amplified at least 10, 20, 30, 40, 50, 60, 70, 80, 90, or 100% less efficiently than the 3' read product. In some embodiments, the 5' read product can be amplified at most 10, 20, 30, 40, 50, 60, 70, 80, 90, or 100% less efficiently than the 3' read product. In some embodiments, the 3' read product can be amplified at least 1, 2, 3, 4, 5, 6, 7, 8, 9, 10, 15, 20, 225, 30, 35, or 40 or more fold more than the 5' read product. In some embodiments, the 3' read product can be amplified at most 1, 2, 3, 4, 5, 6, 7, 8, 9, 10, 15, 20, 225, 30, 35, or 40 or more fold more than the 5' read product. In some embodiments, the second universal label can be a second mechanism for breaking the symmetry of the quasi-symmetric stochastically barcoded nucleic acid (e.g., read products from only one side of the quasi-symmetric stochastically barcoded nucleic acid may be preferentially made).

The sequence of the read products can be determined (e.g., with a sequencing reaction). Reads from the sequencing reaction can preferentially map to the 3' read product. In some embodiments, the number of reads of the 3' read product can be, or be at least, 1, 2, 3, 4, 5, 6, 7, 8, 9, 10, 15, 20, 25, 30, 35, or 40 or more fold more than the reads from the 5' product. In some embodiments, the number of reads of the 3' read product can be at most 1, 2, 3, 4, 5, 6, 7, 8, 9, 10, 15, 20, 25, 30, 35, or 40 or more fold more than the reads from the 5' product. In some embodiments, the 3' products comprising the stochastic barcode (e.g., 3' end) can be used to estimate the number of distinct target nucleic acids in the sample by counting the unique stochastic barcodes on the products.

In some embodiments, the read products can be prepared for a sequencing reaction. For example, the read products can be fragmented for adaptor ligation. Fragmentation can include fragmentation using a mechanical (Covaris focused electroacoustic, Nebulizer, sonication, vortex) or enzymatic (e.g. Fragmentase) fragmentation. Fragments can be any length. For example, fragments can be from 1 to 3,000,000 nucleotides in length.

Figure 27:
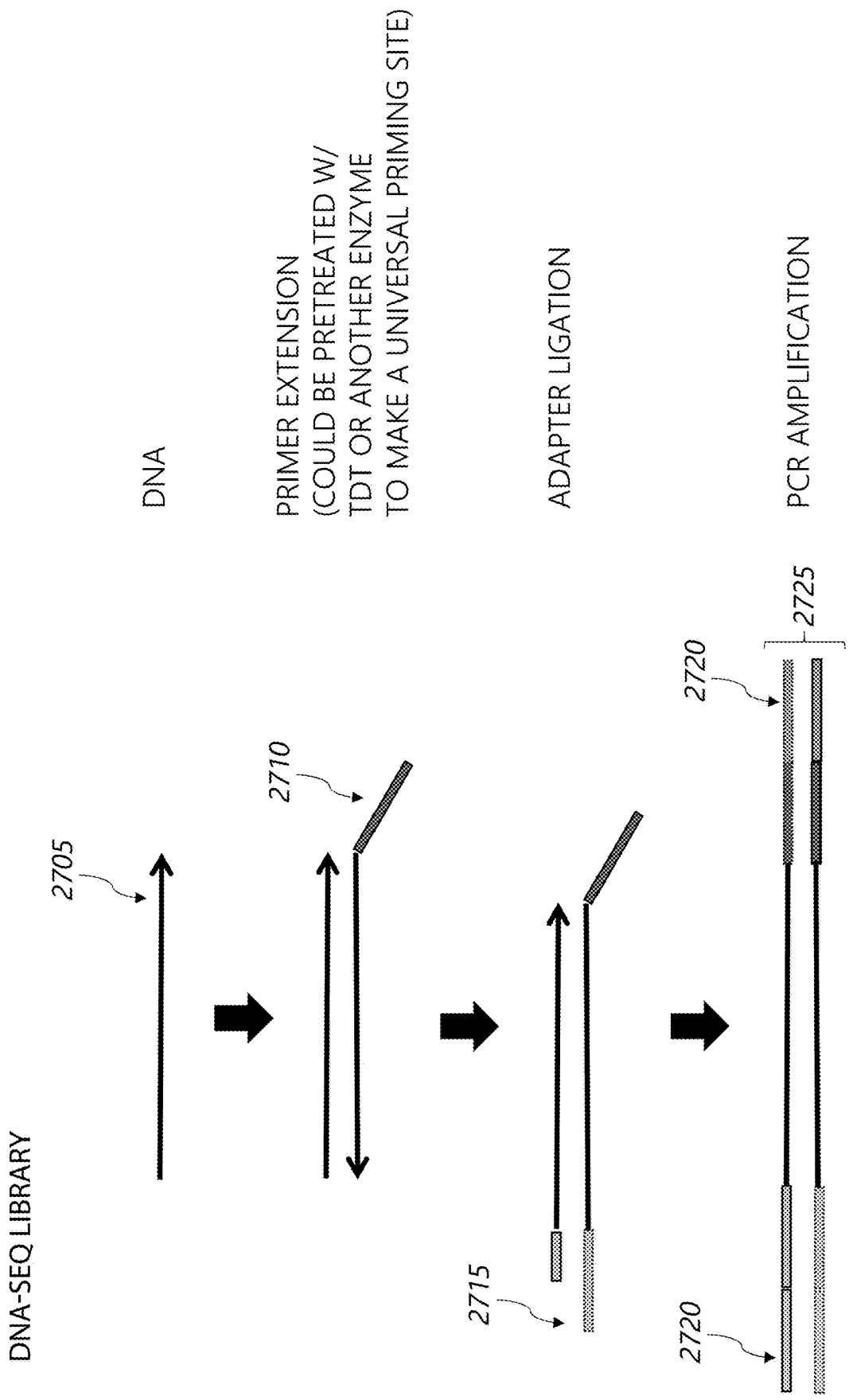
FIG. 27 illustrates an exemplary embodiment of DNA-seq library preparation using the adaptor ligation method of the disclosure.

In some embodiments, the disclosure provides for library preparation methods that may result in an asymmetric double-stranded cDNA (e.g., may not result in a quasi-symmetric stochastically barcoded nucleic acid, e.g., have ends that comprise different sequences, e.g., may not undergo suppressive PCR). As shown in FIGS. 26 and 27, a nucleic acid (e.g., RNA, mDNA, DNA) can be reverse transcribed, and copied, or duplicated into a double-stranded cDNA. The reverse transcription or primer extension event (depending on if the starting material is RNA or DNA, respectively), can be performed with a primer that comprises a first sequence. The first sequence can, for example, comprise at least a portion of a first sequencing primer sequence (e.g., Illumina Read 1). In some embodiments, the first sequence can comprise at least 10, 20, 30, 40, 50, 60, 70, 80, 90, or 100% of the sequencing primer sequence. In some embodiments, the first sequence can comprise at most 10, 20, 30, 40, 50, 60, 70, 80, 90, or 100% of the sequencing primer sequence.

The double-stranded cDNA comprising the first sequencing can be contacted with adaptors. The adaptors can be double stranded. The adaptors can be single-stranded. The adaptors can ligate to the 3' ends of the double-stranded cDNA. The adaptors can ligate to the 5' ends of the double-stranded cDNA. One strand of a double-stranded adaptor can ligate to the 3' end of one strand of the double-stranded cDNA.

The adaptors can comprise a second sequence. The second sequence can comprise at least a portion of a second sequencing primer sequence (e.g., Illumina Read 2). In some embodiments, the second sequence can comprise at least 10, 20, 30, 40, 50, 60, 70, 80, 90, or 100% of the sequence of the flow cell sequence. In some embodiments, the second sequence can comprise at most 10, 20, 30, 40, 50, 60, 70, 80, 90, or 100% of the sequence of the flow cell sequence.

The adaptor ligated double-stranded cDNA can be amplified. Amplification can be used to complete the sequence of the first and second sequences (e.g., add in the full sequence that can be used in downstream applications, i.e., adding the full sequence for sequencing primer sequences (e.g., Illumina Read 1 and 2) and flow cell adaptor hybridization). The flow cell sequences (e.g., Illumina flow cell sequences) can be added during amplification. Amplification can be used to increase the amount of the adaptor ligated double-stranded cDNA. Amplification can be performed with primers comprising at least a portion of the adaptor sequence. The primers can comprise additional sequence to be added (e.g., to complete the sequence of the flow cell primers). The PCR amplified molecules can be used in sequencing.

The strand sequenced can be determined based on the reads from the sequencing. Reads comprising the first sequence originated from a first strand of the double-stranded adaptor ligated molecule. Reads comprise the second sequence originated from a second strand of the double-stranded adaptor ligated molecule. The library preparation methods can be used for RNA-seq or DNA-seq. The methods can be used to determine which strand of an RNA molecule is involved in regulation (e.g., the antisense strand). The methods can be used to determine base pair resolution for footprinting assays (e.g., Chip-Seq). The methods may not comprise degradation of one strand to preserve directionality (e.g., removal of one strand allowing only the other strand to be sequenced).

Sequencing

Determining the number of different stochastically labeled nucleic acids can comprise determining the sequence of the labeled target, the spatial label, the molecular label, the sample label, and the cellular label or any product thereof (e.g. labeled-amplicons, labeled-cDNA molecules). An amplified target can be subjected to sequencing. Determining the sequence of the stochastically labeled nucleic acid or any product thereof can comprise conducting a sequencing reaction to determine the sequence of at least a portion of a sample label, a spatial label, a cellular label, a molecular label, and/or at least a portion of the stochastically labeled target, a complement thereof, a reverse complement thereof, or any combination thereof.

Determination of the sequence of a nucleic acid (e.g. amplified nucleic acid, labeled nucleic acid, cDNA copy of a labeled nucleic acid, etc.) can be performed using variety of sequencing methods including, but not limited to, sequencing by synthesis (SBS) sequencing by hybridization (SBH), sequencing by ligation (SBL), quantitative incremental fluorescent nucleotide addition sequencing (QIF-NAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads, wobble sequencing, multiplex sequencing, polymerized colony (POLONY) sequencing; nanogrid rolling circle sequencing (ROLONY), allele-specific oligo ligation assays (e.g., oligo ligation assay (OLA), single template molecule OLA using a ligated linear probe and a rolling circle amplification (RCA) readout, ligated padlock probes, or single template molecule OLA using a ligated circular padlock probe and a rolling circle amplification (RCA) readout), and the like.

In some embodiments, determining the sequence of the labeled nucleic acid or any product thereof comprises paired-end sequencing, nanopore sequencing, high-throughput sequencing, shotgun sequencing, dye-terminator sequencing, multiple-primer DNA sequencing, primer walking, Sanger dideoxy sequencing, Maxim-Gilbert sequencing, pyrosequencing, true single molecule sequencing, or any combination thereof. Alternatively, the sequence of the labeled nucleic acid or any product thereof can be determined by electron microscopy or a chemical-sensitive field effect transistor (chemFET) array.

High-throughput sequencing methods, such as cyclic array sequencing using platforms such as Roche 454, Illumina Solexa, ABI-SOLiD, ION Torrent, Complete Genomics, Pacific Bioscience, Helicos, or the Polonator platform, can also be utilized. Sequencing can comprise MiSeq sequencing. Sequencing can comprise HiSeq sequencing.

In some embodiments, the stochastically labeled targets can comprise nucleic acids representing from about 0.01% of the genes of an organism's genome to about 100% of the genes of an organism's genome. For example, about 0.01% of the genes of an organism's genome to about 100% of the genes of an organism's genome can be sequenced using a target complimentary region comprising a plurality of multimers by capturing the genes containing a complimentary sequence from the sample. In some embodiments, the labeled nucleic acids comprise nucleic acids representing from about 0.01% of the transcripts of an organism's transcriptome to about 100% of the transcripts of an organism's transcriptome. For example, about 0.501% of the transcripts of an organism's transcriptome to about 100% of the transcripts of an organism's transcriptome can be sequenced using a target complimentary region comprising a poly-T tail by capturing the mRNAs from the sample.

In some embodiments, sequencing can comprise sequencing at least about 10, 20, 30, 40, 50, 60, 70, 80, 90, 100 or more nucleotides or base pairs of the labeled nucleic acid and/or stochastic barcode. In some embodiments, sequencing can comprise sequencing at most about 10, 20, 30, 40, 50, 60, 70, 80, 90, 100 or more nucleotides or base pairs of the labeled nucleic acid and/or stochastic barcode. In some embodiments, sequencing can comprise sequencing at least about 200, 300, 400, 500, 600, 700, 800, 900, 1,000 or more nucleotides or base pairs of the labeled nucleic acid and/or stochastic barcode. In some embodiments, sequencing can comprise sequencing at most about 200, 300, 400, 500, 600, 700, 800, 900, 1,000 or more nucleotides or base pairs of the labeled nucleic acid and/or stochastic barcode. In some embodiments, sequencing can comprise sequencing at least about 1,500; 2,000; 3,000; 4,000; 5,000; 6,000; 7,000; 8,000; 9,000; or 10,000 or more nucleotides or base pairs of the labeled nucleic acid and/or stochastic barcode. In some embodiments, sequencing can comprise sequencing at most about 1,500; 2,000; 3,000; 4,000; 5,000; 6,000; 7,000; 8,000; 9,000; or 10,000 or more nucleotides or base pairs of the labeled nucleic acid and/or stochastic barcode.

In some embodiments, sequencing can comprise at least about 200, 300, 400, 500, 600, 700, 800, 900, 1,000 or more sequencing reads per run. In some embodiments, sequencing can comprise at most about 200, 300, 400, 500, 600, 700, 800, 900, 1,000 or more sequencing reads per run. In some embodiments, sequencing comprises sequencing at least about 1,500; 2,000; 3,000; 4,000; 5,000; 6,000; 7,000; 8,000; 9,000; or 10,000 or more sequencing reads per run. In some embodiments, sequencing comprises sequencing at most about 1,500; 2,000; 3,000; 4,000; 5,000; 6,000; 7,000; 8,000; 9,000; or 10,000 or more sequencing reads per run. In some embodiments, sequencing can comprise sequencing at least 10, 50, 100, 150, 200, 250, 300, 350, 400, 450, 500, 550, 600, 650, 700, 750, 800, 850, 900, 950 or 1000 or more millions of sequencing reads per run. In some embodiments, sequencing can comprise sequencing at most 10, 50, 100, 150, 200, 250, 300, 350, 400, 450, 500, 550, 600, 650, 700, 750, 800, 850, 900, 950 or 1000 or more millions of sequencing reads per run. In some embodiments, sequencing can comprise sequencing at least 100, 200, 300, 400, 500, 600, 700, 800, 900, 1000, 1100, 1200, 1300, 1400, 1500, 1600, 2000, 3000, 4000, or 5000 or more millions of sequencing reads in total. In some embodiments, sequencing can comprise sequencing at most 100, 200, 300, 400, 500, 600, 700, 800, 900, 1000, 1100, 1200, 1300, 1400, 1500, 1600, 2000, 3000, 4000, or 5000 or more millions of sequencing reads in total. In some embodiments, sequencing can comprise less than or equal to about 1,600,000,000 sequencing reads per run. In some embodiments, sequencing can comprise less than or equal to about 200,000,000 reads per run.

RNA-Seq Library Generation Using Adaptor Ligation

In some instances, the disclosure provides for a method for generating an RNA-seq library using adaptor ligation. Sequencing on next generation sequencers can use platform specific adapter sequences on both ends of the nucleic acid to be sequenced. An adaptor can be ligated to both strands of second-strand cDNA followed by PCR amplification, however, the adaptors can be prone to dimer formation, which can lead to artifacts. The directionality of the original sample may be lost (e.g., differentiation of the 5' and 3' end of the sample). New methods in adaptor ligation can be useful for improving library preparation for next generation sequencing, such as those shown in FIGS. 26 and 27.

As shown in FIG. 26, an RNA 2605 (e.g., mRNA or fragmented RNA) can be contacted with a primer 2610 comprising a first sequence (e.g., a portion of a first sequencing primer sequence, e.g., Illumina Read 1). The RNA 2605 can be reverse transcribed, thereby generating a first cDNA strand. The first cDNA strand can be copied during second strand synthesis, thereby generating a double-stranded cDNA 2615. Adaptors 2620 can be ligated to the double-stranded DNA 2615. The adaptors 2620 can comprise a second sequence (e.g., a portion of a second sequencing primer sequence, e.g., Illumina Read 2). The adaptors 2620 can ligated to the 3', 5' end, or both the 3' and 5' end of the double-stranded cDNA 2615. The adaptors 2620 can be double-stranded, but only one strand of the adaptor can ligate to one strand of the double-stranded cDNA 2615. The first and second sequencing primer sequences can be completed by PCR amplification using primers 2625. The amplification primers 2625 can comprise a portion of the sequencing primer sequences. The amplification primers 2625 can comprise a flow cell sequencing primer. The resulting molecule 2630 can be sequenced. Reads comprising the adaptor sequence 2620 can correspond to a first strand of the molecule 2630. Reads comprising the first sequence 2610 can correspond to a second strand of the molecule 2630. In this way, an RNA-seq library can be prepared with adaptors that preserve the directionality of the molecule.

DNA-Seq Library Generation Using Adaptor Ligation

In some embodiments, the disclosure provides for an adaptor ligation method for preparing DNA sequencing libraries as shown in FIG. 27. A DNA 2705 can be contacted with a primer 2710 comprising a first sequence (e.g., a portion of a first primer sequence, e.g., Illumina Read 1 sequence). The DNA can be extended thereby generating a double-stranded cDNA. Adaptors 2715 can be ligated to the double-stranded cDNA. The adaptors 2715 can comprise a second sequence (e.g., a portion of a second primer sequence, e.g., Illumina Read 2 sequence). The adaptors 2715 can be ligated to the 3', 5' end, or both 3' and 5' end of the double-stranded cDNA. The adaptors 2715 can be double-stranded, but only one strand of the adaptor can ligate to one strand of the double-stranded cDNA. The first and second sequencing primer sequences can be completed by PCR amplification using primers 2720. The amplification primers 2720 can comprise a portion of the sequencing primer sequences. The amplification primers 2720 can comprise a flow cell sequencing primer. The resulting molecule 2725 can be sequenced. Reads comprising the adaptor sequence 2715 can correspond to a first strand of the molecule 2725. Reads comprising the first sequence 2710 can correspond to a second strand of the molecule 2735. In this way, a DNA-seq library can be prepared with adaptors that preserve the directionality of the molecule.

Diffusion Across a Substrate

When a sample (e.g., cell) is stochastically barcoded according to the methods of the disclosure, the cell can be lysed. Lysis of a cell can result in the diffusion of the contents of the lysis (e.g., cell contents) away from the initial location of lysis. In other words, the lysis contents can move into a larger surface area than the surface area taken up by the cell.

Diffusion of sample lysis mixture (e.g., comprising targets) can be modulated by various parameters including, but not limited to, viscosity of the lysis mixture, temperature of the lysis mixture, the size of the targets, the size of physical barriers in a substrate, the concentration of the lysis mixture, and the like. For example, the temperature of the lysis reaction can be performed at a temperature of at least 1, 2, 3, 4, 5, 10, 15, 20, 25, 30, 35, or 40 C or more. In some embodiments, the temperature of the lysis reaction can be performed at a temperature of at most 1, 2, 3, 4, 5, 10, 15, 20, 25, 30, 35, or 40 C or more. The viscosity of the lysis mixture can be altered by, for example, adding thickening reagents (e.g., glycerol, beads) to slow the rate of diffusion. The viscosity of the lysis mixture can be altered by, for example, adding thinning reagents (e.g., water) to increase the rate of diffusion. A substrate can comprise physical barriers (e.g., wells, microwells, microhills) that can alter the rate of diffusion of targets from a sample. The concentration of the lysis mixture can be altered to increase or decrease the rate of diffusion of targets from a sample. In some embodiments, the concentration of a lysis mixture can be increased or decreased by at least 1, 2, 3, 4, 5, 6, 7, 8, or 9 or more fold. In some embodiments, the concentration of a lysis mixture can be increased or decreased by at most 1, 2, 3, 4, 5, 6, 7, 8, or 9 or more fold.

The rate of diffusion can be increased or decreased. In some embodiments, the rate of diffusion of a lysis mixture can be increased or decreased by at least 1, 2, 3, 4, 5, 6, 7, 8, 9, or 10 or more fold compared to an un-altered lysis mixture. In some embodiments, the rate of diffusion of a lysis mixture can be increased or decreased by at most 1, 2, 3, 4, 5, 6, 7, 8, 9, or 10 or more fold compared to an un-altered lysis mixture. In some embodiments, the rate of diffusion of a lysis mixture can be increased or decreased by at least 10, 20, 30, 40, 50, 60, 70, 80, 90 or 100% compared to an un-altered lysis mixture. In some embodiments, the rate of diffusion of a lysis mixture can be increased or decreased by at least 10, 20, 30, 40, 50, 60, 70, 80, 90 or 100% compared to an un-altered lysis mixture.

Data Analysis and Display Software
Data Analysis and Visualization of Spatial Resolution of Targets The disclosure provides for methods for estimating the number and position of targets with stochastic barcoding and digital counting using spatial labels. The data obtained from the methods of the disclosure can be visualized on a map. A map of the number and location of targets from a sample can be constructed using information generated using the methods described herein. The map can be used to locate a physical location of a target. The map can be used to identify the location of multiple targets. The multiple targets can be the same species of target, or the multiple targets can be multiple different targets. For example a map of a brain can be constructed to show the digital count and location of multiple targets.

The map can be generated from data from a single sample. The map can be constructed using data from multiple samples, thereby generating a combined map. The map can be constructed with data from tens, hundreds, and/or thousands of samples. A map constructed from multiple samples can show a distribution of digital counts of targets associated with regions common to the multiple samples. For example, replicated assays can be displayed on the same map. In some embodiments, at least 1, 2, 3, 4, 5, 6, 7, 8, 9, or 10 or more replicates can be displayed (e.g., overlaid) on the same map. In some embodiments, at most 1, 2, 3, 4, 5, 6, 7, 8, 9, or 10 or more replicates can be displayed (e.g., overlaid) on the same map. The spatial distribution and number of targets can be represented by a variety of statistics.

Combining data from multiple samples can increase the locational resolution of the combined map. The orientation of multiple samples can be registered by common landmarks, wherein the individual locational measurements across samples are at least in part non-contiguous. A particular example is sectioning a sample using a microtome on one axis and then sectioning a second sample along a different access. The combined dataset can give three dimensional spatial locations associated with digital counts of targets. Multiplexing the above approach can allow for high resolution three dimensional maps of digital counting statistics.

In some embodiments, the system comprises computer-readable media that includes code for providing data analysis for the sequence datasets generated by performing single cell, stochastic barcoding assays. Examples of data analysis functionality that can be provided by the data analysis software include, but are not limited to, (i) algorithms for decoding/demultiplexing of the sample label, cell label, spatial label, and molecular label, and target sequence data provided by sequencing the stochastic barcode library created in running the assay, (ii) algorithms for determining the number of reads per gene per cell, and the number of unique transcript molecules per gene per cell, based on the data, and creating summary tables, (iii) statistical analysis of the sequence data, e.g. for clustering of cells by gene expression data, or for predicting confidence intervals for determinations of the number of transcript molecules per gene per cell, etc., (iv) algorithms for identifying sub-populations of rare cells, for example, using principal component analysis, hierarchical clustering, k-mean clustering, self-organizing maps, neural networks etc., (v) sequence alignment capabilities for alignment of gene sequence data with known reference sequences and detection of mutation, polymorphic markers and splice variants, and (vi) automated clustering of molecular labels to compensate for amplification or sequencing errors. In some embodiments, commercially-available software can be used to perform all or a portion of the data analysis, for example, the Seven Bridges (https://www.sbgenomics.com/) software can be used to compile tables of the number of copies of one or more genes occurring in each cell for the entire collection of cells. In some embodiments, the data analysis software can include options for outputting the sequencing results in useful graphical formats, e.g. heatmaps that indicate the number of copies of one or more genes occurring in each cell of a collection of cells. In some embodiments, the data analysis software can further comprise algorithms for extracting biological meaning from the sequencing results, for example, by correlating the number of copies of one or more genes occurring in each cell of a collection of cells with a type of cell, a type of rare cell, or a cell derived from a subject having a specific disease or condition. In some embodiment, the data analysis software can further comprise algorithms for comparing populations of cells across different biological samples.

In some embodiments all of the data analysis functionality can be packaged within a single software package. In some embodiments, the complete set of data analysis capabilities can comprise a suite of software packages. In some embodiments, the data analysis software can be a standalone package that is made available to users independently of the assay instrument system. In some embodiments, the software can be web-based, and can allow users to share data.

System Processors and Networks

In general, the computer or processor included in the presently disclosed instrument systems, can be further understood as a logical apparatus that can read instructions from media or a network port, which can optionally be connected to server having fixed media. The system can include a CPU, disk drives, optional input devices such as keyboard or mouse and optional monitor. Data communication can be achieved through the indicated communication medium to a server at a local or a remote location. The communication medium can include any means of transmitting or receiving data. For example, the communication medium can be a network connection, a wireless connection or an internet connection. Such a connection can provide for communication over the World Wide Web. It is envisioned that data relating to the present disclosure can be transmitted over such networks or connections for reception or review by a party.

An exemplary embodiment of a first example architecture of a computer system can be used in connection with example embodiments of the present disclosure. The example computer system can include a processor for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, or personal data assistant devices.

A high speed cache can be connected to, or incorporated in, the processor to provide a high speed memory for instructions or data that have been recently, or are frequently, used by processor. The processor can be connected to a north bridge by a processor bus. The north bridge is connected to random access memory (RAM) by a memory bus and manages access to the RAM by the processor. The north bridge can also be connected to a south bridge by a chipset bus. The south bridge is, in turn, connected to a peripheral bus. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus. In some alternative architectures, the functionality of the north bridge can be incorporated into the processor instead of using a separate north bridge chip.

The system can include an accelerator card attached to the peripheral bus. The accelerator can include field programmable gate arrays (FPGAs) or other hardware for accelerating certain processing. For example, an accelerator can be used for adaptive data restructuring or to evaluate algebraic expressions used in extended set processing.

Software and data can be stored in external storage and can be loaded into RAM or cache for use by the processor. The system includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present invention.

For example, system also includes network interface cards (NICs) and connected to the peripheral bus for providing network interfaces to external storage, such as Network Attached Storage (NAS) and other computer systems that can be used for distributed parallel processing.

An exemplary diagram of a network can comprise a plurality of computer systems, a plurality of cell phones and personal data assistants, and Network Attached Storage (NAS). In example embodiments, systems can manage data storage and optimize data access for data stored in Network Attached Storage (NAS). A mathematical model can be used for the data and be evaluated using distributed parallel processing across computer systems, and cell phone and personal data assistant systems. Computer systems, and cell phone and personal data assistant systems can also provide parallel processing for adaptive data restructuring of the data stored in Network Attached Storage (NAS). A wide variety of other computer architectures and systems can be used in conjunction with the various embodiments of the present invention. For example, a blade server can be used to provide parallel processing. Processor blades can be connected through a back plane to provide parallel processing. Storage can also be connected to the back plane or as Network Attached Storage (NAS) through a separate network interface.

In some embodiments, processors can maintain separate memory spaces and transmit data through network interfaces, back plane or other connectors for parallel processing by other processors. In other embodiments, some or all of the processors can use a shared virtual address memory space.

An exemplary block diagram of a multiprocessor computer system can comprise a shared virtual address memory space in accordance with an example embodiment. In some embodiments, the system can include a plurality of processors that can access a shared memory subsystem. In some embodiments, the system can incorporate a plurality of programmable hardware memory algorithm processors (MAPs) in the memory subsystem. Each MAP can comprise a memory and one or more field programmable gate arrays (FPGAs). The MAP can provide a configurable functional unit and particular algorithms or portions of algorithms can be provided to the FPGAs for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory, allowing it to execute tasks independently of, and asynchronously from the respective microprocessor. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In some embodiments, the computer subsystem of the present disclosure can be implemented using software modules executing on any of the above or other computer architectures and systems. In other embodiments, the functions of the system can be implemented partially or completely in firmware, programmable logic devices such as field programmable gate arrays (FPGAs), system on chips (SOCs), application specific integrated circuits (ASICs), or other processing and logic elements. For example, the Set Processor and Optimizer can be implemented with hardware acceleration through the use of a hardware accelerator card, such as accelerator card.

Kits

Disclosed herein are kits for performing single cell, stochastic barcoding assays. The kit can comprise one or more substrates (e.g., microwell array), either as a free-standing substrate (or chip) comprising one or more microwell arrays, or packaged within one or more flow-cells or cartridges. In some embodiments, the kits comprise one or more solid support suspensions, wherein the individual solid supports within a suspension comprise a plurality of attached stochastic barcodes of the disclosure. In some embodiments, the kits comprise stochastic barcodes that may not be attached to a solid support. In some embodiments, the kit can further comprise a mechanical fixture for mounting a free-standing substrate in order to create reaction wells that facilitate the pipetting of samples and reagents into the substrate. The kit can further comprise reagents, e.g. lysis buffers, rinse buffers, or hybridization buffers, for performing the stochastic barcoding assay. In some embodiments, the kit further comprise reagents (e.g. enzymes, primers, dNTPs, NTPs, RNAse inhibitors, or buffers) for performing nucleic acid extension reactions, for example, reverse transcription reactions and primer extension reactions. In some embodiments, the kit further comprises reagents (e.g. enzymes, universal primers, sequencing primers, target-specific primers, or buffers) for performing amplification reactions to prepare sequencing libraries. In some embodiments, the kit can comprise a ligase, a transposase, a reverse transcriptase, a DNA polymerase, an RNase, an exonuclease, or any combination thereof. In some embodiments, the kit comprises reagents for homopolymer tailing of molecules (e.g., a terminal transferase enzyme, and dNTPs). The kit can comprise reagents for, for example, any enzymatic cleavage of the disclosure (e.g., ExoI nuclease, restriction enzyme). In some embodiments, the kit can comprise reagents for adaptor ligation (e.g., ligase enzyme, reducing reagent). In some embodiments, the kit can comprise reagents for library preparation (e.g., addition of sequencing library/flow cell primers) which can include, sequencing/flow cell primers, enzymes for attaching the primers, dNTPs, etc.).

In some embodiments, the kit comprises a whole transcriptome amplification primer of the disclosure. In some embodiments, the kit can comprise sequencing library amplification primers of the disclosure. In some embodiments, the kit can comprise a second strand synthesis primer of the disclosure. For example, the second strand synthesis primer can comprise a second universal label, a gene specific sequence, a random multimer sequence, a restriction enzyme cleavage site, and a sequence complementary to a homopolymer tail, or any combination thereof. The kit can comprise any primers of the disclosure (e.g., gene-specific primers, random multimers, sequencing primers, and universal primers).

In some embodiments, the kit can comprise one or more molds, for example, molds comprising an array of micropillars, for casting substrates (e.g., microwell arrays), and one or more solid supports (e.g., bead), wherein the individual beads within a suspension comprise a plurality of attached stochastic barcodes of the disclosure. In some embodiments, the kit can further comprise a material for use in casting substrates (e.g. agarose, a hydrogel, PDMS, optical adhesive. and the like).

In some embodiments, the kit can comprise one or more substrates that are pre-loaded with solid supports comprising a plurality of attached stochastic barcodes of the disclosure. In some instances, there can be one solid support per microwell of the substrate. In some embodiments, the plurality of stochastic barcodes can be attached directly to a surface of the substrate, rather than to a solid support. In any of these embodiments, the one or more microwell arrays can be provided in the form of free-standing substrates (or chips), or they can be packed in flow-cells or cartridges.

In some embodiments, the kit can comprise one or more cartridges that incorporate one or more substrates. In some embodiments, the one or more cartridges can further comprise one or more pre-loaded solid supports, wherein the individual solid supports within a suspension comprise a plurality of attached stochastic barcodes of the disclosure. In some embodiments, the beads can be pre-distributed into the one or more microwell arrays of the cartridge. In some embodiments, the beads, in the form of suspensions, can be pre-loaded and stored within reagent wells of the cartridge. In some embodiments, the one or more cartridges can further comprise other assay reagents that are pre-loaded and stored within reagent reservoirs of the cartridges.

Kits can also include instructions for carrying out one or more of the methods described herein. Instructions included in kits can be affixed to packaging material or can be included as a package insert. While the instructions are typically written or printed materials they are not limited to such. Any medium capable of storing such instructions and communicating them to an end user is contemplated by the disclosure. Such media can include, but are not limited to, electronic storage media (e.g., magnetic discs, tapes, cartridges, chips, or any combination thereof), optical media (e.g., CD ROM), RF tags, and the like. As used herein, the term "instructions" can include the address of an internet site that provides the instructions.

Systems

Disclosed herein are systems for generating a whole transcriptome amplification (WTA) product from a plurality of single cells. In some embodiments, the systems disclosed herein can comprise a substrate comprising a plurality of partitions each comprising a single cell and a solid support immobilized with a plurality of nucleic acids. In some embodiments, the systems disclosed herein can comprise one or more solid support suspensions, wherein the individual solid supports within a suspension comprise a plurality of attached stochastic barcodes of the disclosure. In some embodiments, the systems disclosed herein can comprise stochastic barcodes that may not be attached to a solid support. In some embodiments, the systems disclosed herein can further comprise a mechanical fixture for mounting a free-standing substrate in order to create reaction wells that facilitate the pipetting of samples and reagents into the substrate. In some embodiments, the systems disclosed herein further comprise reagents, e.g. lysis buffers, rinse buffers, or hybridization buffers, for performing the stochastic barcoding assay. In some embodiments, the systems disclosed herein can further comprise reagents (e.g. enzymes, primers, dNTPs, NTPs, RNAse inhibitors, or buffers) for performing nucleic acid extension reactions, for example, reverse transcription reactions and primer extension reactions. In some embodiments, the systems disclosed herein can further comprise reagents (e.g. enzymes, universal primers, sequencing primers, target-specific primers, or buffers) for performing amplification reactions to prepare sequencing libraries. In some embodiments, the systems disclosed herein can comprise a ligase, a transposase, a reverse transcriptase, a DNA polymerase, an RNase, an exonuclease, or any combination thereof.

Devices

Flow Cells

The microwell array substrate can be packaged within a flow cell that provides for convenient interfacing with the rest of the fluid handling system and facilitates the exchange of fluids, e.g. cell and solid support suspensions, lysis buffers, rinse buffers, etc., that are delivered to the microwell array and/or emulsion droplet. Design features can include: (i) one or more inlet ports for introducing cell samples, solid support suspensions, or other assay reagents, (ii) one or more microwell array chambers designed to provide for uniform filling and efficient fluid-exchange while minimizing back eddies or dead zones, and (iii) one or more outlet ports for delivery of fluids to a sample collection point or a waste reservoir. The design of the flow cell can include a plurality of microarray chambers that interface with a plurality of microwell arrays such that one or more different cell samples can be processed in parallel. The design of the flow cell can further include features for creating uniform flow velocity profiles, i.e. "plug flow", across the width of the array chamber to provide for more uniform delivery of cells and beads to the microwells, for example, by using a porous barrier located near the chamber inlet and upstream of the microwell array as a "flow diffuser", or by dividing each array chamber into several subsections that collectively cover the same total array area, but through which the divided inlet fluid stream flows in parallel. In some embodiments, the flow cell can enclose or incorporate more than one microwell array substrate. In some embodiments, the integrated microwell array/flow cell assembly can constitute a fixed component of the system. In some embodiments, the microwell array/flow cell assembly can be removable from the instrument.

In some embodiments, the dimensions of fluid channels and the array chamber(s) in flow cell designs are optimized to (i) provide uniform delivery of cells and beads to the microwell array, and (ii) to minimize sample and reagent consumption. In some embodiments, the width of fluid channels is between 50 um and 20 mm. In some embodiments, the width of fluid channels can be at least 50 um, at least 100 um, at least 200 um, at least 300 um, at least 400 um, at least 500 um, at least 750 um, at least 1 mm, at least 2.5 mm, at least 5 mm, at least 10 mm, at least 20 mm, at least 50 mm, at least 100 mm, or at least 150 mm. In some embodiments, the width of fluid channels can be at most 150 mm, at most 100 mm, at most 50 mm, at most 20 mm, at most 10 mm, at most 5 mm, at most 2.5 mm, at most 1 mm, at most 750 um, at most 500 um, at most 400 um, at most 300 um, at most 200 um, at most 100 um, or at most 50 um. In some embodiments, the width of fluid channels is about 2 mm. The width of the fluid channels can fall within any range bounded by any of these values (e.g. from about 250 um to about 3 mm).

In some embodiments, the depth of the fluid channels is between 50 um and 2 mm. In other embodiments, the depth of fluid channels can be at least 50 um, at least 100 um, at least 200 um, at least 300 um, at least 400 um, at least 500 um, at least 750 um, at least 1 mm, at least 1.25 mm, at least 1.5 mm, at least 1.75 mm, or at least 2 mm. In yet other embodiments, the depth of fluid channels can at most 2 mm, at most 1.75 mm, at most 1.5 mm, at most 1.25 mm, at most 1 mm, at most 750 um, at most 500 um, at most 400 um, at most 300 um, at most 200 um, at most 100 um, or at most 50 um. In one embodiment, the depth of the fluid channels is about 1 mm. The depth of the fluid channels can fall within any range bounded by any of these values (e.g. from about 800 um to about 1 mm).

Flow cells can be fabricated using a variety of techniques and materials known to those of skill in the art. In some embodiments, the flow cell is fabricated as a separate part and subsequently either mechanically clamped or permanently bonded to the microwell array substrate. Examples of suitable fabrication techniques include conventional machining, CNC machining, injection molding, 3D printing, alignment and lamination of one or more layers of laser or die-cut polymer films, or any of a number of microfabrication techniques such as photolithography and wet chemical etching, dry etching, deep reactive ion etching, or laser micromachining. Once the flow cell part has been fabricated it can be attached to the microwell array substrate mechanically, e.g. by clamping it against the microwell array substrate (with or without the use of a gasket), or it can be bonded directly to the microwell array substrate using any of a variety of techniques (depending on the choice of materials used) known to those of skill in the art, for example, through the use of anodic bonding, thermal bonding, or any of a variety of adhesives or adhesive films, including epoxy-based, acrylic-based, silicone-based, UV curable, polyurethane-based, or cyanoacrylate-based adhesives.

Flow cells can be fabricated using a variety of materials known to those of skill in the art. In some embodiments, the choice of material used depends on the choice of fabrication technique used, and vice versa. Examples of suitable materials include, but are not limited to, silicon, fused-silica, glass, any of a variety of polymers, e.g. polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, metals (e.g. aluminum, stainless steel, copper, nickel, chromium, and titanium), a non-stick material such as teflon (PTFE), or a combination of these materials.

Cartridges

In some embodiments of the system, the microwell array, with or without an attached flow cell, can be packaged within a consumable cartridge that interfaces with the instrument system. Design features of cartridges can include (i) one or more inlet ports for creating fluid connections with the instrument or manually introducing cell samples, bead suspensions, or other assay reagents into the cartridge, (ii) one or more bypass channels, i.e. for self-metering of cell samples and bead suspensions, to avoid overfilling or back flow, (iii) one or more integrated microwell array/flow cell assemblies, or one or more chambers within which the microarray substrate(s) are positioned, (iv) integrated miniature pumps or other fluid actuation mechanisms for controlling fluid flow through the device, (v) integrated miniature valves (or other containment mechanisms) for compartmentalizing pre-loaded reagents (for example, bead suspensions) or controlling fluid flow through the device, (vi) one or more vents for providing an escape path for trapped air, (vii) one or more sample and reagent waste reservoirs, (viii) one or more outlet ports for creating fluid connections with the instrument or providing a processed sample collection point, (ix) mechanical interface features for reproducibly positioning the removable, consumable cartridge with respect to the instrument system, and for providing access so that external magnets can be brought into close proximity with the microwell array, (x) integrated temperature control components or a thermal interface for providing good thermal contact with the instrument system, and (xi) optical interface features, e.g. a transparent window, for use in optical interrogation of the microwell array.

The cartridge can be designed to process more than one sample in parallel. The cartridge can further comprise one or more removable sample collection chamber(s) that are suitable for interfacing with stand-alone PCR thermal cyclers or sequencing instruments. The cartridge itself can be suitable for interfacing with stand-alone PCR thermal cyclers or sequencing instruments. The term "cartridge" as used in this disclosure can be meant to include any assembly of parts which contains the sample and beads during performance of the assay.

The cartridge can further comprise components that are designed to create physical or chemical barriers that prevent diffusion of (or increase pathlengths and diffusion times for) large molecules in order to minimize cross-contamination between microwells. Examples of such barriers can include, but are not limited to, a pattern of serpentine channels used for delivery of cells and solid supports (e.g., beads) to the microwell array, a retractable platen or deformable membrane that is pressed into contact with the surface of the microwell array substrate during lysis or incubation steps, the use of larger beads, e.g. Sephadex beads as described previously, to block the openings of the microwells, or the release of an immiscible, hydrophobic fluid from a reservoir within the cartridge during lysis or incubation steps, to effectively separate and compartmentalize each microwell in the array.

The dimensions of fluid channels and the array chamber(s) in cartridge designs can be optimized to (i) provide uniform delivery of cells and beads to the microwell array, and (ii) to minimize sample and reagent consumption. For example, the width of fluid channels can be between 50 micrometers and 20 mm. In some embodiments, the width of fluid channels can be at least 50 micrometers, at least 100 micrometers, at least 200 micrometers, at least 300 micrometers, at least 400 micrometers, at least 500 micrometers, at least 750 micrometers, at least 1 mm, at least 2.5 mm, at least 5 mm, at least 10 mm, or at least 20 mm. In some embodiments, the width of fluid channels can at most 20 mm, at most 10 mm, at most 5 mm, at most 2.5 mm, at most 1 mm, at most 750 micrometers, at most 500 micrometers, at most 400 micrometers, at most 300 micrometers, at most 200 micrometers, at most 100 micrometers, or at most 50 micrometers. In some embodiments, the width of fluid channels can be about 2 mm. In some embodiments, the width of the fluid channels can fall within any range bounded by any of these values (e.g. from about 250 um to about 3 mm).

The fluid channels in the cartridge can have a depth. The depth of the fluid channels in cartridge designs can be, for example, between 50 micrometers and 2 mm. In some embodiments, the depth of fluid channels can be at least 50 micrometers, at least 100 micrometers, at least 200 micrometers, at least 300 micrometers, at least 400 micrometers, at least 500 micrometers, at least 750 micrometers, at least 1 mm, at least 1.25 mm, at least 1.5 mm, at least 1.75 mm, or at least 2 mm. In some embodiments, the depth of fluid channels can at most 2 mm, at most 1.75 mm, at most 1.5 mm, at most 1.25 mm, at most 1 mm, at most 750 micrometers, at most 500 micrometers, at most 400 micrometers, at most 300 micrometers, at most 200 micrometers, at most 100 micrometers, or at most 50 micrometers. In some embodiments, the depth of the fluid channels can be about 1 mm. In some embodiments, the depth of the fluid channels can fall within any range bounded by any of these values (e.g. from about 800 micrometers to about 1 mm).

Cartridges can be fabricated using a variety of techniques and materials known to those of skill in the art. In some embodiments, the cartridges are fabricated as a series of separate component parts and subsequently assembled using any of a number of mechanical assembly or bonding techniques. Examples of suitable fabrication techniques include, but are not limited to, conventional machining, CNC machining, injection molding, thermoforming, and 3D printing. Once the cartridge components have been fabricated they can be mechanically assembled using screws, clips, and the like, or permanently bonded using any of a variety of techniques (depending on the choice of materials used), for example, through the use of thermal bonding/welding or any of a variety of adhesives or adhesive films, including epoxy-based, acrylic-based, silicone-based, UV curable, polyurethane-based, or cyanoacrylate-based adhesives.

Cartridge components can be fabricated using any of a number of suitable materials, including but not limited to silicon, fused-silica, glass, any of a variety of polymers, e.g. polydimethylsiloxane (PDMS; elastomer), polymethylmethacrylate (PMMA), polycarbonate (PC), polypropylene (PP), polyethylene (PE), high density polyethylene (HDPE), polyimide, cyclic olefin polymers (COP), cyclic olefin copolymers (COC), polyethylene terephthalate (PET), epoxy resins, non-stick materials such as teflon (PTFE), metals (e.g. aluminum, stainless steel, copper, nickel, chromium, and titanium), or any combination thereof.

The inlet and outlet features of the cartridge can be designed to provide convenient and leak-proof fluid connections with the instrument, or can serve as open reservoirs for manual pipetting of samples and reagents into or out of the cartridge. Examples of convenient mechanical designs for the inlet and outlet port connectors can include, but are not limited to, threaded connectors, Luer lock connectors, Luer slip or "slip tip" connectors, press fit connectors, and the like. The inlet and outlet ports of the cartridge can further comprise caps, spring-loaded covers or closures, or polymer membranes that can be opened or punctured when the cartridge is positioned in the instrument, and which serve to prevent contamination of internal cartridge surfaces during storage or which prevent fluids from spilling when the cartridge is removed from the instrument. The one or more outlet ports of the cartridge can further comprise a removable sample collection chamber that is suitable for interfacing with stand-alone PCR thermal cyclers or sequencing instruments.

The cartridge can include, for example, integrated miniature pumps or other fluid actuation mechanisms for control of fluid flow through the device. Examples of suitable miniature pumps or fluid actuation mechanisms can include, but are not limited to, electromechanically- or pneumatically-actuated miniature syringe or plunger mechanisms, membrane diaphragm pumps actuated pneumatically or by an external piston, pneumatically-actuated reagent pouches or bladders, or electro-osmotic pumps.

The cartridge can include, for example, miniature valves for compartmentalizing pre-loaded reagents or controlling fluid flow through the device. Examples of suitable miniature valves can include, but are not limited to, one-shot "valves" fabricated using wax or polymer plugs that can be melted or dissolved, or polymer membranes that can be punctured; pinch valves constructed using a deformable membrane and pneumatic, magnetic, electromagnetic, or electromechanical (solenoid) actuation, one-way valves constructed using deformable membrane flaps, and miniature gate valves.

The cartridge can include, for example, vents for providing an escape path for trapped air. Vents can be constructed according to a variety of techniques, for example, using a porous plug of polydimethylsiloxane (PDMS) or other hydrophobic material that allows for capillary wicking of air but blocks penetration by water.

The mechanical interface features of the cartridge can provide for easily removable but highly precise and repeatable positioning of the cartridge relative to the instrument system. Suitable mechanical interface features can include, but are not limited to, alignment pins, alignment guides, mechanical stops, and the like. The mechanical design features can include relief features for bringing external apparatus, e.g. magnets or optical components, into close proximity with the microwell array chamber.

In some embodiments, the cartridge can include temperature control components or thermal interface features for mating to external temperature control modules. Examples of suitable temperature control elements can include, but are not limited to, resistive heating elements, miniature infrared-emitting light sources, Peltier heating or cooling devices, heat sinks, thermistors, thermocouples, and the like. Thermal interface features can be fabricated from materials that are good thermal conductors (e.g. copper, gold, silver, etc.) and can comprise one or more flat surfaces capable of making good thermal contact with external heating blocks or cooling blocks.

In some embodiments, the cartridge can include optical interface features for use in optical imaging or spectroscopic interrogation of the microwell array. The cartridge can include an optically transparent window, e.g. the microwell substrate itself or the side of the flow cell or microarray chamber that is opposite the microwell array, fabricated from a material that meets the spectral requirements for the imaging or spectroscopic technique used to probe the microwell array. Examples of suitable optical window materials can include, but are not limited to, glass, fused-silica, polymethylmethacrylate (PMMA), polycarbonate (PC), cyclic olefin polymers (COP), or cyclic olefin copolymers (COC).

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

EXAMPLES

The following examples are offered to illustrate but not to limit the invention.

In order to facilitate understanding, the specific embodiments are provided to help interpret the technical proposal, that is, these embodiments are only for illustrative purposes, but not in any way to limit the scope of the invention. Unless otherwise specified, embodiments do not indicate the specific conditions, are in accordance with the conventional conditions or the manufacturer's recommended conditions.

Example 1: First Strand cDNA Synthesis Using an Oligo dT Primer with a Universal Sequence at the 5' End This example describes the adaptor ligation method of the disclosure. First strand cDNA synthesis using an oligo dT primer with a universal sequence at its 5' end was performed. Following first strand synthesis, second strand cDNA was synthesized by the Gubler-Hoffman method (DNA PolI, RNaseH, and E. coli DNA Ligase). Following second strand synthesis, the ends of the cDNA were optionally further processed (i.e. blunting or dA-tailing), and the 3' ends of the cDNA is ligated to a 5' phosphorylated adapter with the same or different universal priming sequence. Because the adapter was partially single stranded and 5' phosphorylated, it may only ligate to the cDNA with negligible self-ligation. The cDNA was the amplified by PCR using the universal sequences from the original RT primer and ligated adapter as priming sites. The priming sites could be the same sequence, or the first and second universal primer sequences of the disclosure, and could involve semi-suppressive PCR to prevent artifact formation.

Figure 6A:
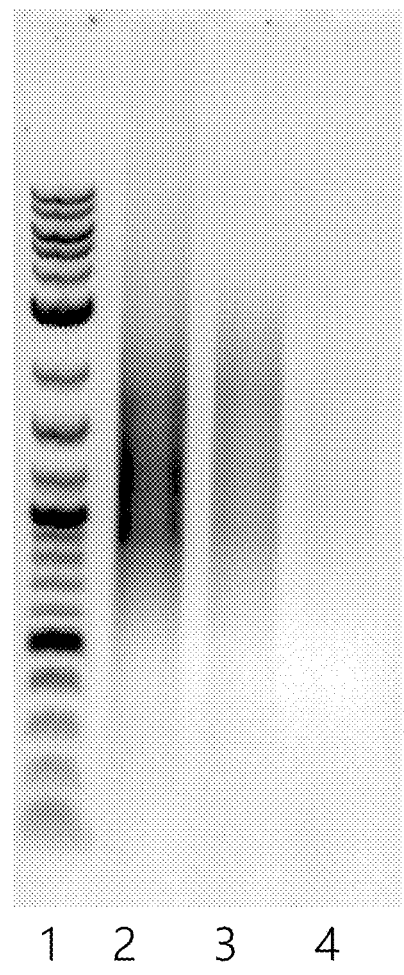
Figure 6B:
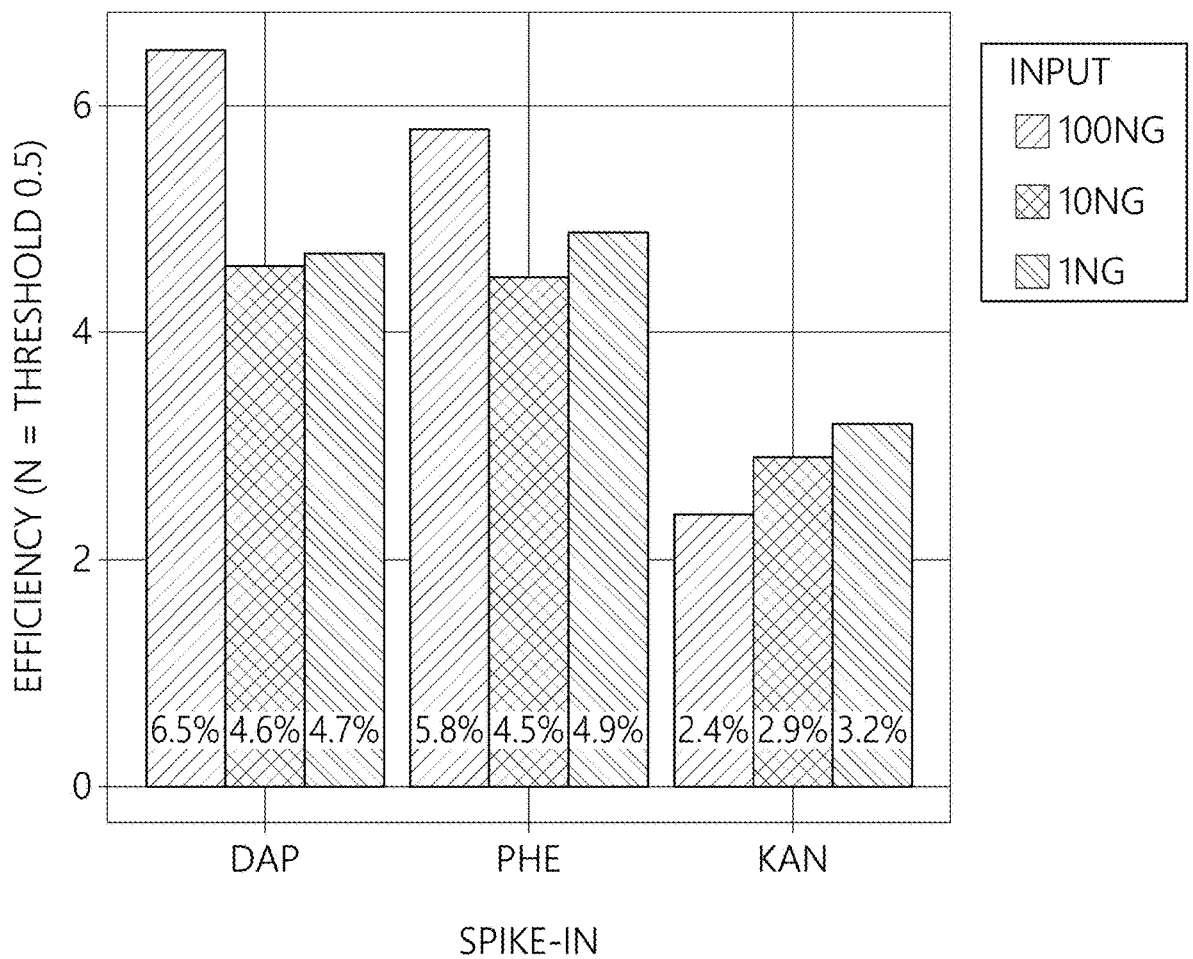

In a specific exemplary embodiment, the method was used to generate amplified cDNA from individual samples ranging from 1-100 ng total RNA, and from 96 1 ng samples simultaneously. 1 ng, 10 ng, 100 ng Human Brain Reference RNA (HBRR) spiked with 10,000 barcoded control RNAs per reaction was used as the template for first strand cDNA synthesis using 200 nM RT primer consisting of a pool of all 96 RT primers from the Precisem assay. Second strand cDNA was generated using the NEBNext $2^{nd}$ strand cDNA module according to manufacturer's protocol. Five minutes before the end of the reaction, 3 U of T4 DNA polymerase is added to ensure blunt cDNA, the reaction was terminated by addition of EDTA, and purified using a 1.8× ratio of AmpureXP beads. 300 nM phosphorylated adapter CBO102/103 (annealed /5Phos/GCGATCGCGATCG-GAAGAGCACACGTCTGA (SEQ ID NO: 1) and CTTCC-GATCGCGATCGC (SEQ ID NO: 2)) was ligated to the blunted cDNA using the NEBNext Quick ligation module. Ligated cDNA was purified with a 1× volume of AmpureXP beads and the eluted product was amplified using 2× Q5 HotStart Mastermix (NEB) and 500 nM of the primer CBO23 (sequence: TCAGACGTGTGCTCTTCC (SEQ ID NO: 3)). 5 µl of the resulting PCR product was resolved on a 1% TBE Agarose gel (See FIG. 6A, Lanes: 1) NEB 2-log ladder 2) 100 ng HBRR, 3) 10 ng HBRR 4) 1 ng HBRR). Efficiency of second strand synthesis and ligation was determined by the mass yield of WTA product as determined by Nanodrop (See FIG. 6C), as well as counting control spike-in molecules (kan, dap, phe) with the Pixel™ instrument (See FIG. 6B).

Example 2: First Strand cDNA Synthesis Using an Oligo dT Primer with a Universal Sequence at the 5' End 1 ng Human Brain Reference RNA or Human Universal Reference RNA was added to each well of a 96 well plate (e.g., Precise™ Assay plate). First strand cDNA was synthesized according to the manufacturer's protocol (e.g., 42 C for 30 min, followed by 80 C for 5 min, hold at 4 C) and purified using a 1× ratio of AmpureXP beads, with elution into water.

Figure 7:
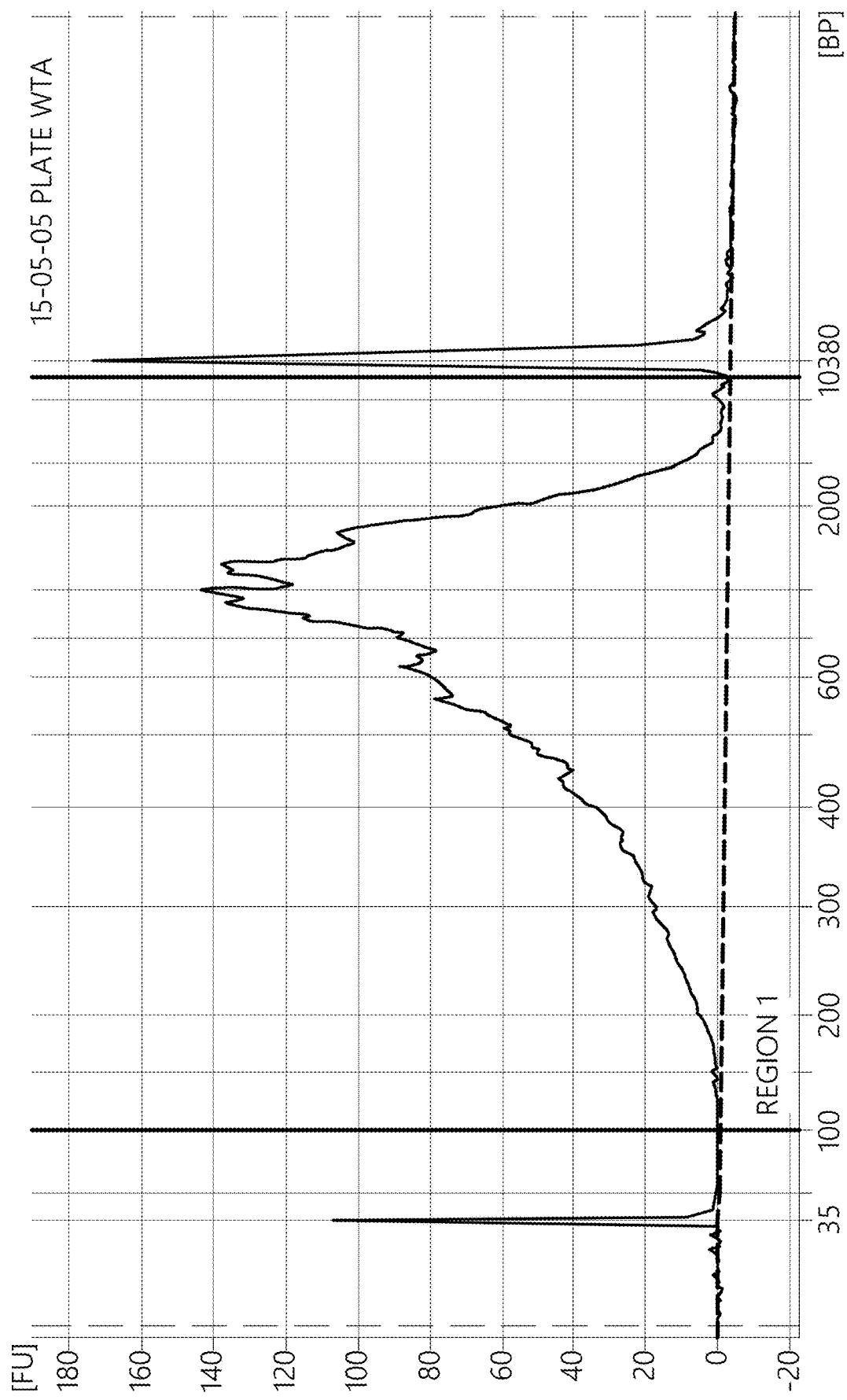
FIG. 7 depicts the nucleic acid size distribution of the WTA product using an exemplary adaptor ligation method used in Example 2.

Second strand cDNA was generated using the NEBNext $2^{nd}$ strand cDNA module according to manufacturer's protocol (e.g., combination of buffers, incubation of 2.5 hours at 16 C). Five minutes before the end of the reaction, 3 U of T4 DNA polymerase was added to ensure blunt cDNA, the reaction is terminated by addition of EDTA, and purified using a 1.8× ratio of AmpureXP beads, with elution into water. 300 nM phosphorylated adapter CBO105/106 (annealed /5Phos/GCGATCGCGGAAGAGCACACGTCTGA (SEQ ID NO: 4) and GCTCTTCCGCGATCGC (SEQ ID NO: 5)) was ligated to the blunted cDNA using the NEBNext Quick ligation module by incubation at 30 min at room temperature. Ligated cDNA was purified with a 1× volume of AmpureXP beads and the eluted product is amplified using 2× Q5 HotStart Mastermix (NEB) and 500 nM of the primer CBO23 (sequence: TCAGACGTGTGCTCTTCC (SEQ ID NO: 6)). Amplification comprised one cycle of 98 C at 30 seconds, 15 cycles of 98 C for 20 s, 65 C for 15 s, 72 C for 3 minutes, and one cycle of 72 C for 5 min. The size distribution of the WTA product was determined by Agilent Bioanalyzer. To determine the size distribution of the WTA product 30 ng/µl WTA product from 96×1 ng WTA plate was diluted 1:10 and run on an Agilent Bioanalyzer high sensitivity assay. FIG. 7 shows the WTA size distribution, which ranges from ~200 bp-3 kb, with the peak at ~1.2 kb.

Figure 8A:
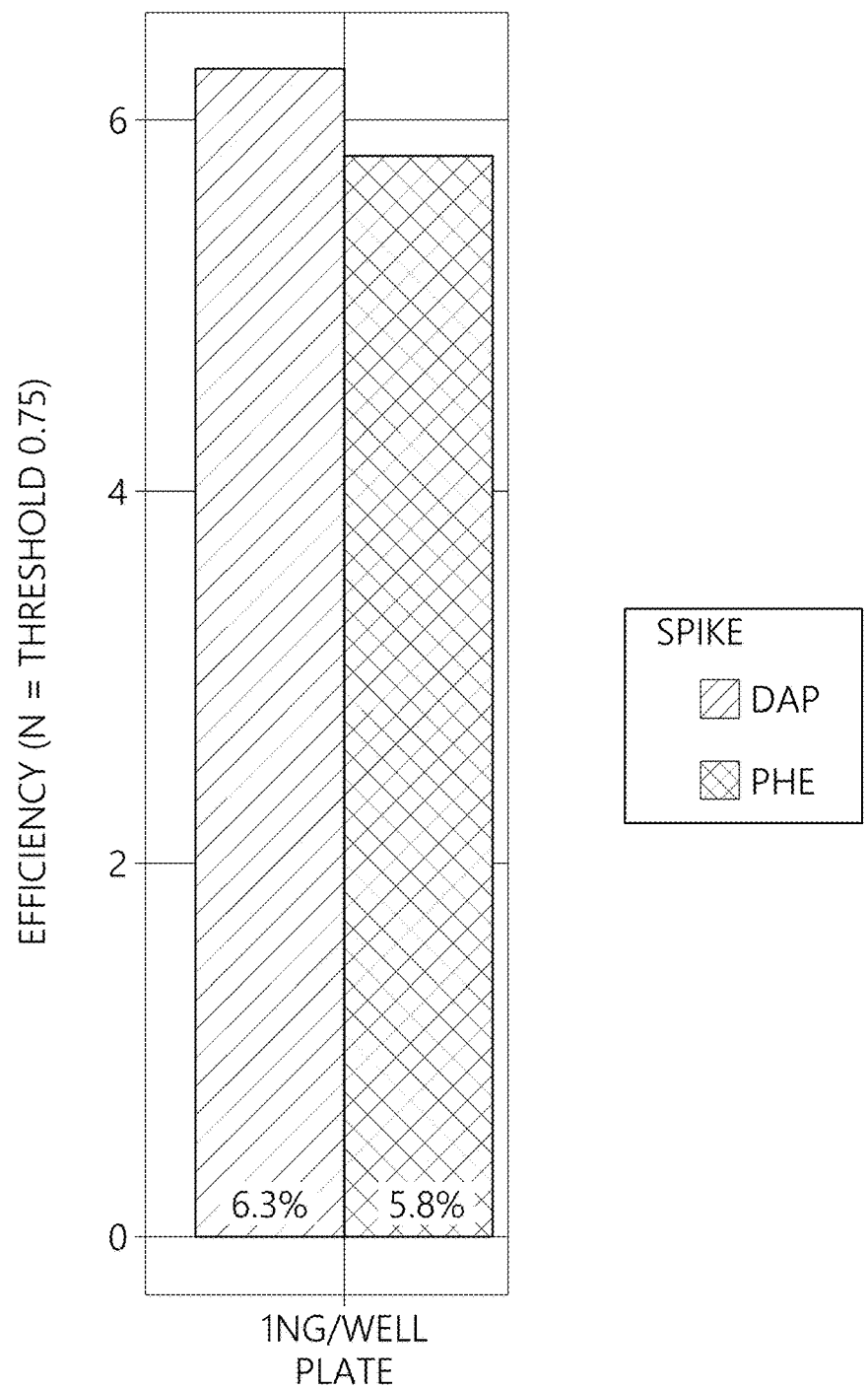
FIGS. 8A and 8B depict the efficiency of exemplary methods used in Examples 2 and 3.

The overall efficiency of second strand synthesis and adaptor ligation was measured by counting the 4320 control molecules with Pixel™, as shown in FIG. 8A. Following the 96×1 ng WTA as described above, Dap and Phe plate spike ins were quantified by Pixel™. The Pixel™ counts were then compared to the total number of spike-in molecules in the plate, 4320, to determine overall reaction efficiency.

Example 3: Second Strand Synthesis with RNaseH and a Strand Displacing Polymerase The method disclosed in this example was used to amplify cDNA from 10 ng total RNA. cDNA is synthesized according to the method of Example 1. Second strand synthesis was performed using RNaseH and a strand-displacing polymerase or mixture of polymerases at least one of which has strand displacement activity. This resulted in the generation of many overlapping second-strand cDNAs biased towards the 3' of the original RNA and containing the complement to the universal priming sequence at their 3' ends. After synthesis, the RNA primer portion of the second strands was optionally removed by RNase or alkali treatment. This can aid full length extension by DNA polymerases. These second strand cDNAs were primed with a universal primer and extended to generate double stranded molecules. These double stranded molecules were ligated and amplified as described in Example 1. Using strand displacing polymerase can amplify the signal amplification by generating several second strand cDNAs for every first strand.

In a specific exemplary embodiment, 10 ng Human Brain Reference RNA (HBRR) spiked with 10,000 barcoded control RNAs per reaction was used as the template for first strand cDNA synthesis using 200 nM RT primer consisting of a pool of all 96 RT primers from the Precise™ assay. Second strand synthesis was performed using 18 U Klenow (Exo-) and 15 U RNaseH for 2 hrs at 16° C., followed by 30 min at 37° C., either done in either NEB $2^{nd}$ strand buffer or ThermoPol buffer+200 nM dNTPs). The enzymes were heat inactivated, or the reaction is purified using 1.8× AmpureXP beads and eluted cDNA added to 1× ThermoPol buffer+ dNTPs. 200 nM primer CBO17 (sequence: TCAGACGTGTGCTCTTCCGAT (SEQ ID NO: 7)) and 5 U of Taq DNA polymerase was added and the reactions were incubated at 94° C. for 3 min, 55° C. 30 sec, and 72° C. for 40 min to generate the complementary strand and A-tail the product. Reactions were purified using 1.8× ratio AmpureXP beads. 300 nM phosphorylated adapter CBO105/107 (annealed /5Phos/GCGATCGCGGAAGAGCACACGTCTGA (SEQ ID NO: 8) and GCTCTTCCGCGATCGC*T (SEQ ID NO: 9)) was ligated to the tailed cDNA using the NEBNext Quick ligation module. Ligated cDNA was purified with a 1× volume of AmpureXP beads and the eluted product is amplified using 2× Q5 HotStart Mastermix (NEB) and 500 nM of the primer CBO23 (sequence: TCAGACGTGTGCTCTTCC (SEQ ID NO: 10)). 5 µl of the resulting PCR product was resolved on a 1% TBE Agarose gel (See FIG. 9A, Lanes: 1) NEB 2-log ladder 2) 10 ng HBRR second strand synthesis and Taq extension done in NEB second strand buffer, 3) 10 ng HBRR second strand synthesis and Taq extension done in NEB ThermoPol buffer 4) 10 ng HBRR second strand synthesis done in NEB second strand buffer followed by purification and Taq extension in ThermoPol buffer).

Figure 8B:
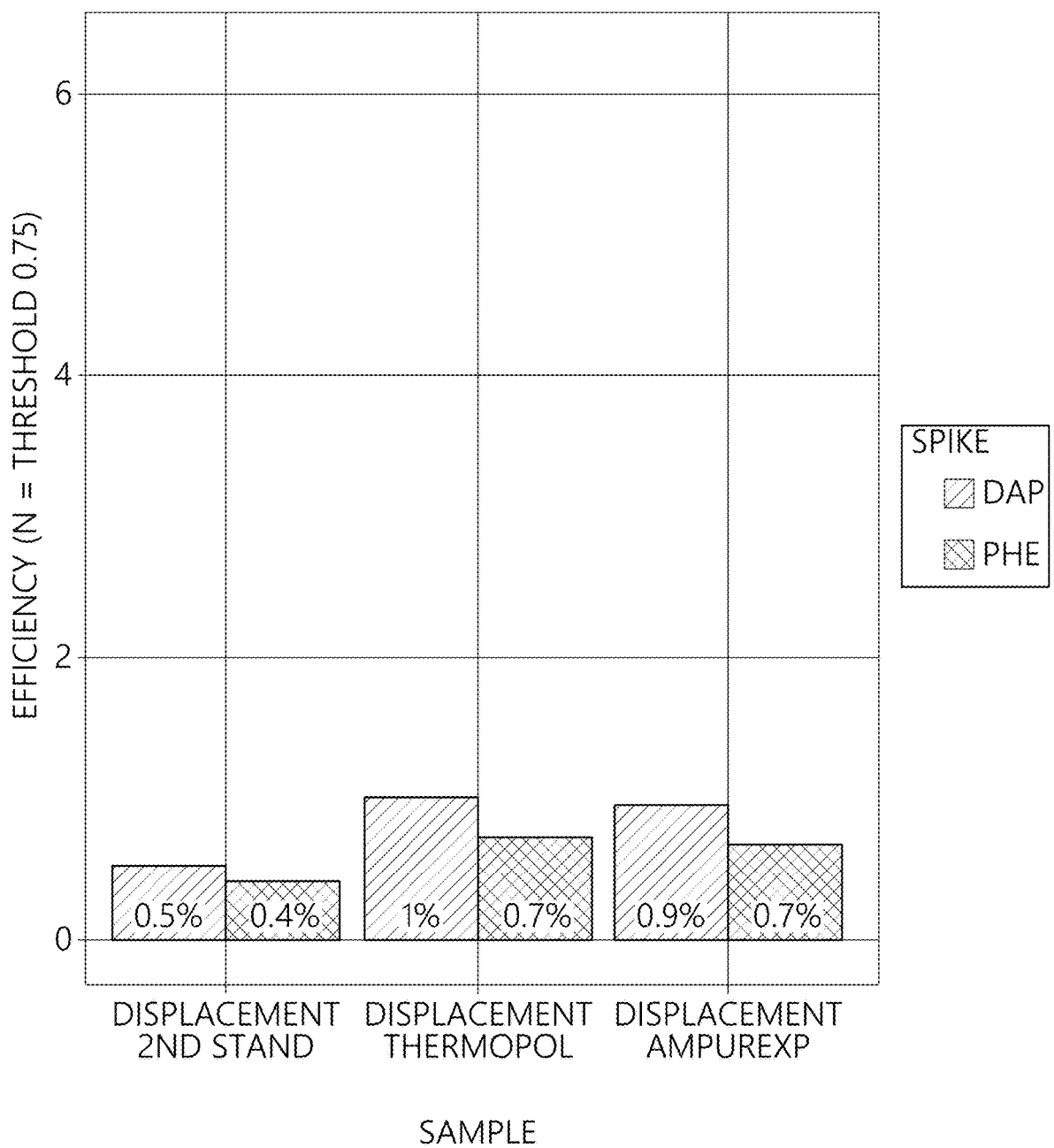

Efficiency of second strand synthesis was determined by the mass yield of WTA product (See FIG. 9B), as well as counting control spike-in molecules with the Pixel instrument (See FIG. 8B).

Example 4: Homopolymer Tailing

This example describes the homopolymer tailing method of the disclosure. 96 10 µl reverse transcription reactions each made up of 1 ng lymphocyte total RNA, 12.5 nM RT primers (e.g., comprising stochastic barcodes of the disclosure) pool, 500 µM dNTPs, 1× Protoscript buffer, 40 U ProtoscriptII reverse transcriptase (NEB), and 4 U Murine Rnase Inhibitor (NEB) were carried out at 42° C. for 30 minutes and heat inactivated at 80° C. for 5 min.

Reactions were combined into eight tubes and purified using a 1× ratio of AmpureXP beads. cDNA was eluted in 20 µl ExoI digestion mix (1× CutSmart buffer, 20 ExonucleaseI (NEB)) and incubated at 37° C. for 30 minutes followed by inactivation at 80° C. for 20 minutes.

5 µl Tailing mix (1× CutSmart buffer, 1.25 mM dATP, 12.5 µM ddATP, 10 U Terminal transferase (NEB) 1 U RNaseH(NEB)) was added to each reaction and incubated at 37° C. for 15 minutes followed by inactivation at 75° C. for 10 minutes.

25 µl PCR Mastermix (1× Q5 buffer, 400 µM dNTPs, 100 nM CBO16 TCAGACGTGTGCTCTTCCGATCTgcgatcgcTTTTTTTTTTTTTTTTTTTTTTTT (SEQ ID NO: 11), 1.76 µM CBO20 TCAGACGTGTGCTCTTCCGAT, 1 U Q5 HotStart Polymerase (NEB)) was added to each reaction and thermocycled with the program: 98° C. 2 min, 45° C. 30 s, 72° C. 2 min, 15× of (98° C. 10 s, 65° C. 15 s, 72° C. 1.5 min), and 72° C. 1.5 min. PCR reactions were pooled together and cleaned with 0.7× ratio of AmpureXP beads and eluted in 50 µl 10 mM Tris pH8.0, 0.05% Tween-20. The total reaction yield was ~1.5 µg.

Figure 10:
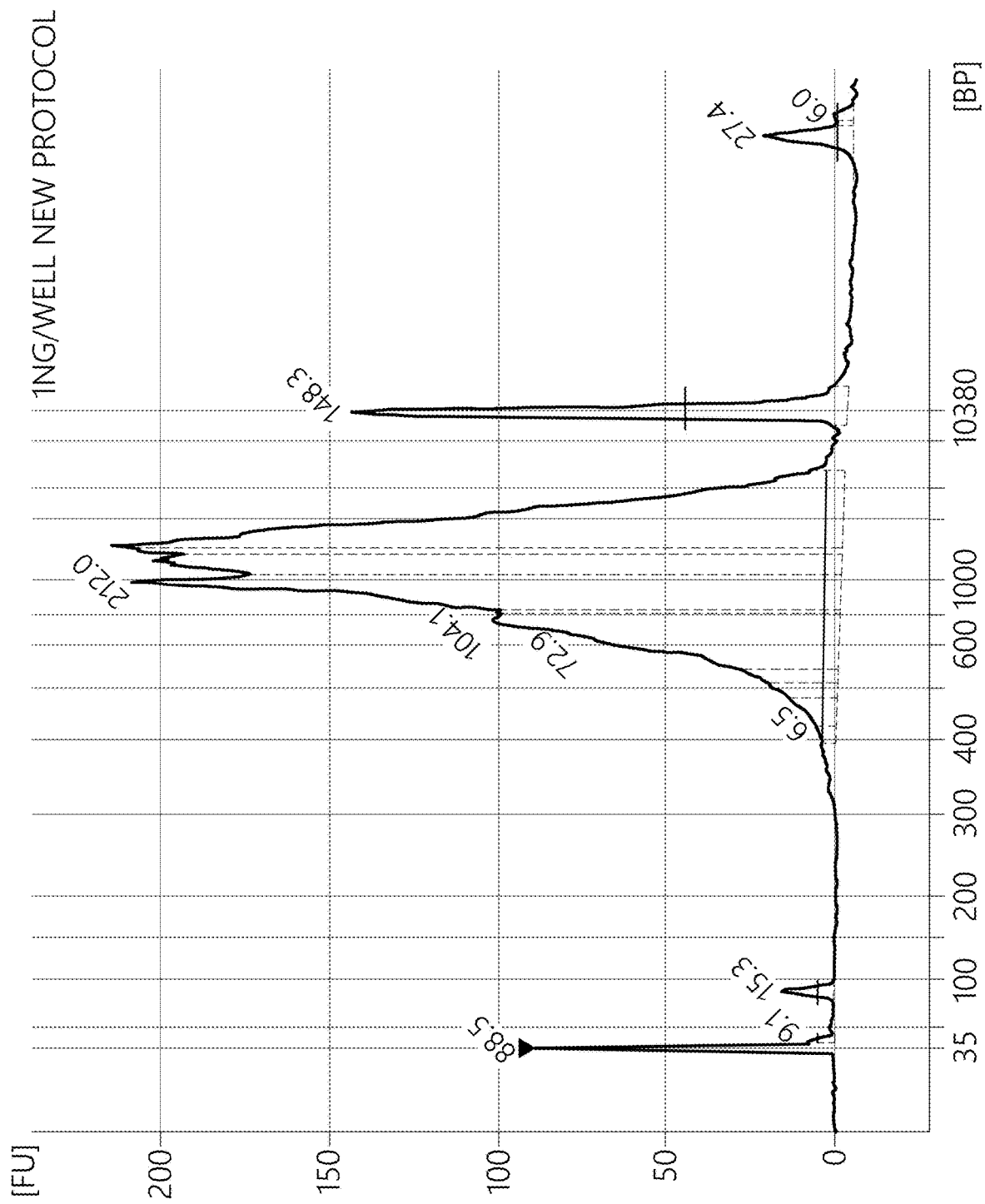
FIG. 10 depicts a bioanalyzer trace of the WTA product using an exemplary homopolymer tailing method in Example 4.

The WTA product (e.g., quasi-symmetric stochastically barcoded nucleic acid) was diluted and run on the high sensitivity DNA assay of an Agilent bioanalyzer as shown in FIG. 10.

Example 5: Library Generation Protocol Using Homopolymer Tailing

This example describes library generation of the WTA product from the homopolymer tailing method (e.g., described in Example 4). 100 ng of WTA product was digested in 20 µl with 10 U AsiSI (NEB) in 1× CutSmart Buffer for at 37° C. for 30 min. Reactions were heated to 95° C. for 2 min, and then placed on ice for 5 min.

30 µl Random priming mix (1× CutSmart buffer, 333 µM dNTPs, 1.66 µM CBO12 CCCTACACGACGCTCTTCC-GATCTNNNNNN (SEQ ID NO: 12), 5 U Klenow(exo-) (NEB)) was added to each reaction and incubated at 37° C. for 30 min.

Volume was adjusted to 150 µl and bound to 120 µl AmpureXP beads for 5 min. Beads were bound to a magnet and the supernatant was transferred to a new tube and the beads discarded. The supernatant was then purified with 60 µl Ampure XP beads and eluted in 22 µl water. 28 µl PCR mix was added to each reaction (1.79× Q5 buffer, 357 nM dNTP, 800 nM CBO32 AATGATACGGCGAC-CACCGAGATCTACACTATAGCCTACACTCTTTCCC-TACACG ACGCTCTTCCGATC*T (SEQ ID NO: 13), 800 nM CBO33 CAAGCAGAAGACGGCAT-ACGAGATCGAGTAATGTGACTGGAGTTCA-GACGTGTG CTCTTCCGATC*T (SEQ ID NO: 14), and 1 U Q5 HotStart DNA Polymerase (NEB))) was added to each reaction and thermocycled with the program: 98° C. 30 s, 15× of (98° C. 10 s, 65° C. 15 s, 72° C. 20 s) and 72° C. 2 min.

PCR reactions were cleaned with 1× ratio of AmpureXP beads and eluted in 30 µl 10 mM Tris pH8.0, 0.05% Tween-20. The final product concentration was ~20 ng/µl.

Figure 11:
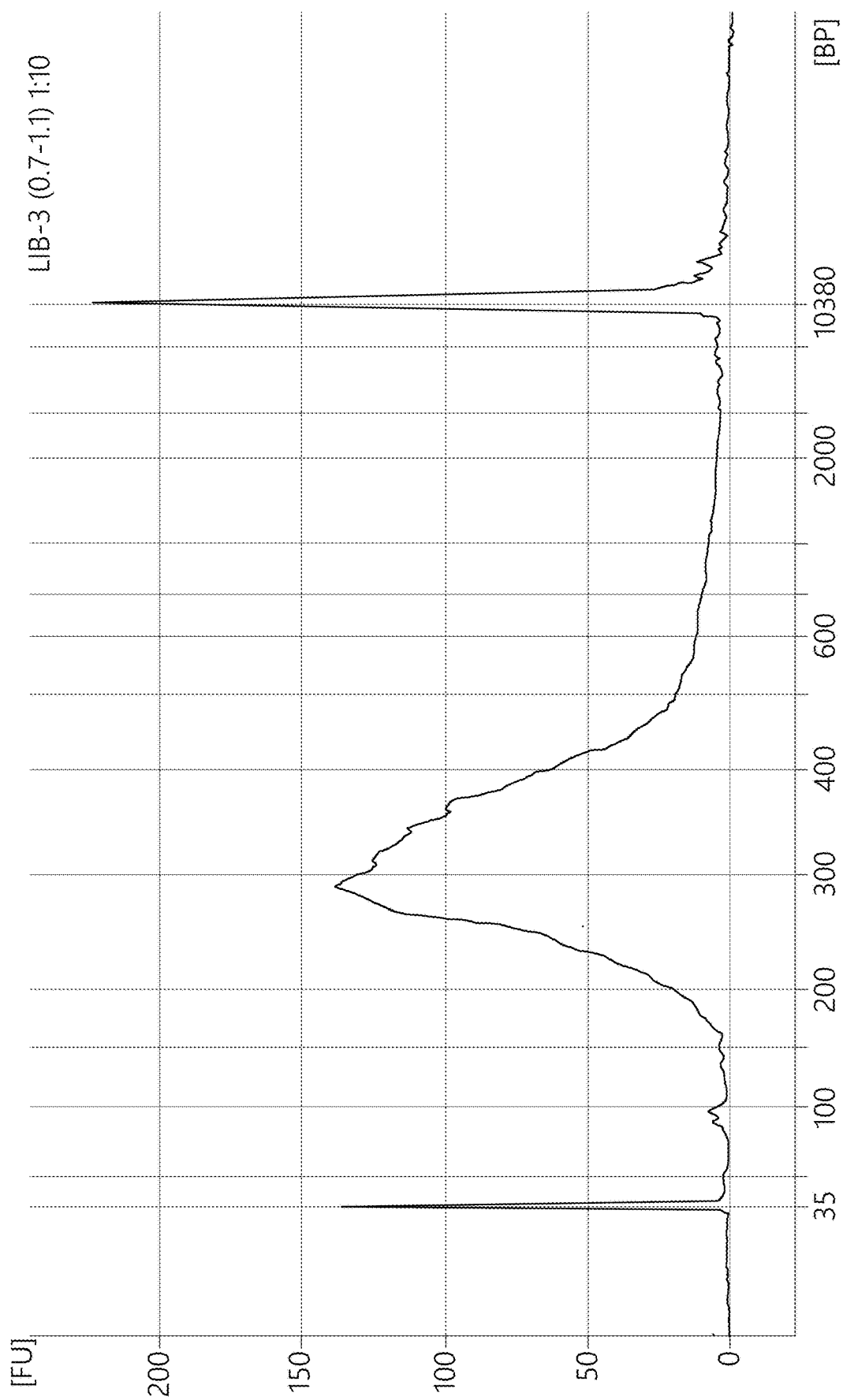
FIG. 11 depicts a bioanalyzer trace of the sequencing library made from the WTA product made with an exemplary homopolymer tailing method in Example 5.

Sequencing library was diluted and run on the high sensitivity DNA assay of an Agilent Bioanalyzer as shown in FIG. 11.

Example 6: Removal of Restriction Enzyme Site

This example compares various methods to remove the restriction enzyme binding site from the quasi-symmetric stochastically barcoded nucleic acid product of the disclosure, thereby breaking the symmetry of the molecule.

Figure 12:
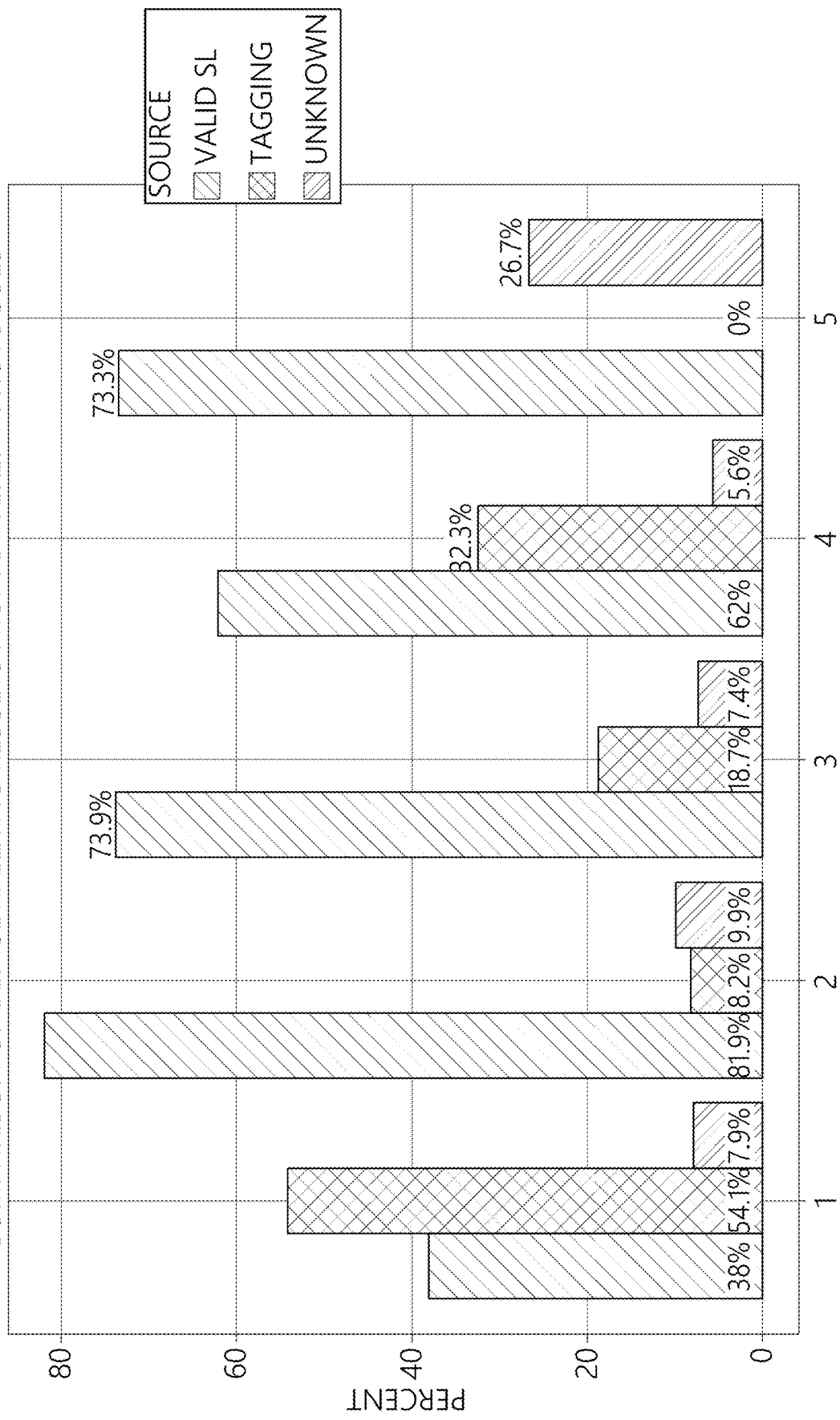
FIG. 12 depicts percent of read mapping with exemplary restriction enzyme digestion methods in Example 6.

Libraries were created using different protocols as described herein to remove the tagging sequence from libraries before, during, or after library construction. FIG. 12 shows a comparison of the demultiplexing results of the sequencing runs from WTA samples made with different restriction enzyme binding site removal protocols. Group 1 of FIG. 12 were samples made by the homopolymer tailing and restriction digestion protocol of the disclosure. The first bar of the triplicate indicates the percent of reads that mapped to a valid stochastic barcode (e.g., a stochastic barcode used in the assay). The second bar of the triplicate indicates sequences unique to the tagging primer/ligated adapter (e.g., the restriction cleavage site directly after the WTA primer annealing site). This indicates reads that were on the 5' end.

The third bar of the triplicate indicates the percent of reads that were of unknown origin. Group 2 of FIG. 12 was a WTA sample prepared with homopolymer tailing and digested with 10 U of AsiSI. Group 3 of FIG. 12 was a WTA sample prepared with homopolymer tailing with 10 U of the AsiSI restriction enzyme included during the random priming step after the WTA amplification. Group 4 of FIG. 12 was a WTA sample prepared with homopolymer tailing with 10 U of the AsiSI restriction enzyme included during the random priming step after the WTA amplification and was heat inactivated. Group 5 of FIG. 12 was a WTA sample prepared with an alternate tagging primer of the disclosure (CBO10 TCA-GACGTGTGCTCTTCCGATgcgatcgcTTTTTTTTTTT-TTTTTTTTTTTTT (SEQ ID NO: 15)). The primer has a 2 nt mismatch to the 3' most nucleotides of the WTA amplification primer. The library was constructed omitting AsiSI digestion.

Figure 13A:
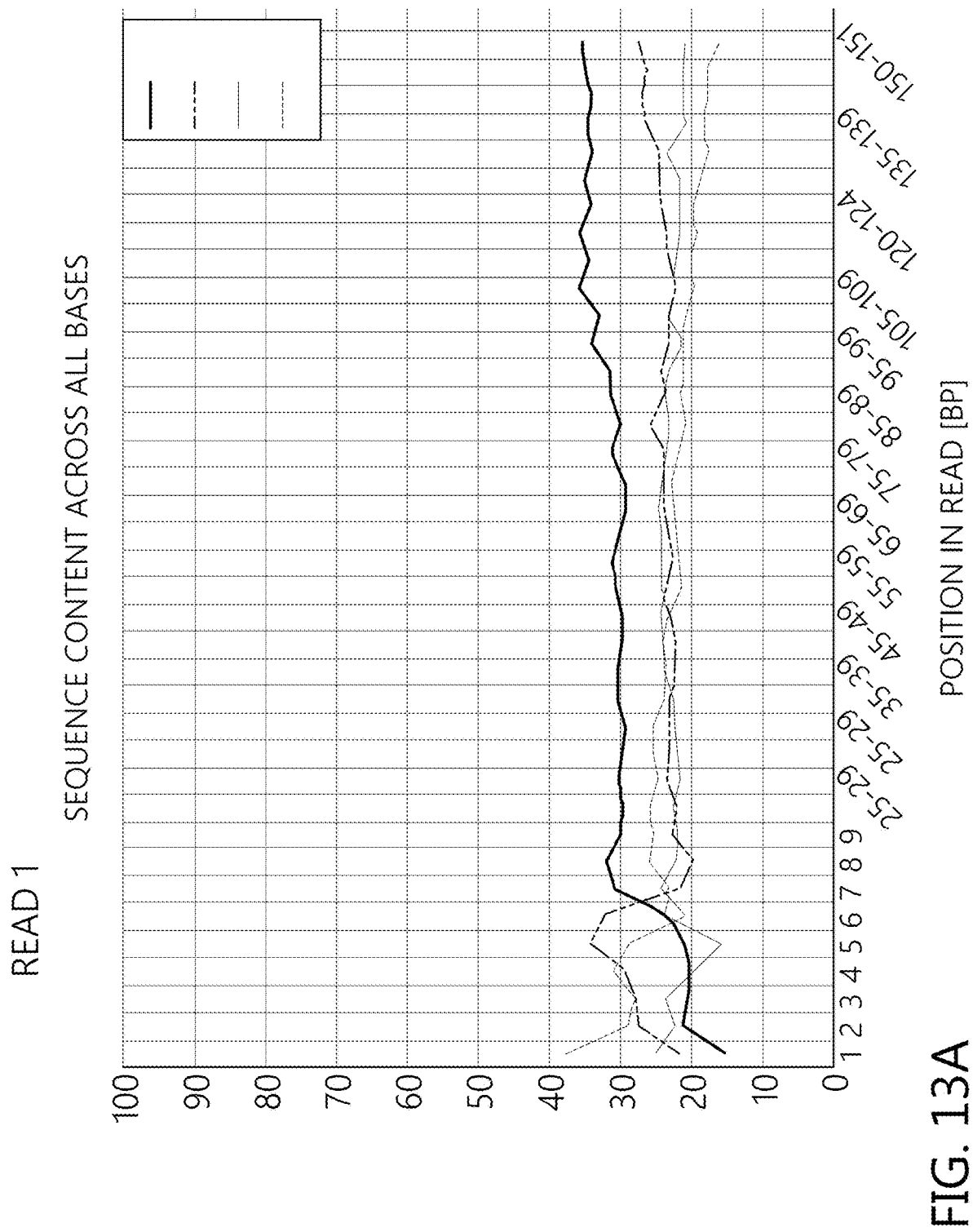
FIGS. 13A and 13B depict fastQC data of the base content of a sample using an exemplary adaptor ligation method in Example 6.
Figure 13B:
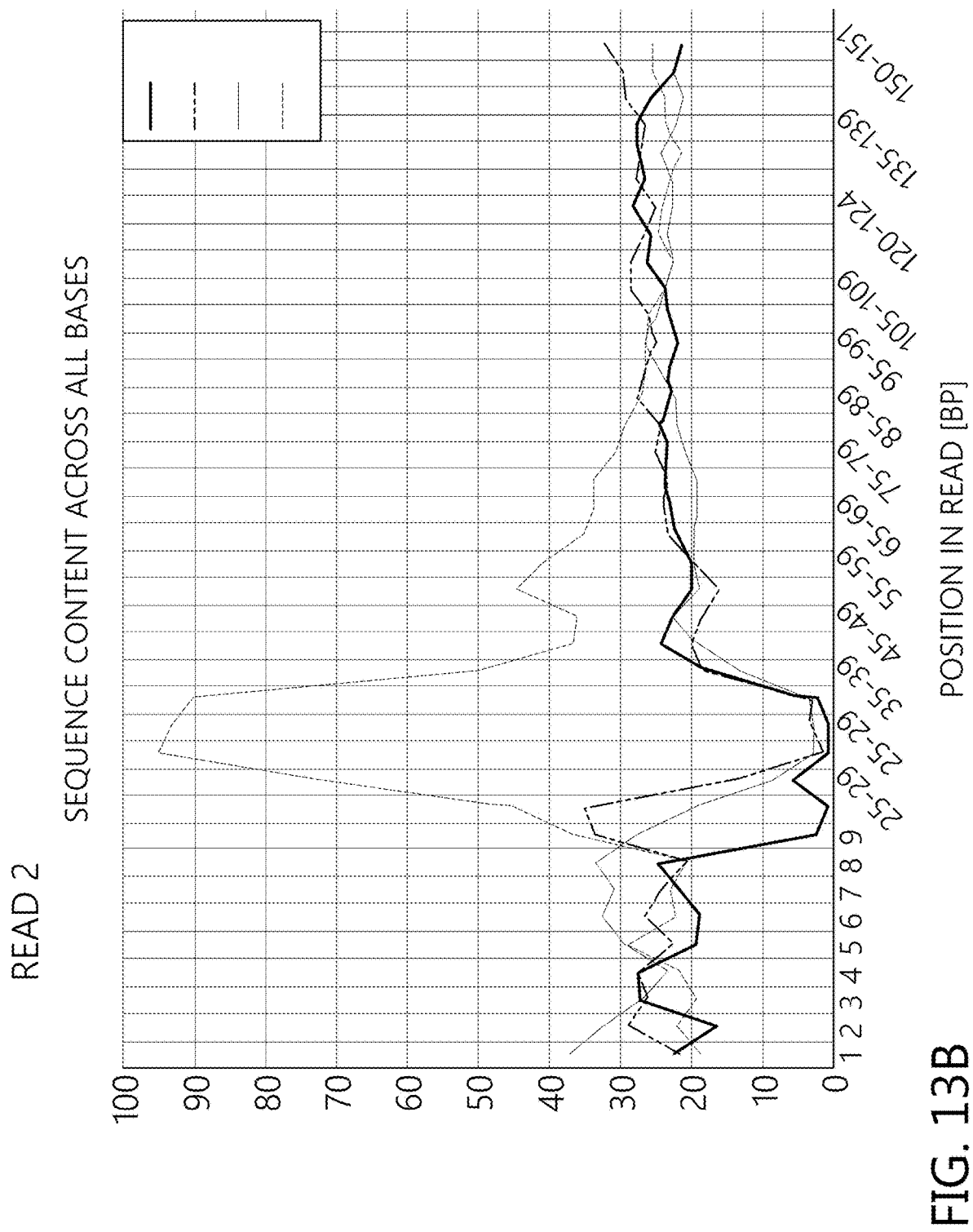
Figure 14:
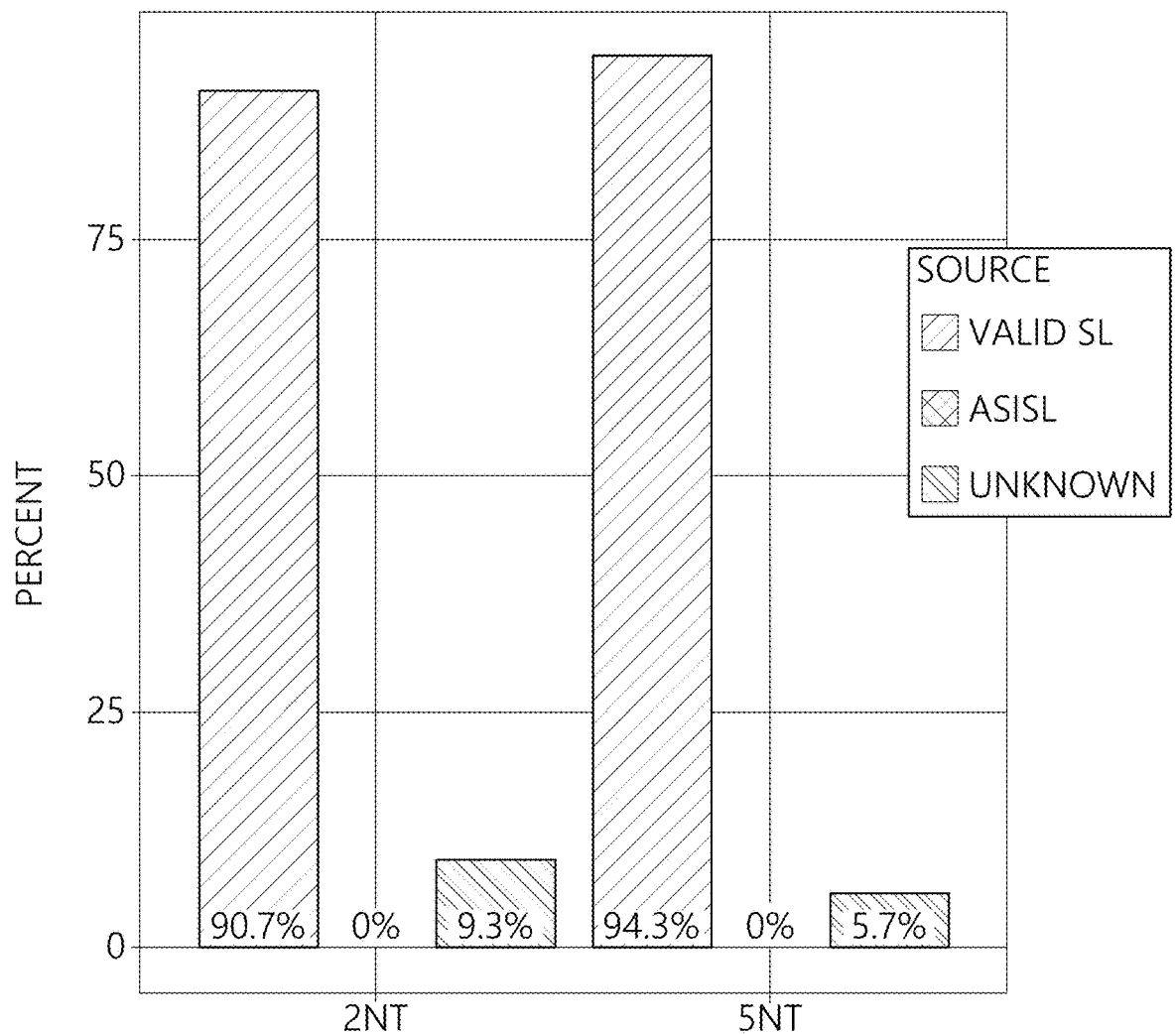
FIG. 14 shows the percent of read mapping with simultaneous use of restriction enzyme cleavage and a mismatched WTA primer (e.g., second universal primer).

The base distribution of the sequencing reads from the library prepared in FIG. 14 is shown in FIGS. 13A and 13B. The bases are distributed evenly indicating there isn't any contaminating AsiSI sequence from the WTA primer (e.g., second universal primer). The library from FIG. 14 was made from a combination of using CBO10 and simultaneous AsiSI treatment like group 3.

Example 7: Combination of Adaptor Addition Methods and Simultaneous Restriction Enzyme Treatment This example shows the percentage of reads based on the first 8 bp of the sequence mapping to either a valid stochastic barcode, the WTA primer (e.g., second universal primer) that comprises the restriction enzyme binding site (i.e., immediately downstream of the read2 sequence), or an unknown sequence.

WTA products were generated either by the homopolymer tailing method, or $2^{nd}$ strand/ligation protocols. The homopolymer protocol utilized a tagging primer with 2 nt of mismatch to the 3' end of the library amplification primer, while the ligation based method described herein had 5 nt of mismatch.

Libraries were generated by random priming with Klenow (Exo-), but with the inclusion of 10 U AsiSI during the primer extension. Libraries were sequenced with paired end chemistry on an Illumina MiSeq.

As shown in FIG. 14, combining enzyme digestion and 3' mismatches to the library amplification primer perform the best, with more mismatches being better.

Example 8: Adaptor Ligation Method on Beads

This example illustrates the method and data for ligating an adaptor of the disclosure to the second strand of a barcoded cDNA on a bead. The method comprises:

Bead Preparation: 40 µl 2.5M beads/ml Resolve beads were put in a 1.5 ml tube. The beads were bound to a magnet and supernatant was removed. The beads were washed 2× with 200 µl RNase-free water. The beads were resuspended in 21.5 µl Annealing mix and incubated 3 min @ 65° C. in the heat block with occasional vortexing. The beads were placed on ice.

$1^{st}$ Strand Synthesis: 18.5 µl RT Mastermix was added to the beads. The reaction mixture was incubated at 42° C. for 10 min in the thermomixer and 80° C. for 5 min on a heat block. The beads were bound to a magnet to remove the supernatant.

$2^{nd}$ Strand Synthesis: 80 µl 2nd Strand Synthesis Mix was added to the beads. The reaction mixture was incubated 2.5 hrs at 16° C. in the thermomixer and 1 µl 3 U/µl T4 DNA Polymerase was added and incubated 5 min at 16° C. (blunt the cDNA). The reaction mixture was transferred to ice, and 5 µl 0.5M EDTA was added and mixed to stop all enzymatic activity followed by 1×100 µl 10 mM Tris Ph8.0.

Adaptor Ligation: 50 µl Ligation Mix was added to each tube and incubated 30 min @ room temp on the rotator. The beads were bound to a magnet and washed 2×200 µl Tris-Tween and resuspended in 50 µl Tris-Tween and store at 4° C.

WTA Amplification: WTA PCR reactions were set up with 1 µl resuspended beads in WTA Mastermix and PCR was conducted.

| Annealing mix | | |
|---|---|---|
| 1 | 1 X | Reagent |
| 1 | 1 µl | 1 µg/µl Ambion Human Brain RNA (not HBRR) |
| 1 | 1 µl | 1 pg/µl spike-in |
| 19.5 | 19.5 µl | water |
| 21.5 | 21.5 µl | Total |

| RT Mastermix | | |
|---|---|---|
| 1 | 1 X | Reagent |
| 8 | 8 µl | 5X Protoscipt buffer |
| 4 | 4 µl | 1 mg/ml BSA |
| 2 | 2 µl | 10 mM dNTP |
| 2 | 2 µl | 100 mM DTT |
| 2 | 2 µl | ProtoscriptII |
| 0.5 | 0.5 µl | Murine Rnasin |
| 18.5 | 18.5 µl | Total |

| 2nd Strand Synthesis Mix | | |
|---|---|---|
| 1 | 1 X | Reagent |
| 60 | 60 µl | water |
| 8 | 8 µl | 1 mg/ml BSA |
| 8 | 8 µl | 10X 2nd Strand Synthesis Buffer |
| 4 | 4 µl | 2nd Strand Enzyme Mix |
| 80 | 80 µl | Total |

| Ligation Mix | | |
|---|---|---|
| 1 | 1 X | Reagent |
| 32 | 32 µl | water |
| 5 | 5 µl | 1 mg/ml BSA |
| 10 | 10 µl | 5X Quick Ligation Reaction Buffer |
| 1 | 1 µl | Quick T4 DNA Ligase |
| 2 | 2 µl | 5 µM Anealed CBO123/106 |
| 50 | 50 µl | Total |

| WTA Mastermix | | |
|---|---|---|
| 1 | 2 X | Reagent |
| 21.5 | 43 µl | Water |
| 1 | 2 µl | Ligated Resolve Beads |
| 2.5 | 5 µl | 30 µM CBO40 |
| 25 | 50 µl | 2X Q5 HotStart Mastermix |
| 50 | 100 µl | Total |

| Cycling Conditions for PCR | | |
|---|---|---|
| 98° C. | 30 s | |
| 98° C. | 10 s | 20X |
| 65° C. | 15 s | |
| 72° C. | 3 min | |
| 72° C. | 5 min | |
| 4° C. | hold | |

Figure 22A:
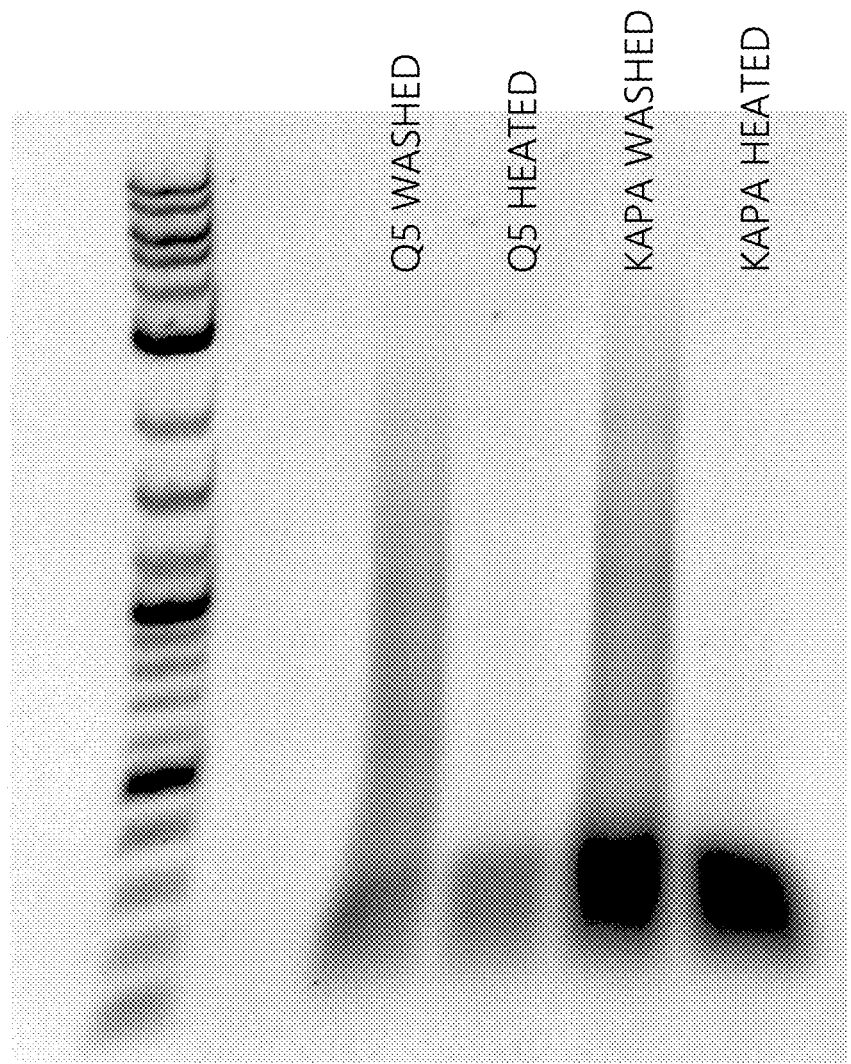
FIGS. 22A and 22B show data demonstrating an exemplary adaptor ligation onto nucleic acids attached to solid supports method of Example 7.
Figure 22B:
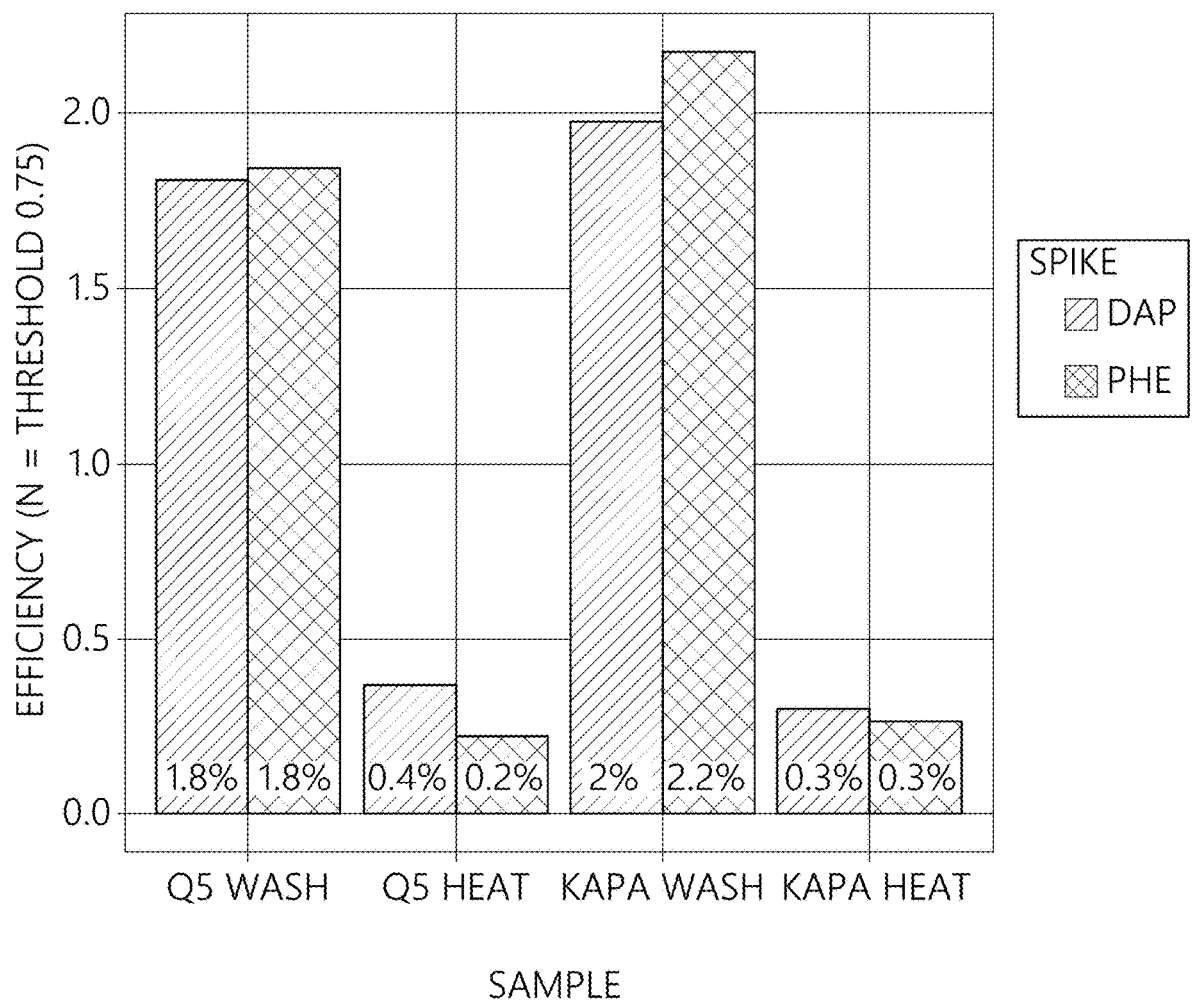

The results of the above method are shown in FIG. 22. The gel depicted on the left shows the WTA amplification product. The Q5 wash and KAPA washed lanes show the WTA amplification product, as the smear represents the amplified transcriptome. Removal of $2^{nd}$ strand enzymes by washing was much more effective than heat inactivation. No major difference was seen between the polymerases.

The samples shown on the left were quantified for efficiency using the Pixel™ method as described herein.

Example 9: Characterization of the Suppressive Adaptor

This example shows the characterization of the suppression capabilities of different adaptors. The method followed the adaptor ligation WTA protocol (Example 8) with either the high or low suppression adapter and then amplified with varying concentrations of WTA primer. The method comprises:

Bead Preparation: 40 µl 2.5M beads/ml Resolve beads were put in a 1.5 ml tube. The beads were bound to a magnet and supernatant was removed. The beads were washed 2× with 200 µl RNase-free water. The beads were resuspended in 21.5 µl Annealing mix and incubated 3 min @ 65° C. in the heat block with occasional vortexing. The beads were placed on ice.

$1^{st}$ Strand Synthesis: 18.5 µl RT Mastermix was added to the beads. The reaction mixture was incubated at 42° C. for 10 min in the thermomixer and 80° C. for 5 min on a heat block. The beads were bound to a magnet to remove the supernatant.

$2^{nd}$ Strand Synthesis: 80 µl 2nd Strand Synthesis Mix was added to the beads. The reaction mixture was incubated 2.5 hrs at 16° C. in the thermomixer and 1 µl 3 U/µl T4 DNA Polymerase was added and incubated 5 min at 16° C. (blunt the cDNA). The reaction mixture was transferred to ice, and 5 µl 0.5M EDTA was added and mixed to stop all enzymatic activity followed by 1×100 µl 10 mM Tris Ph8.0. The cleaned 2nd strand reaction was split into two tubes.

Adaptor Ligation: 50 µl Ligation Mix was added to each tube and incubated 30 min @ room temp on the rotator. The beads were bound to a magnet and washed 2×200µl Tris-Tween and resuspended in 50 µl Tris-Tween and store at 4° C.

WTA Amplification: WTA PCR reactions were set up with 1 µl resuspended beads in WTA Mastermix and PCR was conducted.

| Annealing mix | | | |
|---|---|---|---|
| 1 | 1 X | Reagent | |
| 1 | 1 µl | 1 µg/µl Ambion Human Brain RNA (not HBRR) | |
| 1 | 1 µl | 1 pg/µl spike-in | |
| 19.5 | 19.5 µl | water | |
| 21.5 | 21.5 µl | Total | |

| RT Mastermix | | |
|---|---|---|
| 1 | 1 X | Reagent |
| 8 | 8 µl | 5X Protoscipt buffer |
| 4 | 4 µl | 1 mg/ml BSA |
| 2 | 2 µl | 10 mM dNTP |
| 2 | 2 µl | 100 mM DTT |
| 2 | 2 µl | ProtoscriptII |
| 0.5 | 0.5 µl | Murine Rnasin |
| 18.5 | 18.5 µl | Total |

| 2nd Strand Synthesis Mix | | |
|---|---|---|
| 1 | 1 X | Reagent |
| 60 | 60 µl | water |
| 8 | 8 µl | 1 mg/ml BSA |
| 8 | 8 µl | 10X 2nd Strand Synthesis Buffer |
| 4 | 4 µl | 2nd Strand Enzyme Mix |
| 80 | 80 µl | Total |

| Ligation Mix | | |
|---|---|---|
| 1 | 1 X | Reagent |
| 32 | 32 µl | water |
| 5 | 5 µl | 1 mg/ml BSA |
| 10 | 10 µl | 5X Quick Ligation Reaction Buffer |
| 1 | 1 µl | Quick T4 DNA Ligase |
| 2 | 2 µl | 5 µM Anealed CBO122/103 or CBO 123/105 |
| 50 | 50 µl | Total |

| WTA Mastermix | | |
|---|---|---|
| 1 | 2 X | Reagent |
| 21.5 | 43 µl | Water |
| 1 | 2 µl | Ligated Resolve Beads |
| 2.5 | 5 µl | 30 µM, 10 µM, or 5 µM CBO40 |
| 25 | 50 µl | 2X Q5 HotStart Mastermix |
| 50 | 100 µl | Total |

| Cycling Conditions for PCR | | |
|---|---|---|
| 98° C. | 30 s | |
| 98° C. | 10 s | 20X |
| 65° C. | 15 s | |
| 72° C. | 3 min | |
| 72° C. | 5 min | |
| 4° C. | hold | |

Figure 23:
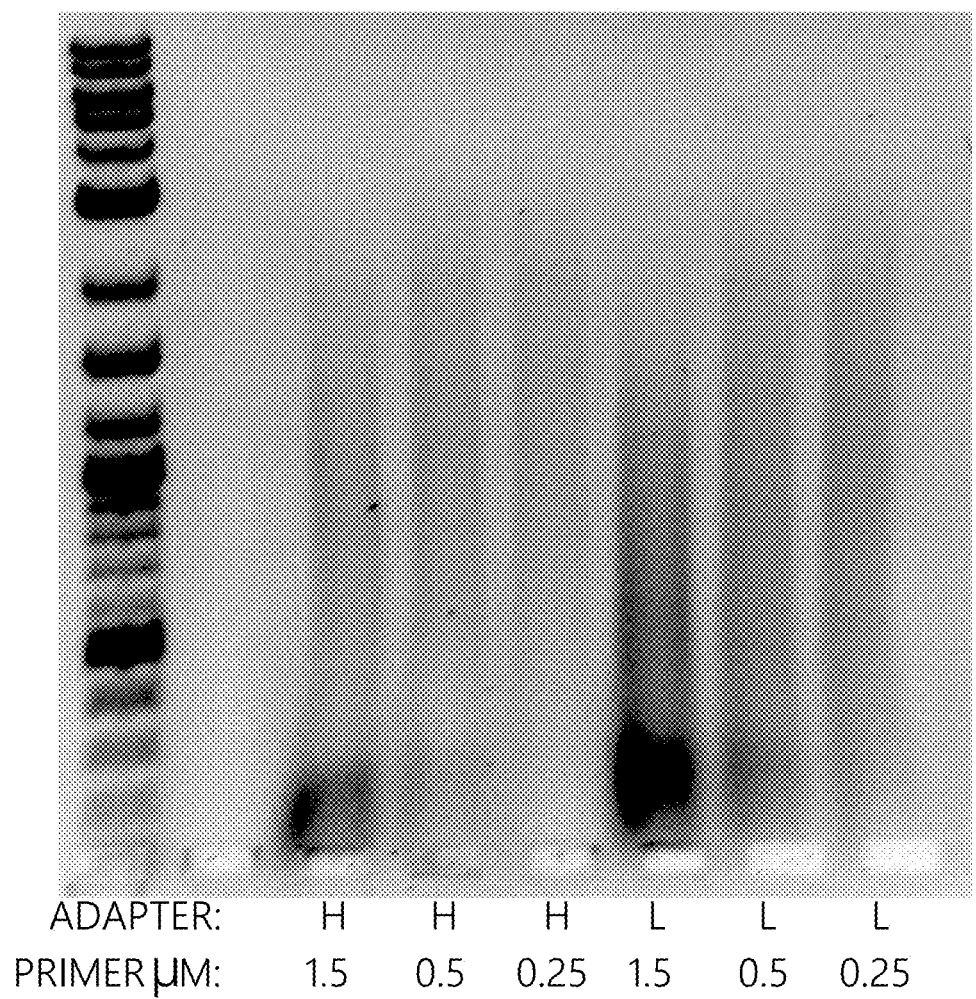
FIG. 23 shows that the high suppression adaptor prevents primer-dimer formation.

The results of the method are shown in FIG. 23. H refers to high suppression adaptor. L refers to low suppression adaptor. The primer concentration variation is shown beneath each lane. FIG. 23 shows that while all samples had similar levels of transcriptome amplification, the high suppression adapter at lower primer concentrations had the fewest primer-artifacts (as evidenced by the lack of primer-dimer band at the bottom of the gel).

Example 10: Testing Bead Capacity for WTA Amplification

This example describes experiments done to test the bead capacity for WTA amplification. The method comprises:

Bead Preparation: 80 µl 2M beads/ml uncoupled beads were put in a 1.5 ml tube and bound to a magnet to remove supernatant. The beads were washed 2× with 200 µl RNase-free water and resuspended in two 10 µl aliquots in water.

WTA Amplification: WTA PCR reactions were set up with 1 µl resuspended beads.

| Tube | WTA beads | Bare Beads | Water | Polymerase |
|---|---|---|---|---|
| 1 | 0 | 0 | 20 | Q5 |
| 2 | 1 | 0 | 19 | Q5 |
| 3 | 10 | 0 | 10 | Q5 |
| 4 | 10 | 10 | 0 | Q5 |
| 5 | 0 | 0 | 20 | KAPA |
| 6 | 1 | 0 | 19 | KAPA |
| 7 | 10 | 0 | 10 | KAPA |
| 8 | 10 | 10 | 0 | KAPA |

| WTA Mastermix | | |
|---|---|---|
| 1 | 2 X | Reagent |
| 2.5 | 5 µl | Water |
| 2.5 | 5 µl | 5 µM CBO40 |
| 25 | 50 µl | 2X Q5 HotStart Mastermix or APA Hifi |
| 30 | 60 µl | Total |

| Cycling Conditions | | |
|---|---|---|
| 98° C. | 2 min | |
| 98° C. | 20 s | 20X |

| Cycling Conditions | | |
|---|---|---|
| 58° C. | 15 s | |
| 72° C. | 3 min | |
| 72° C. | 5 min | |
| 4° C. | hold | |

Bead Preparation: Beads were in ~100 µl Tris-Tween, two 10 µl bead amplifications were performed, one with and one without BSA.

WTA Amplification: WTA PCR reactions were set up with 1 µl resuspended beads.

| WTA Mastermix | | |
|---|---|---|
| 1 | 2 X | Reagent |
| 7.5 | 15 µl | Water |
| 10 | 20 µl | Resolve Beads |
| 5 | 10 µl | 10X BSA or water |
| 2.5 | 5 µl | 5 µM CBO40 |
| 25 | 50 µl | 2X KAPA Hifi |
| 50 | 100 µl | Total |

| Cycling Conditions | | |
|---|---|---|
| 98° C. | 2 min | |
| 98° C. | 20 s | 20X |
| 58° C. | 15 s | |
| 72° C. | 3 min | |
| 72° C. | 5 min | |
| 4° C. | hold | |

Figure 24B:
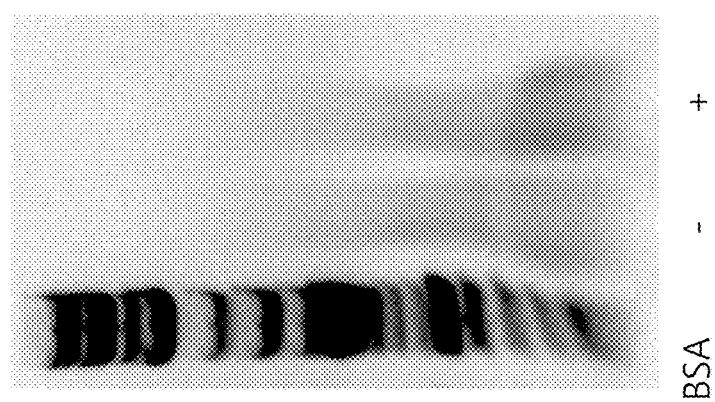
FIGS. 24A and 24B show whole transcriptome amplification product generated from beads either alone (A) or in combination with cells (B).
Figure 24A:
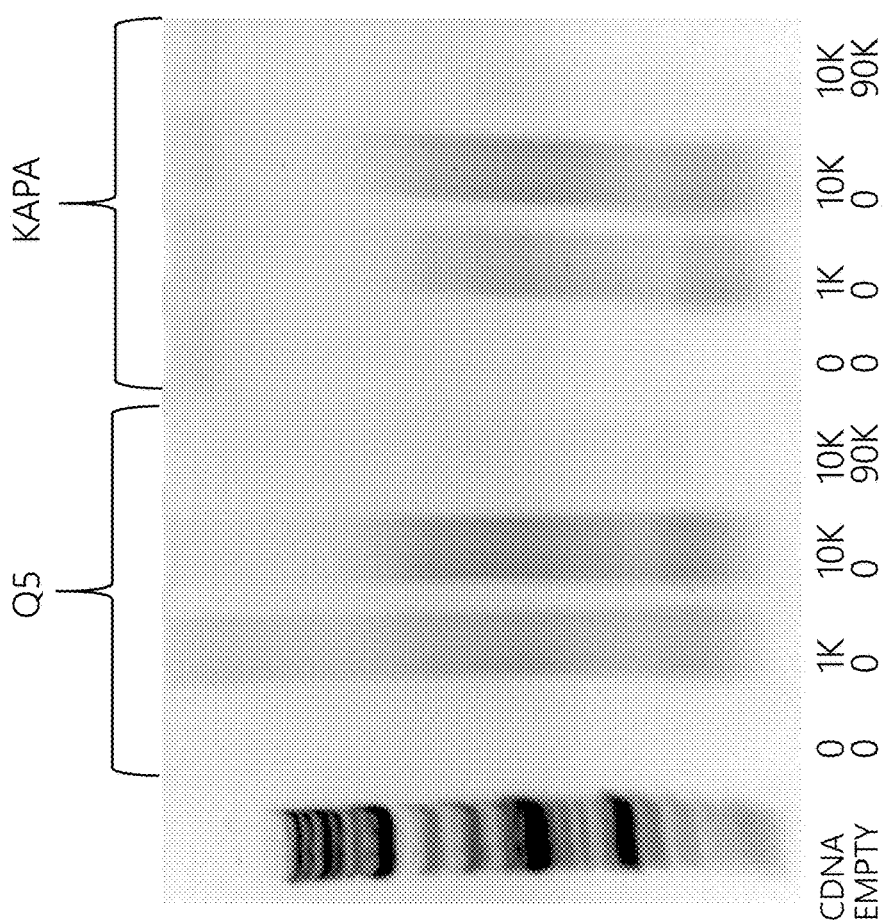

The results of the method are shown in FIG. 24. As shown on the left, different amount of beads with cDNA transcribed from bulk RNA (cDNA) were mixed with uncoupled beads (Empty) (e.g., beads without conjugated oligonucleotides) to mimic the loaded and unloaded beads from a typical experiment. Different amount of the beads were added to a standard 50 µl PCR reaction with either Q5 polymerase 2× mastermix or KAPA Hifi polymerase. In both cases, the maximum amount of beads per PCR was ~10,000.

As shown on the right in FIG. 24, the WTA protocol was prepared from a sample that had been contacted with cells (as opposed to the left image of FIG. 24 which had no cells). Then about 10,000 beads from the experiment were added in each of two PCR reactions, either with or without BSA. The BSA was used to counter bead inhibition. The smear above the primer dimers indicates amplification of some RNA species.

The samples above were used to prepare a library. The WTA product and the library were analyzed with the Bioanalyzer. The protocol for generating the library comprises: Annealing mix was added to 50 ng WTA product, heated to 95° C. for 2 min and cooled to 4° C. for 5 min. 7 µl Klenow(exo-) mastermix was added to each tube. The reaction mixture was incubated at 37° C. for 30 min and at 80° C. for 20 min, and cleaned up with 35 µl AmpureXP, followed by elution in 22 µl water.

Library Preparation: 28 µl Q5 Mastermix was added, and PCR was conducted using the cycling conditions below. Clean up was done with the same ratio of beads as used for library size selection and eluted in 30 µl Tris-Tween.

| Annealing mix | | |
|---|---|---|
| 1 | 2.5 X | Reagent |
| 5 | 12.5 µl | 10 µM R2-N9 (CBO121) |
| 1 | 2.5 µl | 10 mM dNTP |
| 5 | 12.5 µl | WTA Product |
| 32 | 80 µl | Water |
| 43 | 107.5 µl | Total |

| Klenow Mastermix | | |
|---|---|---|
| 1 | 3 X | Reagent |
| 5 | 15 µl | 10X NEB2.1 |
| 1 | 3 µl | AsiSI |
| 1 | 3 µl | Klenow exo- (NEB) |
| 7 | 21 µl | Total |

| Q5 Mastermix | | |
|---|---|---|
| 1 | 2.5 X | Reagent |
| 25 | 62.5 µl | 2X Q5 HotStart Mastermix |
| 1.5 | 3.75 µl | D501 |
| 1.5 | 3.75 µl | D70X |
| 28 | 62.5 µl | Total |

| Cycling Conditions | | |
|---|---|---|
| 98° C. | 30 s | |
| 98° C. | 10 s | 12X |
| 65° C. | 15 s | |
| 72° C. | 20 s | |
| 72° C. | 2 min | |
| 4° C. | hold | |

| Tube | Index |
|---|---|
| 1 | D707 |
| 2 | D708 |

Figure 25A:
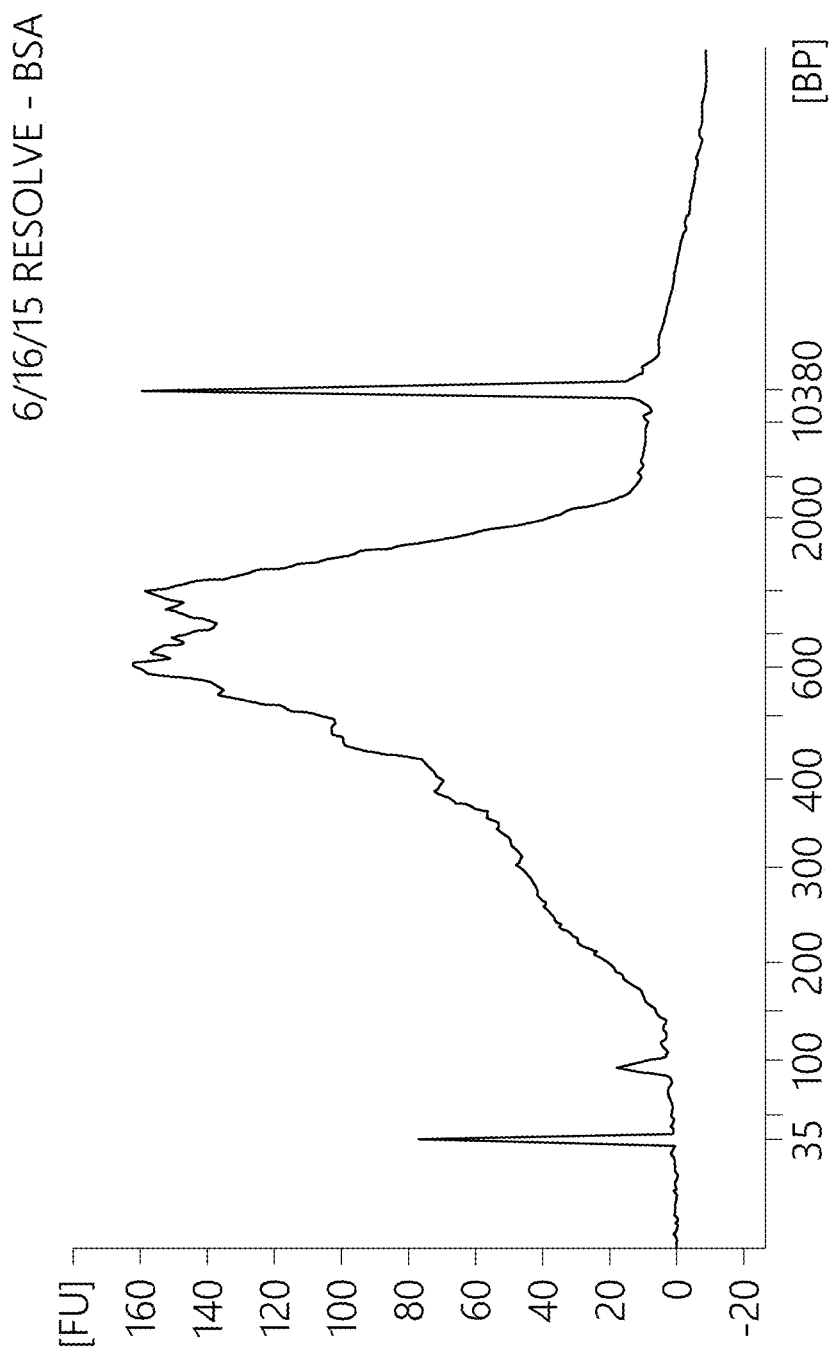
FIGS. 25A and 25B show Bioanalyzer traces of the WTA product (A) and library preparation (B) of the samples generated from FIG. 24.
Figure 25B:
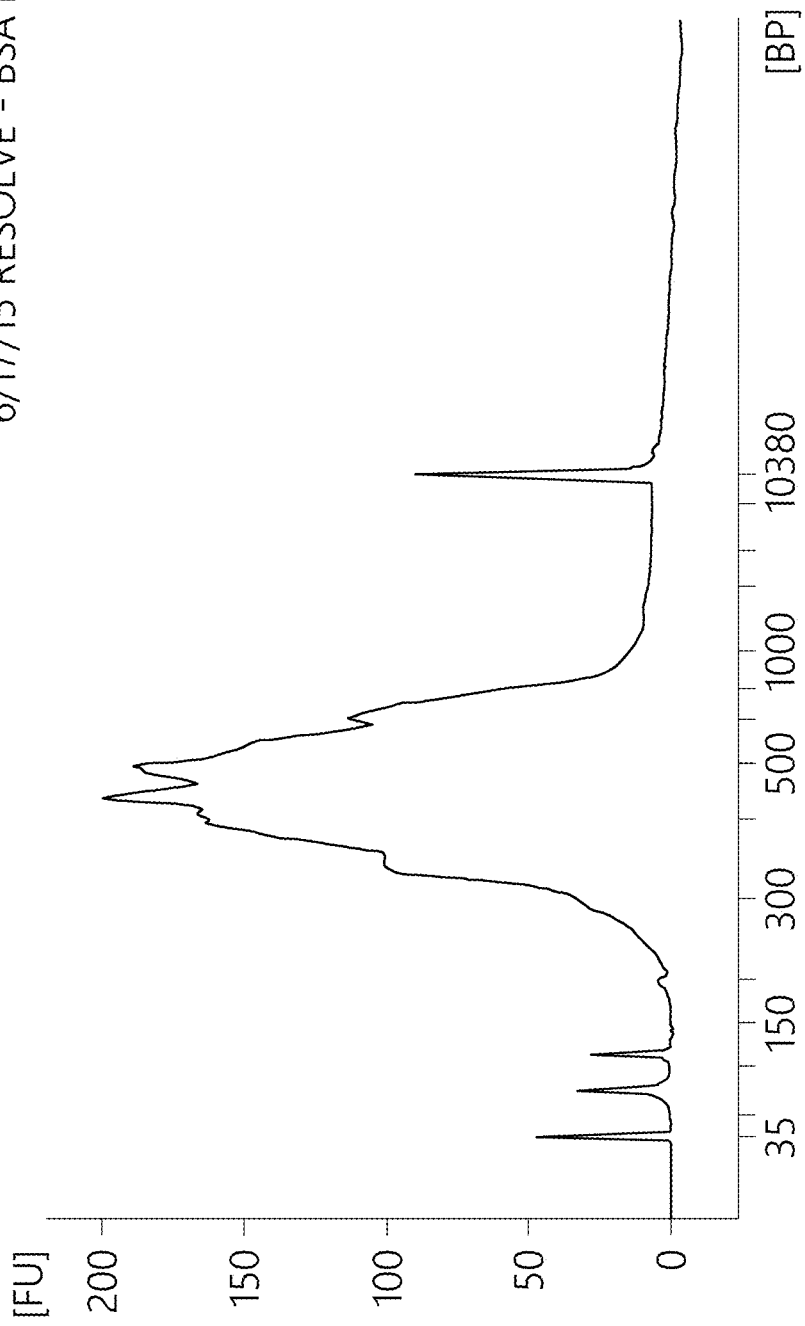

As shown FIG. 25, the left trace shows the WTA products resulting from FIG. 24 right-hand side. The right trace in FIG. 25 is from the library of WTA product. The product for each was the right size, as evidenced by the trace. This indicates that the right sequences were added to the WTA ligation and library preparation methods and a valid library can be prepared from solid supports.

Example 12: Analysis of Exonuclease Treatment

This example was performed to test the effect of exonuclease treatment on the beads using the adaptor ligation methods of the disclosure. The method comprises:

Bead Preparation: 16 µl 2.5M beads/ml Resolve beads were put in a 1.5 ml tube. 144 µl beads were put in a separate tube. The beads were bound to a magnet and supernatant was removed. The beads were resuspended in 100 µl Trsi-Tween and heated to 95° C. for 2 min. The beads were washed 2× with 200 µl RNase-free water (set aside the 144 µl beads for later). The beads were resuspended in 21.5 µl Annealing mix and incubated 3 min @ 65° C. in the heat block with occasional vortexing. The beads were placed on ice.

1$^{st}$ Strand Synthesis: 18.5 µl RT Mastermix was added to the beads. The reaction mixture was incubated at 42° C. for 30 min in the thermomixer and 80° C. for 5 min on a heat block. The beads were bound to a magnet to remove the supernatant. The beads from the 1st strand reaction were mixed with the no RT beads, and washed 2× with 200 µl Tris-Tween. After resuspending for the second wash, the beads were split into four 50 µl tubes. For tubes #3&4 only (other tubes go straight to 2nd strand reaction), the beads were bound to magnet and supernatant was removed. The beads were resuspended in 40 µl ExoI mastermix. The reaction mixture was incubated at 37° C. for 30 min and at 80° C. for 20 min. The beads were washed 1× in 200 µl Tris-Tween.

$2^{nd}$ Strand Synthesis: 80 µl 2nd Strand Synthesis Mix was added to the beads. 20 µl 2nd Strand Buffer Mix without enzyme was added. The reaction mixture was incubated 2.5 hrs at 16° C. in the thermomixer and 1 µl 3 U/µl T4 DNA Polymerase was added and incubated 5 min at 16° C. (blunt the cDNA) to tube #1 (or #3). The reaction mixture was transferred to ice, and 5 µl 0.5M EDTA was added and mixed to stop all enzymatic activity followed by wash 2× in 100µl Wash Buffer (10 mM Tris pH8.0, 150 mM NaCl, 5 mM EDTA, 0.05% tween-20) and 2×100 µl Tris-Tween to remove 2nd strand enzymes.

Adaptor Ligation: 50 µl Ligation Mix was added to each tube and incubated 30 min @ room temp on the rotator. The beads were bound to a magnet and washed 2×200 µl Tris-Tween and resuspended in 50 µl Tris-Tween and store at 4° C.

WTA Amplification: WTA PCR reactions were set up with 5 µl resuspended beads in WTA Mastermix and PCR was conducted.

| Annealing mix | | | |
|---|---|---|---|
| 1 | 1 X | | Reagent |
| 4 | 4 µl | | 1 ng/µl K562 RNA |
| 0.5 | 0.5 µl | | 1 pg/µl spike-in |
| 17 | 17 µl | | water |
| 21.5 | 53.75 µl | | Total |

| RT Mastermix | | | |
|---|---|---|---|
| 1 | 2.5 X | | Reagent |
| 8 | 20 µl | | 5X Protoscipt buffer |
| 4 | 10 µl | | 1 mg/ml BSA |
| 2 | 5 µl | | 10 mM dNTP |
| 2 | 5 µl | | 100 mM DTT |
| 2 | 5 µl | | ProtoscriptII |
| 0.5 | 1.25 µl | | Murine Rnasin |
| 18.5 | 46.25 µl | | Total |

| ExoI Mastermix | | | |
|---|---|---|---|
| 1 | 2.5 X | | Reagent |
| 4 | 10 µl | | 10X ExoI buffer |
| 2 | 5 µl | | ExoI |
| 34 | 85 µl | | Water |
| 40 | 100 µl | | Total |

| 2nd Strand Synthesis Mix | | | |
|---|---|---|---|
| 1 | 2.2 X | | Reagent |
| 8 | 17.6 µl | | 1 mg/ml BSA |
| 8 | 17.6 µl | | 10X 2nd Strand Synthesis Buffer |
| 4 | 8.8 µl | | 2nd Strand Enzyme Mix |
| 60 | 132 µl | | water |
| 16 | 35.2 µl | | Total |

| Ligation Mix | | | |
|---|---|---|---|
| 1 | 2.2 X | | Reagent |
| 32 | 70.4 µl | | water |
| 5 | 11 µl | | 1 mg/ml BSA |
| 10 | 22 µl | | 5X Quick Ligation Reaction Buffer |
| 1 | 2.2 µl | | Quick T4 DNA Ligase |
| 2 | 4.4 µl | | 5 µM Anealed CBO122/103 |
| 50 | 110 µl | | Total |

| WTA Mastermix | | | |
|---|---|---|---|
| 1 | 4.2 X | | Reagent |
| 17.5 | 73.5 µl | | Water |
| 2.5 | 10.5 µl | | 5 µM CBO40 |
| 25 | 105 µl | | 2X KAPA Hifi |
| 45 | 189 µl | | Total |

| Cycling Conditions | | |
|---|---|---|
| 98° C. | 2 min | |
| 98° C. | 20 s | 20X |
| 65° C. | 15 s | |
| 72° C. | 3 min | |
| 72° C. | 5 min | |
| 4° C. | hold | |

Figure 28A:
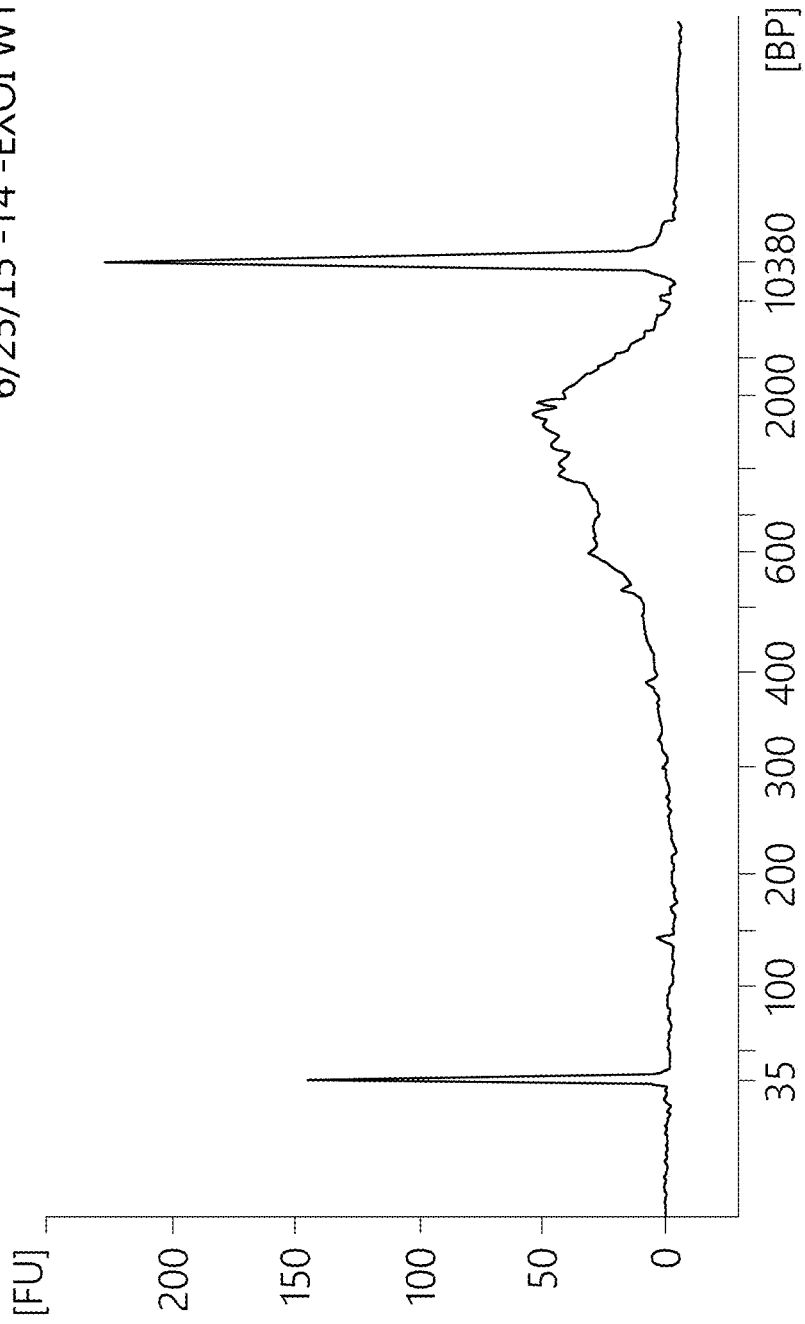
FIGS. 28A and 28B show the effect of exonuclease treatment on the WTA adaptor ligation method of the disclosure.
Figure 28B:
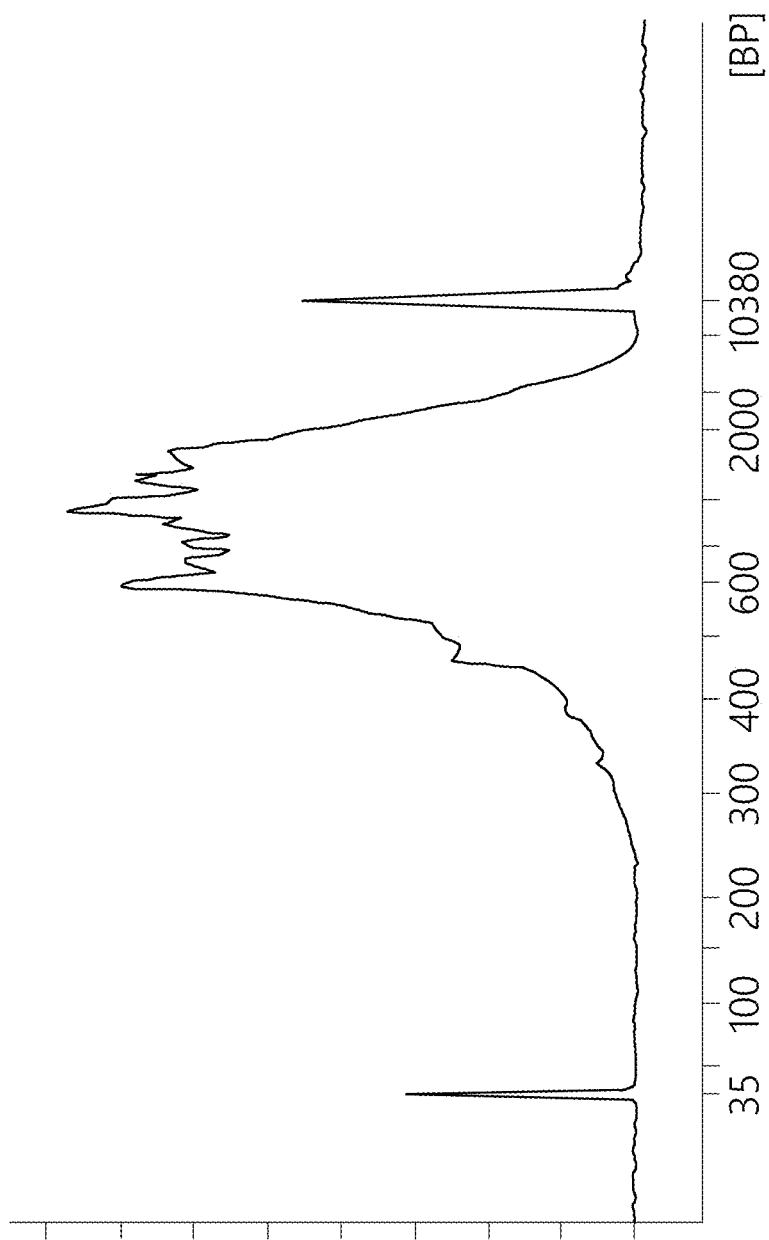
Figure 31A:
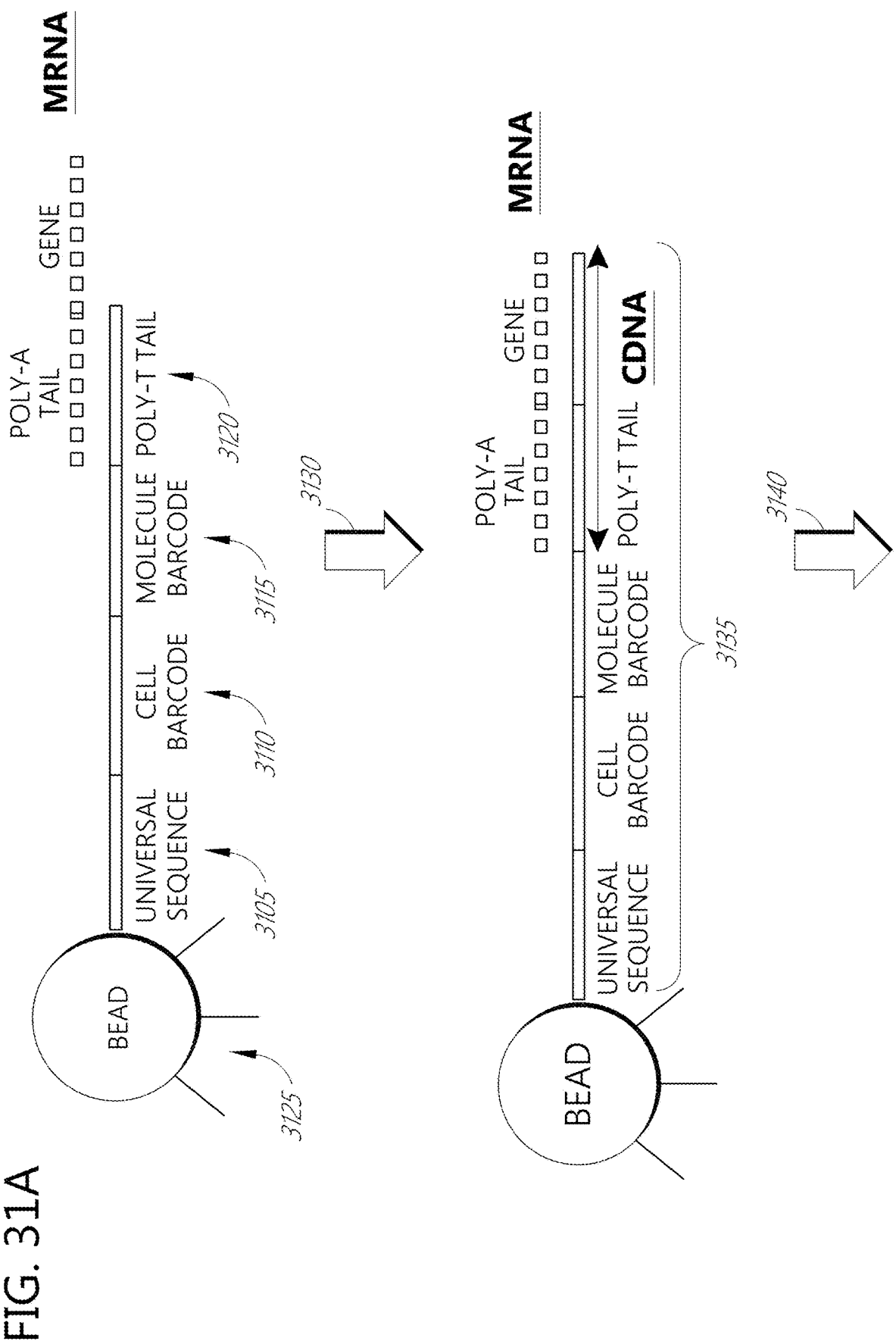
FIGS. 31A-31D show a schematic illustrating an exemplary embodiment of the whole transcriptome amplification method of the disclosure using adaptor ligation with beads.
Figure 31B:
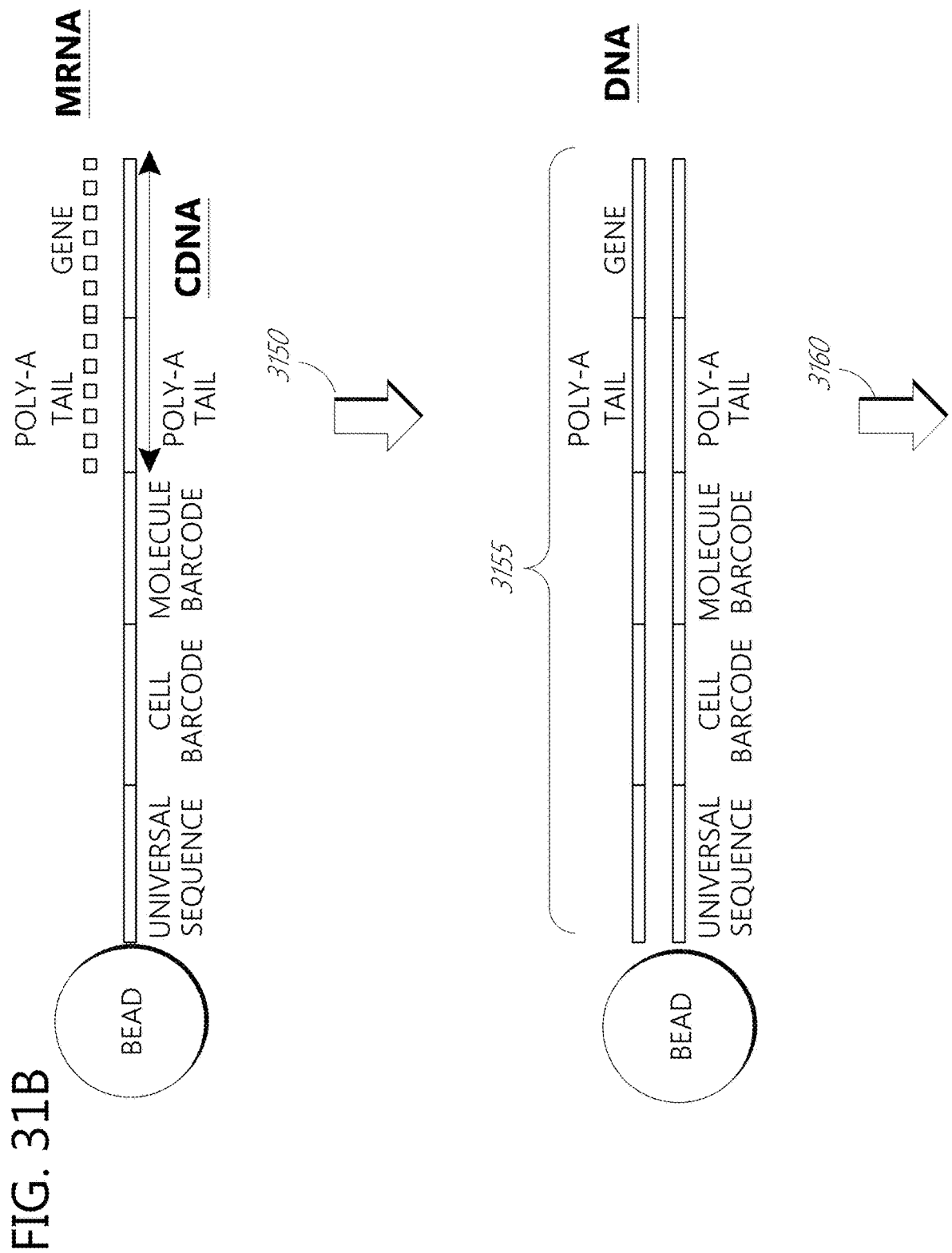
Figure 31C:
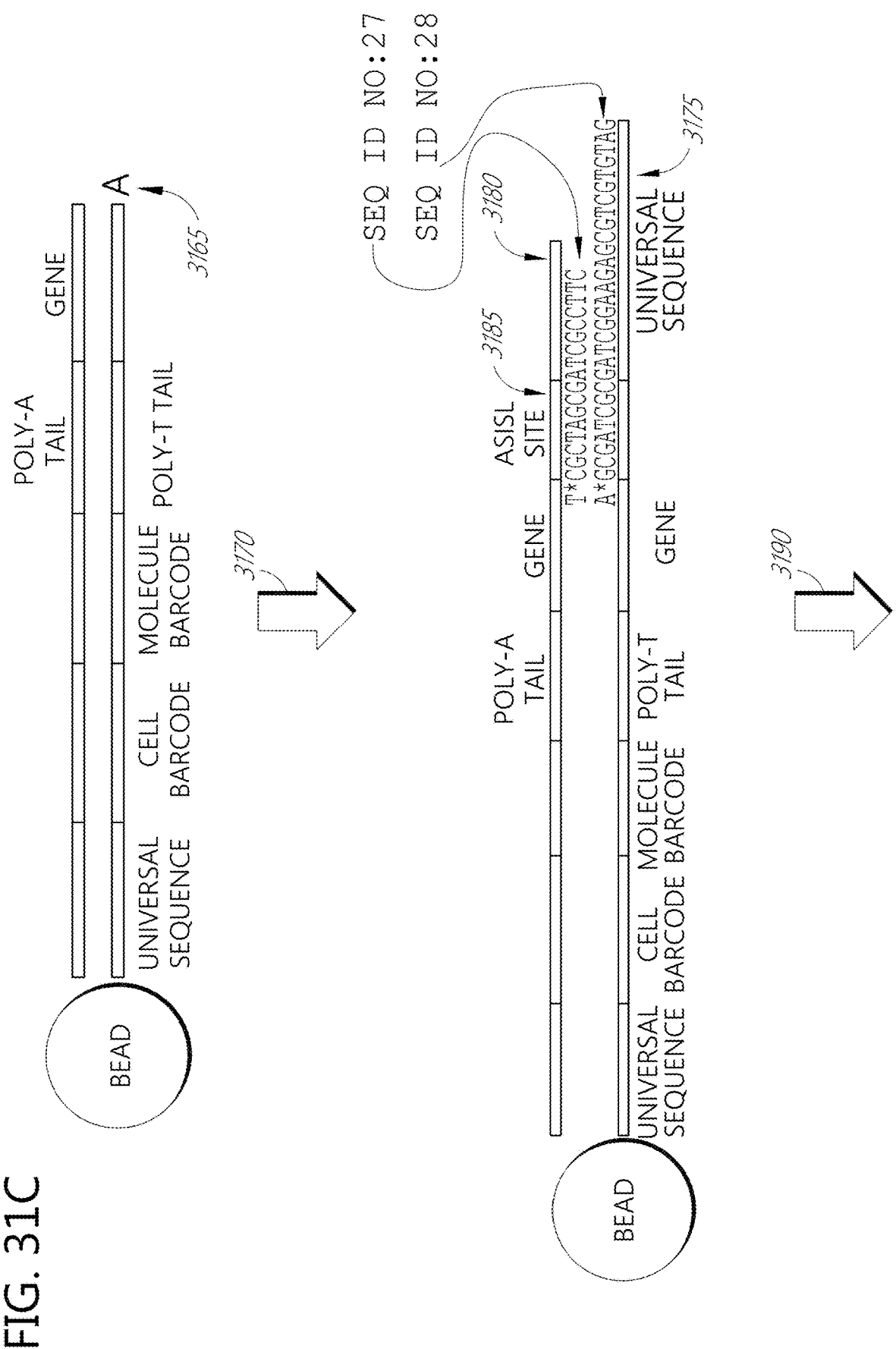
Figure 31D:
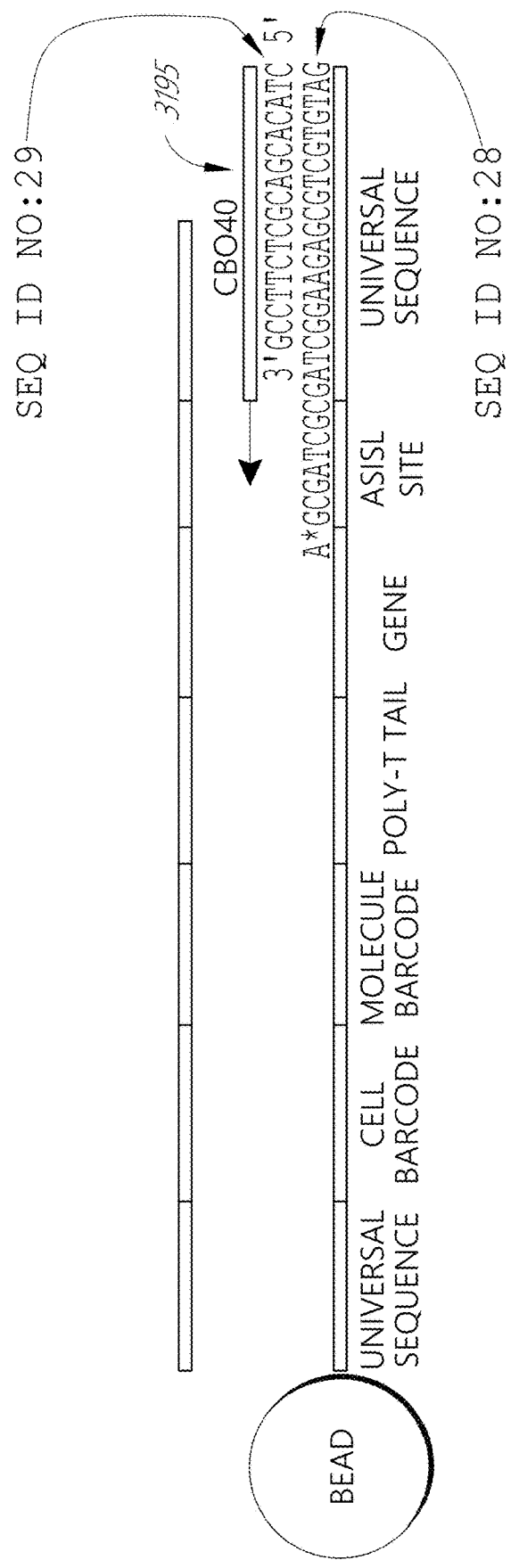
Figure 32A:
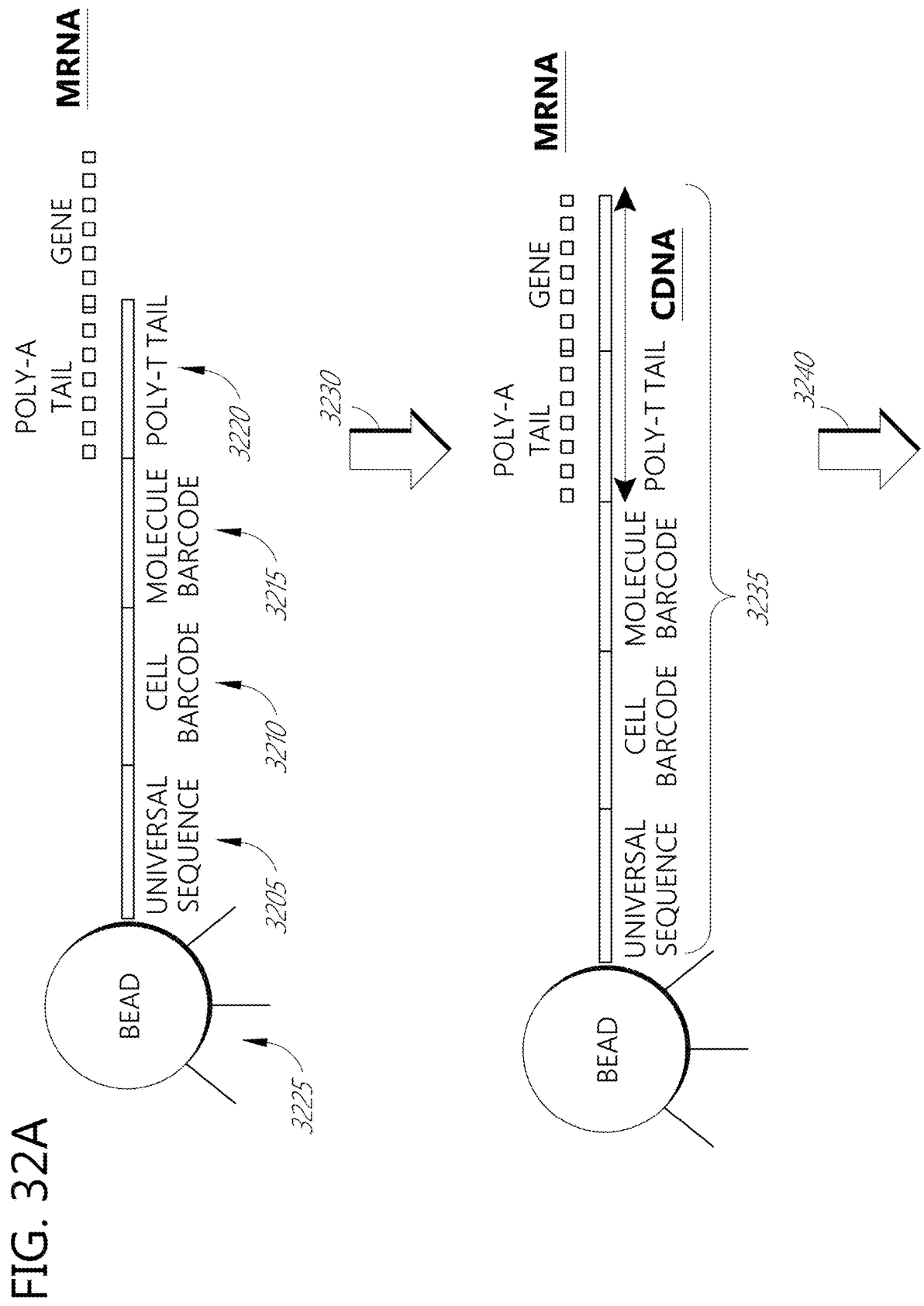
FIGS. 32A-32E show a schematic illustrating an exemplary embodiment of the whole transcriptome amplification method of the disclosure using transposome-based fragmentation and ligation with beads.
Figure 32B:
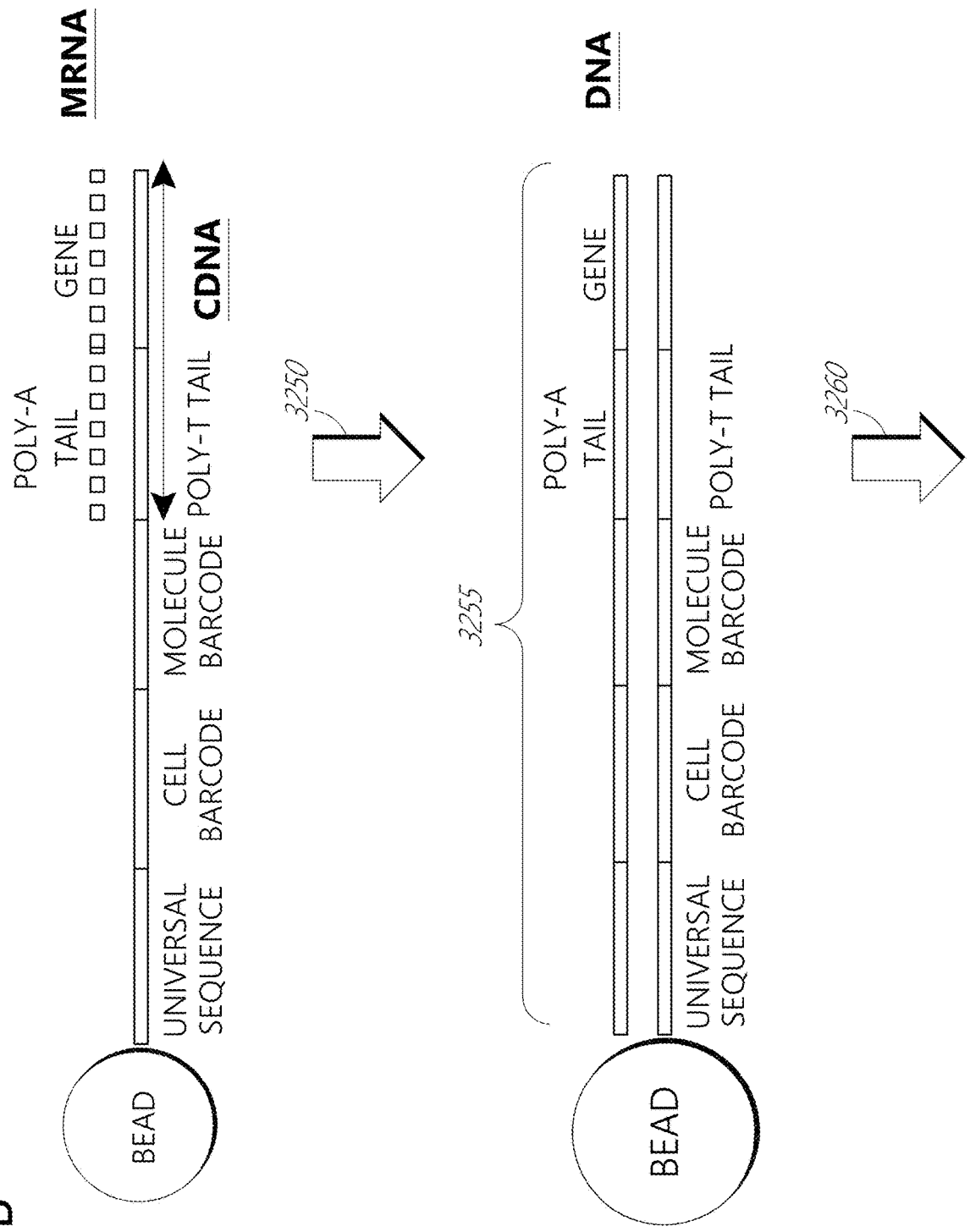
Figure 32C:
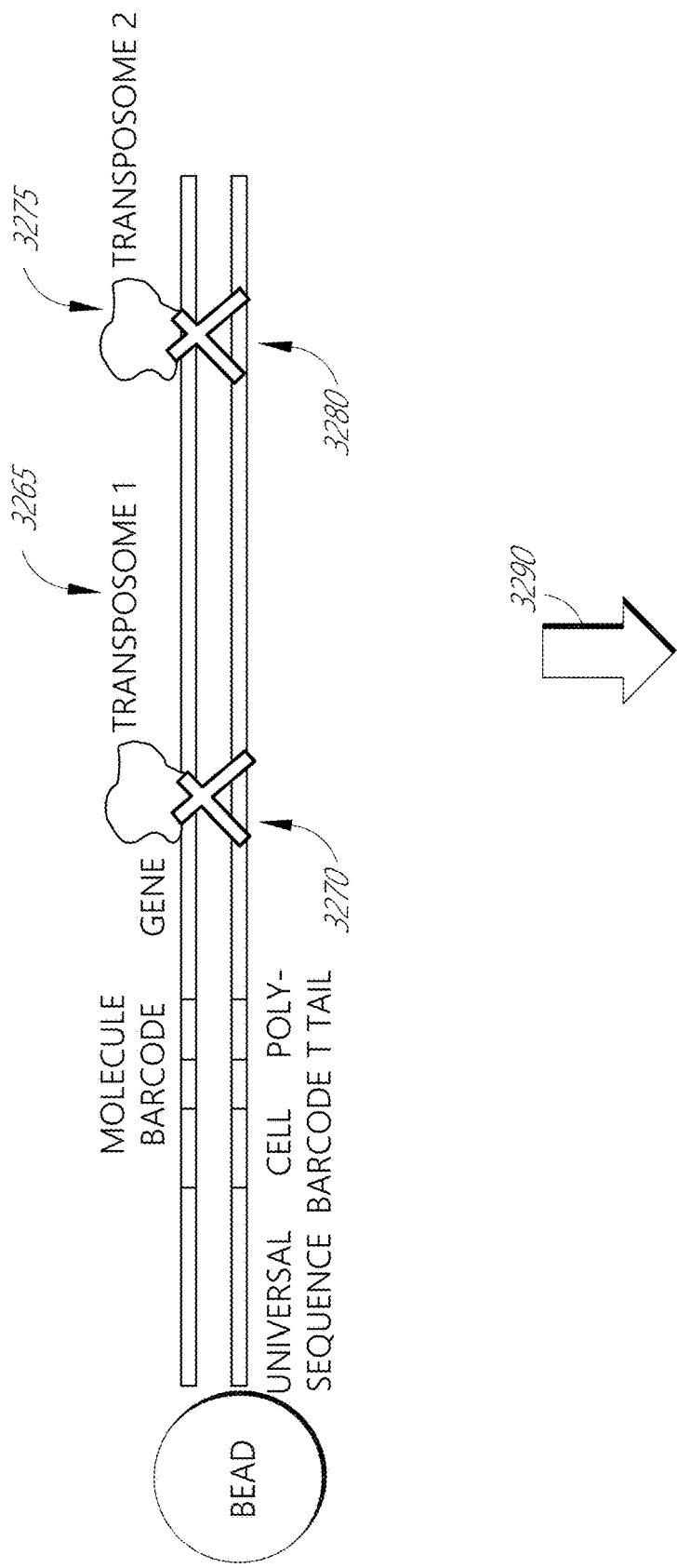
Figure 32D:
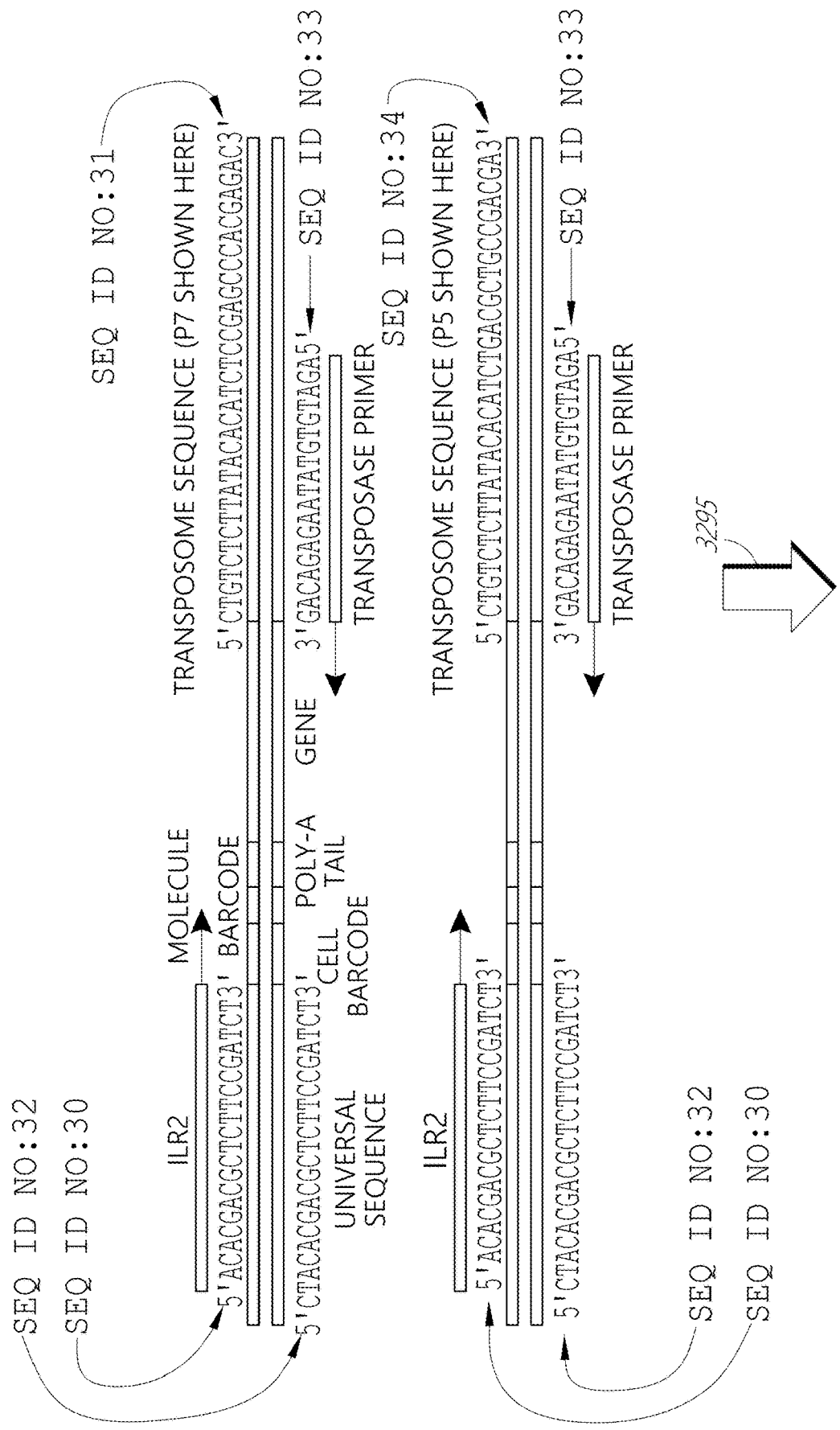
Figure 32E:
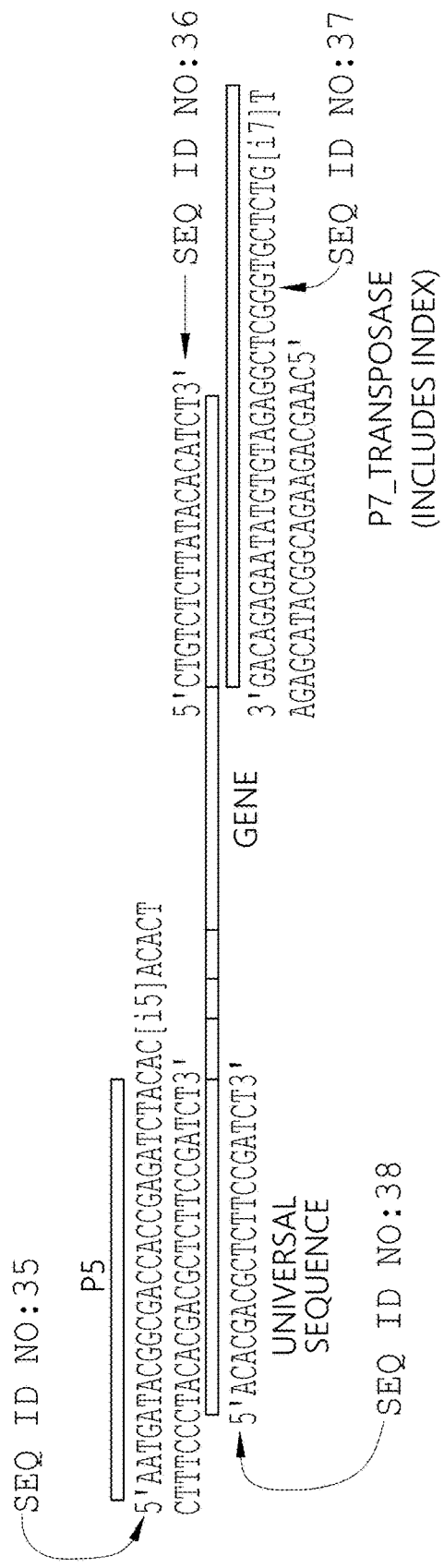
Figure 33A:
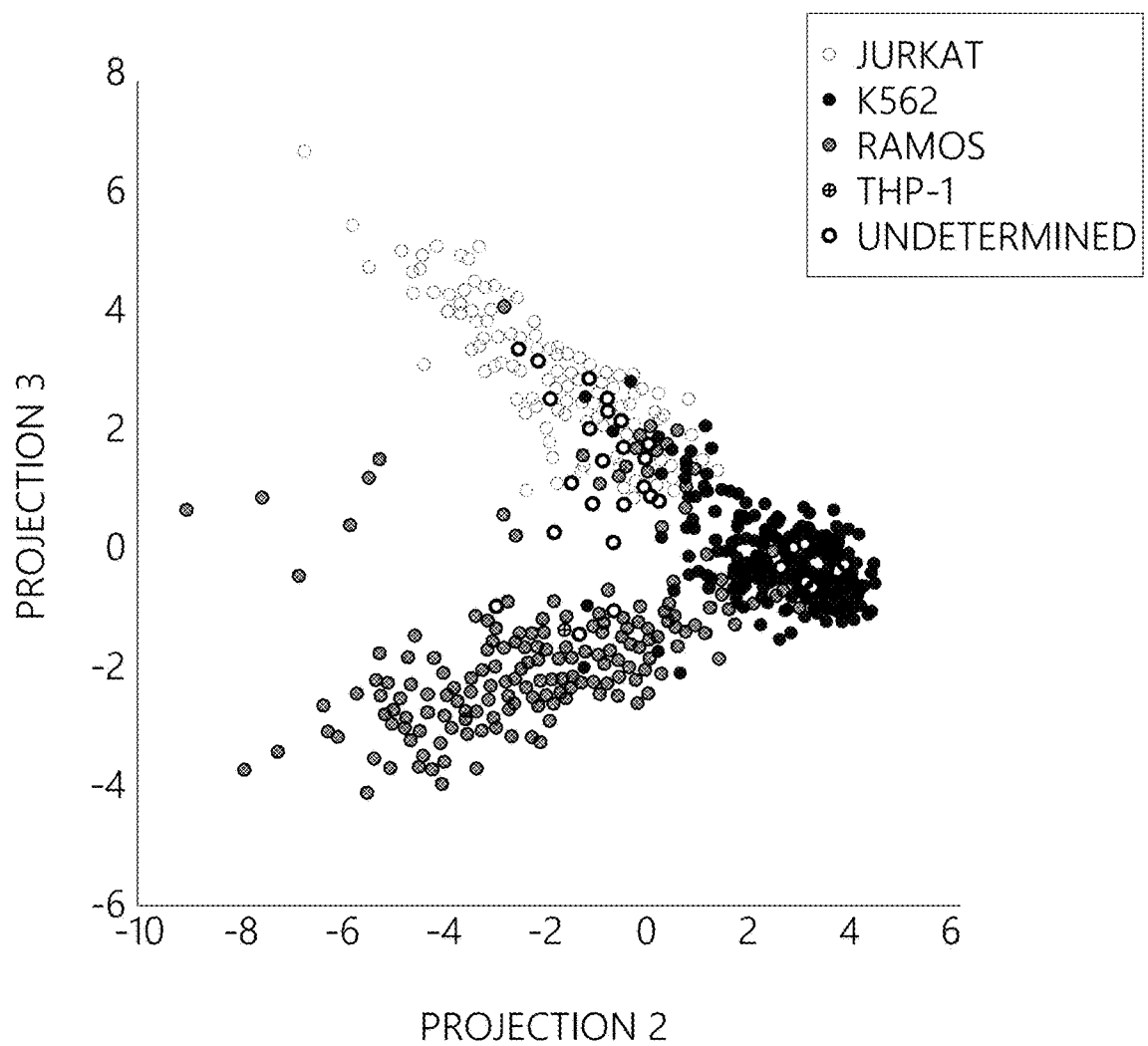
FIGS. 33A, 33B, 33C and 33D show exemplary results of TWA analysis using transposome-based fragmentation and ligation with beads and adaptor ligation with beads.
Figure 33B:
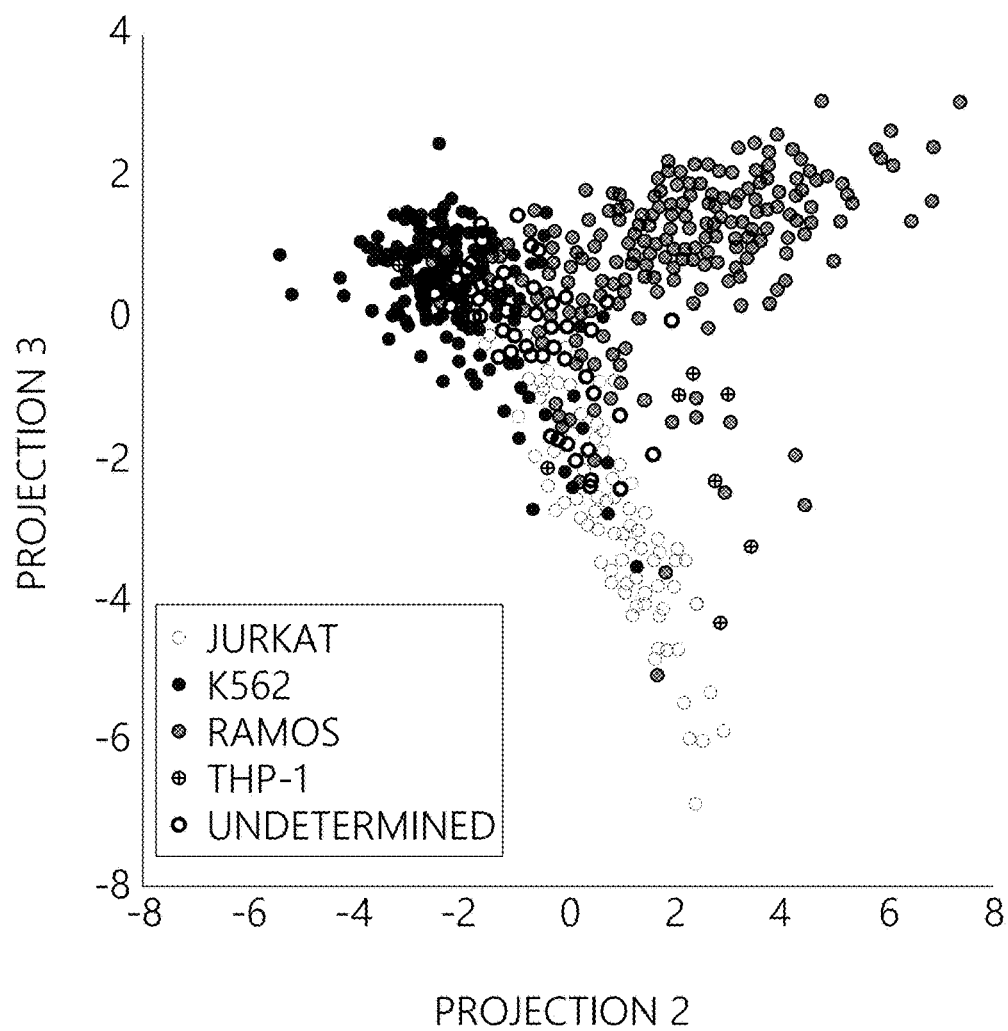
Figure 33C:
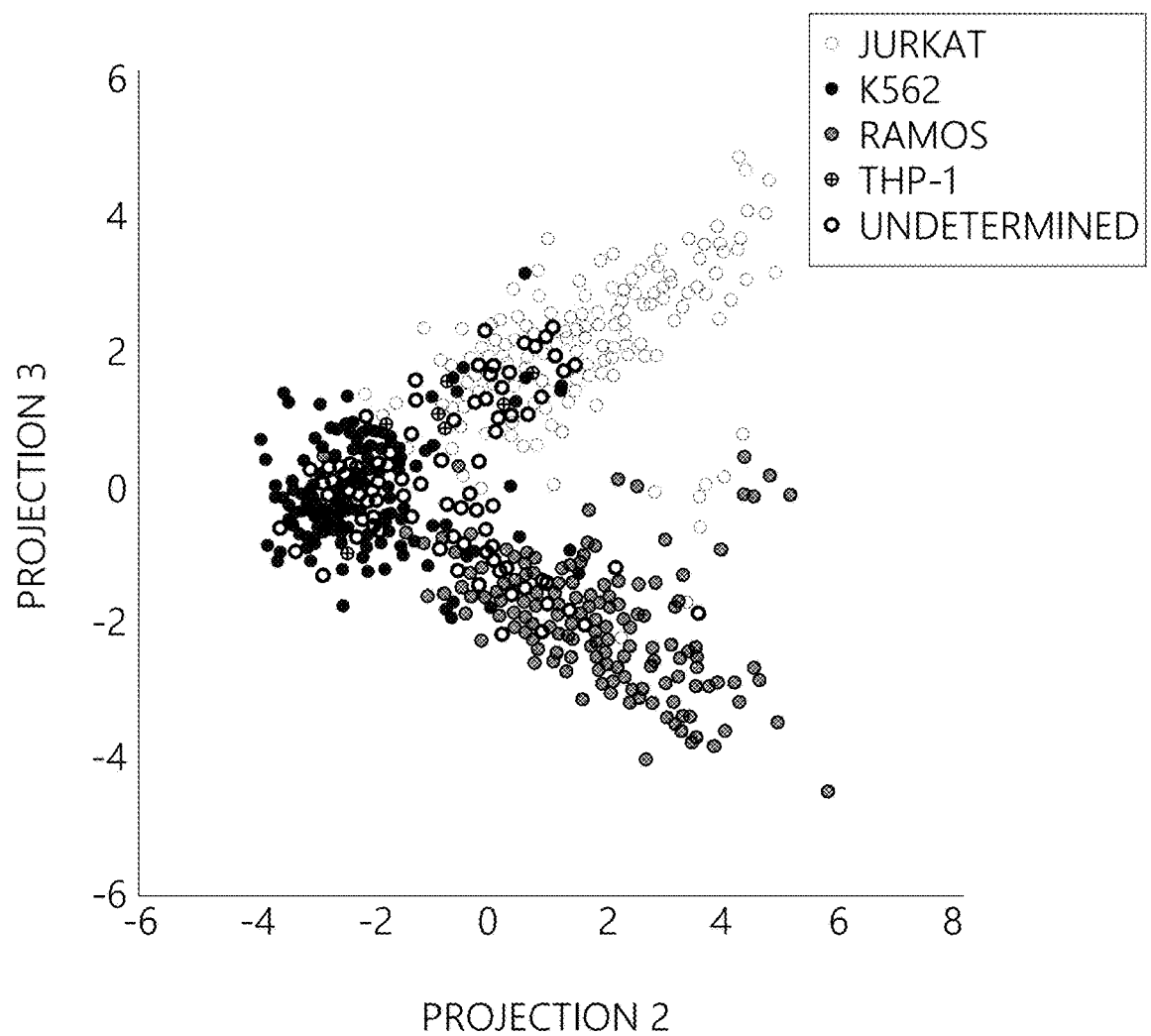
Figure 33D:
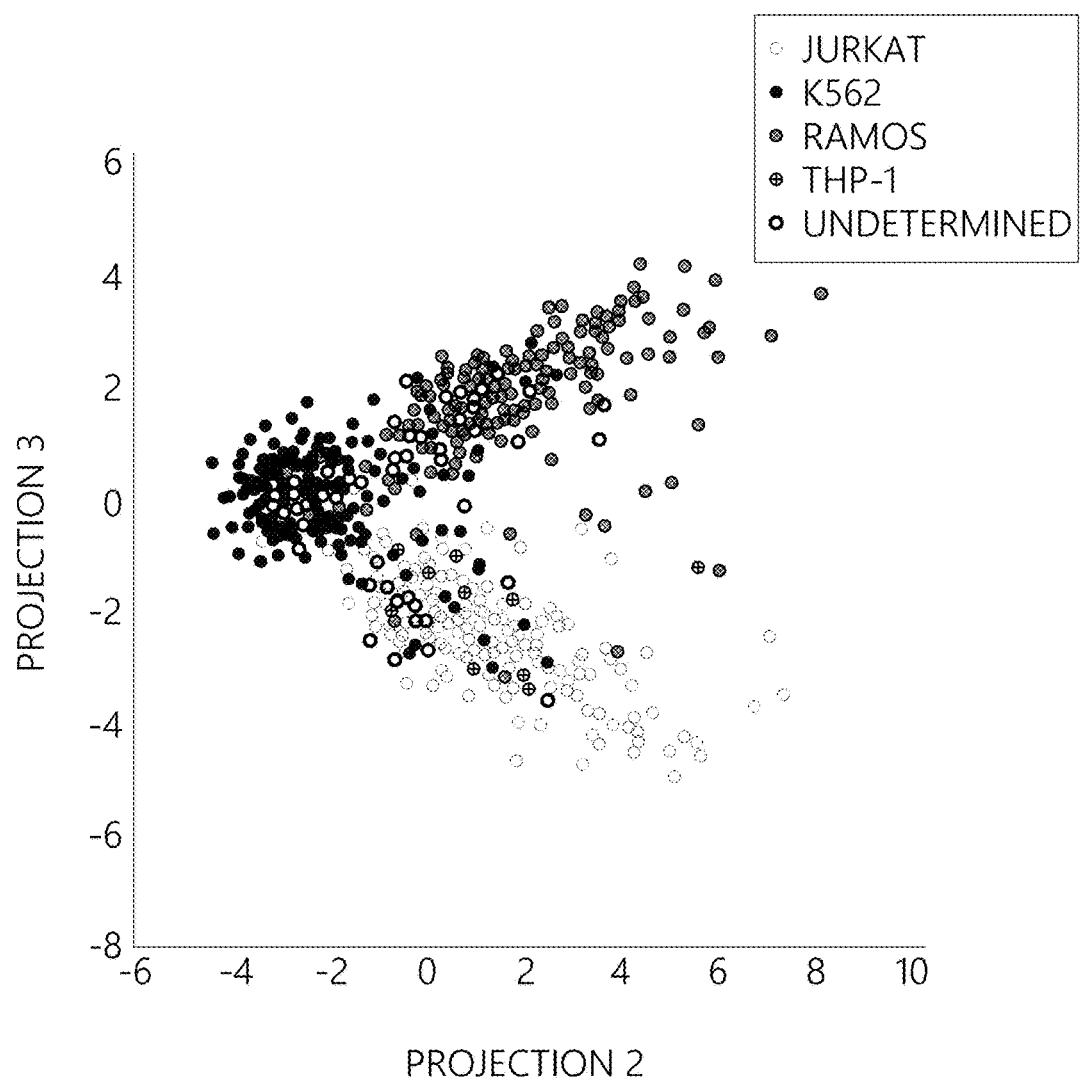

The results of the experiment are shown in FIG. 28. The no treatment trace is shown on the left. cDNA sample treated with exonuclease is shown on the right. Treatment occurred before proceeding with second strand synthesis and adaptor ligation. WTA PCR showed that there was a much higher yield when there was an ExoI treatment.

Example 13: WTA Analysis Using 1 ng and 10 pg RNA

This example describes the methods of the disclosure using primers unconjugated to beads. The protocol for analyzing 1 ng RNA is described in FIGS. 29A and 29B. The protocol for analyzing 10 pg RNA is described in FIGS. 30A and 30B.

Figure 18A:
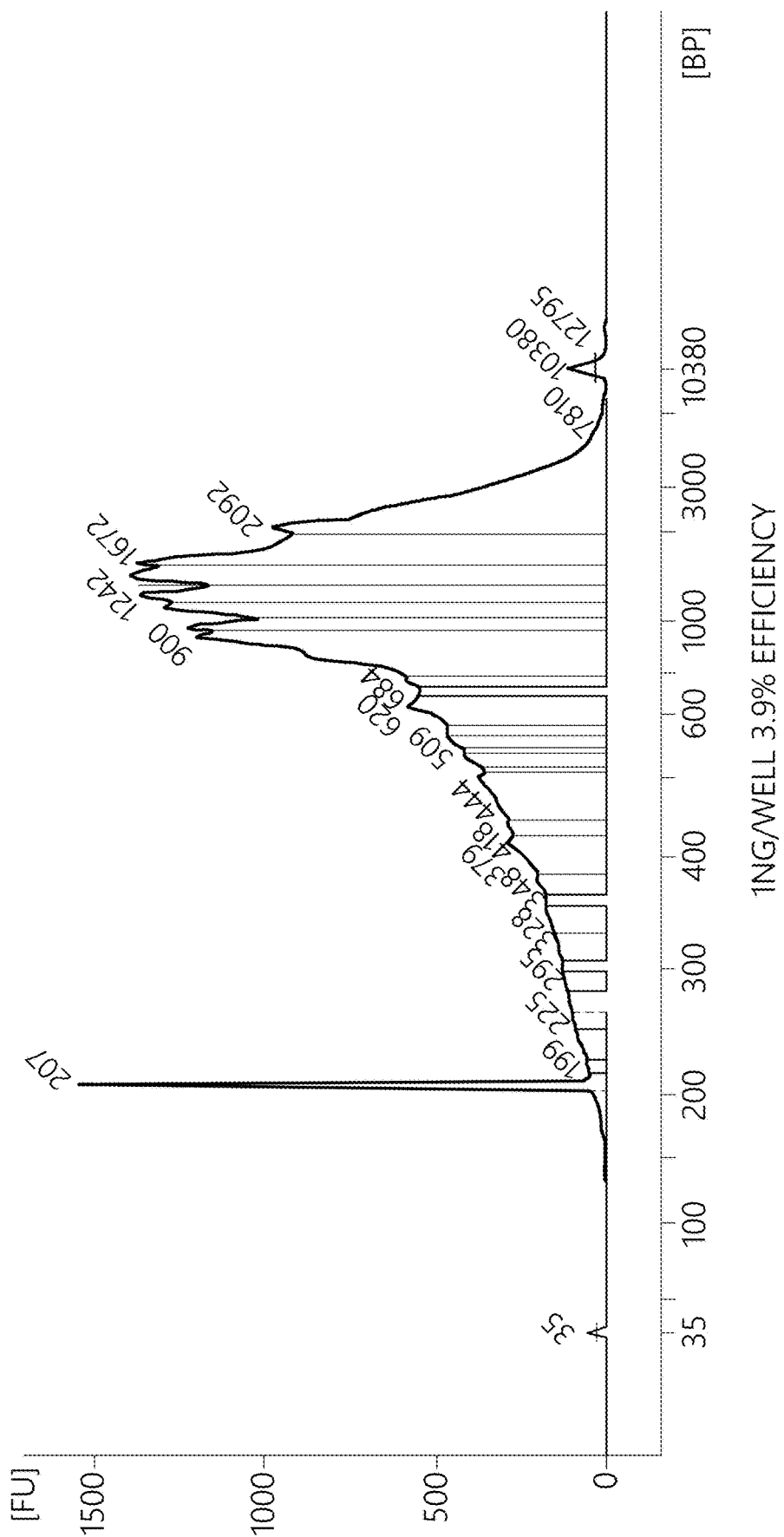
FIGS. 18A and 18B compare efficiency of an exemplary adaptor ligation method of Example 13 using 1 ng RNA per well (A) and 10 pg RNA/well (B).
Figure 18B:
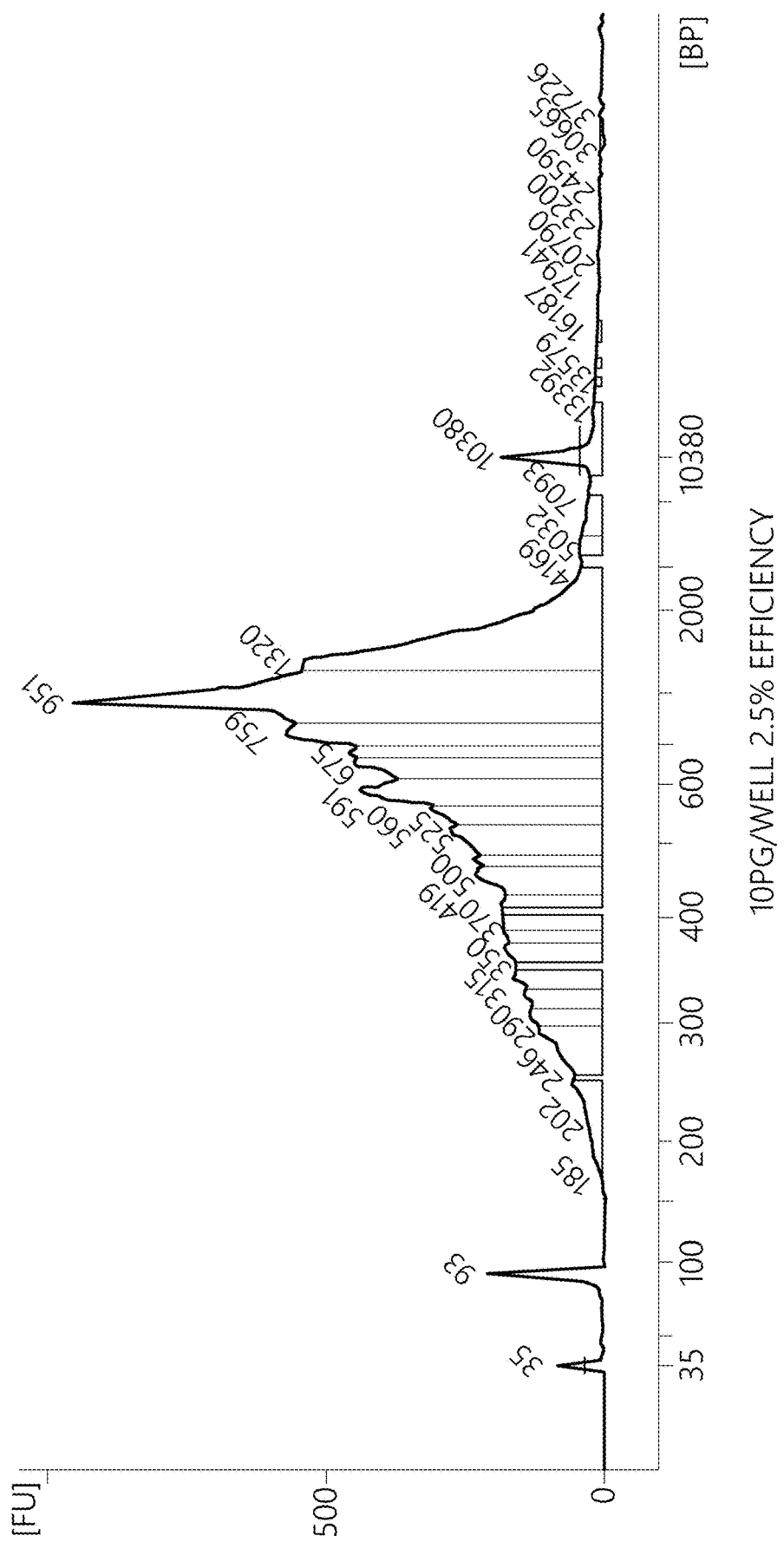

Using both 1 ng/well or 10 pg/well produced a proper WTA product, as evidenced by the correct size distribution of the Bioanalyzer traces shown in FIG. 18.

Figure 19:
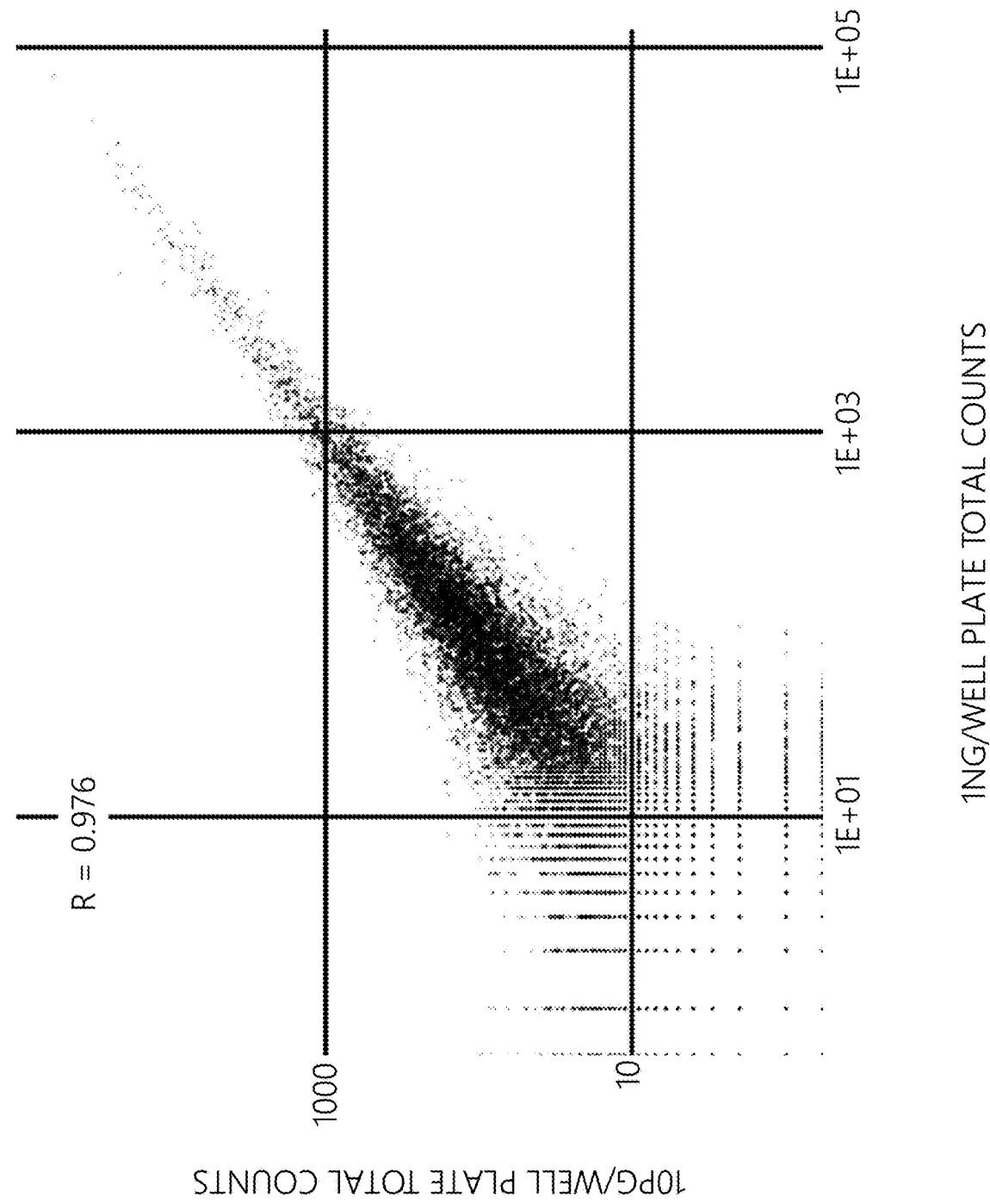
FIG. 19 shows correlation between 1 ng/well or 10 pg/well total RNA using an exemplary adaptor ligation method of Example 13.

Furthermore, both the 1 ng/well and 10 pg/well experiments resulted in a correspondence in the number of reads for each experiment. FIG. 19 shows the number of reads for each gene in the assay. The number of reads for both samples was similar. This showed the robustness of the assay.

Figure 20A:
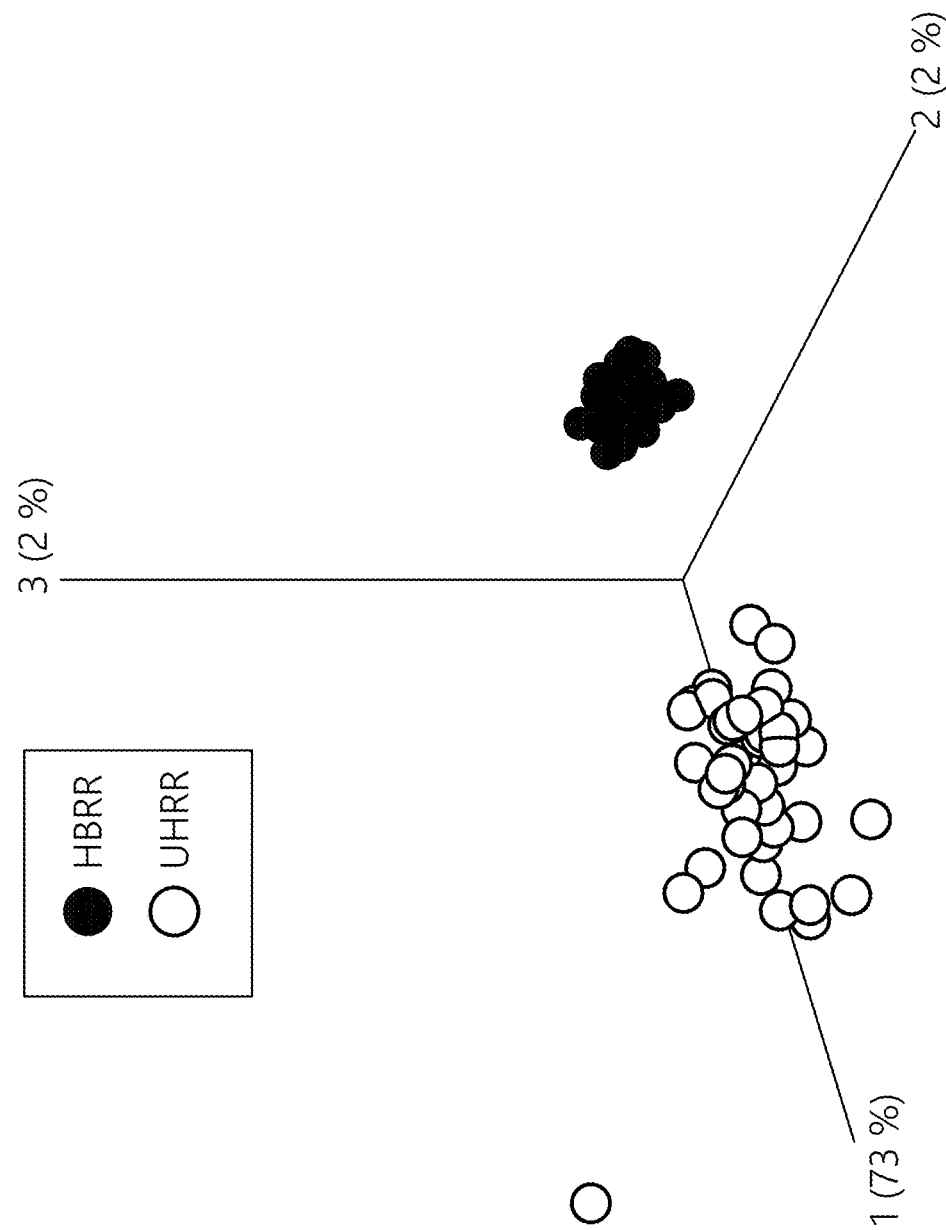
FIGS. 20A and 20B are graphical representations of the data generated in FIGS. 18 and 19.
Figure 20B:
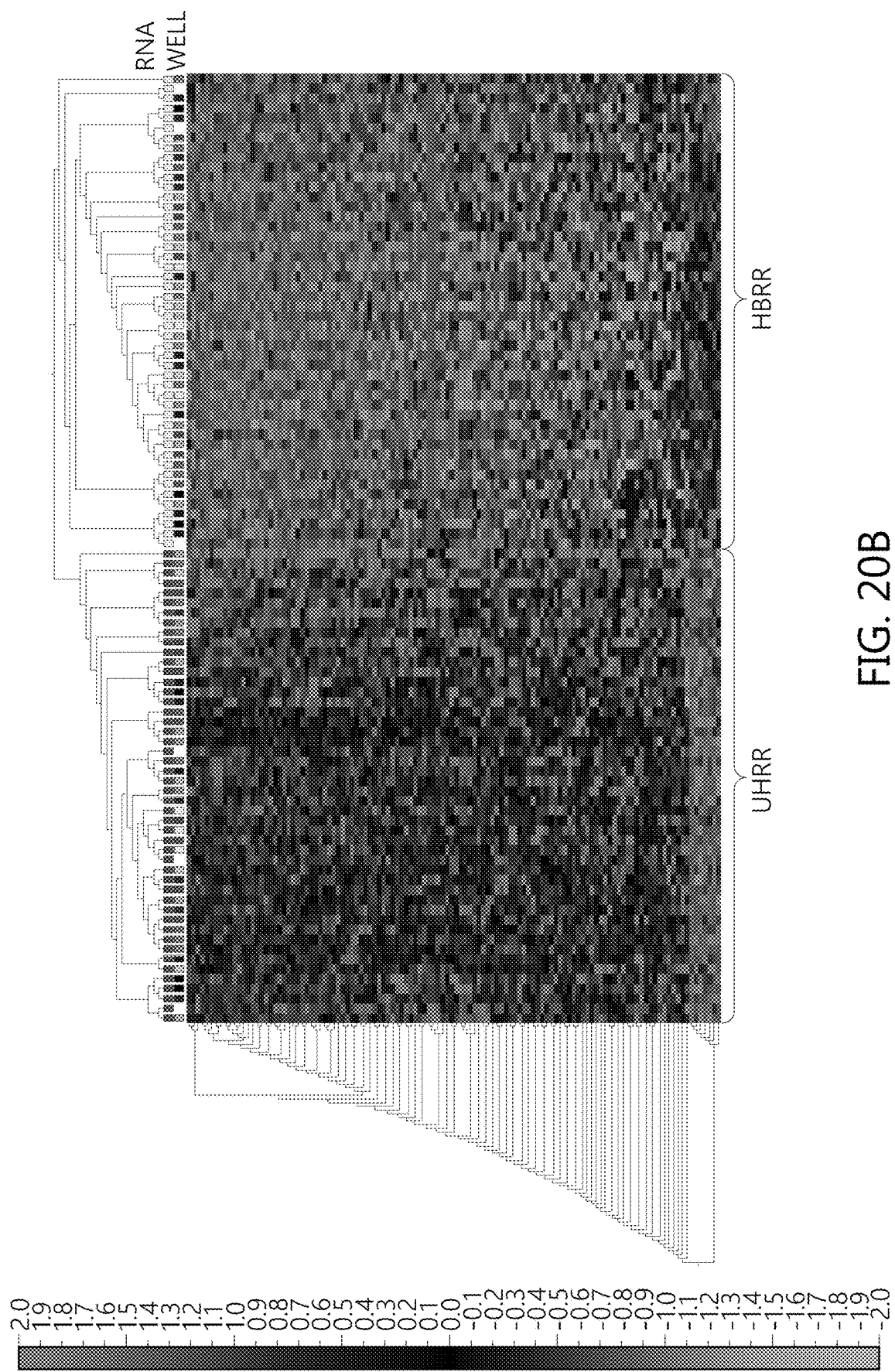

The sequencing output from the reads (e.g., FIG. 19) was graphically displayed, as shown in FIG. 20. Left, a PCA plot that clearly separates the UHRR (universal human reference RNA) wells from the Human Brain Reference RNA (HBRR)

wells. Right, a heatmap of the genes used for PCA along with hierarchical clustering that shows all of the like RNA types clustering together. FIG. 20 shows that different cell types can be identified using the methods of the disclosure.

Example 14: Comparison of Ligation-Based and Transposome-Based WTA

The Nextera XT or Nextera kit (Illumina) was used to generate sequencing libraries directly from beads. The Tn5 transposase was used to randomly fragment captured mRNA (either still in original form in a RNA/DNA complex, or converted to cDNA) and attach adapters. Primers that can hybridize to these adapter sequences were used to attach P5 and P7 indices for multiplexed Illumina sequencing runs. No further library preparation was required. While proof of principle experiments were done with commercial Nextera sequencing library kits, only the transposome component of the kit was used. Transposases can be purchased commercially and transposomes can be custom built to allow the attachment of any oligo sequence of choice (in this case, a universal sequence). If custom built, transposomes can be built with oligos containing unique molecular index, such that when the transposase cuts the DNA, a unique molecular index is attached in addition to the universal sequence. This will add a second molecular index to each of the molecules (one molecular index already added as the cDNA is transcribed using primer on the Resolve bead).

FIG. 33 shows the PCA plots for WTA analysis of 3 cell types using either ligation-based or transposome-based protocols with beads. The results show that with or without second strand synthesis, the transposome-based WTA analysis was able to distinguish the 3 cell types based on WTA. Ligation-based WTA analysis also was able to distinguish the 3 cell types.

All publications, patents, and patent applications mentioned in this specification are herein incorporated by reference for all purposes to the same extent as if each individual publication, patent, or patent application was specifically and individually indicated to be incorporated by reference.

In at least some of the previously described embodiments, one or more elements used in an embodiment can interchangeably be used in another embodiment unless such a replacement is not technically feasible. It will be appreciated by those skilled in the art that various other omissions, additions and modifications may be made to the methods and structures described above without departing from the scope of the claimed subject matter. All such modifications and changes are intended to fall within the scope of the subject matter, as defined by the appended claims.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity. As used in this specification and the appended claims, the singular forms "a," "an," and "the" include plural references unless the context clearly dictates otherwise. Any reference to "or" herein is intended to encompass "and/or" unless otherwise stated.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible sub-ranges and combinations of sub-ranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into sub-ranges as discussed above. Finally, as will be understood by one skilled in the art, a range includes each individual member. Thus, for example, a group having 1-3 articles refers to groups having 1, 2, or 3 articles. Similarly, a group having 1-5 articles refers to groups having 1, 2, 3, 4, or 5 articles, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for labeling a plurality of nucleic acid targets from a sample, comprising:
   hybridizing the plurality of nucleic acid targets from the sample with a plurality of labeling nucleic acids each comprising a first universal label;
   extending the plurality of labeling nucleic acids to generate a plurality of first strand polynucleotides, wherein the plurality of nucleic acid targets are single-stranded;
   synthesizing a plurality of second strand polynucleotides using the plurality of first strand polynucleotides as templates to generate a plurality of double-stranded polynucleotides;
   ligating an adaptor to the plurality of double-stranded polynucleotides, wherein said adaptor comprises a second universal label; and
   amplifying the plurality of double-stranded polynucleotides using the first universal label and the second universal label as primer sequences, thereby generating a plurality of amplicons comprising the plurality of nucleic acid targets.

2. The method of claim 1, wherein each of the plurality of labeling nucleic acids comprises a stochastic barcode.

3. The method of claim 2, wherein said stochastic barcode comprises a molecular label, a cellular label, a target-specific region, or any combination thereof.

4. The method of claim 1, wherein the plurality of nucleic acid targets are mRNAs.

5. The method of claim 4, wherein synthesizing the plurality of second strand polynucleotides comprises nicking the plurality of mRNAs with an RNase, thereby generating one or more mRNA primers.

6. The method of claim 4, wherein the plurality of nucleic acid targets are nucleic acids from a single cell selected from the group consisting of a bacterial cell, a fungal cell, a protozoan cell, an animal cell, and a plant cell.

7. The method of claim 4, wherein the plurality of amplicons comprises a whole transcriptome amplification (WTA) product.

8. The method of claim 1, wherein each of the plurality of labeling nucleic acids is immobilized on a solid support.

9. The method of claim 8, wherein said solid support is a bead.

10. The method of claim 8, wherein at least two of said plurality of labeling nucleic acids immobilized on a single solid support comprises different molecular labels.

11. The method of claim 8, wherein said plurality of labeling nucleic acids attached to a solid support comprises the same cellular label.

12. The method of claim 1, wherein the sample comprises a single cell.

13. The method of claim 1, wherein the first universal label and the second universal label are different.

14. A method for labeling a plurality of nucleic acid targets from a sample comprising:
   hybridizing the plurality of nucleic acid targets from the sample with a plurality of labeling nucleic acids each comprising a first universal label;
   extending the plurality of labeling nucleic acids to generate a plurality of first strand polynucleotides, wherein the plurality of first stand polynucleotides and the plurality of nucleic acid targets form a plurality of double-stranded polynucleotides;
   contacting the plurality of double-stranded polynucleotides with a first transposome comprising a first transposase and a first adaptor, wherein said first adaptor comprises a second universal label;
   ligating the first adaptor to the double-stranded polynucleotides with the first transposase to generate a plurality of double stranded polynucleotides that are ligated with the first adaptor; and
   amplifying the plurality of double-stranded polynucleotides that are ligated with the first adaptor using the first universal label and the second universal label as primer sequences, thereby generating a plurality of amplicons comprising the plurality of nucleic acid targets.

15. The method of claim 14, further comprising synthesizing a plurality of second strand polynucleotides using the plurality of first strand polynucleotides as templates.

16. The method of claim 14, wherein said first adaptor comprises a stochastic barcode.

17. The method of claim 14, wherein said second universal label is a transposome sequence.

18. The method of claim 14, wherein each of the plurality of labeling nucleic acids is immobilized on a solid support.

19. The method of claim 18, wherein said solid support is a bead.

20. The method of claim 19, comprising purifying double-stranded polynucleotides that are immobilized on beads, wherein the double-stranded polynucleotides are double-stranded polynucleotides that are ligated with the first adaptor, the second adaptor, or both.

21. A method for labeling a plurality of nucleic acid target sequences from a single cell, comprising:
   providing the single cell to a partition comprising a solid support immobilized with a plurality of labeling nucleic acids each comprising a first universal label, wherein the single cell is a bacterial cell, a fungal cell, a protozoan cell, an animal cell, or a plant cell;
   lysing the single cell to release the plurality of nucleic acid target sequences, wherein the nucleic acid target sequences are mRNAs;
   hybridizing the plurality of nucleic acid target sequences from the single cell with the plurality of labeling nucleic acids;

extending the plurality of labeling nucleic acids to generate a plurality of first strand polynucleotides;

adding an adaptor sequence to the plurality of first strand polynucleotides, wherein said adaptor sequence comprises a second universal label; and amplifying the plurality of first strand polynucleotides using the first universal label and the second universal label as primer sequences, thereby generating a plurality of amplicons comprising the plurality of nucleic acid target sequences.

22. The method of claim 21, wherein said adaptor sequence is added by a transposome.

23. The method of claim 21, wherein said adaptor is added by a ligation step.

* * * * *

```
                              SEQUENCE LISTING

<160> NUMBER OF SEQ ID NOS: 38

<210> SEQ ID NO 1
  <211> LENGTH: 30
  <212> TYPE: DNA
  <213> ORGANISM: Artificial Sequence
  <220> FEATURE:
  <223> OTHER INFORMATION: CBO102

<400> SEQUENCE: 1
gcgatcgcga tcggaagagc acacgtctga                                           30

<210> SEQ ID NO 2
  <211> LENGTH: 17
  <212> TYPE: DNA
  <213> ORGANISM: Artificial Sequence
  <220> FEATURE:
  <223> OTHER INFORMATION: CBO103

<400> SEQUENCE: 2
cttccgatcg cgatcgc                                                         17

<210> SEQ ID NO 3
  <211> LENGTH: 18
  <212> TYPE: DNA
  <213> ORGANISM: Artificial Sequence
  <220> FEATURE:
  <223> OTHER INFORMATION: CBO23

<400> SEQUENCE: 3
tcagacgtgt gctcttcc                                                        18

<210> SEQ ID NO 4
  <211> LENGTH: 26
  <212> TYPE: DNA
  <213> ORGANISM: Artificial Sequence
  <220> FEATURE:
  <223> OTHER INFORMATION: CBO105

<400> SEQUENCE: 4
gcgatcgcgg aagagcacac gtctga                                               26

<210> SEQ ID NO 5
  <211> LENGTH: 16
  <212> TYPE: DNA
  <213> ORGANISM: Artificial Sequence
  <220> FEATURE:
  <223> OTHER INFORMATION: CBO106

<400> SEQUENCE: 5
gctcttccgc gatcgc                                                          16

<210> SEQ ID NO 6
  <211> LENGTH: 18
  <212> TYPE: DNA
  <213> ORGANISM: Artificial Sequence
  <220> FEATURE:
  <223> OTHER INFORMATION: CBO23

<400> SEQUENCE: 6
```
tcagacgtgt gctcttcc                                                18

<210> SEQ ID NO 7
<211> LENGTH: 21
<212> TYPE: DNA
<213> ORGANISM: Artificial Sequence
<220> FEATURE:
<223> OTHER INFORMATION: CBO17

<400> SEQUENCE: 7
tcagacgtgt gctcttccga t                                            21

<210> SEQ ID NO 8
<211> LENGTH: 26
<212> TYPE: DNA
<213> ORGANISM: Artificial Sequence
<220> FEATURE:
<223> OTHER INFORMATION: CBO105

<400> SEQUENCE: 8
gcgatcgcgg aagagcacac gtctga                                       26

<210> SEQ ID NO 9
<211> LENGTH: 17
<212> TYPE: DNA
<213> ORGANISM: Artificial Sequence
<220> FEATURE:
<223> OTHER INFORMATION: CBO107

<400> SEQUENCE: 9
gctcttccgc gatcgct                                                 17

<210> SEQ ID NO 10
<211> LENGTH: 18
<212> TYPE: DNA
<213> ORGANISM: Artificial Sequence
<220> FEATURE:
<223> OTHER INFORMATION: CBO23

<400> SEQUENCE: 10
tcagacgtgt gctcttcc                                                18

<210> SEQ ID NO 11
<211> LENGTH: 55
<212> TYPE: DNA
<213> ORGANISM: Artificial Sequence
<220> FEATURE:
<223> OTHER INFORMATION: CBO16

<400> SEQUENCE: 11
tcagacgtgt gctcttccga tctgcgatcg ctttttttttt ttttttttt ttttt       55

<210> SEQ ID NO 12
<211> LENGTH: 30
<212> TYPE: DNA
<213> ORGANISM: Artificial Sequence
<220> FEATURE:
<223> OTHER INFORMATION: CBO12
<220> FEATURE:
<221> NAME/KEY: misc_feature
<222> LOCATION: (25)...(30)
<223> OTHER INFORMATION: n = random nucleotide

<400> SEQUENCE: 12
ccctacacga cgctcttccg atctnnnnnn                                   30

<210> SEQ ID NO 13
<211> LENGTH: 70
<212> TYPE: DNA
<213> ORGANISM: Artificial Sequence
<220> FEATURE:
<223> OTHER INFORMATION: CBO32

<400> SEQUENCE: 13
aatgatacgg cgaccaccga gatctacact atagcctaca ctctttccct acacgacgct    60
cttccgatct                                                          70

<210> SEQ ID NO 14
<211> LENGTH: 66
<212> TYPE: DNA
<213> ORGANISM: Artificial Sequence
<220> FEATURE:
<223> OTHER INFORMATION: CBO33

<400> SEQUENCE: 14
caagcagaag acggcatacg agatcgagta atgtgactgg agttcagacg tgtgctcttc    60
cgatct                                                              66

<210> SEQ ID NO 15
<211> LENGTH: 53
<212> TYPE: DNA
<213> ORGANISM: Artificial Sequence
<220> FEATURE:
<223> OTHER INFORMATION: CBO10

<400> SEQUENCE: 15
tcagacgtgt gctcttccga tgcgatcgct tttttttttt tttttttttt ttt          53

<210> SEQ ID NO 16
<211> LENGTH: 24
<212> TYPE: DNA
<213> ORGANISM: Artificial Sequence
<220> FEATURE:
<223> OTHER INFORMATION: Illumina Read 1

<400> SEQUENCE: 16
ccctacacga cgctcttccg atct                                          24

<210> SEQ ID NO 17
<211> LENGTH: 17
<212> TYPE: DNA
<213> ORGANISM: Artificial Sequence
<220> FEATURE:
<223> OTHER INFORMATION: CBO122

<400> SEQUENCE: 17
cttccgatcg cgatcgc                                                  17

<210> SEQ ID NO 18
<211> LENGTH: 29
<212> TYPE: DNA
<213> ORGANISM: Artificial Sequence
<220> FEATURE:
<223> OTHER INFORMATION: CBO103

<400> SEQUENCE: 18
gcgatcgcga tcggaagagc gtcgtgtag                                     29

<210> SEQ ID NO 19
<211> LENGTH: 16

```
<212> TYPE: DNA
<213> ORGANISM: Artificial Sequence
<220> FEATURE:
<223> OTHER INFORMATION: CBO123

<400> SEQUENCE: 19
gctcttccgc gatcgc                                                         16

<210> SEQ ID NO 20
<211> LENGTH: 25
<212> TYPE: DNA
<213> ORGANISM: Artificial Sequence
<220> FEATURE:
<223> OTHER INFORMATION: CBO106

<400> SEQUENCE: 20
gcgatcgcgg aagagcgtcg tgtag                                               25

<210> SEQ ID NO 21
<211> LENGTH: 14
<212> TYPE: DNA
<213> ORGANISM: Artificial Sequence
<220> FEATURE:
<223> OTHER INFORMATION: Poly-A

<400> SEQUENCE: 21
aaaaaaaaaa aaaa                                                           14

<210> SEQ ID NO 22
<211> LENGTH: 14
<212> TYPE: DNA
<213> ORGANISM: Artificial Sequence
<220> FEATURE:
<223> OTHER INFORMATION: Oligo dT

<400> SEQUENCE: 22
tttttttttt tttt                                                           14

<210> SEQ ID NO 23
<211> LENGTH: 14
<212> TYPE: DNA
<213> ORGANISM: Artificial Sequence
<220> FEATURE:
<223> OTHER INFORMATION: Poly-A

<400> SEQUENCE: 23
aaaaaaaaaa aaaa                                                           14

<210> SEQ ID NO 24
<211> LENGTH: 14
<212> TYPE: DNA
<213> ORGANISM: Artificial Sequence
<220> FEATURE:
<223> OTHER INFORMATION: Oligo dT

<400> SEQUENCE: 24
tttttttttt tttt                                                           14

<210> SEQ ID NO 25
<211> LENGTH: 13
<212> TYPE: DNA
<213> ORGANISM: Artificial Sequence
<220> FEATURE:
<223> OTHER INFORMATION: Poly-A

<400> SEQUENCE: 25
```

```
aaaaaaaaaa aaa                                                    13

<210> SEQ ID NO 26
<211> LENGTH: 14
<212> TYPE: DNA
<213> ORGANISM: Artificial Sequence
<220> FEATURE:
<223> OTHER INFORMATION: Oligo dT

<400> SEQUENCE: 26
tttttttttt tttt                                                   14

<210> SEQ ID NO 27
<211> LENGTH: 18
<212> TYPE: DNA
<213> ORGANISM: Artificial Sequence
<220> FEATURE:
<223> OTHER INFORMATION: Universal sequence 1

<400> SEQUENCE: 27
cttccgctag cgatcgct                                               18

<210> SEQ ID NO 28
<211> LENGTH: 30
<212> TYPE: DNA
<213> ORGANISM: Artificial Sequence
<220> FEATURE:
<223> OTHER INFORMATION: Universal sequence 2

<400> SEQUENCE: 28
agcgatcgcg atcggaagag cgtcgtgtag                                  30

<210> SEQ ID NO 29
<211> LENGTH: 18
<212> TYPE: DNA
<213> ORGANISM: Artificial Sequence
<220> FEATURE:
<223> OTHER INFORMATION: CBO40

<400> SEQUENCE: 29
ctacacgacg ctcttccg                                               18

<210> SEQ ID NO 30
<211> LENGTH: 20
<212> TYPE: DNA
<213> ORGANISM: Artificial Sequence
<220> FEATURE:
<223> OTHER INFORMATION: ILR2

<400> SEQUENCE: 30
acacgacgct cttccgatct                                             20

<210> SEQ ID NO 31
<211> LENGTH: 34
<212> TYPE: DNA
<213> ORGANISM: Artificial Sequence
<220> FEATURE:
<223> OTHER INFORMATION: Transposome sequence P7

<400> SEQUENCE: 31
ctgtctctta tacacatctc cgagcccacg agac                             34

<210> SEQ ID NO 32
<211> LENGTH: 22
<212> TYPE: DNA
<213> ORGANISM: Artificial Sequence
```

```
<220> FEATURE:
<223> OTHER INFORMATION: Universal sequence 3

<400> SEQUENCE: 32
ctacacgacg ctcttccgat ct                                             22

<210> SEQ ID NO 33
<211> LENGTH: 19
<212> TYPE: DNA
<213> ORGANISM: Artificial Sequence
<220> FEATURE:
<223> OTHER INFORMATION: Transposase primer

<400> SEQUENCE: 33
agatgtgtat aagagacag                                                 19

<210> SEQ ID NO 34
<211> LENGTH: 33
<212> TYPE: DNA
<213> ORGANISM: Artificial Sequence
<220> FEATURE:
<223> OTHER INFORMATION: Transposome sequence P5

<400> SEQUENCE: 34
ctgtctctta tacacatctg acgctgccga cga                                 33

<210> SEQ ID NO 35
<211> LENGTH: 62
<212> TYPE: DNA
<213> ORGANISM: Artificial Sequence
<220> FEATURE:
<223> OTHER INFORMATION: P5

<400> SEQUENCE: 35
aatgatacgg cgaccaccga gatctacaca cactctttcc ctacacgacg ctcttccgat    60
ct                                                                   62

<210> SEQ ID NO 36
<211> LENGTH: 19
<212> TYPE: DNA
<213> ORGANISM: Artificial Sequence
<220> FEATURE:
<223> OTHER INFORMATION: Transposome sequence

<400> SEQUENCE: 36
ctgtctctta tacacatct                                                 19

<210> SEQ ID NO 37
<211> LENGTH: 58
<212> TYPE: DNA
<213> ORGANISM: Artificial Sequence
<220> FEATURE:
<223> OTHER INFORMATION: P7

<400> SEQUENCE: 37
caagcagaag acggcatacg agatgtctcg tgggctcgga gatgtgtata agagacag      58
```

```
<210> SEQ ID NO 38
<211> LENGTH: 20
<212> TYPE: DNA
<213> ORGANISM: Artificial Sequence
<220> FEATURE:
<223> OTHER INFORMATION: Universal sequence 4

<400> SEQUENCE: 38
acacgacgct cttccgatct                                                    20
```